United States Patent
Francis et al.

(10) Patent No.: US 9,885,071 B2
(45) Date of Patent: Feb. 6, 2018

(54) POLYMER ENHANCEMENT OF ENZYMATIC ACTIVITY

(71) Applicant: The Regents of the University of California, Oakland, CA (US)

(72) Inventors: Matthew B. Francis, Berkeley, CA (US); Katherine J. Mackenzie, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 157 days.

(21) Appl. No.: 14/731,381

(22) Filed: Jun. 4, 2015

(65) Prior Publication Data

US 2015/0344924 A1    Dec. 3, 2015

Related U.S. Application Data

(63) Continuation of application No. PCT/US2013/073712, filed on Dec. 6, 2013.

(60) Provisional application No. 61/801,982, filed on Mar. 15, 2013, provisional application No. 61/734,918, filed on Dec. 7, 2012.

(51) Int. Cl.
| | |
|---|---|
| *A01N 65/00* | (2009.01) |
| *C12P 19/14* | (2006.01) |
| *C12P 19/12* | (2006.01) |
| *C12N 11/08* | (2006.01) |
| *C08F 220/56* | (2006.01) |
| *C12P 19/02* | (2006.01) |
| *C12N 9/16* | (2006.01) |
| *C12N 9/20* | (2006.01) |
| *C12N 9/24* | (2006.01) |
| *C12N 9/26* | (2006.01) |
| *C12N 9/42* | (2006.01) |
| *C12N 9/96* | (2006.01) |

(52) U.S. Cl.
CPC ........... *C12P 19/14* (2013.01); *C08F 220/56* (2013.01); *C12N 9/16* (2013.01); *C12N 9/20* (2013.01); *C12N 9/2402* (2013.01); *C12N 9/248* (2013.01); *C12N 9/2411* (2013.01); *C12N 9/2437* (2013.01); *C12N 9/2477* (2013.01); *C12N 9/96* (2013.01); *C12N 11/08* (2013.01); *C12P 19/02* (2013.01); *C12P 19/12* (2013.01); *C12P 2203/00* (2013.01)

(58) Field of Classification Search
CPC ...... C08F 220/56; C08F 220/60; C12N 11/08; C12N 9/16; C12N 9/20; C12N 9/2402; C12N 9/2411; C12N 9/2437; C12N 9/2477; C12N 9/248; C12N 9/96; C12N 19/02; C12N 19/12; C12P 19/02; C12P 19/12; C12P 19/14; C12P 2203/00; Y02P 20/52

See application file for complete search history.

(56) References Cited

U.S. PATENT DOCUMENTS 8,309,331 B2    11/2012   Banerjee et al.

FOREIGN PATENT DOCUMENTS

| JP | 2009-207461 A | 9/2009 |
| WO | WO 95/33047 A1 * | 5/1995 |

OTHER PUBLICATIONS

Milasinovic et al.(Reactive Functional Polymers (2010) 70: 807-814.*
Milasinovic et al. Int. J. Phamracuetics (2012; available online Jun. 30, 2012) 436: 332-340.*
Ogawa et al. Langmuir (2001) 17: 4704-4707.*
Takac et al. Process Biochem. (2007) 42: 1021-1027.*
Weise et al. Angewandte Int. Ed. (2013; published online Nov. 26, 2012) 52: 576-579.*
International Search Report and Written Opinion received for PCT Patent Application No. PCT/US2013/073712, dated Mar. 10, 2014, 12 pages.
International Preliminary Report on Patentability received for PCT Patent Application No. PCT/US2013/073712, dated Jun. 18, 2015, 8 pages.
Chearúil et al., "Thermosensitivity and Release from Poly N-Isopropylacrylamide—Polylactide Copolymers", International Journal of Pharmaceutics, vol. 366, 2009, pp. 21-30.
Chen et al., "Immobilization of α-Amylase to Temperature-Responsive Polymers by Single or Multiple Point Attachments", Journal of Chemical Technology and Biotechnology, vol. 69, 1997, pp. 421-428.

(Continued)

*Primary Examiner* — Susan M Hanley
(74) *Attorney, Agent, or Firm* — Richard Aron Osman

(57) ABSTRACT

Provided herein are methods for enhancing enzymatic activity using certain polymers that may be optionally attached to an enzyme. The polymers may be thermally-responsive polymers, including poly N-isopropylacrylamide or poly N-isopropylmethacrylamide. The polymer may also be a copolymer with at least two different monomer residues. The monomer residues may have a structure of formula (I):

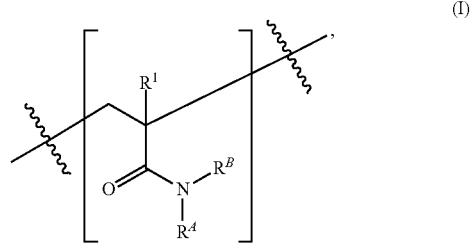

wherein $R^1$, $R^A$ and $R^B$ are as described herein. Examples of such monomer residues may include N-isopropylacrylamide (NIPAm) or N-isopropylmethacrylamide (NIPMa). The polymer may include additional monomer residues, such as aminooxy-bearing methacrylamide monomer residues that can be modified to vary the lower critical solution temperature (LCST) of the polymer.

14 Claims, 49 Drawing Sheets

(56) References Cited

OTHER PUBLICATIONS

Chen, Jyh-Ping, "Immobilization of α-Chymotrypsin to a Temperature-Responsive Reversibly Soluble-Insoluble Oligomer Based on N-Isopropylacrylamide", Journal of Chemical Technology and Biotechnology, vol. 73, 1998, pp. 137-143.
Chen et al., "Immobilization of α-Amylase to a Composite Temperature-Sensitive Membrane for Starch Hydrolysis", Biotechnol. Prog. vol. 14, No. 3, 1998, pp. 473-478.
Ding et al., "Synthesis and Purification of Thermally Sensitive Oligomer-Enzyme Conjugates of Poly(N-Isopropylacrylamide)-Trypsin", Bioconjugate Chem. vol. 7, No. 1, 1996, pp. 121-125.
Ding et al., "Unusual Properties of Thermally Sensitive Oligomer-Enzyme Conjugates of Poly(N-Isopropylacrylamide)-Trypsin", J. Biomed Mater Res, vol. 39, 1998, pp. 498-505.
Eriksson et al., "Mechanism of Surfactant Effect in Enzymatic Hydrolysis of Lignocellulose", Enzyme and Microbial Technology, vol. 31, 2002, pp. 353-364.
Esser-Kahn et al., "Protein-Cross-Linked Polymeric Materials through Site-Selective Bioconjugation", Angewandte Chem. Int. Ed., vol. 47, 2008, pp. 3751-3754.
Hao et al., "Stability Properties of Thermoresponsive Poly (N-Isopropylacrylamide)-Trypsin Conjugates", Biocatalysis and Biotransformation, vol. 19, 2001, pp. 341-359.
Huang et al., "Construction of Smart Glutathione Peroxidase Mimic Based on Hydrophilic Block Copolymer with Temperature Responsive Activity", Macromolecular Bioscience, vol. 9, 2009, pp. 1202-1210.
Ivanov et al., "Conjugation of Penicillin Acylase with the Reactive Copolymer of N-Isopropylacrylamide: A Step Toward a Thermosensitive Industrial Biocatalyst", Biotechnol. Prog. vol. 19, No. 4, 2003, pp. 1167-1175.
Jiang et al., "Thermo-sensitive Amphiphilic Block Copolymer Poly (styrene-b-N-Isopropylacrylamide) with Switchable Catalytic Activity Immobilizing Pectinase", Biotechnology and Bioprocess Engineering, vol. 16, 2011, pp. 1187-1195.
Kaar et al., "Benefits from Tween During Enzymatic Hydrolysis of Corn Stover", Biotechnology and Bioengineering, vol. 59, No. 4, Aug. 20, 1998, pp. 419-427.
Kim et al., "Surface Deactivation of Cellulase and Its Prevention", Enzyme Microb. Technol., vol. 4, Mar. 1982, pp. 99-103.
Kim et al., "Thermo-Sensitive Microparticles of PNIPAM-Grafted Ethylcellulose by Spray-Drying Method", Journal of Microencapsulation, vol. 19, No. 5, 2002, pp. 661-669.
Kristensen et al., "Use of Surface Active Additives in Enzymatic Hydrolysis of Wheat Straw Lignocellulose", Enzyme and Microbial Technology, vol. 40, 2007, pp. 888-895.
Kumar et al., "Effect of Additives on the Digestibility of Corn Stover Solids Following Pretreatment by Leading Technologies", Biotechnology and Bioengineering, vol. 102, No. 6, Apr. 15, 2009, pp. 1544-1557.
Liang et al., "Preparation of a pH-Sensitive Polyacrylate Amphiphilic Copolymer and its Application in Cellulase Immobilization", Bioresource Technology, vol. 116, 2012, pp. 140-146.
Mackenzie et al., "Effects of NIPAm Polymer Additives on the Enzymatic Hydrolysis of Avicel and Pretreated Miscanthus", Biotechnology and Bioengineering, vol. 111, No. 9, Sep. 2014, pp. 1792-1800.
Mackenzie, et al., "Recyclable Thermoresponsive Polymer-Cellulase Bioconjugates for Biomass Depolymerization", Journal of the American Chemical Society, vol. 135. 2013, pp. 293-300.
Mackenzie, Katherine J., "Applications of NIPAm Copolymers in Lignocellulosic Biomass Depolymerization for Biofuels Production", University of California, Berkeley, 2014, 119 pages.

Matsukata et al., "Temperature Modulated Solubility-Activity Alterations for Poly(N-Isopropylacrylamide)-Lipase Conjugates", J. Biochem.,vol. 116, 1994, pp. 682-686.
Milasinovic et al., "Hydrogel s of N-Isopropylacrylamide Copolymers with Controlled Release of a Model Protein", International Journal of Pharmaceutics, vol. 383, 2010, pp. 53-61.
Molawi et al., "Reversible Switching of Substrate Activity of Poly-N-Isopropylacrylamide Peptide Conjugates", Chemical Communications, 2007, pp. 5173-5175.
Mora et.al., "Mechanism of Rate Enhancement of Wood Fiber Saccharification by Cationic Polyelectrolytes", Biotechnol. Lett., vol. 33, 2011, pp. 1805-1808.
Nagel et al., "Enzyme Activity Control by Responsive Redoxpolymers", Langmuir, vol. 23, No. 12, 2007, pp. 6807-6811.
Overstreet et al., "Bioresponsive Copolymers of Poly (N-Isopropylacrylamide) with Enzyme-Dependent Lower Critical Solution Temperatures", Biomacromolecules, vol. 11, No. 5, 2010, pp. 1154-1159.
Park et al., "Effect of Temperature Cycling on the Activity and Productivity of Immobilized β-Galactosidase in a Thermally Reversible Hydrogel Bead Reactor", Applied Biochemistry and Biotechnology, vol. 19, 1988, pp. 1-9.
Park et al., "Immobilization and Characterization of β-Galactosidase in Thermally Reversible Hydrogel Beads", Journal of Biomedical Materials Research, vol. 24, 1990, pp. 21-38.
Park, Tae Gwan, "Stabilization of Enzyme Immobilized in Temperature-Sensitive Hydrogels", Biotechnology Letters, vol. 15, No. 1, Jan. 1993, pp. 57-60.
Qing et al., "Impact of Surfactants on Pretreatment of Corn Stover", Bioresource Technology, vol. 101, 2010, pp. 5941-5951.
Raghava et al., "Preparation and Properties of Thermoresponsive Bioconjugates of Trypsin", Artificial Cells, Blood Substitutes, and Biotechnology, vol. 34, 2006, pp. 323-336.
Reye et al., "Cationic Polyacrylamides Enhance Rates of Starch and Cellulose Saccharification", Biotechnol. Lett., vol. 31, 2009, pp. 1613-1616.
Reye et al., "Cationic Polyacrylamides Promote Binding of Cellulase and Amylase", Journal of Biotechnology, vol. 154, 2011, pp. 269-273.
Sipos et al., "Mechanism of the Positive Effect of Poly(Ethylene Glycol) Addition in Enzymatic Hydrolysis of Steam Pretreated Lignocelluloses", Comptes Rendus Biologies, vol. 334, 2011, pp. 812-823.
Sun et al., "Preparation and Characterization of α-Amylase-Immobilized Thermal-Responsive Composite Hydrogel Membranes", J. Biomed. Mater. Res., vol. 45, 1999, pp. 125-132.
Taniguchi et al., "Properties of a Reversible Soluble-Insoluble Cellulase and its Application to Repeated Hydrolysis of Crystalline Cellulose", Biotechnology and Bioengineering, vol. 34, 1989, pp, 1092-1097.
Welsch et al., "Enhanced Activity of Enzymes Immobilized in Thermoresponsive Core-Shell Microgels", J. Phys. Chem. B., vol. 113, No. 49, 2009, pp. 16039-16045.
Yu et al., "Synthesis and Characterization of Thermoresponsive Hydrogels Cross-Linked with Acryloyloxyethylaminopolysuccinimide", Colloid and Polymer Science, vol. 285, 2007, pp. 1553-1560.
Zhang et al., "Preparation and Properties of an Immobilized Cellulase on the Reversibly Soluble Matrix Eudragit L-100", Biocatalysis and Biotransformation, vol. 28, Sep.-Dec. 2010, pp. 313-319.
Zheng et al., "Non-Ionic Surfactants and Non-Catalytic Protein Treatment on Enzymatic Hydrolysis of Pretreated Creeping Wild Ryegrass", Appl. Biochem. Biotechnol., vol. 146, 2008, pp. 231-248.

\* cited by examiner

POLYMER ENHANCEMENT OF ENZYMATIC ACTIVITY

CROSS-REFERENCE TO RELATED APPLICATIONS

This is a continuation of International Application PCT/US2013/073712, with an international filing date of Dec. 6, 2013, which claims the benefit of U.S. provisional patent application Ser. Nos. 61/734,918 filed Dec. 7, 2012, and 61/801,982, filed Mar. 15, 2013, the disclosures of which are hereby incorporated by reference in their entireties.

FIELD

The present disclosure relates generally to the enhancing enzymatic activity, and more specifically to the use of certain polymers to increase enzymatic activity and stability, for example, in the production of sugars from cellulose in biomass.

BACKGROUND

Enzymes are used in a variety of commercial applications, including the food and agriculture industry, the pharmaceutical industry, and the chemical and biofuels industry. For example, cellulases, such as endoglucanase, exoglucanase, and β-glucosidase, may be used to convert the cellulosic component of biomass into fermentable sugars for biofuel production. Collectively, these cellulases have been isolated from a broad assortment of organisms, and exhibit a range of temperature, pH, and substrate optima. The cost of cellulases, however, generally presents a barrier to the commercialization of processes using such enzymes.

The costs associated with enzymatic hydrolysis can be lowered by increasing hydrolysis yields or by increasing reactor throughput with the same enzyme loading. Molecular biology methods have been investigated to improve enzyme function and decrease substrate recalcitrance. See Wilson D B., *Curr. Opin. Biotech.*, 2009, 20: 295-299. Alternative methods involving the inclusion of large molecule "additives", such as surfactants, to hydrolysis mixtures have also been used to increase yields with enzymes. See Eriksson T, et al., *Enzyme Microb. Tech.*, 2002, 31: 353-364; Kaar W E & Holtzapple M T., *Biotechnol. Bioeng.*, 1998, 59(4):419-427; Kristensen J B, et al., *Enzyme Microb. Tech.*, 2007, 40: 888-895; Kumar R & Wyman C E., *Biotechnol. Bioeng.*, 2008, 102(6):1544-1557; Qing Q, et al., *Bioresource Technol.*, 2010, 101:5941-5951; Sipos B, et al., C. R. Biol., 2011, 334: 812-823; and Zheng Y, et al., *Appl. Biochem. Biotechnol.*, 2008, 146:231-248. However, the level at which these additives enhance enzymatic activity can vary based on several factors, including enzyme loading, substrate pretreatment, hydrolysis temperature, and substrate and enzymatic choice. Thus, what are needed in the art are more consistent and reliable methods, viable on an industrial scale that can improve enzymatic activity and stability.

The costs associated with enzymatic hydrolysis can also be lowered by collecting and reusing enzymes through multiple rounds of processing. For example, work has been done in the field of immobilizing cellulases, including their covalent attachment or adsorption onto substrates such as silicon dioxide wafers, silica, glass beads, calcium alginate beads, and magnetic nanoparticles. See e.g., Ogeda et al., *J. Biotechnol.* 2012, 157, 246-252; Lupoi, et al., *Biotechnol. Bioeng.* 2011, 108, 2835-2843; Mandali & Dalaly, *ASTM Intern.* 2010, 7, 1-10; Andriani, et al., *Bioprocess. Biosyst. Eng.* 2012, 35, 29-33; Jordan, et al. gala, C. *J. Mol. Catal. B-Enzym.* 2011, 68, 139-146; Xu, et al., *Biocatal. Biotransfor.* 2011, 29, 71-76. Work has also been done in the field involving reversibly soluble-insoluble polymer-cellulase materials, most commonly utilizing pH-sensitive polymers such as Eudragit L-100 or methacrylic acid polymers. See e.g., Taniguchi, et al., *Biotechnol. Bioeng.* 1989, 34, 1092-1097; Liang & Cao, X. *Bioresource Technol.* 2012, 116, 140-146; Zhang, et al., *Biocatal. Biotransfor.* 2010, 28, 313-319. These materials, however, limit industrial processes to a fairly narrow pH range and require multiple pH adjustments to recover and reuse the enzyme. Thus, what is also needed in the art are alternatives, viable on an industrial scale, that can reduce enzyme costs by recycling enzymes through multiple rounds of processing.

BRIEF SUMMARY

Provided herein are methods for increasing enzymatic activity or decreasing denaturation of an enzyme or a mixture of enzymes during the breaking down (e.g., the hydrolysis) of one or more substrates, by contacting the substrate(s) with an enzyme or a mixture of enzymes and at least one of the polymers described herein. Any suitable enzymes or mixture of enzymes that can break down at least a portion of a substrate in the presence of the polymers described herein may be used in the methods provided. Suitable enzymes may, for example, include cellulases, hemicellulases, ligninases, lipases, amylases, phosphatases, and xylanases. For example, the enzyme may be an endoglucanase, an exoglucanase, a β-glucosidase, or a polysaccharide monooxygenase, or any mixtures of such enzymes, and the substrate may be, for example, biomass, cellulose, disaccharides and other polysaccharides. Such enzymes may hydrolyze the substrate in the presence of the polymers described herein to produce sugars.

Provided herein are also methods for pretreating a substrate by contacting a substrate with an enzyme and at least one of the polymers described herein, including at least one of the polymers descried herein, to produce a pretreated substrate, wherein the subsequent hydrolysis of the pretreated substrate results in a higher yield compared to hydrolysis of the substrate without such pretreatment.

The polymers used in any of the methods described herein may include a plurality of monomer residues having the structure of formula (I):

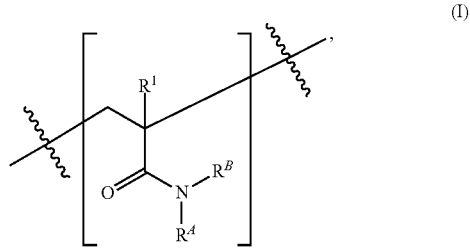

wherein:
$R^1$ at each occurrence is independently H or alkyl; and
$R^A$ and $R^B$ at each occurrence is independently H, unsubstituted or substituted aliphatic group, unsubstituted or substituted alicyclic group, unsubstituted or substituted aryl, unsubstituted or substituted heteroaryl, or unsubstituted or substituted heterocyclyl.

In some embodiments, the monomer residues of formula (I) have a structure wherein: $R^A$ and $R^B$ at each occurrence is independently H, unsubstituted or substituted alkyl, unsubstituted or substituted cycloalkyl, unsubstituted or substituted aryl, unsubstituted or substituted heterocycloalkyl, or unsubstituted or substituted heteroaryl.

In certain embodiments, the monomer residues of formula (I) are N-isopropylacrylamide (NIPAm), N-isopropylmethacrylamide (NIPMa), or any combination thereof.

In certain embodiments, the monomer residues of formula (I) are monomer residues of formula (I-A1):

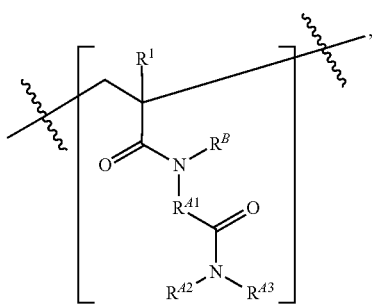

(I-A1)

wherein:

$R^1$ and $R^B$ are as defined above for formula (I);

$R^{A1}$ at each occurrence is unsubstituted or substituted -aliphatic group-, unsubstituted or substituted -alicyclic group-, unsubstituted or substituted -aryl-, unsubstituted or substituted -heteroaryl-, or unsubstituted or substituted -heterocyclyl-; and $R^{A2}$ and $R^{A3}$ at each occurrence is independently H, unsubstituted or substituted aliphatic group, unsubstituted or substituted alicyclic group, unsubstituted or substituted aryl, unsubstituted or substituted heteroaryl, or unsubstituted or substituted heterocyclyl.

In some embodiments, the monomer residues of formula (I-A1) have a structure wherein: $R^{A1}$ at each occurrence is unsubstituted or substituted -alkyl-, unsubstituted or substituted -cycloalkyl-, unsubstituted or substituted -aryl-, unsubstituted or substituted -heterocycloalkyl-, or unsubstituted or substituted -heteroaryl-.

In some embodiments, the monomer residues of formula (I-A1) have a structure wherein: $R^{A2}$ and $R^{A3}$ at each occurrence is independently unsubstituted or substituted alkyl, unsubstituted or substituted cycloalkyl, unsubstituted or substituted aryl, unsubstituted or substituted heterocycloalkyl, or unsubstituted or substituted heteroaryl.

In certain embodiments, the monomer residues of formula (I) are monomer residues of formula (I-A2):

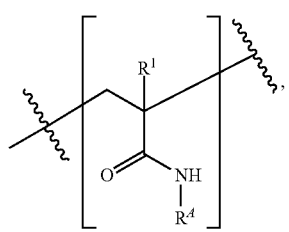

(I-A2)

wherein $R^1$ and $R^A$ are as defined above for formula (I).

In certain embodiments, the monomer residues of formula (I-A2) have a structure wherein: $R^A$ is unsubstituted or substituted aliphatic group, unsubstituted or substituted alicyclic group, unsubstituted or substituted aryl, unsubstituted or substituted heteroaryl, or unsubstituted or substituted heterocyclyl. In one embodiment, $R^A$ is other than H.

In some embodiments, the polymer having monomer residues of formula (I), (I-A1), (I-A2), or (I-A2a), or any combinations of such residues, may be a thermally-responsive polymer. In one embodiment, the thermally-responsive polymer is poly N-isopropylacrylamide. In another embodiment, the thermally-responsive polymer is poly N-isopropylmethacrylamide.

In one embodiment, the monomer residues of formula (I-A2) have the structure of formula (I-A2a):

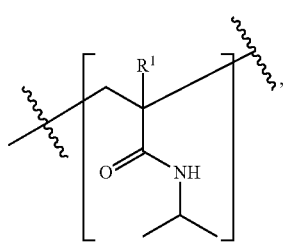

(I-A2a)

wherein $R^1$ is as defined above for formula (I).

In other embodiments, the polymer may be a copolymer made up of a plurality of first monomer residues and a plurality of second monomer residues. Such a copolymer can be made up of a plurality of first monomer residues having the structure of formula (I), (I-A1), (I-A2), or (I-A2a) as described above, and a plurality of aminooxy-bearing methacrylamide monomer residues.

In certain embodiments, the aminooxy-bearing methacrylamide monomer residues at each occurrence independently have the structure of formula (II-B1) or (II-B2):

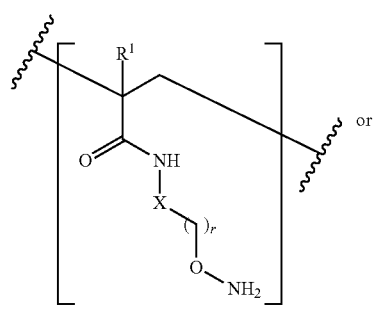

(II-B1)

or

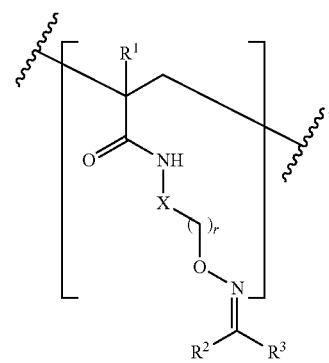

(II-B2)

wherein:

R¹ at each occurrence is independently H or alkyl;

r at each occurrence is independently an integer greater than or equal to 1;

X at each occurrence is independently unsubstituted or substituted -aliphatic group-, unsubstituted or substituted -alicyclic group-, unsubstituted or substituted -aryl-, unsubstituted or substituted -heteroaryl-, unsubstituted or substituted -heterocyclyl-, unsubstituted or substituted -ether-, or —(CH₂)ⱼNHCO—, wherein j is an integer, and j at each occurrence is independently at least 1; and R² and R³ at each occurrence is independently H, unsubstituted or substituted aliphatic group, unsubstituted or substituted alicyclic group, unsubstituted or substituted aryl, unsubstituted or substituted heteroaryl, unsubstituted or substituted heterocyclyl, or —C(O)Rᵃ¹, wherein Rᵃ is H, alkyl, or hydroxy; or R² and R³ are taken together with the carbon to which they are attached to form a 5- or 6-membered unsubstituted or substituted heterocyclyl.

In some embodiments, the aminooxy-bearing methacrylamide monomer residues of formula (II-B1) or (II-B2) have a structure wherein:

R¹ is methyl (i.e., CH₃);

r at each occurrence is an integer greater than or equal to 1;

X at each occurrence is independently unsubstituted or substituted -alkyl-, unsubstituted or substituted -alkenyl-, unsubstituted or substituted -alkynyl-, unsubstituted or substituted -aryl-, unsubstituted or substituted -heteroaryl-, unsubstituted or substituted -cycloalkyl-, unsubstituted or substituted -heterocycloalkyl-, unsubstituted or substituted -ether-, or —(CH₂)ⱼNHCO—, wherein j is an integer, and j at each occurrence is independently at least 1; and R² and R³ at each occurrence is independently H, unsubstituted or substituted alkyl, unsubstituted or substituted alkenyl, unsubstituted or substituted alkynyl, unsubstituted or substituted aryl, unsubstituted or substituted heteroaryl, unsubstituted or substituted cycloalkyl, unsubstituted or substituted heterocycloalkyl, or —C(O)Rᵃ¹, wherein Rᵃ is H, alkyl, or hydroxy; or R² and R³ are taken together with the carbon to which they are attached to form a 5- or 6-membered unsubstituted or substituted heterocyclyl.

In some embodiments, the polymer may be a thermally-responsive copolymer, wherein each of the first monomer residues may independently be N-isopropylacrylamide, N-isopropylmethacrylamide, or any combinations thereof; and each of the second monomer residues is an aminooxy-bearing methacrylamide monomer residue. In one embodiment, the copolymer is a random copolymer.

In certain embodiments, the aminooxy-bearing methacrylamide monomer residues of the copolymer independently have the structure of formula (II-B1a) or (II-B2a):

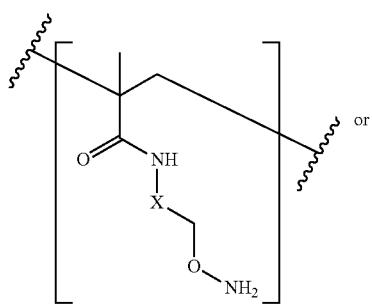

(II-B1a)

or

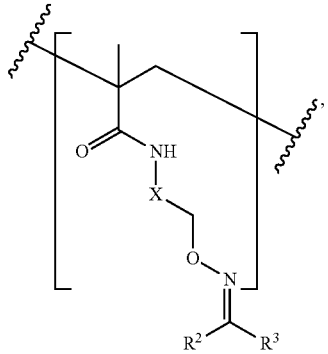

(II-B2a)

wherein:

X at each occurrence is independently unsubstituted or substituted -aliphatic group-, unsubstituted or substituted -alicyclic group-, unsubstituted or substituted -aryl-, unsubstituted or substituted -heteroaryl-, unsubstituted or substituted -heterocyclyl-, unsubstituted or substituted -ether-, or —(CH₂)ⱼNHCO—, wherein j is an integer, and j at each occurrence is independently at least 1; and R² and R³ (in the case of formula II-B2a) at each occurrence is independently H, unsubstituted or substituted aliphatic group, unsubstituted or substituted alicyclic group, unsubstituted or substituted aryl, unsubstituted or substituted heteroaryl, unsubstituted or substituted heterocyclyl, or —C(O)Rᵃ¹, wherein Rᵃ is H, alkyl, or hydroxy; or R² and R³ are taken together with the carbon to which they are attached to form a 5- or 6-membered unsubstituted or substituted heterocyclyl.

In some embodiments, the aminooxy-bearing methacrylamide monomer residues of formula (II-B1a) and (II-B2a) have a structure wherein: X at each occurrence is independently unsubstituted or substituted -alkyl-, unsubstituted or substituted -alkenyl-, unsubstituted or substituted -alkynyl-, unsubstituted or substituted -aryl-, unsubstituted or substituted -heteroaryl-, unsubstituted or substituted -cycloalkyl-, unsubstituted or substituted -heterocycloalkyl-, unsubstituted or substituted -ether-, or —(CH₂)ⱼNHCO—, wherein j is an integer, and j at each occurrence is independently at least 1.

In some embodiments, the aminooxy-bearing methacrylamide monomer residues of formula (II-B2a) have a structure wherein: R² and R³ at each occurrence is independently H, unsubstituted or substituted alkyl, unsubstituted or substituted alkenyl, unsubstituted or substituted alkynyl, unsubstituted or substituted aryl, unsubstituted or substituted heteroaryl, unsubstituted or substituted cycloalkyl, unsubstituted or substituted heterocycloalkyl, or —C(O)Rᵃ¹, wherein Rᵃ is H, alkyl, or hydroxy; or R² and R³ are taken together with the carbon to which they are attached to form a 5- or 6-membered unsubstituted or substituted heterocyclyl.

The methods provided herein may further include recovering at least one of the polymers after enzymatic reaction (e.g., hydrolysis). In embodiments where at least one of the polymers is recovered, the method further includes: contacting additional substrate with additional enzyme or mixture of enzymes in the presence of the recovered polymer(s), and breaking down (including, for example, hydrolyzing) at least a portion of the additional substrate. For example, in one embodiment where the polymer(s) is/are recovered, the method further includes: i) providing additional biomass, additional hydrolysis enzyme or mixture of hydrolysis enzymes, and the recovered polymer(s); ii) contacting the biomass with the additional hydrolysis enzyme in the presence of the recovered the polymer(s); and iii) hydrolyzing at least a portion of the additional biomass to produce additional sugars.

Provided herein are also compositions that include: at least one substrate, at least one enzyme, and at least one of the polymers described herein, including at least one polymer comprising monomer residues of formula (I), (I-A1), (I-A2), or (I-A2a), and optionally further comprising aminooxy-bearing methacrylamide monomer residues of formula (II-B1), (II-B2), (II-B1a) or (II-B2a). For example, in one embodiment, the composition includes: biomass, a hydrolysis enzyme, and a thermally-responsive polymer selected from poly N-isopropylacrylamide, poly N-isopropylmethacrylamide, and a copolymer as described above.

Provided herein are also residual substrate compositions that include: at least one residual substrate, at least one hydrolysis product, at least one enzyme, and at least one of the polymers described herein, including at least one polymer comprising monomer residues of formula (I), (I-A1), (I-A2), or (I-A2a), and aminooxy-bearing methacrylamide monomer residues of formula (II-B1), (II-B2), (II-B1a) or (II-B2a). For example, in some embodiments, provided is a residual biomass composition that includes: residual biomass, sugars, a hydrolysis enzyme, and at least one polymer as described herein. In one embodiment, the residual biomass composition includes: residual biomass, sugars, a hydrolysis enzyme, and a thermally-responsive polymer selected from poly N-isopropylacrylamide, poly N-isopropylmethacrylamide, and a copolymer as described above.

In yet other aspects, provided is a method of preparing the copolymer described above, by: a) providing N-isopropylacrylamide (NIPAm) or N-isopropylmethacrylamide (NIPMa); b) providing an aminooxy-bearing methacrylamide; c) copolymerizing the NIPAm or NIPMa with the aminooxy-bearing methacrylamide to produce a copolymer; and d) reacting the copolymer with a quencher to produce a modified copolymer.

Provided is also a polymer-enzyme conjugate that includes: a hydrolysis enzyme, wherein the hydrolysis enzyme has a transaminated N-terminus; and a polymer, wherein the polymer is attached to the transaminated N-terminus of the enzyme. In certain embodiments, the polymer is a copolymer made up of a plurality of first monomer residues and a plurality of second monomer residues, where the first monomer residues at each occurrence may independently be N-isopropylacrylamide, N-isopropylmethacrylamide, and any combinations thereof, and the second monomer residues at each occurrence are aminooxy-bearing methacrylamide monomer residues, as described above. In certain embodiments, the polymer of the polymer-enzyme conjugate is a thermally-responsive polymer as described herein.

In another aspect, provided is a composition that includes biomass, and a polymer-enzyme conjugate as described above. In yet other aspects, provided is a residual biomass composition that includes residual biomass, sugars, and a polymer-enzyme conjugate as described above.

In yet another aspect, provided is a method of hydrolyzing biomass by: a) providing biomass, and a polymer-enzyme conjugate as described above; b) contacting the biomass with the polymer-enzyme conjugate, and c) hydrolyzing at least a portion of the biomass to produce sugars. In some embodiments, the method further includes providing additional polymer as described above (in an unconjugated form), and contacting the biomass with the polymer-enzyme conjugate in the presence of the additional polymer in step (b).

Provided is also method of preparing the polymer-enzyme conjugate described above, by: a) providing N-isopropylacrylamide (NIPAm) or N-isopropylmethacrylamide (NIPMa); b) providing an aminooxy-bearing methacrylamide; c copolymerizing the NIPAm or NIPMa with the aminooxy-bearing methacrylamide to produce a copolymer; d) reacting the copolymer with a quencher to produce a modified copolymer; e) providing a hydrolysis enzyme, wherein the hydrolysis enzyme has an N-terminus; f) transaminating the N-terminus of the hydrolysis enzyme; and g) conjugating the modified copolymer with the transaminated N-terminus of the hydrolysis enzyme to produce a polymer-enzyme conjugate, wherein the conjugate is thermally-responsive.

DESCRIPTION OF THE FIGURES

The present application can be best understood by references to the following description taken in conjunction with the accompanying figures.

DETAILED DESCRIPTION

Figure 1:
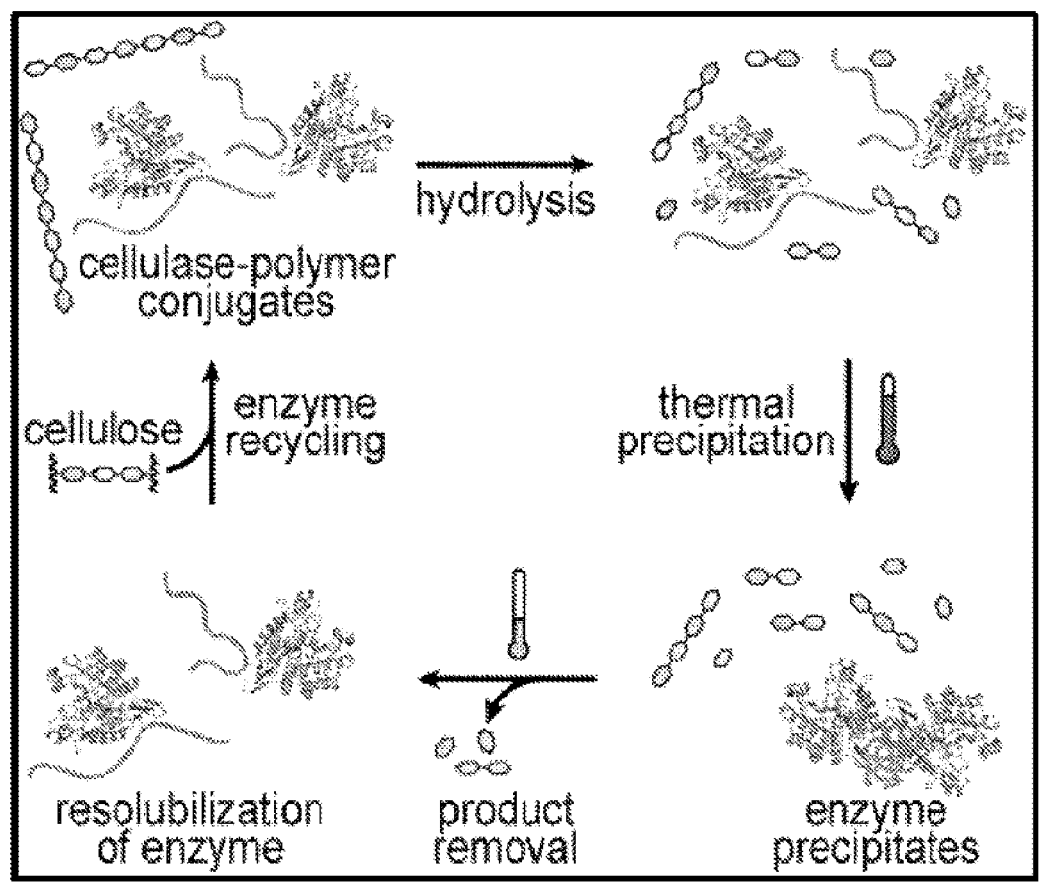
FIG. 1 is an exemplary scheme depicting the activity cycle of a polymer-cellulase conjugate.

The following description is presented to enable a person of ordinary skill in the art to make and use the various embodiments. Descriptions of specific methods, compositions, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Provided herein are methods of increasing enzymatic activity by breaking down (including, for example, hydrolyzing) a substrate in the presence of any one or more of the polymers of the invention, including at least one polymer comprising at least one polymer comprising monomer residues of formula (I), (I-A1), (I-A2), or (I-A2a), and optionally further comprising aminooxy-bearing methacrylamide monomer residues of formula (II-B1), (II-B2), (II-B1a) or (II-B2a) as described in further detail below. Any suitable enzymes may be used in the methods described herein, including any suitable enzymes that may be used to break down at least a portion of the substrate provided in the presence of the polymers or polymer-enzymes conjugates described herein. When such enzymes are used with the polymers of the invention, an increase in enzymatic activity and/or a decrease in denaturation of such enzymes may be observed during the enzymatic reaction. Suitable enzymes may, for example, include cellulases, hemicellulases, ligninases, lipases, amylases, phosphatases, xylanases, or any suitable mixtures of such enzymes.

The use of the polymers described herein unexpectedly increases the activity of the enzyme and/or decreases denaturation of an enzyme during the enzymatic reaction. For example, the polymers described herein have been unexpectedly observed to stabilize enzymes at the air-liquid interface of a hydrolysis reaction, thereby reducing deactivation of the enzyme. Furthermore, such polymers can be recyclable. In certain embodiments, the polymers are thermally-responsive polymers that exhibit reversible phase transition at their lower critical solution temperatures (LCSTs). These polymers may also be further modified to include a quencher that can affect the LCSTs of the polymers. Controlling the LCSTs allows for recovery of the polymers at specific temperatures.

The structure and characteristics of the polymers are described in further detail below, along with their methods of use in various applications.

The Polymers

The polymers described herein may be added to a mixture of enzymes and substrates to break down the substrate. For example, the polymers described herein, including thermally-responsive polymers, may be added to a hydrolysis mixture of biomass and enzymes to increase the activity of the enzymes and/or to stabilize the enzyme and decrease denaturation.

In some embodiments, the polymer is a homopolymer. A "homopolymer" is a polymer with one monomer residue. A "monomer residue" refers to a type of repeating unit, e.g., unit A, unit B, etc.

In other embodiments, the polymer is a copolymer. A "copolymer" is a polymer with two or more monomer residues. The number of times each monomer residue (e.g., unit A, unit B, etc.) appears in a copolymer may vary. The copolymer may be an alternating copolymer, a periodic copolymer, a random copolymer, or a block copolymer. An alternating copolymer has alternating monomer residues (e.g., -A-B-A-B-A-B-). A periodic copolymer has monomer residues arranged in a repeating sequence (e.g., (-A-B-A-A-A-B-)$_n$). A random copolymer has monomer residues arranged such that the probability of finding a given type of unit at a particular point in the chain is equal to the mole fraction of that unit in the chain. A block copolymer is made up of blocks of different polymerized monomer residues (e.g., [(-A-)$_n$-(-B-)$_m$]. It should be understood that while the aforementioned copolymers depict two monomer residues, A and B, the copolymers described herein may in some embodiments have three or more monomer residues. In some embodiments, the polymer is a random copolymer.

Homopolymers

In some embodiments, the polymer is a homopolymer made up of repeating monomer residues having the structure of formula (I):

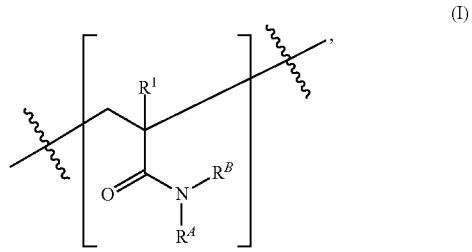

wherein:

$R^1$ is H or alkyl; and $R^A$ and $R^B$ is independently H, unsubstituted or substituted aliphatic group, unsubstituted or substituted alicyclic group, unsubstituted or substituted aryl, unsubstituted or substituted heteroaryl, or unsubstituted or substituted heterocyclyl.

In some embodiments, the monomer residues of formula (I) have a structure wherein: the aliphatic group, the alicyclic group, aryl, heteroaryl, or heterocyclyl of $R^A$ and $R^B$ may be optionally substituted with one or more (e.g., 1 to 5 substituents, 1 to 4 substituents, or 1 to 3 substituents, or 1 or 2 substituents) selected from cycloalkyl, aryl, heterocycloalkyl, heteroaryl, amine, —C(O)NR'R", —C(O)R', —C(O)OR', —OR', a cationic moiety, and an anionic moiety.

In some embodiments, the monomer residues of formula (I) have a structure wherein:

$R^1$ is H or alkyl; and $R^A$ and $R^B$ is independently H, unsubstituted or substituted alkyl, unsubstituted or substituted cycloalkyl, unsubstituted or substituted aryl, unsubstituted or substituted heterocycloalkyl, or unsubstituted or substituted heteroaryl.

In some embodiments, the monomer residues of formula (I) have a structure wherein: the alkyl, the cycloalkyl, the aryl, he heterocycloalkyl, or the heteroaryl of $R^A$ and $R^B$ may be optionally substituted with one or more (e.g., 1 to 5 substituents, 1 to 4 substituents, or 1 to 3 substituents, or 1 or 2 substituents) selected from cycloalkyl, aryl, heterocycloalkyl, heteroaryl, amine, —C(O)NR'R", —C(O)R', —C(O)OR, —OR', a cationic moiety, and an anionic moiety.

In some embodiments, the monomer residues of formula (I) have a structure wherein $R^A$ and $R^B$ is independently:

H;

unsubstituted alkyl;

alkyl substituted with 1 to 5 substituents selected from cycloalkyl, aryl, heterocycloalkyl, heteroaryl, amine, —C(O)NR'R", —C(O)R", —C(O)OR", —OR", a cationic moiety, or an anionic moiety;

unsubstituted cycloalkyl;

cycloalkyl substituted with 1 to 5 substituents selected from alkyl, aryl, heterocycloalkyl, heteroaryl, amine, —C(O)NR'R", —C(O)R', —C(O)OR', —OR', a cationic moiety, or an anionic moiety;

unsubstituted aryl;

aryl substituted with 1 to 5 substituents selected from alkyl, cycloalkyl, heterocycloalkyl, heteroaryl, amine, —C(O)NR'R", —C(O)R', —C(O)OR', —OR', a cationic moiety, or an anionic moiety;

unsubstituted heterocycloalkyl;

heterocycloalkyl substituted with 1 to 5 substituents selected from alkyl, cycloalkyl, aryl, heteroaryl, amine, —C(O)NR'R", —C(O)R', —C(O)OR', —OR', a cationic moiety, or an anionic moiety;

unsubstituted heteroaryl; or heteroaryl substituted with 1 to 5 substituents selected from alkyl, cycloalkyl, aryl, heterocycloalkyl, amine, —C(O)NR'R", —C(O)R', —C(O)OR', —OR', a cationic moiety, or an anionic moiety;

wherein each R' and R" at each occurrence is independently H, alkyl, cycloalkyl, heterocycloalkyl, aryl, or heteroaryl.

In certain embodiments, the monomer residues of formula (I) have a structure wherein $R^A$ and $R^B$ is independently:

unsubstituted alkyl;

alkyl substituted with 1 to 5 substituents selected from amine, —C(O)R', and —OR'; unsubstituted cycloalkyl;

cycloalkyl substituted with 1 to 5 substituents selected from amine, —C(O)R', and —OR'; unsubstituted aryl;

aryl substituted with 1 to 5 substituents selected from amine, —C(O)R', and —OR'; unsubstituted heterocycloalkyl;

heterocycloalkyl substituted with 1 to 5 substituents selected from amine, —C(O)R', and —OR';

unsubstituted heteroaryl; or heteroaryl substituted with 1 to 5 substituents selected from amine, —C(O)R', and —OR';

wherein each R' and R" at each occurrence is independently H or alkyl.

In one embodiment, the monomer residues of formula (I) have a structure wherein $R^A$ and $R^B$ is independently H; unsubstituted alkyl; or alkyl substituted with 1 to 5 —OH groups.

In some embodiments of formula (I), the alkyl, cycloalkyl, aryl, heterocycloalkyl, or heteroaryl may be substituted with an anionic moiety or a cationic moiety. In certain embodiments, the alkyl, cycloalkyl, aryl, heterocycloalkyl, or heteroaryl may be substituted with a sulfate moiety), a phosphate moiety, a nitrate moiety, or a carboxylate moiety.

In some embodiments, the monomer residues of formula (I) have a structure wherein $R^B$ is H. In other embodiments, the monomer residues of formula (I) have a structure wherein $R^A$ is H or alkyl. The alkyl of $R^A$ may be linear or branched.

In certain embodiments, the monomer residues of formula (I) have a structure wherein: $R^1$ is H or alkyl; $R^A$ is alkyl; and $R^B$ is H. In one embodiment, the monomer residues of formula (I) have a structure wherein: $R^1$ is H or methyl; $R^A$ is methyl, ethyl, propyl (including, for example, isopropyl) or butyl; and $R^B$ is H.

In some embodiments that may be combined with any of the embodiments described herein for the monomer residues of formula (I), at least one of $R^A$ and $R^B$ is other than H. In other embodiments, at least one of $R^A$ and $R^B$ is alkyl.

In other embodiments, the monomer residues of formula (I) are monomer residues of formula (I-A1):

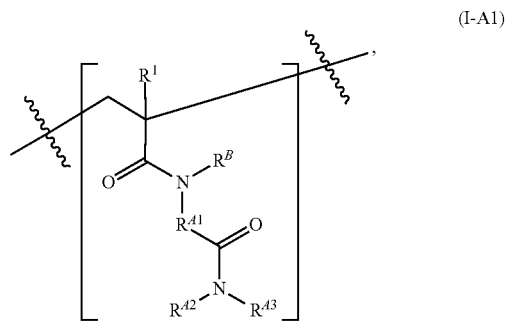

(I-A1)

wherein:

$R^1$ and $R^B$ are as defined above for formula (I);

$R^{41}$ is unsubstituted or substituted -aliphatic group-, unsubstituted or substituted -alicyclic group-, unsubstituted or substituted -aryl-, unsubstituted or substituted -heteroaryl-, or unsubstituted or substituted -heterocyclyl-; and $R^{42}$ and $R^{43}$ is independently H, unsubstituted or substituted aliphatic group, unsubstituted or substituted alicyclic group, unsubstituted or substituted aryl, unsubstituted or substituted heteroaryl, or unsubstituted or substituted heterocyclyl.

In some embodiments, the monomer residues of formula (I-A1) have a structure wherein:

$R^{41}$ is unsubstituted or substituted -alkyl-, unsubstituted or substituted -alkenyl-, unsubstituted or substituted -alkynyl-, unsubstituted or substituted -aryl-, unsubstituted or substituted -heteroaryl-, unsubstituted or substituted -cycloalkyl-, or unsubstituted or substituted -heterocycloalkyl-; and $R^{42}$ and $R^{43}$ is independently H, unsubstituted or substituted alkyl, unsubstituted or substituted cycloalkyl, unsubstituted or substituted aryl, unsubstituted or substituted heterocycloalkyl, or unsubstituted or substituted heteroaryl.

In certain embodiments, the monomer residues of formula (I-A1) have a structure in which $R^{41}$ is unsubstituted or substituted -alkyl-. In one embodiment, the monomer residues of formula (I-A1) have a structure in which $R^{41}$ is unsubstituted or substituted —$C_{1-10}$ alkyl-. In certain embodiments, the monomer residues of formula (I-A1) have a structure in which $R^{41}$ is unsubstituted -alkyl-. In certain embodiments, the monomer residues of formula (I-A1) have a structure in which $R^{41}$ is unsubstituted —$C_{1-10}$ alkyl-.

In certain embodiments, the monomer residues of formula (I-A1) have a structure in which $R^{42}$ and $R^{43}$ are independently H, or unsubstituted or substituted alkyl. In one embodiment, the monomer residues of formula (I-A1) have a structure in which $R^{42}$ is H; and $R^{43}$ is unsubstituted or substituted alkyl.

In yet other embodiments, the monomer residues of formula (I) are monomer residues of formula (I-A2):

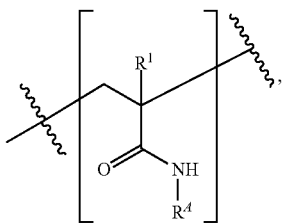

(I-A2)

wherein $R^1$ and $R^B$ are as defined above for formula (I).

In certain embodiments, $R^1$ is H or alkyl; and $R^A$ is alkyl. In one embodiment, $R^1$ is H or alkyl; and $R^A$ is isopropyl. In one variation, $R^1$ is H or methyl; and $R^A$ is isopropyl.

In certain embodiments, the monomer residues of formula (I-A2) have the structure of formula (I-A2a):

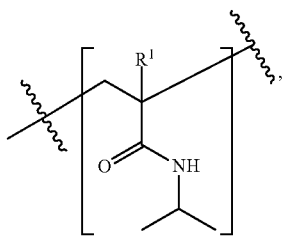

(I-A2a)

wherein $R^1$ is as defined above for formula (I).

In one variation, the monomer residues of formula (I-A2) are N-isopropylacrylamide (NIPAm), and the polymer is poly N-isopropylacrylamide (also referred to as "pNIPAm"), which has the following structure:

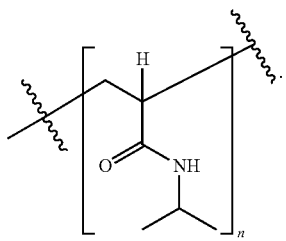

In another variation, the monomer residues of formula (I-A2) are N-isopropylmethacrylamide (NIPMa), and the polymer is poly N-isopropylmethacrylamide (also referred to as "pNIPMa"), which has the following structure:

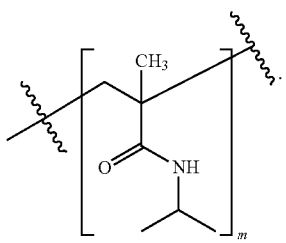

Copolymers

In some embodiments, the polymer is a copolymer made up of a plurality of monomer residues having the structure of formula (I), (I-A1), (I-A2), or (I-A2a), or any combinations of such monomer residues, as described in any of the embodiments described above. In certain embodiments, the copolymer may have at least two, at least three, or at least four, or two, three or four types of monomer residues.

In certain embodiments, the copolymer may have at least two, at least three, or at least four, or two, three or four types of monomer residues of formula (I), (I-A1), (I-A2), or (I-A2a), or any combinations of such monomer residues, as described in any of the embodiments described above. In one embodiment, the copolymer may have at least two, at least three, or at least four, or two, three or four types of monomer residues of formula (I-A2).

In one embodiment, the copolymer is made up of:

a plurality of first monomer residues of formula (I-A2), in which:

$R^1$ is H or alkyl;

$R^A$ is unsubstituted alkyl; and $R^B$ is H; and a plurality of second monomer residues of formula (I-A2), in which:

$R^1$ is H or alkyl;

$R^A$ is unsubstituted alkyl, or alkyl substituted with 1 to 5 —OH groups;

$R^B$ is H, provided that at least one of $R^1$, $R^A$ and $R^B$ of the first monomer residues is different from $R^1$, $R^A$ and $R^B$ of the second monomer residues. In certain embodiments, at least one of $R^A$ and $R^B$ of the first monomer residues is different from $R^A$ and $R^B$ of the second monomer residues.

Examples of such copolymers include:

copolymers having

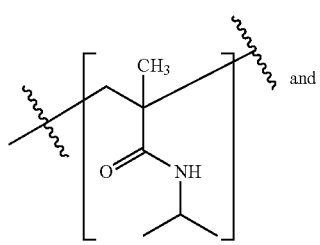 and

-continued

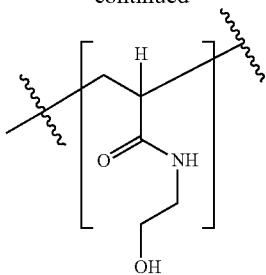

as the first and second monomer residues, respectively; copolymers having

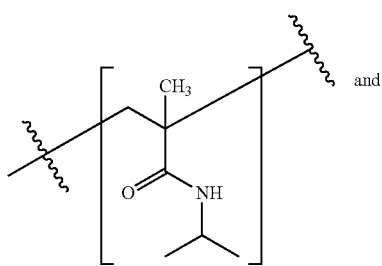 and

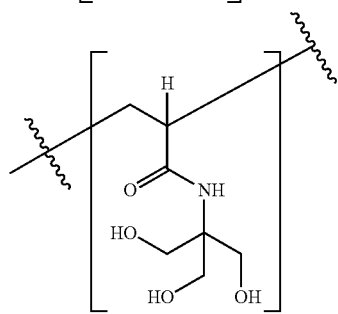

as the first and second monomer residues, respectively; and copolymers having

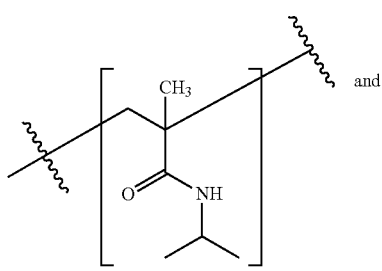 and

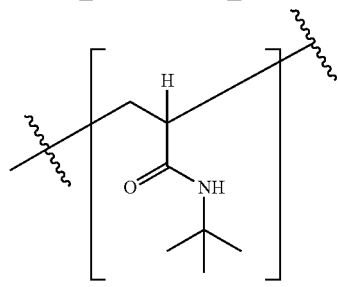

as the first and second monomer residues, respectively.

In some variations, the first and second monomer residues of the exemplary copolymers above may be arranged such that the copolymer is an alternative copolymer, a periodic copolymer, a random copolymer or a block copolymer.

In other embodiments, the polymer is a copolymer comprising a plurality of monomer residues independently having the structure of formula (I), (I-A1), (I-A2), or (I-A2a), as described in any of the embodiments above; and a plurality of aminooxy-bearing methacrylamide monomer residues.

In certain embodiments, the aminooxy-bearing methacrylamide monomer residues have the structure of formula (II-B1) or (II-B2):

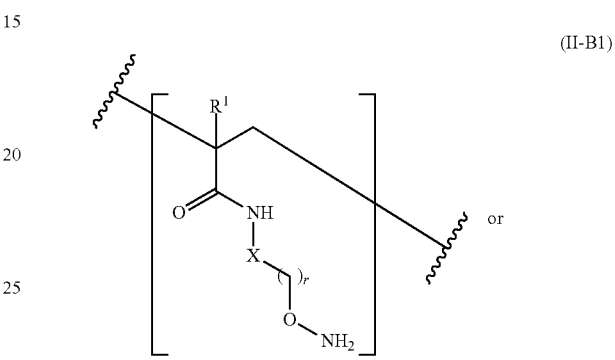

(II-B1)

or

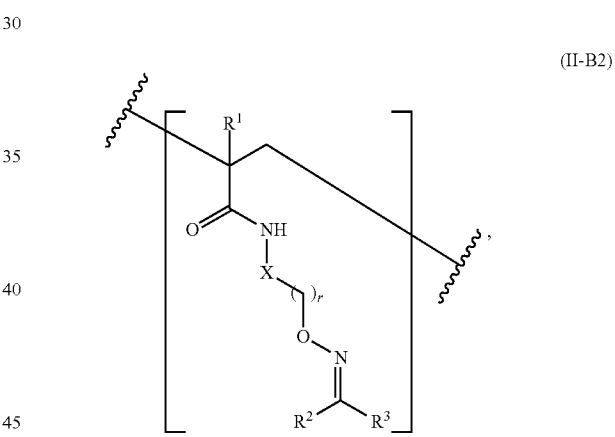

(II-B2)

wherein:

$R^1$ at each occurrence is independently H or alkyl;

r at each occurrence is independently an integer greater than or equal to 1;

X at each occurrence is independently unsubstituted or substituted -aliphatic group-, unsubstituted or substituted -alicyclic group-, unsubstituted or substituted -aryl-, unsubstituted or substituted -heteroaryl-, unsubstituted or substituted -heterocyclyl-, unsubstituted or substituted -ether-, or —$(CH_2)_j$NHCO—, wherein j is an integer, and j at each occurrence is independently at least 1; and $R^2$ and $R^3$ at each occurrence is independently H, unsubstituted or substituted aliphatic group, unsubstituted or substituted alicyclic group, unsubstituted or substituted aryl, unsubstituted or substituted heteroaryl, unsubstituted or substituted heterocyclyl, or —$C(O)R^a$, wherein $R^a$ is H, alkyl, or hydroxy; or $R^2$ and $R^3$ are taken together with the carbon to which they are attached to form a 5- or 6-membered unsubstituted or substituted heterocyclyl.

In some embodiments, the aminooxy-bearing methacrylamide monomer residues of formulae (II-B1) and (II-B2) have a structure wherein:

$R^1$ is methyl (i.e., $CH_3$);

r is an integer greater than or equal to 1;

X at each occurrence is independently unsubstituted or substituted -alkyl-, unsubstituted or substituted -alkenyl-, unsubstituted or substituted -alkynyl-, unsubstituted or substituted -aryl-, unsubstituted or substituted -heteroaryl-, unsubstituted or substituted -cycloalkyl-, unsubstituted or substituted -heterocycloalkyl-, unsubstituted or substituted -ether-, or —$(CH_2)_j$NHCO—, wherein j is an integer, and j at each occurrence is independently at least 1; and $R^2$ and $R^3$ at each occurrence is independently H, unsubstituted or substituted alkyl, unsubstituted or substituted alkenyl, unsubstituted or substituted alkynyl, unsubstituted or substituted aryl, unsubstituted or substituted heteroaryl, unsubstituted or substituted cycloalkyl, unsubstituted or substituted heterocycloalkyl, or —$C(O)R^{a\prime}$, wherein $R^a$ is H, alkyl, or hydroxy; or $R^2$ and $R^3$ are taken together with the carbon to which they are attached to form a 5- or 6-membered unsubstituted or substituted heterocyclyl.

In some embodiments of formulae (II-B1) and (II-B2), $R^1$ is H. In other embodiments, $R^1$ is methyl.

In some embodiments of formulae (II-B1) and (II-B2), r is 1 to 10. In one embodiment of formulae (II-B1) and (II-B2), r is 1, 2, 3, 4, or 5.

In certain embodiments, the aminooxy-bearing methacrylamide monomer residues at each occurrence independently have a structure of formula (II-B1a):

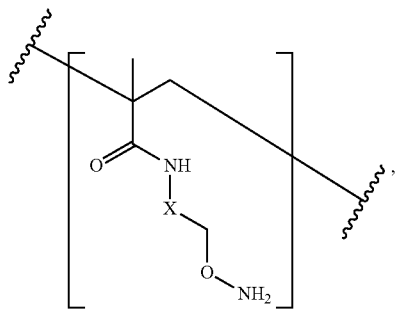

(II-B1a)

wherein X is as defined for formula (II-B1).

In other embodiments, the aminooxy-bearing methacrylamide monomer residues at each occurrence independently have a structure of formula (II-B2a):

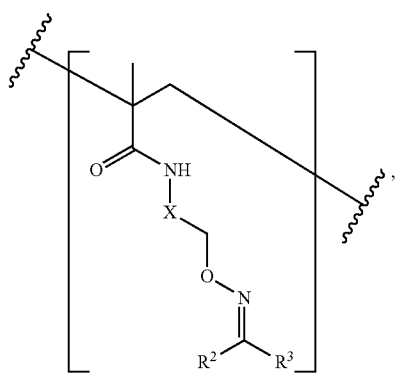

(II-B2a)

wherein X, $R^2$ and $R^3$ are as defined for formula (II-B2).

The presence of the $R^2$ and $R^3$ groups in the aminooxy-bearing methacrylamide monomer residues of formula (II-B2) and (II-B2a) may provide a handle through which the LCST can be adjusted through small molecule quenching. This allows a wide range of LCSTs to be accessed starting from a common supply of copolymer. Quenching also prevents the aminooxy functional groups from reacting with adventitious aldehydes, such as those of the glucose molecules produced during cellulose depolymerization.

In some embodiments, the aminooxy-bearing methacrylamide monomer residues of formulae (II-B2) and (II-B2a) have a structure wherein $R^2$ and $R^3$ at each occurrence is independently:

H;

unsubstituted $C_{1-10}$ alkyl;

$C_{1-10}$ alkyl substituted with one or more groups independently selected from hydroxy, amino, oxo, nitrate, phosphate, and sulfate;

unsubstituted $C_{2-10}$ alkenyl;

$C_{2-10}$ alkenyl substituted with one or more groups independently selected from hydroxy, amino, oxo, nitrate, phosphate, and sulfate;

unsubstituted $C_{2-10}$ alkynyl;

$C_{2-10}$ alkynyl substituted with one or more groups independently selected from hydroxy, amino, oxo, nitrate, phosphate, and sulfate;

unsubstituted $C_{6-12}$ aryl;

$C_{6-12}$ aryl substituted with one or more groups independently selected from alkyl, halo, hydroxy, amino, oxo, nitrate, phosphate, and sulfate;

unsubstituted $C_{4-12}$ heteroaryl with 1 to 3 ring heteroatoms independently selected from the group consisting of nitrogen, oxygen and sulfur;

$C_{4-12}$ heteroaryl with 1 to 3 ring heteroatoms independently selected from the group consisting of nitrogen, oxygen and sulfur, wherein the heteroaryl is substituted with one or more groups independently selected from alkyl, halo, hydroxy, amino, oxo, nitrate, phosphate, and sulfate;

unsubstituted $C_{3-12}$ cycloalkyl;

$C_{3-12}$ cycloalkyl substituted with one or more groups selected from alkyl, halo, hydroxy, amino, oxo, nitrate, phosphate, and sulfate;

unsubstituted $C_{3-12}$ heterocycloalkyl with 1 to 3 ring heteroatoms independently selected from the group consisting of nitrogen, oxygen and sulfur;

$C_{3-12}$ heterocycloalkyl with 1 to 3 ring heteroatoms independently selected from the group consisting of nitrogen, oxygen and sulfur, wherein the heterocycloalkyl is substituted with one or more groups selected from alkyl, halo, hydroxy, amino, oxo, nitrate, phosphate, and sulfate;

$R^2$ and $R^3$ are taken together with the carbon to which they are attached to form a 5- or 6-membered unsubstituted $C_{4-12}$ heterocyclyl with 1 to 3 ring heteroatoms independently selected from the group consisting of nitrogen, oxygen and sulfur; or $R^2$ and $R^3$ are taken together with the carbon to which they are attached to form a 5- or 6-membered $C_{4-12}$ heterocyclyl with 1 to 3 ring heteroatoms independently selected from the group consisting of nitrogen, oxygen and sulfur, wherein the heterocyclyl is substituted with one or more groups selected from alkyl, halo, hydroxy, amino, oxo, nitrate, phosphate, and sulfate.

In certain embodiments of formulae (II-B2) and (II-B2a), $R^2$ and $R^3$ at each occurrence are independently H, unsubstituted $C_{1-5}$ alkyl, or $C_{1-5}$ alkyl substituted with 1-5 hydroxyl groups.

In some embodiments of formulae (II-B2) and (II-B2a),

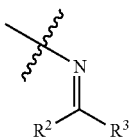

at each occurrence is independently selected from:

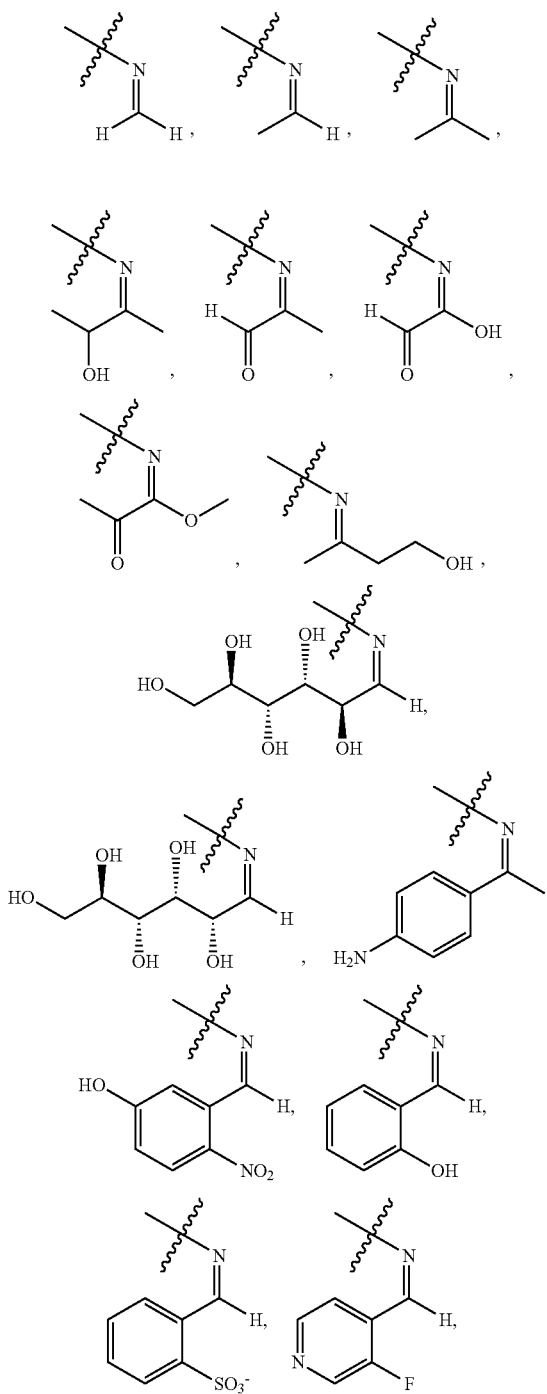

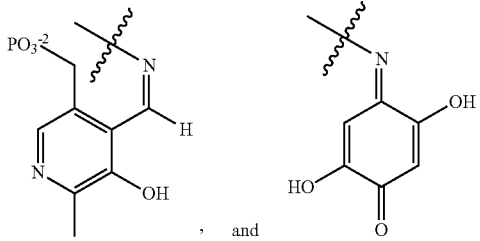

In some embodiments, the aminooxy-bearing methacrylamide monomer residues of formula (II-B1), (II-B2), (II-B1a) and (II-B2a) have a structure wherein X at each occurrence is:

unsubstituted $C_{1-10}$-alkyl-;

$C_{1-10}$-alkyl- substituted with one or more groups independently selected from hydroxy, amino, oxo, nitrate, phosphate, and sulfate;

unsubstituted $C_{2-10}$-alkenyl-;

$C_{2-10}$-alkenyl- substituted with one or more groups independently selected from hydroxy, amino, oxo, nitrate, phosphate, and sulfate;

unsubstituted $C_{2-10}$-alkynyl-;

$C_{2-10}$-alkynyl- substituted with one or more groups independently selected from hydroxy, amino, oxo, nitrate, phosphate, and sulfate;

unsubstituted $C_{6-12}$-aryl-;

$C_{6-12}$-aryl- substituted with one or more groups independently selected from alkyl, halo, hydroxy, amino, oxo, nitrate, phosphate, and sulfate;

unsubstituted $C_{4-12}$-heteroaryl- with 1 to 3 ring heteroatoms independently selected from the group consisting of nitrogen, oxygen and sulfur;

$C_{4-12}$-heteroaryl- with 1 to 3 ring heteroatoms independently selected from the group consisting of nitrogen, oxygen and sulfur, wherein the heteroaryl is substituted with one or more groups independently selected from alkyl, halo, hydroxy, amino, oxo, nitrate, phosphate, and sulfate;

unsubstituted $C_{3-12}$-cycloalkyl-;

$C_{3-12}$-cycloalkyl- substituted with one or more groups selected from alkyl, halo, hydroxy, amino, oxo, nitrate, phosphate, and sulfate;

unsubstituted $C_{3-12}$-heterocycloalkyl- with 1 to 3 ring heteroatoms independently selected from the group consisting of nitrogen, oxygen and sulfur;

$C_{3-12}$-heterocycloalkyl- with 1 to 3 ring heteroatoms independently selected from the group consisting of nitrogen, oxygen and sulfur, wherein the heterocycloalkyl is substituted with one or more groups selected from alkyl, halo, hydroxy, amino, oxo, nitrate, phosphate, and sulfate;

unsubstituted $C_{2-10}$-ether-;

$C_{2-10}$-ether- substituted with one or more groups selected from alkyl, halo, hydroxy, amino, oxo, nitrate, phosphate, and sulfate; or —$(CH_2)_j$NHCO—, wherein j is an integer of at least 1.

In some embodiments, the aminooxy-bearing methacrylamide monomer residues of formula (II-B1), (II-B2), (II-B1a) and (II-B2a) have a structure wherein: X at each occurrence is -ethylene glycol- or —$(CH_2)_j$NHCO—. In certain embodiments, j at each occurrence is between 1 and 10, between 1 and 8, or between 2 and 5. In one embodiment, X at each occurrence is —$(CH_2)_3$NHCO—.

With respect to variable $R^{41}$ in formula (I-A1) and variable X in formulae (II-B1), (II-B2), (II-B1a) and (II-B2a), it should be understood that "-moiety-" refers to a moiety having bivalency. For example, -alkyl- has the same residues as alkyl but has bivalency. Thus, -methyl- is methylene (—$CH_2$—).

In some embodiments, the aminooxy-bearing methacrylamide monomer residues described herein may be neutral. In other embodiments, the aminooxy-bearing methacrylamide monomer residues may be charged. In one embodiment, the aminooxy-bearing methacrylamide monomer residues are positively charged. In another embodiment, the aminooxy-bearing methacrylamide monomer residues are negatively charged. It should be understood that the charge of the residues may be selected based on the charge of the enzyme and physiological conditions.

It is intended and understood that each and every combination of the aminooxy-bearing methacrylamide monomer residues described herein (e.g., residues of formulae (II-B1), (II-B2), (II-B1a) and (II-B2a)) may be combined with any descriptions of the monomer residues of formula (I) (e.g., residues of formula (I), (I-A1), (I-A2), and (I-A2a)), the same as if each and every combination were individually listed.

Figure 2A:
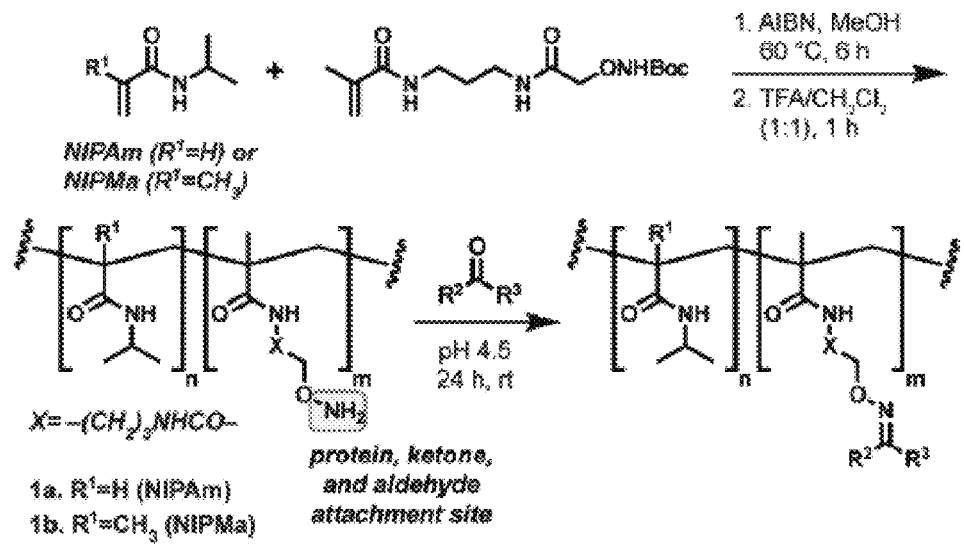
FIG. 2A is an exemplary reaction scheme for preparing a copolymer with two monomer residues, where the first monomer residue is N-isopropylacrylamide (NIPAm) or N-isopropylmethacrylamide (NIPMa), and the second monomer residue is an aminooxy-bearing methacrylamide monomer residue.
Figure 2B:
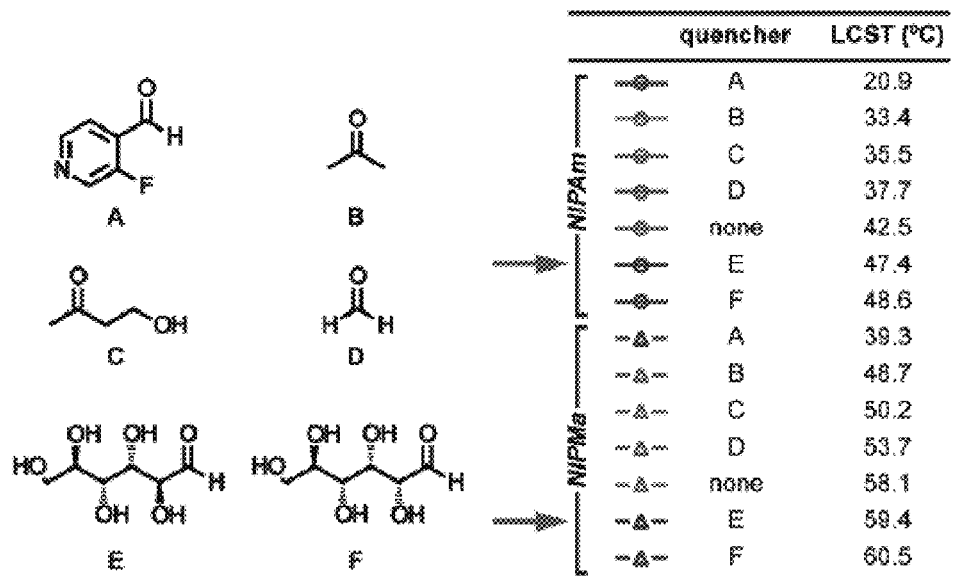
FIG. 2B provides a table of lower critical solution temperature (LCSTs) for NIPAm and NIPMa copolymers modified by small molecule quenchers A-F.

The polymers described herein may be synthesized using any suitable methods known in the art. With reference to FIG. 2A, in one exemplary reaction, the copolymers may be synthesized by free-radical copolymerization with a Boc-aminooxy methacrylamide and N-isopropylacrylamide (NIPAm) or N-isopropylmethacrylamide (NIPMa) using azobisisobutyronitrile (AIBN) as a radical initiator. The copolymers may be further modified, as described above, using small-molecule quenchers using any suitable chemistry known in the art. Exemplary small molecule quenchers are depicted in FIG. 2B.

As used herein, "aliphatic" refers to a linear or branched hydrocarbon structure, and can be saturated or have any degree of unsaturation. Aliphatic groups include, for example, alkyl, alkenyl, and alkynyl. In some embodiments, an aliphatic group as used herein, such as in monomer residues of formulae (I), (I-A1), (I-A2), (I-A2a), (II-B1), (II-B2), (II-B1a) and (II-B2a), has 1 to 10 carbon atoms (i.e., $C_{1-10}$ aliphatic group), 1 to 10 carbon atoms (i.e., $C_{1-9}$ aliphatic group), 1 to 8 carbon atoms (i.e., $C_{1-8}$ aliphatic group), 1 to 7 carbon atoms (i.e., $C_{1-7}$ aliphatic group), 1 to 6 carbon atoms (i.e., $C_{1-6}$ aliphatic group), 1 to 5 carbon atoms (i.e., $C_{1-5}$ aliphatic group), 1 to 4 carbon atoms (i.e., $C_{1-4}$ aliphatic group), 1 to 3 carbon atoms (i.e., $C_{1-5}$ aliphatic), or 1 or carbon atoms (i.e., $C_{1-2}$ aliphatic).

"Alkyl" refers to a linear or branched saturated hydrocarbon chain. In some embodiments, alkyl as used herein, such as in monomer residues of formulae (I), (I-A1), (I-A2), (I-A2a), (II-B1), (II-B2), (II-B1a) and (II-B2a), has 1 to 10 carbon atoms (i.e., $C_{1-10}$ alkyl), 1 to 10 carbon atoms (i.e., $C_{1-9}$ alkyl), 1 to 8 carbon atoms (i.e., $C_{1-8}$ alkyl), 1 to 7 carbon atoms (i.e., $C_{1-7}$ alkyl), 1 to 6 carbon atoms (i.e., $C_{1-6}$ alkyl), 1 to 5 carbon atoms (i.e., $C_{1-5}$ alkyl), 1 to 4 carbon atoms (i.e., $C_{1-4}$ alkyl), 1 to 3 carbon atoms (i.e, $C_{1-3}$ alkyl), 1 to 2 carbon atoms (i.e., $C_{1-2}$ alkyl), or 1 carbon atom (i.e., $C_1$ alkyl). Examples of alkyl groups include methyl, ethyl, n-propyl, iso-propyl, n-butyl, sec-butyl, tart-butyl, n-pentyl, 2-pentyl, iso-pentyl, neo-pentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, iso-butyl and tert-butyl; "propyl" can include n-propyl and iso-propyl.

"Alkenyl" refers to a linear or branched hydrocarbon chain with one or more double bonds. In some embodiments, alkenyl as used herein, such as in monomer residues of formulae (I), (I-A1), (I-A2), (I-A2a), (II-B1), (II-B2), (II-B1a) and (II-B2a), has 2 to 10 carbon atoms (i.e., $C_{2-10}$ alkenyl), 2 to 10 carbon atoms (i.e., $C_{2-9}$ alkenyl), 2 to 8 carbon atoms (i.e., $C_{2-8}$ alkenyl), 2 to 7 carbon atoms (i.e., $C_{2-7}$ alkenyl), 2 to 6 carbon atoms (i.e., $C_{2-6}$ alkenyl), 2 to 5 carbon atoms (i.e., $C_{2-5}$ alkenyl), 2 to 4 carbon atoms (i.e., alkenyl), 2 or 3 carbon atoms (i.e., $C_{2-3}$ alkyl), "Alkynyl" refers to a linear or branched hydrocarbon chain with one or more triple bonds. In some embodiments, alkynyl as used herein, such as in monomer residues of formulae (I), (I-A1), (I-A2), (I-A2a), (II -B1), (II-B2), (II-B1a) and (II-B2a), has 2 to 10 carbon atoms (i.e., $C_{2-10}$ alkynyl), 2 to 10 carbon atoms (i.e., $C_{2-9}$ alkynyl), 2 to 8 carbon atoms (i.e., $C_{2-8}$ alkynyl), 2 to 7 carbon atoms (i.e., $C_{2-7}$ alkynyl), 2 to 6 carbon atoms (i.e., $C_{2-6}$ alkynyl), 2 to 5 carbon atoms (i.e., $C_{2-5}$ alkynyl), 2 to 4 carbon atoms (i.e., $C_{2-4}$ alkynyl), 2 or 3 carbon atoms (i.e., $C_{2-3}$ alkynyl).

"Alicyclic" refers to acyclic aliphatic group, including cycloalkyl, cycloalkenyl, or cycloalkynyl. An alicyclic group can comprise one or more rings, includes fused and bridged groups, and can be saturated or have any degree of unsaturation. In some embodiments, alicyclic group as used herein, such as in formulae (I), (I-A1), (I-A2), (I-A2a), (II-B1), (II-B2), (II-B1a) and (II-B2a), has from 3 to 10 ring carbon atoms (i.e., $C_{3-10}$ alicyclic group), or 3 to 9 ring carbon atoms (i.e., $C_{3-9}$ alicyclic group), 3 to 8 ring carbon atoms (i.e., $C_{3-8}$ alicyclic group), 3 to 7 ring carbon atoms (i.e., $C_{3-7}$ alicyclic group), 3 to 6 ring carbon atoms (i.e., $C_{3-6}$ alicyclic group), or 5 ring carbon atoms (i.e., $C_5$ alicyclic group), or 6 ring carbon atoms (i.e., $C_6$ alicyclic group).

"Cycloalkyl" refers to acyclic alkyl group. In some embodiments, cycloalkyl as used herein, such as in monomer residues of formulae (I), (I-A1), (I-A2), (I-A2a), (II-B1), (II-B2), (II-B1a) and (II-B2a), has from 3 to 10 ring carbon atoms (i.e., $C_{3-10}$ cycloalkyl), or 3 to 9 ring carbon atoms (i.e., $C_{3-9}$ cycloalkyl), 3 to 8 ring carbon atoms (i.e., $C_{3-8}$ cycloalkyl), 3 to 7 ring carbon atoms (i.e., $C_{3-7}$ cycloalkyl), 3 to 6 ring carbon atoms (i.e., $C_{3-6}$ cycloalkyl), or 5 ring carbon atoms (i.e., $C_{3-7}$ cycloalkyl), or 6 ring carbon atoms (i.e., $C_6$ cycloalkyl). Examples of cycloalkyl groups include cyclopropyl, cyclobutyl, cyclopentyl, and cyclohexyl.

"Heterocyclyl" refer to acyclic aliphatic group with one or more ring heteroatoms independently selected from nitrogen, oxygen and sulfur. Heterocyclyl includes, for example, heterocycloalkyl, heterocycloalkenyl, and heterocycloalkynyl. Heterocycles can be group can comprise one or more rings, include fused and bridged groups, and can be saturated or have any degree of unsaturation. In some embodiments, the heterocyclyl as used herein, such as in monomer residues of formulae (I), (I-A1), (I-A2a), (II-B1), (II-B2), (II-B1a) and (II-B2a), has 2 to 20 ring carbon atoms (i.e., $C_{2-20}$ heterocyclyl), 2 to 12 ring carbon atoms (i.e., $C_{2-12}$ heterocyclyl), or 2 to 8 ring carbon atoms (i.e., $C_{2-8}$ heterocyclyl); and 1 to 5 ring heteroatoms, 1 to 4 ring heteroatoms, 1 to 3 ring heteroatoms, 1 or 2 ring heteroatoms, or 1 ring heteroatom independently selected from nitrogen, sulfur or oxygen.

"Heterocycloalkyl" refers to a cyclic alkyl group, with one or more ring heteroatoms independently selected from nitrogen, oxygen and sulfur. In some embodiments, the heterocycloalkyl as used herein, such as in monomer residues of formulae (I), (I-A1), (I-A2), (I-A2a), (II-B1), (II-B2), (II-B1a) and (II-B2a), has 2 to 20 ring carbon atoms (i.e., $C_{2-20}$ heterocycloalkyl), 2 to 12 ring carbon atoms (i.e., $C_{2-12}$ heterocycloalkyl), or 2 to 8 ring carbon atoms (i.e., $C_{2-8}$ heterocycloalkyl); and 1 to 5 ring heteroatoms, 1 to 4 ring heteroatoms, 1 to 3 ring heteroatoms, 1 or 2 ring heteroatoms, or 1 ring heteroatom independently selected from nitrogen, sulfur or oxygen. In one example, a heterocycloalkyl has 2 to 8 ring carbon atoms, with 1 to 3 ring heteroatoms independently selected from nitrogen, oxygen and sulfur. Examples of heterocycloalkyl groups may include pyrrolidinyl, piperidinyl, piperazinyl, oxetanyl, dioxolanyl, azetidinyl, and morpholinyl. Heterocycloalkyl may also include such groups in charged form, e.g., 1-methylpiperidinyl-1-ium.

"Aryl" refers to an aromatic carbocyclic group having a single ring (e.g., phenyl), multiple rings (e.g., biphenyl), or multiple fused rings (e.g., naphthyl, fluorenyl, and anthryl). In certain embodiments, aryl as used herein, such as in monomer residues of formulae (I), (I-A1), (I-A2a), (II-B1), (II-B2), (II-B1a) and (II-B2a), has 6 to 20 ring carbon atoms (i.e., $C_{6-20}$ aryl), or 6 to 12 carbon ring atoms (i.e., $C_{6-12}$ aryl). Aryl, however, does not encompass or overlap in any way with heteroaryl, separately defined below. In certain embodiments, if one or more aryl groups are fused with a heteroaryl ring, the resulting ring system is heteroaryl.

"Heteroaryl" refers to an aromatic group having a single ring, multiple rings, or multiple fused rings, with one or more ring heteroatoms independently selected from nitrogen, oxygen, and sulfur. In some embodiments, heteroaryl is an aromatic, monocyclic or bicyclic ring containing one or more heteroatoms independently selected from nitrogen, oxygen and sulfur with the remaining ring atoms being carbon. In certain embodiments, heteroaryl as used herein, such as in monomer residues of formula (I) and (I-A1), has 3 to 20 ring carbon atoms (i.e., $C_{3-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 or 2 ring heteroatoms, or 1 ring heteroatom independently selected from nitrogen, oxygen, and sulfur. In one example, a heteroaryl has 3 to 8 ring carbon atoms, with 1 to 3 ring heteroatoms independently selected from nitrogen, oxygen and sulfur. Examples of heteroaryl groups include pyridyl, pyridazinyl, pyrimidinyl, benzothiazolyl, and pyrazolyl. Heteroaryl may also include such groups in charged form, e.g., 1-methylpyridinyl-1-ium. Heteroaryl does not encompass or overlap with aryl as defined above.

"Amine" refers to —$NR^aR^b$, wherein each $R^a$ and $R^b$ is independently H, aliphatic group, alicyclic group, aryl, heteroaryl, and heterocyclyl. In some embodiments, an amine has a structure where each $R^a$ and $R^b$ is independently H, alkyl, cycloalkyl, heterocycloalkyl, aryl, or heteroaryl. In particular embodiments, amine may also be in charged form.

Polymer-Enzyme Conjugates

Polymer-enzyme conjugates (also referred to herein as "conjugates"), including thermally-responsive polymer-enzyme conjugates, may also be used in the methods described herein to increase the activity of the enzymes and/or to stabilize the enzyme and decrease denaturation. For example, in some embodiments, the polymer-enzyme conjugate is used to increase enzymatic hydrolysis of biomass to produce sugars. Such polymer-enzyme conjugates may also be easily recovered based on the LCST of the polymer, and can be recycled in one or more subsequent hydrolysis reactions. As depicted in FIG. 1, the polymer-enzyme conjugate may be soluble in solution. Then, a cellulosic substrate is added, and the substrate is degraded by the conjugate. By raising the temperature of the soluble above the LCST of the conjugate, the polymer-enzyme conjugate can be precipitated out, and the soluble sugars can then be removed. To resolubilize the polymer-enzyme conjugate, the temperature of the solution can be decreased below the LCST.

The polymer-enzyme conjugates may include at least one of the aminooxy-bearing methacrylamide monomer residues described herein (including, for example, aminooxy-bearing methacrylamide monomer residues of formula (II-B1), (II-B2), (II-B1a) or (II-B2a), or any combinations of such residues, modified for attachment to an enzyme. The aminooxy-bearing methacrylamide monomer residues described herein can be attached to an enzyme by transaminating the N-terminus of the enzyme. Such a bioconjugation strategy allows the introduction of the polymer at a position in the enzyme that is typically remotely disposed from the active site of enzyme.

In some embodiments, the copolymer of the polymer-enzyme conjugate has at least two monomer residues, wherein at least a portion of the monomer residues are modified for attachment to an enzyme. For example, a plurality of the monomer residues of the polymer-enzyme conjugate may independently have a structure of formula (I), (I-A1), (I-A2), or (I-A2a), or any combination of such residues, as described herein; and a plurality of the monomer residues of the polymer-enzyme conjugate may be aminooxy-bearing methacrylamide monomer residues independently having a structure of formula (II-B1), (II-B2), (II-B1a) and (II-B2a), or any combination of such residues, wherein at least a portion of the aminooxy-bearing methacrylamide monomer residues are modified for attachment to an enzyme.

In certain embodiments of the polymer-enzyme conjugate, at least one of the aminooxy-bearing methacrylamide monomer residues independently has the structure of formula (II-B1) or (II-B2):

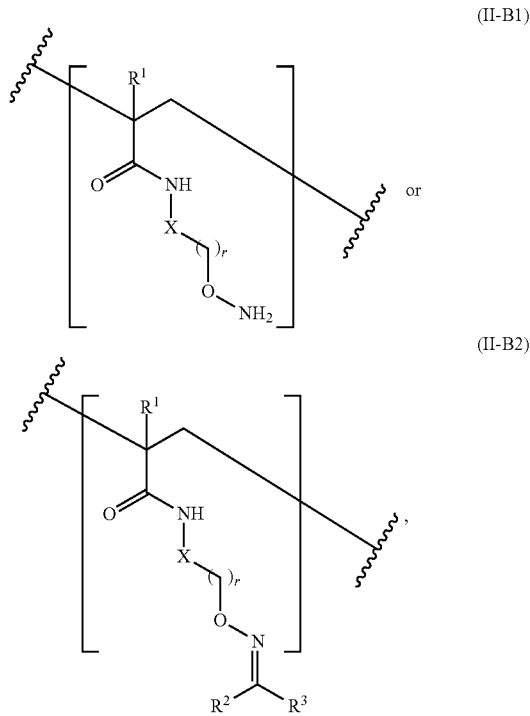

wherein X, r, $R^1$, $R^2$ and $R^3$ are each as defined above in the context of the monomer residues for the polymer; and at least one of the aminooxy-bearing methacrylamide monomer residues has the structure of formula (II-B3):

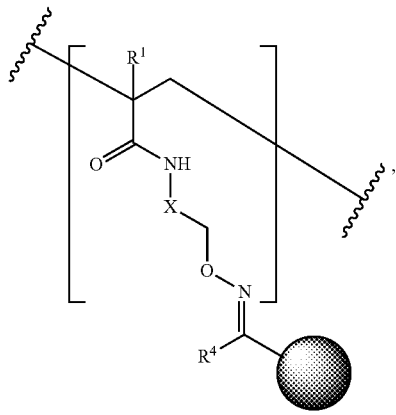

(II-B3)

wherein:
$R^1$ and X are as defined above in the context of the monomer residues for the polymer;
$R^4$ is an amino acid side chain; and

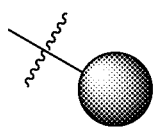

is the point of attachment to the enzyme.

In certain embodiments of the polymer-enzyme conjugate, at least one of the aminooxy-bearing methacrylamide monomer residues independently has the structure of formula (II-B1a) or (II-B2a):

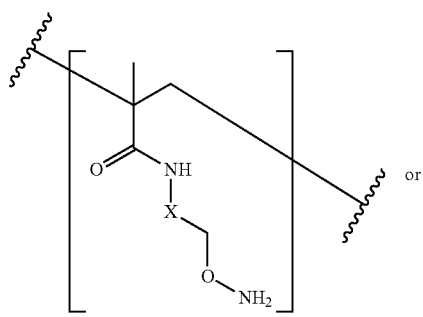

(II-B1a)

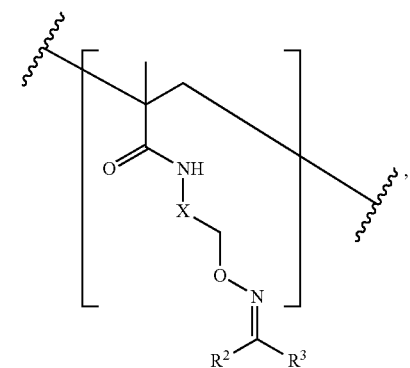

(II-B2a)

wherein X, $R^2$ and $R^3$ are each as defined above in the context of the monomer residues for the polymer; and at least one of the plurality of aminooxy-bearing methacrylamide monomer residues has the structure of formula (II-B3) as described above.

In some embodiments of formula (II-B3), $R^4$ may be any suitable amino acid side chain. Suitable amino acid side chains may include, for example, the side chains of alanine, glycine, aspartic acid, glutamic acid, asparagine, arginine, cysteine, threonine, tyrosine, leucine, serine, methionine, phenylalanine, valine, histidine, isoleucine, lysine, glutamine, tryptophan, and proline. In some embodiments of formula (II-B3), $R^4$ is a side chain of alanine, glycine, aspartic acid, glutamic acid, asparagine, arginine, cysteine, threonine, tyrosine, leucine, serine, or methionine. In certain embodiments of formula (II-B3), $R^4$ is a side chain of alanine, glycine, aspartic acid, or glutamic acid. In one embodiment of formula (II-B3), $R^4$ is an alanine side chain (i.e., $R^4$ is $CH_3$). In another embodiment of formula (II-B3), $R^4$ is a glycine side chain (i.e., $R^4$ is H).

In other embodiments of the polymer-enzyme conjugate, the aminooxy-bearing methacrylamide monomer residues may be a mixture of monomer residues having the structure of formula (II-B1) or (II-B1a), and (II-B3); or having the structure of formula (II-B2) or (II-B2a), and (B3); or having the structure of formula (II-B1) or (II-B1a); (II-B2) or (II-B2a); and (II-B3).

Alternatively, in other embodiments, the enzyme be conjugated to the residues of formula (I), (I-A1), (I-A2), or (I-A2a). For example, a plurality of the monomer residues of the polymer-enzyme conjugate may independently have a structure of formula (I), (I-A1), (I-A2), or (I-A2a), or any combinations of such residues, as described herein, wherein at least one of the plurality of such residues are modified for attachment to an enzyme.

LCST Tuning

The polymers and polymer-enzyme conjugates described above may, in certain embodiments, be thermally-responsive. Such thermally-responsive polymers and polymer-enzyme conjugates allow for recovery and reuse of the polymers and polymer-enzyme conjugates. The thermal responsiveness of such polymers and polymer-enzyme conjugates may be described by their LCST behavior.

Such thermally-responsive polymers or conjugates become soluble in an aqueous solution below the LCST; however, above the LCST, the polymers become insoluble, and may precipitate out of the aqueous solution. It should be understood that at the LCST, some of the polymers may be partially soluble (or partially insoluble). In some embodiments, the thermally-responsive polymer or conjugate is at least partially insoluble in water at a temperature above about 15° C., or between about 20° C. and about 100° C., or between about 20° C. and about 70° C. In certain embodiments, the thermally-responsive polymer is at least 1%, 2%, 3%, 4%, 5%, 6%, 7%, 8%, 9%, 10%, 15%, 20%, 25%, 30%, 40%, 50%, 60%, 70%, 80%, 90%, 95%, 99%, or 99.9% insoluble.

The LCST behavior of such polymers and polymer-enzyme conjugates may depend, in part, on the balance of hydrophilic and hydrophobic regions of the polymer or polymer-enzyme conjugate. Thus, the LCST of the polymers and polymer-enzyme conjugates can be tuned based on (1) the identity of thermally-responsive monomer residues, such as NIPAm or NIPMa; (2) the amount of aminooxy-bearing methacrylamide monomer residues in the copolymer; and/or (3) the small molecule used to modify the copolymer.

By varying one or more factors described above, polymers and polymer-enzyme conjugates can have LCSTs between 0° C. and 100° C., between 20° C. and 100° C., between 20° C. and 95° C., between 20° C. and 90° C., between 20° C. and 80° C., between 20° C. and 70° C., between 20° C. and 60° C., between 30° C. and 55° C., between 30° C. and 35° C., between 35° C. and 45° C., between 35° C. and 40° C., or between 35° C. and 55° C.

The choice of the thermally-responsive monomer residues can affect the starting point for the LCST of the polymer or polymer-enzyme conjugate. In some embodiments, the polymer or polymer-enzyme conjugate is made up of monomer residues having the structure of formula (I) as described above, wherein the monomer residues have a LCST of at least 0° C., at least 20° C., at least 30° C., at least 40° C., or at least 50° C.; or between 0° C. and 100° C., 20° C. and 70° C., between 20° C. and 60° C., between 30° C. and 60° C. between 30° C. and 55° C., between 30° C. and 35° C., or between 35° C. and 45° C. For example, if NIPAm or NIPMa is the thermally-responsive monomer residue, the LCST is typically about 32° C. or 42° C., respectively.

The aminooxy-bearing methacrylamide monomer residue may be hydrophilic. Increasing the amount of the aminooxy-bearing methacrylamide monomer residues present in the copolymer can increase the LCST of the copolymer. In some embodiments, the molar ratio of the thermally-responsive monomer residues to the aminooxy-bearing methacrylamide monomer residues is between 50:50 and 99:1. In one embodiment, the molar ratio of the NIPAm or NIPMa monomer residues to the aminooxy-bearing methacrylamide monomer residues is between 50:50 and 99:1, or between 70:30 and 90:10, or between about 80:20 and 90:10. In another embodiment, the molar ratio of the NIPAm or NIPMa monomer residues to the aminooxy-bearing methacrylamide monomer residues is about 92:8.

For example, copolymers having

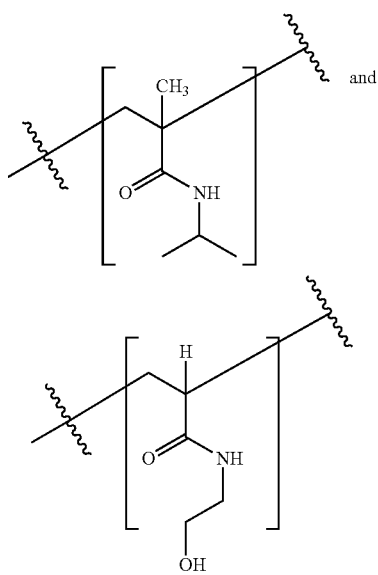

as the first and second monomer residues, respectively, are present in a ratio of about 80:20, and the LCST of such copolymer may be about 55° C. to 60° C.

In another example, copolymers having

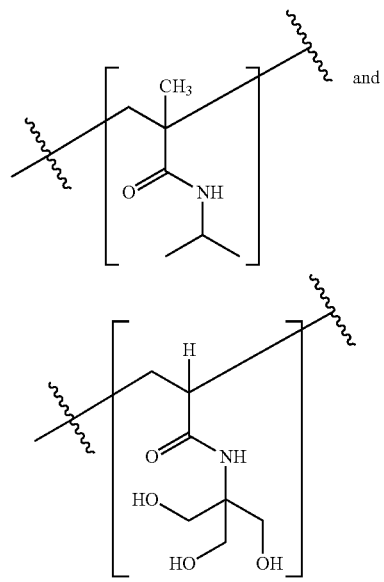

as the first and second monomer residues, respectively, are present in a ratio of about 85:15, and the LCST of such copolymer may be about 45° C. to 50° C.

In yet another example, copolymers having

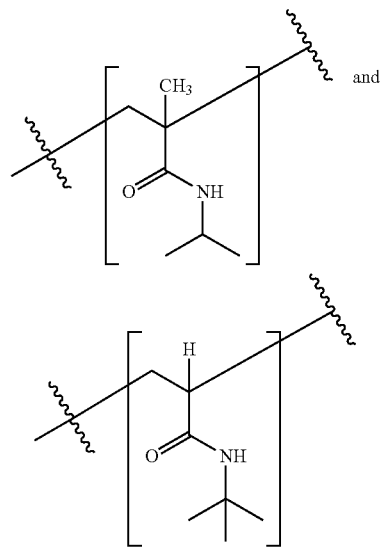

as the first and second monomer residues, respectively, are present in a ratio of about 85:15, and the LCST of such copolymer may be about 35° C. to 40° C.

As discussed above, the LCST can be further adjusted by modification with small molecules. The identity and the amount of small molecule can determine the final LCST of a modified polymer. For example, a NIPAm copolymer with 8.5% aminooxy-bearing methacrylamide monomer residues may initially have an LCST of about 42.5° C. When modified with 3-fluoroisonicotinaldehyde, which is slightly hydrophobic, the LCST may drop to about 20.9° C. However, if a NIPAm copolymer with 15% aminooxy-bearing methacrylamide monomer residues is modified with 3-fluoroisonicotinaldehyde, the final material may have a LCST lower than about 33.4° C. because it would contain more hydrophobically-modified monomer residues, since there are more reactive aminooxy-bearing methacrylamide monomer residues present to modify.

Other suitable small molecule quenchers may include, for example, acetaldehyde, 3-hydroxy-2-butanone, pyruvaldehyde, 4'-aminoacetophenone, 5-hydroxy-2-nitrobenzaldehyde, salicyaldehyde, 2-formylbenzene-sulfonic acid, glyoxylic acid, 2,5-hydroxy-1,4-benzoquinone, pyridoxal-5'-phosphate, or methyl pyruvate.

In some embodiments, a polymer or conjugate can be modified to have a LCST between 33-37° C. using, for example, acetaldehyde, 3-hydroxy-2-butanone, or pyruvaldehyde as the quencher. In other embodiments, a polymer can be modified to have a LCST less than 20° C. using, for example, 4'-aminoacetophenone, 5-hydroxy-2-nitrobenzaldehyde, or salicyaldehyde as the quencher. In yet other embodiments, a polymer or conjugate can be modified to have a LCST greater than 95° C. using, for example, 2-formylbenzene-sulfonic acid, glyoxylic acid, 2,5-hydroxy-1,4-benzoquinone, pyridoxal-5'-phosphate, or methyl pyruvate.

Figure 4A:
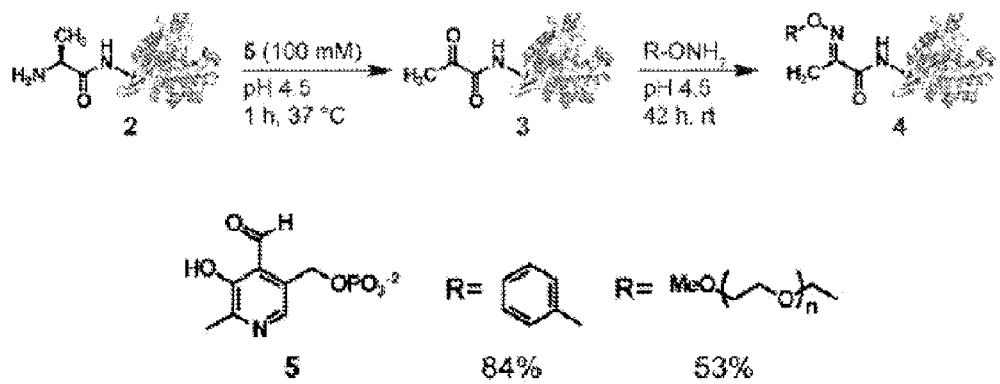
FIG. 4A is an exemplary reaction scheme for modifying EGPh with benzylalkoxyamine or 5k-PEG-ONH$_2$.

For example, with reference to FIG. 4A, in one exemplary embodiment, the N-terminus of cellulase may be transaminated by reacting the cellulase with pyridoxal-5'-phosphate (PLP), and then modifying the PLP-cellulase with benzylalkoxyamine or 5k-PEG-ONH$_2$. The transaminated cellulase can then be conjugated to the terminally-responsive polymer using any suitable methods known in the art.

Other Properties of the Polymers and Polymer-Enzyme Conjugates

In some embodiments, the polymer (either in free form or as part of the polymer-enzyme conjugate) has a $M_w$ of between about 500 Da and about 1,000,000 Da, between about 1000 Da and about 1,000,000 Da, between about 5,000 Da and about 1,000,000 Da, between about 5,000 Da and about 175,000 Da, or between 10,000 Da and 90,000 Da, or between 13,000 Da and 70,000 Da.

In other embodiments, the polymer (either in free form or as part of the polymer-enzyme conjugate) has a $M_n$ of between about 500 Da and about 1,000,000 Da, between about 1000 Da and about 1,000,000 Da, between about 5,000 Da and about 1,000,000 Da, between about 5,000 Da and about 175,000 Da, or between 10,000 Da and 90,000 Da, or between 13,000 Da and 70,000 Da.

Any suitable methods or techniques to measure $M_w$ and $M_n$ may be employed. For example, the values listed above may be measured based on gel permeation chromatography (GPC) using particular solvents and standards, such as dimethylformamide (DMF) as the solvent and poly(methyl methacrylate) (PMMA) as the standard. One of skill in the art would recognize that varying the solvents and standards, for example to chloroform and polyethylene glycol (PEG), could change the values of $M_w$ and $M_n$.

In yet other embodiments, the polymer (either in free form or as part of the polymer-enzyme conjugate) has a polydispersity index (PDI) of between about 1 and about 3, between about 2 and about 3, or between about 1 and about 2. Any suitable methods or techniques to measure PDI may be employed.

The polymers and polymer-enzyme conjugates described above may, in certain embodiments, be nonionic and/or nonsurfactant. As used herein, "nonionic" refers to a polymer and polymer-enzyme conjugate that has no electric charge. As used herein, "nonsurfactant" refers to a polymer and polymer-enzyme conjugate that has the ability to decrease surface tension of water like a surfactant, but is structurally different from a surfactant. In particular, a nonsurfactant does not have the hydrophobic head and hydrophilic tail of a typical surfactant.

The polymers and polymer-enzyme conjugates described above may, in certain embodiments, increase yield of enzymatic reaction; stabilize the enzyme, e.g., at the air-liquid interface; and reduce or prevent denaturation or deactivation of enzyme.

In certain embodiments, the polymers and polymer-enzyme conjugates described above may reduce or prevent nonspecific adsorption to lignin in biomass, and increase binding to lignocellulo sic substrates.

Mixture of Polymers and/or Polymer-Enzyme Conjugates

The methods described herein may employ one polymer or polymer-enzyme conjugate as described herein, or a mixture of such polymers and/or polymer-enzyme conjugates. The use of a mixture of polymers and/or polymer-enzyme conjugates can allow for the addition of two or more polymers or polymer-enzyme conjugates with different enzymes and different LCSTs, which may work cooperatively to break down substrates. The different LCSTs may allow for sequential recovery of each polymer or polymer-enzyme conjugate used in the mixture.

For example, when a first exemplary polymer of the invention (Polymer A) and a second exemplary polymer of the invention (Polymer B) are used to hydrolyze a substrate, these polymers may be recovered separately by: (i) increasing the temperature of the solution to above the LCST of Polymer A, but below the LCST of Polymer B; (ii) recovering Polymer A using any suitable methods or techniques known in the art; (iii) raising the temperature of the remaining solution above the LCST of Polymer B; and (iv) recovering Polymer B.

Alternatively, in another example, polymer-enzyme conjugate with one LCST could be supplemented by polymer with a second LCST, and following enzymatic reaction, each polymer and polymer-enzyme conjugate may be sequentially recovered as described above. In yet another example, two polymers with different LCSTs could be added for reaction with free enzyme, and following enzymatic reaction, each polymer may be sequentially recovered as described above.

Polymer Loading

The amount of polymer, in either free or conjugated form, used in the methods described herein may be described relative to the amount of substrate, and such ratio may be referred to as "polymer loading". In certain embodiments, the polymer loading of the polymer, in either free or conjugated form, used in the methods described herein is expressed as a ratio of the amount of polymer (g) to the amount of substrate (g). The substrate used in determining polymer loading can be a dried substrate (also referred to as "dry matter" or "DM"). It should be understood, however, that a dry substrate (or dry matter) is typically oven-dried, and may have residual or trace amounts of water.

It should be understood that polymer loading may depend on various factor, including, substrate type, substrate pretreatment, substrate loading, enzyme loading (in the case of a polymer-enzyme bioconjugate), and desirability to recover the polymer. In some embodiments, the polymer loading in the methods described herein is at least 0.0001 g polymer/g DM, at least 0.001 g polymer/g DM, at least 0.01 g polymer/g DM, or at least 0.02 g polymer/g DM, or at least 0.2 g polymer/g DM; or between 0.0001 g polymer/g DM and 0.02, between 0.001 g polymer/g DM and 0.02 g polymer/g DM, between 0.001 g polymer/g DM and 0.2 g polymer/g DM, or between 0.001 g polymer/g DM and 0.5 g polymer/g DM. When the polymer, in either free or conjugated form, are used in the methods described herein at such polymer loadings, the yield of the enzymatic reaction increases by at least 20%, at least 25%, at least 30%, at least 40%, at least 50%, at least 60%, at least 70%, at least 80%, or at least 90%; or between 20% and 90%, between 20% and 80%, between 20% and 70%, between 30% and 90%, between 30% and 80%, between 30% and 70%, between 40% and 90%, or between 40% and 80% compared to the yield of the enzymatic reaction in the absence of the polymer.

Enzymes

Any suitable enzyme or mixture of enzymes may be used in the methods and/or compositions described herein, including any suitable enzyme or mixture of enzymes that can work with the polymers described herein to perform an enzymatic reaction on one or more substrates. The enzymes may either be used in an unconjugated form in the presence of a polymer, or conjugated to a polymer. The enzyme may be a purified protein, or contained in a cellular extract, such as a bacterial or fungal extract, or contained in an biological mixture, such as a sublimating enzyme mixture. The enzyme may be derived from a thermophilic organism or a mesophilic organism. The enzymes may be selected from, for example, cellulases, hemicellulases, lignases, lipases, amylases, phosphatases, and xylanases, or any mixtures thereof.

The enzymes (e.g., cellulases, hemicellulases, lignases, lipases, amylases, phosphatases, and xylanases) provided for the methods described herein may be obtained from any commercially available sources or isolated according to any methods or techniques known in the art. Moreover, the enzymes (e.g., cellulases, hemicellulases, lignases, lipases, amylases, phosphatases, and xylanases) provided for the methods described herein may be produced recombinantly using any methods and techniques known in the art.

In some embodiments, the enzyme is a cellulase or a mixture of cellulases. For example, the enzyme may be an endoglucanase, an exoglucanase, a β-glucosidase, a polysaccharide monooxygenase, or any mixture thereof. In one embodiment, the enzyme is a thermostable endoglucanase, such as EGPh. In another embodiment, the enzyme is CBHI. In another embodiment, the enzyme is a complex cellulase mixture such as Celluclast®. For example, the endoglucanase may be from *Pyrococcus horikoshii*. In some embodiments the enzyme may be obtained from *Aspergillus niger*, *Trichoderma longibrachiatum*, or *Trichoderma reesei*.

In some embodiments, the enzyme is a hemicellulase or a mixture of hemicellulases. In other embodiments, the enzyme is a mixture of cellulases and hemicellulases. In other embodiments, the enzyme is a lignase. In yet other embodiments, the enzyme is a mixture of two or more enzymes selected from cellulases, hemicellulases, and lignases.

In some embodiments, the enzyme is a lipase or a mixture of lipases. One of skill in the art would recognize that suitable lipases may come from various organisms, including both eukaryotic and prokaryotic organisms. For example, bacterial lipases may include species such as *Pseudomonas*, *Burkholderia*, *Alcaligenes*, *Acinetobacter*, *Bacillus*, and *Chromobacter*. For example, fungal lipases may include species such as *Candida*, *Humicola*, *Penicillium*, *Yarrowia*, *Mucor*, *Rhizopus*, and *Aspergillus*. In one embodiment, the lipase may be obtained from *Candida rugosa*. In another example, mammalian lipases may include pigs and human gastric lipase, as well as recombinant lipases from various organisms. Lipases from the following structural families of acetylcholinesterase-like, gastric lipase, fungal lipase, bacterial lipase, pancreatic lipase N-terminal domain, and cutinase-like lipase may be used in the methods described herein. Mixtures of lipases may also be used, including any commercially available enzyme mixtures, such as Lecitase®, Lecitase®, Lipopan®, Lipozyme®, Palatase®, and Noopazyme®.

In some embodiments, the enzyme is a phosphatase or a mixture of phosphates. One of skill in the art would recognize that suitable alkaline phosphatases can be obtained from various organisms. For example, suitable alkaline phosphatases may be commercially obtained enzymes from bovines, chickens, shrimp (e.g., *Pandalus borealis*), and bacterial sources (e.g., *E. coli*).

In some embodiments, the enzyme is an amylase or a mixture of amylases. In other embodiments, the enzyme is an xylanase or a mixture of xylanases.

It should be understood that the enzyme may carry a charge, e.g., a positive charge or negative charge, under certain physiologic conditions. In certain embodiments, the positively-charged enzyme may be contacted with a positively-charged polymer described herein. In other embodiments, the negatively-charged enzyme may be contacted with a negatively-charged polymer disclosed herein.

Enzyme Loading

The amount of enzyme used may vary depending on the type and amount of substrate, and the type and amount of polymer, in either free or conjugated form, present during the enzymatic reaction. In one embodiment, the ratio of the enzyme to the polymer (including the thermally-responsive polymer), in either free or conjugated form, is between 0.1-5 μM (enzyme) to 0.1-5 wt % (polymer). In one embodiment, the ratio is about 0.2 μM to 0.2 wt %. In other embodiments, the weight ratio of the enzyme to the polymer, in either free or conjugated form, is between 1:2 and 1:2500, or between 1:10 and 1:2000, or between 1:250, or between 1:100, or between 1:50, or between 1:20, or about 1:100, about 1:200, or about 1:300. It should be understood that, with this respect to this enzyme:polymer ratio, the enzyme and the polymer may be in free and/or conjugated form. For example, in methods where biomass is contacted with the polymer-enzyme conjugate, additional polymer in its unconjugated form may be added to the hydrolysis reaction. In such a scenario, the ratio of enzyme to polymer would be a comparison of the amount of enzyme in the conjugate with the amount of polymer in the conjugate and the amount of free polymer added.

In some embodiments, the reaction yields at least 2, at least 3, at least 4, at least 5, at least 6, at least 7, at least 8, at least 9, or at least 10-fold more products in the presence of the polymer than in the absence of the polymer.

Substrates

The type of substrate(s) used in the methods described herein may vary depending on the type of enzyme or mixture of enzymes used. One of skill in the art would recognize and be able to select suitable substrates to use for a given enzyme or mixture of enzymes. The substrates provided for the methods described herein may be obtained from any commercially available sources or produced using any methods or techniques known in the art.

In some embodiments where the enzyme is a cellulase (such as endoglucanase, an exoglucanase, a β-glucosidase, or a polysaccharide monooxygenase) or a mixture of cellulases, the substrate may be selected from biomass, cellulose, disaccharides and other polysaccharides. In one embodiment where the enzyme is an exoglucanase, the substrate may be a cellulosic biomass, such as Avicel. In other embodiment where the enzyme is an endoglucanase or an enzyme mixture, such as celluclast, the substrate may be a lignocellulosic biomass, which may be derived from, for example, *Miscanthus giganteus*.

The biomass used in the methods described herein may contain cellulose and/or hemicellulose. In certain embodiments, cellulosic biomass may be lignocellulosic biomass that contain lignin in addition to cellulose and/or hemicellulose. Cellulose is a polysaccharide that includes a linear chain of β-(1-4)-D-glucose units. Hemicellulose is also a polysaccharide; however, unlike cellulose, hemicellulose is a branched polymer that typically includes shorter chains of sugar units. Suitable sources of biomass include, for example, *Miscanthus*. In certain embodiments, cellobiose may be used as the starting material for enzymatic hydrolysis. When biomass containing cellulose and/or hemicellulose is used as the substrate, the enzyme may be a cellulase or hemicellulase, or mixture of cellulase and hemicellulase. When biomass further contain lignin (e.g., lignocellulosic biomass), lignases may further be used. A lignase enzyme may be used, or a mixture of two or more lignases may be used, or the lignase(s) may be used in combination with cellulase(s) and/or hemicellulase(s).

The biomass used in the methods described herein may be treated before contact with the enzyme or polymer-enzyme conjugate. The biomass may be chemically, physically, or biologically pretreated. A combination of pretreatments may also be used. Suitable pretreatments known in the art may include, for example, dilute acid pretreatment, lime pretreatment, wet oxidation, ammonia fiber/freeze explosion (AFEX), ammonia percolation (APR), and organosolvent pretreatment, steam pretreatment, grinding, milling, or applying lignin-solubilizing microorganisms.

In some embodiments where the enzyme is a lipase or a mixture of lipases, the substrate may be any substrate with at least one ester functional group. In certain embodiments, the substrate is a lipid. For example, the substrate may be a plant oil or algal lipid, wherein the lipase may break down the substrate to produce biofuel. In another example, the substrate may be an oil stain, wherein the lipase in a laundry detergent may break down and remove, or at least partially remove, such oil stain. In yet another example, the substrate may be ester-containing small molecules or pharmaceuticals, wherein the lipase may enantioselectively hydrolyze such molecules or pharmaceuticals to produce a certain chiral product. As lipases can also catalyze transesterification reactions and esterification reactions (the reverse of the hydrolysis reactions given as examples), in other embodiments, other appropriate substrates may include alcohols, carboxylic acids, and/or esters with the goal to achieve a new ester bond.

In some embodiments where the enzyme is a phosphatase or a mixture of phosphatases, the substrate may be any molecule that is made up of at least one phosphate group. Such molecules may include. For example, a suitable substrate may include proteins, DNA, RNA, and deoxy- or ribonucleoside triphosphate.

Conditions for Enzymatic Reaction

One skilled in the art would recognize that suitable processing time, temperature and pH conditions may vary depending on the type and amount of substrate, enzyme, polymer or polymer-enzyme conjugate, and solvent used.

The enzymatic reaction (e.g., hydrolysis) can take from, for example, a few seconds or minutes to several hours. In some embodiments, the enzymatic reaction can take from 5 mins to 96 hours, 10 mins to 96 hours, 15 mins to 96 hours, from 1 to 96 hours, from 12 to 72 hours, or from 12 to 48 hours. In some embodiments, the enzymatic reaction (e.g., hydrolysis) is performed at a temperature between 20° C. and 70° C., between 20° C. and 60° C., between 30° C. and 55° C., between 30° C. and 35° C., or between 35° C. and 45° C. In some embodiments, the enzymatic reaction (e.g., hydrolysis) is performed at a pH of 0-6, or a pH of 3-5

In some embodiments, the substrate may be preincubated with at least one polymer of the invention (including at least one thermally-responsive polymer) prior to addition of the enzyme. For example, biomass may be preincubated with the polymer (including the thermally-responsive polymer) prior to addition of the hydrolysis enzyme (e.g., cellulase(s)). In certain embodiments, this preincubation period is at least 12 hours, 24 hours, or 36 hours.

One of skill in the art would recognize suitable methods and techniques to measure the rate and yield of an enzymatic reaction. Suitable methods and techniques include, for example, the use of HPLC; or the use of an enzyme-paired assay that may provide a colored or fluorescent output quantifiable with spectroscopic instruments (e.g., a UV-vis spectrophotometer or an optical plate reader).

Products of Enzymatic Reaction

The type of product(s) produced according to the methods described herein may vary depending on the type of substrate(s) and type of enzyme(s) used. One of skill in the art would recognize the products formed from a given enzymatic reaction involving a certain substrate and/or certain enzyme.

For example, in embodiments where the substrate is biomass, cellulose, disaccharides and other polysaccharides, the methods described herein can break down such substrates into sugars. For example, the cellulosic component in biomass can be hydrolyzed to form monosaccharides, disaccharides, or oligosaccharides. In one embodiment, the sugars are glucose. The sugars produced from the hydrolysis of biomass according to the methods described herein, using the polymers or polymer-enzyme conjugates, can be used for various downstream products. For example, the sugars may be subsequently fermented to produce biofuels, biochemicals, or other bioproducts.

In another example, the hydrolysis of lipids by lipases may be useful to either break up the lipids themselves (e.g., in the case of oil stains on clothing) or for the hydrolysis products that may result (e.g., the hydrolysis of vegetable oil to produce biodiesel). The esterification or transesterification of substrates by lipases may produce enantiomers of small molecules or pharmaceuticals.

In yet another example, dephosphorylation of chromogenic or fluorogenic small-molecule substrates by alkaline phosphatases provide one way to measure alkaline phosphatase enzyme levels in tissue or blood samples from humans or other animals, which may serve as a measure of various organ functions or overall health.

Recyclability of the Polymer or Polymer-Enzyme Conjugate

As discussed above, the polymer (either in free form or as part of the polymer-enzyme conjugate) may be recovered by increasing the temperature above the LCST of the polymer. The recovered polymer or conjugate may be recycled and used again in one or more subsequent enzymatic reactions.

In some embodiments, the methods provided herein may further include: i) providing additional substrate, additional enzyme, and the recovered polymer; ii) contacting the additional substrate with the additional enzyme in the presence of the recovered the polymer; and iii) hydrolyzing at least a portion of the additional substrate to produce additional hydrolysis products. For example, the method provided herein may further include: i) providing additional biomass, additional hydrolysis enzyme, and the recovered polymer; ii) contacting the additional biomass with the additional hydrolysis enzyme in the presence of the recovered the polymer; and iii) hydrolyzing at least a portion of the additional biomass to produce additional sugars.

The polymer or conjugate may be recovered again from this second enzymatic reaction, and further recycled. The polymer or conjugate may be recycled at least once. In some embodiments, the polymer or conjugate may be recycled one, two, three, or four times. In certain embodiments, the polymer used in this method is a thermally-responsive polymer.

In some embodiments, the recycled polymer or conjugate remains as active as the initial polymer or conjugate. In certain embodiments, the use of the recycled polymer or conjugate increases the amount of enzymatic products by at least 2 fold, at least 2.5 fold, at least 3 fold, at least 5 fold, at least 10 fold over three rounds of use.

Polymer or Polymer-Enzyme Conjugate Compositions

Provided herein is also a composition that includes at least one substrate, at least one enzyme, and at least one polymer as described herein (including at least one thermally-responsive polymer). Provided here is also a composition that includes at least one substrate and at least one polymer-enzyme conjugate as described herein (including at least one thermally-responsive polymer-enzyme conjugate). In some embodiments, the composition may further include additional enzyme(s) in free (unconjugated) form.

For example, in one embodiment, the composition includes a cellulase or a mixture of cellulases (such as endoglucanase, an exoglucanase, a β-glucosidase, a polysaccharide monooxygenase, or any mixture thereof); a suitable substrate (such as biomass, cellulose, disaccharides and/or other polysaccharides); and at least one of the polymers (which may include, for example, at least one thermally-responsive polymers) as described above. In another embodiment, the composition includes a polymer-enzyme conjugate (including a thermally-responsive polymer-enzyme conjugate) as described above, wherein the enzyme is a cellulase or a mixture of cellulase (such as endoglucanase, an exoglucanase, a β-glucosidase, a polysaccharide monooxygenase, or any mixture thereof); and a suitable substrate (such as biomass, cellulose, disaccharides and/or other polysaccharides).

Provided herein is also a residual biomass composition that includes residual substrate, enzymatic reaction product(s), an enzyme or a mixture of enzymes, and at least one polymer (including at least one thermally-responsive polymer) as described above. Residual substrate refers to any substrate that remains after an enzymatic reaction. Provided herein is also a residual biomass composition that includes residual substrate, enzymatic reaction product(s), and at least one polymer-enzyme conjugate (including at least one thermally-responsive polymer-enzyme conjugate) as described above. In some embodiments, the residual biomass composition may further include additional enzyme(s) in free (or unconjugated) form.

For example, in one embodiment, provided herein is a residual biomass composition that includes residual biomass, one or more sugars, a hydrolysis enzyme or a mixture of hydrolysis enzymes, and a polymer (including a thermally-responsive polymer) as described above. Residual biomass refers to any biomass that remains after a hydrolysis reaction, and may include undigested cellulose, hemicellulose and/or lignin, as well as salts and other debris.

In certain embodiments, the composition includes:
at least one enzyme selected from cellulases, hemicellulases, lignases, lipases, amylases, phosphatases, and xylanases;
at least one suitable substrate; and
at least one polymer comprising monomer residues of formula (I), (I-A1), (I-A2), or (I-A2a), and optionally further comprising aminooxy-bearing methacrylamide monomer residues of formula (II-B1), (II-B2), (II-B1a) or (II-B2a).

In one variation, the composition includes:
at least one enzyme selected from cellulases, hemicellulases, and lignases;
at least one suitable substrate; and
at least one polymer comprising monomer residues of formula (I), (I-A1), (I-A2), or (I-A2a), and optionally further comprising aminooxy-bearing methacrylamide monomer residues of formula (II-B1), (II-B2), (II-B1a) or (II-B2a).

In another variation, the composition includes:
at least one enzyme selected from lipases;
at least one suitable substrate; and
at least one polymer comprising monomer residues of formula (I), (I-A1), (I-A2), or (I-A2a), and optionally further comprising aminooxy-bearing methacrylamide monomer residues of formula (II-B1), (II-B2), (II-B1a) or (II-B2a).

In another variation, the composition includes:
at least one enzyme selected from amylases;
at least one suitable substrate; and
at least one polymer comprising monomer residues of formula (I), (I-A1), (I-A2), or (I-A2a), and optionally further comprising aminooxy-bearing methacrylamide monomer residues of formula (II-B1), (II-B2), (II-B1a) or (II-B2a).

In another variation, the composition includes:
at least one enzyme selected from phosphatases;
at least one suitable substrate; and
at least one polymer comprising monomer residues of formula (I), (I-A1), (I-A2), or (I-A2a), and optionally further comprising aminooxy-bearing methacrylamide monomer residues of formula (II-B1), (II-B2), (II-B1a) or (II-B2a).

In another variation, the composition includes:
at least one enzyme selected from xylanases;
at least one suitable substrate; and
at least one polymer comprising monomer residues of formula (I), (I-A1), (I-A2), or (I-A2a), and optionally further comprising aminooxy-bearing methacrylamide monomer residues of formula (II-B1), (II-B2), (II-B1a) or (II-B2a).

In other embodiments, the composition includes: at least one polymer-enzyme conjugate (including at least one thermally-responsive polymer-enzyme conjugate) as provided herein, wherein the enzyme is selected from cellulases, hemicellulases, lignases, lipases, amylases, phosphatases, and xylanases; and a suitable substrate.

Enumerated Embodiments

The following enumerated embodiments are representative of some aspects of the invention.

1. A method of hydrolyzing biomass, comprising:
a) providing biomass, a hydrolysis enzyme, and a thermally-responsive polymer;
b) contacting the biomass with the hydrolysis enzyme in the presence of the thermally-responsive polymer,
wherein the thermally-responsive polymer is:
poly N-isopropylacrylamide,
poly N-isopropylmethacrylamide, or
a copolymer comprising a plurality of first monomer residues and a plurality of second monomer residues,
wherein each of the first monomer residues is independently selected from the group consisting of N-isopropylacrylamide, N-isopropylmethacrylamide, and any combinations thereof, and each of the second monomer residues is an aminooxy-bearing methacrylamide monomer residue; and c) hydrolyzing at least a portion of the biomass to produce sugars.

2. The method of embodiment 1, wherein the thermally-responsive polymer is a copolymer comprising a plurality of first monomer residues and a plurality of second monomer residues, wherein each of the first monomer residues is independently selected from the group consisting of N-isopropylacrylamide, N-isopropylmethacrylamide, and any combinations thereof, and wherein each of the second monomer residues is an aminooxy-bearing methacrylamide monomer residue.

3. The method of embodiment 2, wherein each of the first monomer residues of the copolymer independently has the structure of formula (I-A2):

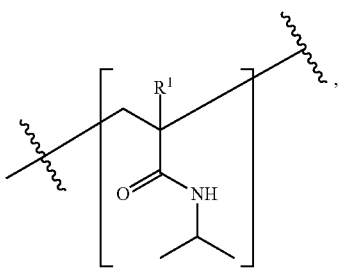

(I-A2)

wherein:

$R^1$ at each occurrence is independently H or alkyl.

4. The method of embodiment 2, wherein each of the second monomer residues of the copolymer independently has the structure of formula (II-B1a) or (II-B2a):

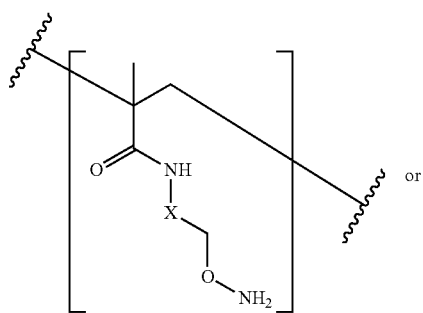

(II-B1a)

or

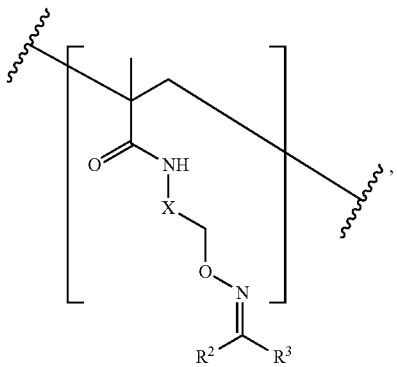

(II-B2a)

wherein:

X at each occurrence is independently unsubstituted or substituted -alkyl-, unsubstituted or substituted -alkenyl-, unsubstituted or substituted -alkynyl-, unsubstituted or substituted -aryl-, unsubstituted or substituted -heteroaryl-, unsubstituted or substituted -cycloalkyl-, unsubstituted or substituted -heterocycloalkyl-, unsubstituted or substituted -ether-, or —$(CH_2)_j$NHCO—, wherein j is an integer, and j at each occurrence is independently at least 1; and $R^2$ and $R^3$ at each occurrence are independently H, unsubstituted or substituted alkyl, unsubstituted or substituted alkenyl, unsubstituted or substituted alkynyl, unsubstituted or substituted aryl, unsubstituted or substituted heteroaryl, unsubstituted or substituted cycloalkyl, unsubstituted or substituted heterocycloalkyl, or —C(O)$R^{a'}$, wherein $R^a$ is H, alkyl, or hydroxy; or $R^2$ and $R^3$ are taken together with the carbon to which they are attached to form a 5- or 6-membered unsubstituted or substituted heterocyclyl.

5. The method of embodiment 4, wherein X at each occurrence is:

unsubstituted $C_{1-10}$ -alkyl-;

$C_{1-10}$ -alkyl- substituted with one or more groups independently selected from hydroxy, amino, oxo, nitrate, phosphate, and sulfate;

unsubstituted $C_{2-10}$ -alkenyl-;

$C_{2-10}$ -alkenyl- substituted with one or more groups independently selected from hydroxy, amino, oxo, nitrate, phosphate, and sulfate;

unsubstituted $C_{2-10}$ -alkynyl-;

$C_{2-10}$ -alkynyl- substituted with one or more groups independently selected from hydroxy, amino, oxo, nitrate, phosphate, and sulfate;

unsubstituted $C_{6-12}$ -aryl-;

$C_{6-12}$ -aryl- substituted with one or more groups independently selected from alkyl, halo, hydroxy, amino, oxo, nitrate, phosphate, and sulfate;

unsubstituted $C_{4-12}$ -heteroaryl- with 1 to 3 ring heteroatoms independently selected from the group consisting of nitrogen, oxygen and sulfur;

$C_{4-12}$ -heteroaryl- with 1 to 3 ring heteroatoms independently selected from the group consisting of nitrogen, oxygen and sulfur, wherein the heteroaryl is substituted with one or more groups independently selected from alkyl, halo, hydroxy, amino, oxo, nitrate, phosphate, and sulfate;

unsubstituted $C_{3-12}$-cycloalkyl-;

$C_{3-12}$-cycloalkyl- substituted with one or more groups selected from alkyl, halo, hydroxy, amino, oxo, nitrate, phosphate, and sulfate;

unsubstituted $C_{3-12}$-heterocycloalkyl- with 1 to 3 ring heteroatoms independently selected from the group consisting of nitrogen, oxygen and sulfur;

$C_{3-12}$-heterocycloalkyl- with 1 to 3 ring heteroatoms independently selected from the group consisting of nitrogen, oxygen and sulfur, wherein the heterocycloalkyl is substituted with one or more groups selected from alkyl, halo, hydroxy, amino, oxo, nitrate, phosphate, and sulfate;

unsubstituted $C_{2-10}$-ether-;

$C_{2-10}$-ether- substituted with one or more groups selected from alkyl, halo, hydroxy, amino, oxo, nitrate, phosphate, and sulfate; or —(CH$_2$)$_j$NHCO—.

6. The method of embodiment 5, wherein X at each occurrence is —(CH$_2$)$_3$NHCO—.

7. The method of embodiment 4, wherein $R^2$ and $R^3$ at each occurrence is independently:

H;

unsubstituted $C_{1-10}$ alkyl;

$C_{1-10}$ alkyl substituted with one or more groups independently selected from hydroxy, amino, oxo, nitrate, phosphate, and sulfate;

unsubstituted $C_{2-10}$ alkenyl;

$C_{2-10}$ alkenyl substituted with one or more groups independently selected from hydroxy, amino, oxo, nitrate, phosphate, and sulfate;

unsubstituted $C_{2-10}$ alkynyl;

$C_{2-10}$ alkynyl substituted with one or more groups independently selected from hydroxy, amino, oxo, nitrate, phosphate, and sulfate;

unsubstituted $C_{6-12}$ aryl;

$C_{6-12}$ aryl substituted with one or more groups independently selected from alkyl, halo, hydroxy, amino, oxo, nitrate, phosphate, and sulfate;

unsubstituted $C_{4-12}$ heteroaryl with 1 to 3 ring heteroatoms independently selected from the group consisting of nitrogen, oxygen and sulfur;

$C_{4-12}$ heteroaryl with 1 to 3 ring heteroatoms independently selected from the group consisting of nitrogen, oxygen and sulfur, wherein the heteroaryl is substituted with one or more groups independently selected from alkyl, halo, hydroxy, amino, oxo, nitrate, phosphate, and sulfate;

unsubstituted $C_{3-12}$ cycloalkyl;

$C_{3-12}$ cycloalkyl substituted with one or more groups selected from alkyl, halo, hydroxy, amino, oxo, nitrate, phosphate, and sulfate;

unsubstituted $C_{3-12}$ heterocycloalkyl with 1 to 3 ring heteroatoms independently selected from the group consisting of nitrogen, oxygen and sulfur;

$C_{3-12}$ heterocycloalkyl with 1 to 3 ring heteroatoms independently selected from the group consisting of nitrogen, oxygen and sulfur, wherein the heterocycloalkyl is substituted with one or more groups selected from alkyl, halo, hydroxy, amino, oxo, nitrate, phosphate, and sulfate;

$R^2$ and $R^3$ are taken together with the carbon to which they are attached to form a 5- or 6-membered unsubstituted $C_{4-12}$ heterocyclyl with 1 to 3 ring heteroatoms independently selected from the group consisting of nitrogen, oxygen and sulfur; or $R^2$ and $R^3$ are taken together with the carbon to which they are attached to form a 5- or 6-membered $C_{4-12}$ heterocyclyl with 1 to 3 ring heteroatoms independently selected from the group consisting of nitrogen, oxygen and sulfur, wherein the heterocyclyl is substituted with one or more groups selected from alkyl, halo, hydroxy, amino, oxo, nitrate, phosphate, and sulfate.

8. The method of embodiment 7, wherein $R^2$ and $R^3$ at each occurrence is independently H, unsubstituted $C_{1-5}$ alkyl, or $C_{1-5}$ alkyl substituted with 1-5 hydroxyl groups.

9. The method of embodiment 4, wherein

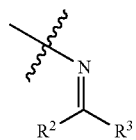

at each occurrence is independently selected from the group consisting of:

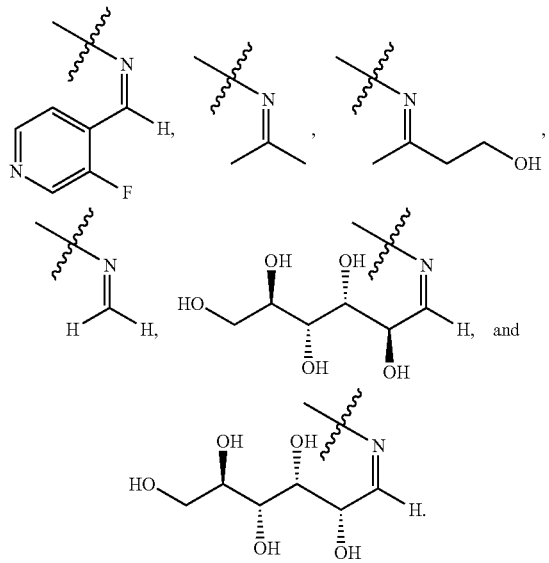

10. The method of embodiment 2, wherein the plurality of the first monomer residues and the plurality of the second monomer residues are present in a molar ratio of between 50:50 and 99:1.

11. The method of embodiment 1, wherein the thermally-responsive polymer is at least partially insoluble in water at a temperature above about 15° C.

12. The method of embodiment 11, wherein the thermally-responsive polymer is at least 1%, 2%, 3%, 4%, 5%, 6%, 7%, 8%, 9%, 10%, 15%, 20%, 25%, 30%, 40%, 50%, 60%, 70%, 80%, 90%, 95%, 99%, or 99.9% insoluble.

13. The method of embodiment 11, wherein the thermally-responsive polymer is at least partially insoluble in water at a temperature between about 20° C. and about 70° C.

14. The method of embodiment 13, wherein the thermally-responsive polymer is at least 1%, 2%, 3%, 4%, 5%, 6%, 7%, 8%, 9%, 10%, 15%, 20%, 25%, 30%, 40%, 50%, 60%, 70%, 80%, 90%, 95%, 99%, or 99.9% insoluble.

15. The method of embodiment 1, wherein the thermally-responsive polymer has a molecular weight of between about 5,000 Da and about 1,000,000 Da.
16. The method of embodiment 1, wherein the thermally-responsive polymer has a polydispersity index (PDI) of between about 1.0 and about 2.0.
17. A method of hydrolyzing biomass, comprising:
    a) providing biomass, a hydrolysis enzyme, and a polymer, wherein polymer comprises a plurality of monomer residues having the structure of formula (I):

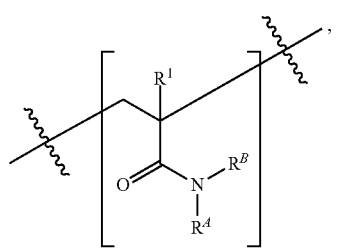

(I)

wherein:
    $R^1$ at each occurrence is independently H or alkyl; and
    $R^A$ and $R^B$ at each occurrence is independently H, unsubstituted or substituted alkyl, unsubstituted or substituted cycloalkyl, unsubstituted or substituted aryl, unsubstituted or substituted heterocycloalkyl, or unsubstituted or substituted heteroaryl;
    c) hydrolyzing at least a portion of the biomass to produce sugars.
    b) contacting the biomass with the hydrolysis enzyme and the polymer; and
    c) hydrolyzing at least a portion of the biomass to produce sugars.
18. The method of embodiment 17, wherein the monomer residues of formula (I) have a structure wherein $R^A$ and $R^B$ at each occurrence is independently:
    H;
    unsubstituted alkyl;
    alkyl substituted with 1 to 5 groups selected from cycloalkyl, aryl, heterocycloalkyl, heteroaryl, amine, —C(O)NR'R", —C(O)R', —C(O)OR', —OR', a cationic moiety, or an anionic moiety;
    unsubstituted cycloalkyl;
    cycloalkyl substituted with 1 to 5 groups selected from alkyl, aryl, heterocycloalkyl, heteroaryl, amine, —C(O)NR'R", —C(O)R', —C(O)OR', —OR', a cationic moiety, or an anionic moiety;
    unsubstituted aryl;
    aryl substituted with 1 to 5 groups selected from alkyl, cycloalkyl, heterocycloalkyl, heteroaryl, amine, —C(O)NR'R", —C(O)R', —C(O)OR', —OR', a cationic moiety, or an anionic moiety;
    unsubstituted heterocycloalkyl;
    heterocycloalkyl substituted with 1 to 5 groups selected from alkyl, cycloalkyl, aryl, heteroaryl, amine, —C(O)NR'R", —C(O)R', —C(O)OR', —OR', a cationic moiety, or an anionic moiety;
    unsubstituted heteroaryl; or
    heteroaryl substituted with 1 to 5 groups selected from alkyl, cycloalkyl, aryl, heterocycloalkyl, amine, —C(O)NR'R", —C(O)R', —C(O)OR', —OR', a cationic moiety, or an anionic moiety;

wherein each R' and R" at each occurrence is independently H, alkyl, cycloalkyl, heterocycloalkyl, aryl, or heteroaryl.
19. The method of embodiment 17, wherein the monomer residues of formula (I) have a structure wherein $R^A$ at each occurrence is independently unsubstituted alkyl; and $R^B$ is hydrogen.
20. The method of embodiment 17, wherein the polymer further comprises a plurality of second monomer residues, wherein the second monomer residues are aminooxy-bearing methacrylamide monomer residues.
21. The method of embodiment 17, wherein the aminooxy-bearing methacrylamide monomer residues at each occurrence independently have the structure of formula (II-B1) or (II-B2):

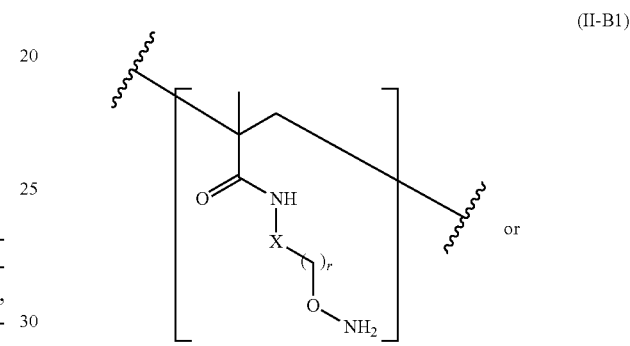

(II-B1)

or

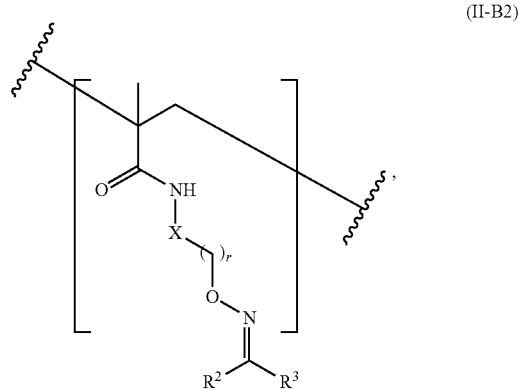

(II-B2)

wherein:
    r at each occurrence is an integer greater than or equal to 1;
    X at each occurrence is independently unsubstituted or substituted -alkyl-, unsubstituted or substituted -alkenyl-, unsubstituted or substituted -alkynyl-, unsubstituted or substituted -aryl-, unsubstituted or substituted -heteroaryl-, unsubstituted or substituted -cycloalkyl-, unsubstituted or substituted -heterocycloalkyl-, unsubstituted or substituted -ether-, or —(CH$_2$)$_j$NHCO—, wherein j is an integer, and j at each occurrence is independently at least 1; and
    $R^2$ and $R^3$ at each occurrence are independently H, unsubstituted or substituted alkyl, unsubstituted or substituted alkenyl, unsubstituted or substituted alkynyl, unsubstituted or substituted aryl, unsubstituted or substituted heteroaryl, unsubstituted or substituted cycloalkyl, unsubstituted or substituted heterocycloalkyl, or —C(O)R$^{a'}$, wherein R$^a$ is H, alkyl, or hydroxy; or $R^2$ and $R^3$ are taken together with the carbon to which they are attached to form a 5- or 6-membered unsubstituted or substituted heterocyclyl.

22. The method of embodiment 21, wherein r is 1 to 5.

23. The method of embodiment 21, wherein the aminooxy-bearing methacrylamide monomer residues have a structure wherein X at each occurrence is:
unsubstituted $C_{1-10}$-alkyl-;
$C_{1-10}$-alkyl- substituted with one or more groups independently selected from hydroxy, amino, oxo, nitrate, phosphate, and sulfate;
unsubstituted $C_{2-10}$-alkenyl-;
$C_{2-10}$-alkenyl- substituted with one or more groups independently selected from hydroxy, amino, oxo, nitrate, phosphate, and sulfate;
unsubstituted $C_{2-10}$-alkynyl-;
$C_{2-10}$-alkynyl- substituted with one or more groups independently selected from hydroxy, amino, oxo, nitrate, phosphate, and sulfate;
unsubstituted $C_{6-12}$-aryl-;
$C_{6-12}$-aryl- substituted with one or more groups independently selected from alkyl, halo, hydroxy, amino, oxo, nitrate, phosphate, and sulfate;
unsubstituted $C_{4-12}$-heteroaryl- with 1 to 3 ring heteroatoms independently selected from the group consisting of nitrogen, oxygen and sulfur;
$C_{4-12}$-heteroaryl- with 1 to 3 ring heteroatoms independently selected from the group consisting of nitrogen, oxygen and sulfur, wherein the heteroaryl is substituted with one or more groups independently selected from alkyl, halo, hydroxy, amino, oxo, nitrate, phosphate, and sulfate;
unsubstituted $C_{3-12}$-cycloalkyl-;
$C_{3-12}$-cycloalkyl- substituted with one or more groups selected from alkyl, halo, hydroxy, amino, oxo, nitrate, phosphate, and sulfate;
unsubstituted $C_{3-12}$-heterocycloalkyl- with 1 to 3 ring heteroatoms independently selected from the group consisting of nitrogen, oxygen and sulfur;
$C_{3-12}$-heterocycloalkyl- with 1 to 3 ring heteroatoms independently selected from the group consisting of nitrogen, oxygen and sulfur, wherein the heterocycloalkyl is substituted with one or more groups selected from alkyl, halo, hydroxy, amino, oxo, nitrate, phosphate, and sulfate;
unsubstituted $C_{2-10}$-ether-;
$C_{2-10}$-ether- substituted with one or more groups selected from alkyl, halo, hydroxy, amino, oxo, nitrate, phosphate, and sulfate; or
—$(CH_2)_j$NHCO—.

24. The method of any one of embodiments 21 to 23, wherein the aminooxy-bearing methacrylamide monomer residues have a structure wherein $R^2$ and $R^3$ at each occurrence is independently:
H;
unsubstituted $C_{1-10}$ alkyl;
$C_{1-10}$ alkyl substituted with one or more groups independently selected from hydroxy, amino, oxo, nitrate, phosphate, and sulfate;
unsubstituted $C_{2-10}$ alkenyl;
$C_{2-10}$ alkenyl substituted with one or more groups independently selected from hydroxy, amino, oxo, nitrate, phosphate, and sulfate;
unsubstituted $C_{2-10}$ alkynyl;
$C_{2-10}$ alkynyl substituted with one or more groups independently selected from hydroxy, amino, oxo, nitrate, phosphate, and sulfate;
unsubstituted $C_{6-12}$ aryl;
$C_{6-12}$ aryl substituted with one or more groups independently selected from alkyl, halo, hydroxy, amino, oxo, nitrate, phosphate, and sulfate;
unsubstituted $C_{4-12}$ heteroaryl with 1 to 3 ring heteroatoms independently selected from the group consisting of nitrogen, oxygen and sulfur;
$C_{4-12}$ heteroaryl with 1 to 3 ring heteroatoms independently selected from the group consisting of nitrogen, oxygen and sulfur, wherein the heteroaryl is substituted with one or more groups independently selected from alkyl, halo, hydroxy, amino, oxo, nitrate, phosphate, and sulfate;
unsubstituted $C_{3-12}$ cycloalkyl;
$C_{3-12}$ cycloalkyl substituted with one or more groups selected from alkyl, halo, hydroxy, amino, oxo, nitrate, phosphate, and sulfate;
unsubstituted $C_{3-12}$ heterocycloalkyl with 1 to 3 ring heteroatoms independently selected from the group consisting of nitrogen, oxygen and sulfur;
$C_{3-12}$ heterocycloalkyl with 1 to 3 ring heteroatoms independently selected from the group consisting of nitrogen, oxygen and sulfur, wherein the heterocycloalkyl is substituted with one or more groups selected from alkyl, halo, hydroxy, amino, oxo, nitrate, phosphate, and sulfate;
$R^2$ and $R^3$ are taken together with the carbon to which they are attached to form a 5- or 6-membered unsubstituted $C_{4-12}$ heterocyclyl with 1 to 3 ring heteroatoms independently selected from the group consisting of nitrogen, oxygen and sulfur; or
$R^2$ and $R^3$ are taken together with the carbon to which they are attached to form a 5- or 6-membered $C_{4-12}$ heterocyclyl with 1 to 3 ring heteroatoms independently selected from the group consisting of nitrogen, oxygen and sulfur, wherein the heterocyclyl is substituted with one or more groups selected from alkyl, halo, hydroxy, amino, oxo, nitrate, phosphate, and sulfate.

25. The method of any one of embodiments 1 to 24, wherein the hydrolysis enzyme is a purified protein.

26. The method of embodiment 25, wherein the hydrolysis enzyme is an endoglucanase, an exoglucanase, a β-glucosidase, a polysaccharide monooxygenase, or CBHI.

27. The method of any one of embodiments 1 to 26, wherein the hydrolysis enzyme is an enzyme mixture.

28. The method of embodiment 27, wherein the hydrolysis enzyme is celluclast.

29. The method of any one of embodiments 1 to 28, wherein the hydrolysis enzyme is derived from a thermophilic organism.

30. The method of embodiment 29, wherein the hydrolysis enzyme is derived from *Pyrococcus horikoshii, Aspergillus niger, Trichoderma longibrachiatum*, or *Trichoderma reesei*.

31. The method of any one of embodiments 1 to 30, wherein the hydrolysis enzyme is derived from a mesophilic organism.

32. The method of embodiment 1, further comprising recovering the thermally-responsive polymer after hydrolysis in step (d).

33. The method of embodiment 32, further comprising:
i) providing second biomass, a second hydrolysis enzyme, and the recovered thermally-responsive polymer;
ii) contacting the biomass with second hydrolysis enzyme in the presence of the recovered the thermally-responsive polymer; and
iii) hydrolyzing at least a portion of the second biomass to produce second sugars.

34. A composition, comprising:
   biomass;
   a hydrolysis enzyme; and
   a thermally-responsive polymer selected from the group consisting of:
      poly N-isopropylacrylamide,
      poly N-isopropylmethacrylamide, and
      a copolymer comprising a plurality of first monomer residues and a plurality of second monomer residues, wherein each of the first monomer residues are independently selected from the group consisting of N-isopropylacrylamide, N-isopropylmethacrylamide and any combinations thereof, and the second monomer residues are aminooxy-bearing methacrylamide monomer residues.

35. A residual biomass composition, comprising:
   residual biomass;
   sugars;
   a hydrolysis enzyme; and
   a thermally-responsive polymer selected from the group consisting of:
      poly N-isopropylacrylamide,
      poly N-isopropylmethacrylamide, and
      a copolymer comprising a plurality of first monomer residues and a plurality of second monomer residues, wherein each of the first monomer residues are independently selected from the group consisting of N-isopropylacrylamide, N-isopropylmethacrylamide and any combinations thereof, and the second monomer residues are aminooxy-bearing methacrylamide monomer residues.

36. The method of embodiment 1 wherein the biomass is contacted with the thermally-responsive polymer first and the hydrolysis enzyme second.

37. The method of embodiment 36 wherein the biomass is contacted with the thermally-responsive polymer for at least 12 hours, 24 hours, or 36 hours.

38. The method of embodiment 1, wherein at least 2, at least 3, at least 4, at least 5, at least 6, at least 7, at least 8, at least 9, or at least 10-fold more sugars are produced in the presence of the thermally-responsive polymer than in the absence of the thermally-responsive polymer.

39. The method of any one of embodiments 1 to 38, wherein the biomass is a cellulosic biomass and the hydrolysis enzyme is an exoglucanase.

40. The method of embodiment 39, wherein the biomass is Avicel.

41. The method of embodiment 38, wherein the biomass is a lignocellulosic biomass and the hydrolysis enzyme is an endoglucanase.

42. The method of embodiment 41, wherein the biomass is derived from *Miscanthus giganteus*.

43. The method of embodiment 38, wherein the biomass is lignocellulosic biomass and the hydrolysis enzyme is celluclast.

44. A method, comprising contacting at least one substrate with at least one and at least one polymer comprising a plurality of monomer residues having the structure of formula (I):

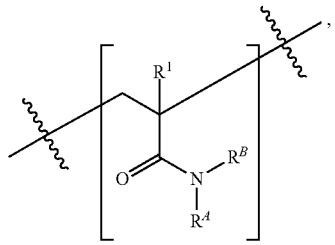

wherein:
   $R^1$ at each occurrence is independently H or alkyl; and
   $R^A$ and $R^B$ at each occurrence is independently H, unsubstituted or substituted aliphatic group, unsubstituted or substituted alicyclic group, unsubstituted or substituted aryl, unsubstituted or substituted heteroaryl, or unsubstituted or substituted heterocyclyl;
   provided that at least one of $R^A$ and $R^B$ is other than H.

45. The method of embodiment 44, further comprising enzymatically breaking down at least a portion of the at least one substrate to produce at least one product.

46. The method of embodiment 44, further comprising enzymatically hydrolyzing at least a portion of the at least one substrate to produce at least one product.

47. The method of embodiment 45 or 46, further comprising recovering at least one of the polymers.

48. The method of embodiment 47, further comprising recovering at least one of the polymers by separating at least one of the polymers from the at least one product.

49. The method of embodiment 47, further comprising:
   i) providing additional substrate, additional enzyme or mixture of enzymes, and the at least one recovered polymer;
   ii) contacting the additional substrate with the additional enzyme in the presence of the at least one recovered polymer; and
   iii) enzymatically breaking down at least a portion of the additional biomass.

50. The method of any one of embodiments 1 to 49, wherein each $R^A$ and $R^B$ at each occurrence is independently:
   H;
   unsubstituted alkyl;
   alkyl substituted with 1 to 5 groups selected from cycloalkyl, aryl, heterocycloalkyl, heteroaryl, amine, —C(O)NR'R", —C(O)R', —C(O)OR', —OR', a cationic moiety, or an anionic moiety;
   unsubstituted cycloalkyl;
   cycloalkyl substituted with 1 to 5 groups selected from alkyl, aryl, heterocycloalkyl, heteroaryl, amine, —C(O)NR'R", —C(O)R', —C(O)OR', —OR', a cationic moiety, or an anionic moiety;
   unsubstituted aryl;
   aryl substituted with 1 to 5 groups selected from alkyl, cycloalkyl, heterocycloalkyl, heteroaryl, amine, —C(O)NR'R", —C(O)R', —C(O)OR', —OR', a cationic moiety, or an anionic moiety;
   unsubstituted heterocycloalkyl;
   heterocycloalkyl substituted with 1 to 5 groups selected from alkyl, cycloalkyl, aryl, heteroaryl, amine, —C(O)NR'R", —C(O)R', —C(O)OR', —OR', a cationic moiety, or an anionic moiety;
   unsubstituted heteroaryl; or
   heteroaryl substituted with 1 to 5 groups selected from alkyl, cycloalkyl, aryl, heterocycloalkyl, amine, —C(O)NR'R", —C(O)R', —C(O)OR', —OR', a cationic moiety, or an anionic moiety;
wherein each R' and R" at each occurrence is independently H, alkyl, cycloalkyl, heterocycloalkyl, aryl, or heteroaryl.

51. The method of any one of embodiments 1 to 49, wherein $R^A$ and $R^B$ at each occurrence is independently H; unsubstituted alkyl; or alkyl substituted with 1 to 5 —OH groups.

52. The method of any one of embodiments 1 to 51, wherein $R^A$ at each occurrence is independently alkyl; and $R^B$ is H.

53. The method of any one of embodiments 1 to 52 wherein $R^1$ at each occurrence is H or alkyl.

54. The method of any one of embodiments 1 to 49, wherein the monomer residues having the structure of formula (I) are monomer residues of formula (I-A1):

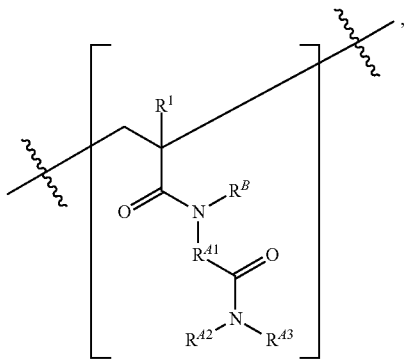

(I-A1)

wherein:
$R^{A1}$ at each occurrence is unsubstituted or substituted -aliphatic group-, unsubstituted or substituted -alicyclic group-, unsubstituted or substituted -aryl-, unsubstituted or substituted -heteroaryl-, or unsubstituted or substituted -heterocyclyl-; and
$R^{A2}$ and $R^{A3}$ at each occurrence is independently H, unsubstituted or substituted aliphatic group, unsubstituted or substituted alicyclic group, unsubstituted or substituted aryl, unsubstituted or substituted heteroaryl, or unsubstituted or substituted heterocyclyl.

55. The method of embodiment 54, wherein:
$R^{A1}$ each occurrence is unsubstituted or substituted -alkyl-, unsubstituted or substituted -alkenyl-, unsubstituted or substituted -alkynyl-, unsubstituted or substituted -aryl-, unsubstituted or substituted -heteroaryl-, unsubstituted or substituted -cycloalkyl-, or unsubstituted or substituted -heterocycloalkyl-; and
$R^{A2}$ and $R^{A3}$ at each occurrence is independently H, unsubstituted or substituted alkyl, unsubstituted or substituted cycloalkyl, unsubstituted or substituted aryl, unsubstituted or substituted heterocycloalkyl, or unsubstituted or substituted heteroaryl.

56. The method of embodiment 54, wherein $R^{A1}$ at each occurrence is unsubstituted or substituted -alkyl-.

57. The method of any one of embodiments 54 to 56, wherein $R^{A2}$ and $R^{A3}$ at each occurrence are independently H, or unsubstituted or substituted alkyl.

58. The method of any one of embodiments 54 to 57, wherein at least one of $R^{A2}$ and $R^{A3}$ is other than H.

59. The method of embodiment 54, wherein:
$R^{A2}$ at each occurrence is H, unsubstituted or substituted aliphatic group, unsubstituted or substituted alicyclic group, unsubstituted or substituted aryl, unsubstituted or substituted heteroaryl, or unsubstituted or substituted heterocyclyl; and
$R^{A3}$ at each occurrence is unsubstituted or substituted aliphatic group, unsubstituted or substituted alicyclic group, unsubstituted or substituted aryl, unsubstituted or substituted heteroaryl, or unsubstituted or substituted heterocyclyl.

60. The method of embodiment 54, wherein:
$R^{A2}$ at each occurrence is H, unsubstituted or substituted alkyl, unsubstituted or substituted cycloalkyl, unsubstituted or substituted aryl, unsubstituted or substituted heterocycloalkyl, or unsubstituted or substituted heteroaryl; and
$R^{A3}$ at each occurrence is unsubstituted or substituted alkyl, unsubstituted or substituted cycloalkyl, unsubstituted or substituted aryl, unsubstituted or substituted heterocycloalkyl, or unsubstituted or substituted heteroaryl.

61. The method of any one of embodiments 1 to 60, wherein the monomer residues having the structure of formula (I) are monomer residues of formula (I-A2):

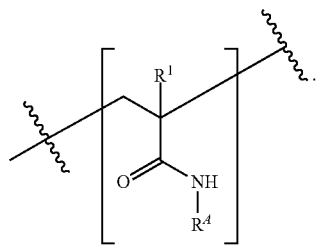

(I-A2)

62. The method of embodiment 61, wherein the monomer residues of formula (I-A2) are monomer residues of formula (I-A2a):

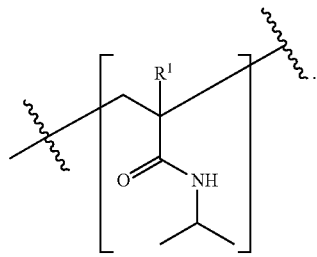

(I-A2a)

63. The method of embodiment 61, wherein the monomer residues of formula (I-A2) are:

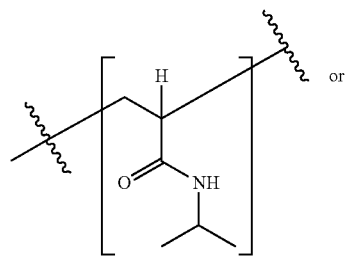

or

-continued

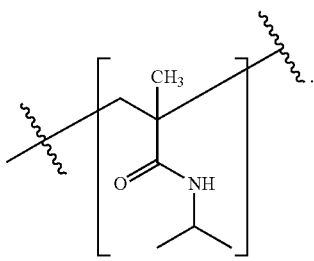

64. The method of any one of embodiments 1 to 63, wherein at least one of the polymers is a homopolymer.

65. The method of any one of embodiments 1 to 63, wherein at least one of the polymers is a copolymer.

66. The method of claim 65, wherein the copolymer is a random copolymer.

67. The method of embodiment 65 or 66, wherein the copolymer comprises:

a plurality of first monomer residues of formula (I-A2):

(I-A2)

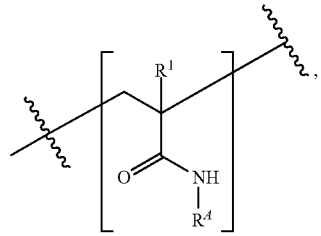

wherein:

$R^1$ is H or alkyl;
$R^A$ is unsubstituted alkyl; and
$R^B$ is H; and a plurality of second monomer residues of formula (I-A2), wherein:

$R^1$ is H or alkyl;
$R^A$ is unsubstituted alkyl, or alkyl substituted with 1 to 5 —OH groups;
$R^B$ is H,
provided that at least one of $R^1$, $R^A$ and $R^B$ of the first monomer residues is different from $R^1$, $R^A$ and $R^B$ of the second monomer residues.

68. The method of embodiment 67, wherein:
the plurality of first monomer residues are

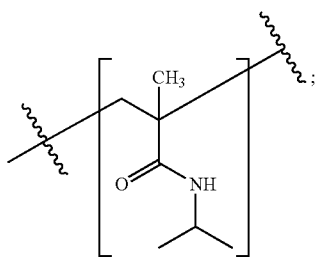

and
the plurality of second monomer residues are selected from the group consisting of

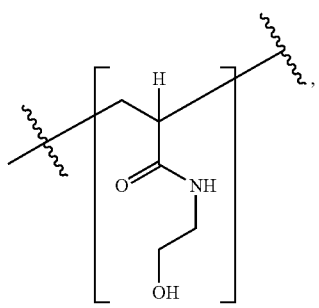

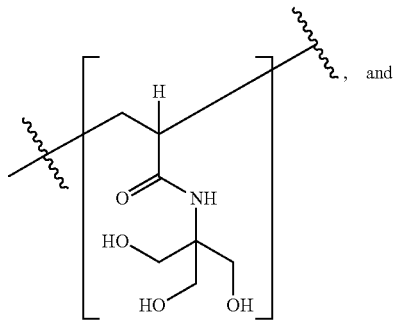

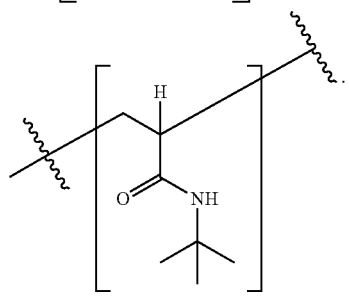

69. The method of embodiment 65 or 66, wherein the copolymer further comprises a plurality of aminooxy-bearing methacrylamide monomer residues.

70. The method of embodiment 69, wherein the aminooxy-bearing methacrylamide monomer residues have a structure of formula (II-B1) or (II-B2):

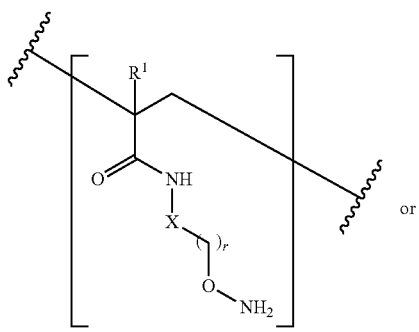

(II-B1)

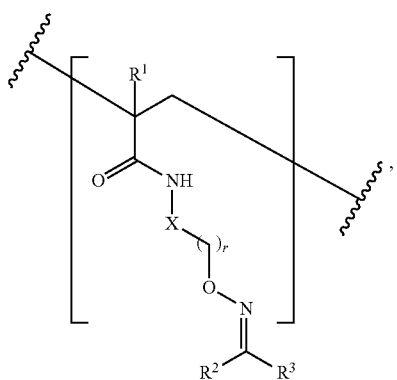

(II-B2)

wherein:

R¹ at each occurrence is independently H or alkyl;

r at each occurrence is independently an integer greater than or equal to 1;

X at each occurrence is independently unsubstituted or substituted -aliphatic group-, unsubstituted or substituted -alicyclic group-, unsubstituted or substituted -aryl-, unsubstituted or substituted -heteroaryl-, unsubstituted or substituted -heterocyclyl-, unsubstituted or substituted -ether-, or —(CH$_2$)$_j$NHCO—, wherein j is an integer, and j at each occurrence is independently at least 1; and R² and R³ at each occurrence is independently H, unsubstituted or substituted aliphatic group, unsubstituted or substituted alicyclic group, unsubstituted or substituted aryl, unsubstituted or substituted heteroaryl, unsubstituted or substituted heterocyclyl, or —C(O)R$^a$, wherein R$^a$ is H, alkyl, or hydroxy; or R² and R³ are taken together with the carbon to which they are attached to form a 5- or 6-membered unsubstituted or substituted heterocyclyl.

71. The method of embodiment 70, wherein:

X at each occurrence is independently unsubstituted or substituted -alkyl-, unsubstituted or substituted -alkenyl-, unsubstituted or substituted -alkynyl-, unsubstituted or substituted -aryl-, unsubstituted or substituted -heteroaryl-, unsubstituted or substituted -cycloalkyl-, unsubstituted or substituted -heterocycloalkyl-, unsubstituted or substituted -ether-, or —(CH$_2$)$_j$NHCO—, wherein j is an integer, and j at each occurrence is independently at least 1; and R² and R³ at each occurrence are independently H, unsubstituted or substituted alkyl, unsubstituted or substituted alkenyl, unsubstituted or substituted alkynyl, unsubstituted or substituted aryl, unsubstituted or substituted heteroaryl, unsubstituted or substituted cycloalkyl, unsubstituted or substituted heterocycloalkyl, or —C(O)R$^a$, wherein R$^a$ is H, alkyl, or hydroxy; or R² and R³ are taken together with the carbon to which they are attached to form a 5- or 6-membered unsubstituted or substituted heterocyclyl.

72. The method of embodiment 70 or 71, wherein at least one of R² and R³ is other than H.

73. The method of embodiment 70, wherein:

R² at each occurrence is H, unsubstituted or substituted aliphatic group, unsubstituted or substituted alicyclic group, unsubstituted or substituted aryl, unsubstituted or substituted heteroaryl, or unsubstituted or substituted heterocyclyl; and R³ at each occurrence is unsubstituted or substituted aliphatic group, unsubstituted or substituted alicyclic group, unsubstituted or substituted aryl, unsubstituted or substituted heteroaryl, or unsubstituted or substituted heterocyclyl.

74. The method of embodiment 71, wherein:

R² at each occurrence is H, unsubstituted or substituted alkyl, unsubstituted or substituted cycloalkyl, unsubstituted or substituted aryl, unsubstituted or substituted heterocycloalkyl, or unsubstituted or substituted heteroaryl; and R³ at each occurrence is unsubstituted or substituted alkyl, unsubstituted or substituted cycloalkyl, unsubstituted or substituted aryl, unsubstituted or substituted heterocycloalkyl, or unsubstituted or substituted heteroaryl.

75. The method of any one of embodiments 70 to 74, wherein r is 1 to 10.

76. The method of embodiment 75, wherein r is 1, 2, 3, 4, or 5.

77. The method of embodiment 70, wherein the aminooxy-bearing methacrylamide monomer residues of formula (II-B1) has a structure of formula (II-B1a):

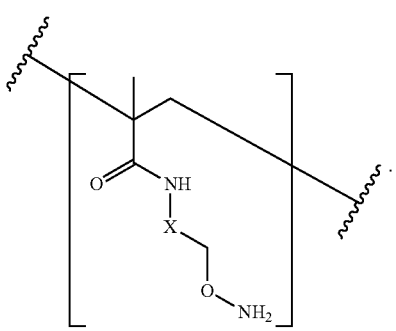

(II-B1a)

78. The method of embodiment 70, wherein the aminooxy-bearing methacrylamide monomer residues of formula (II-B1) has a structure of formula (II-B2a):

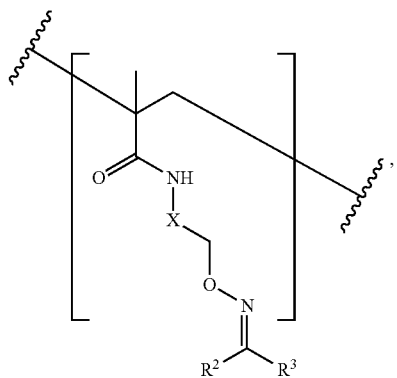

(II-B2a)

79. The method of any one of embodiments 70 to 76 and 78, wherein $R^2$ and $R^3$ at each occurrence is independently:
H;
unsubstituted $C_{1-10}$ alkyl;
$C_{1-10}$ alkyl substituted with one or more groups independently selected from hydroxy, amino, oxo, nitrate, phosphate, and sulfate;
unsubstituted $C_{2-10}$ alkenyl;
$C_{2-10}$ alkenyl substituted with one or more groups independently selected from hydroxy, amino, oxo, nitrate, phosphate, and sulfate;
unsubstituted $C_{2-10}$ alkynyl;
$C_{2-10}$ alkynyl substituted with one or more groups independently selected from hydroxy, amino, oxo, nitrate, phosphate, and sulfate;
unsubstituted $C_{6-12}$ aryl;
$C_{6-12}$ aryl substituted with one or more groups independently selected from alkyl, halo, hydroxy, amino, oxo, nitrate, phosphate, and sulfate;
unsubstituted $C_{4-12}$ heteroaryl with 1 to 3 ring heteroatoms independently selected from the group consisting of nitrogen, oxygen and sulfur;
$C_{4-12}$ heteroaryl with 1 to 3 ring heteroatoms independently selected from the group consisting of nitrogen, oxygen and sulfur, wherein the heteroaryl is substituted with one or more groups independently selected from alkyl, halo, hydroxy, amino, oxo, nitrate, phosphate, and sulfate;
unsubstituted $C_{3-12}$ cycloalkyl;
$C_{3-12}$ cycloalkyl substituted with one or more groups selected from alkyl, halo, hydroxy, amino, oxo, nitrate, phosphate, and sulfate;
unsubstituted $C_{3-12}$ heterocycloalkyl with 1 to 3 ring heteroatoms independently selected from the group consisting of nitrogen, oxygen and sulfur;
$C_{3-12}$ heterocycloalkyl with 1 to 3 ring heteroatoms independently selected from the group consisting of nitrogen, oxygen and sulfur, wherein the heterocycloalkyl is substituted with one or more groups selected from alkyl, halo, hydroxy, amino, oxo, nitrate, phosphate, and sulfate;
$R^2$ and $R^3$ are taken together with the carbon to which they are attached to form a 5- or 6-membered unsubstituted $C_{4-12}$ heterocyclyl with 1 to 3 ring heteroatoms independently selected from the group consisting of nitrogen, oxygen and sulfur; or
$R^2$ and $R^3$ are taken together with the carbon to which they are attached to form a 5- or 6-membered $C_{4-12}$ heterocyclyl with 1 to 3 ring heteroatoms independently selected from the group consisting of nitrogen, oxygen and sulfur, wherein the heterocyclyl is substituted with one or more groups selected from alkyl, halo, hydroxy, amino, oxo, nitrate, phosphate, and sulfate.

80. The method of any one of embodiments 70 to 76 and 78, wherein $R^2$ and $R^3$ at each occurrence is independently H, unsubstituted $C_{1-5}$ alkyl, or $C_{1-5}$ alkyl substituted with 1-5 hydroxyl groups.

81. The method of embodiment or 78, wherein

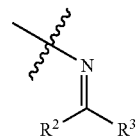

at each occurrence is independently selected from:

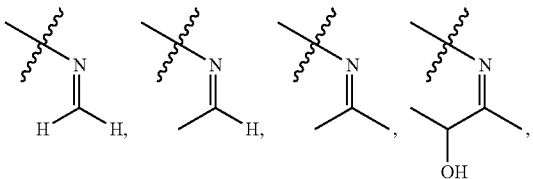

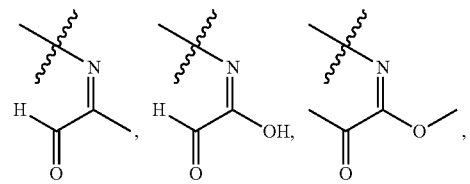

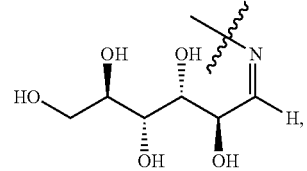

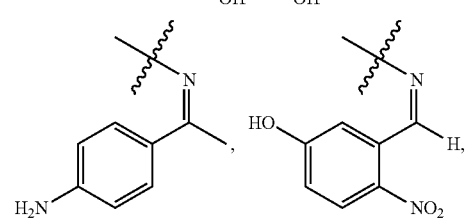

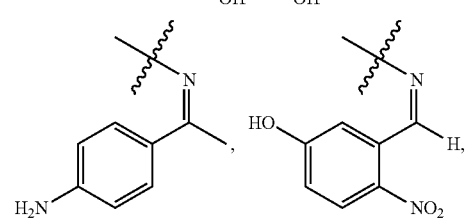

-continued

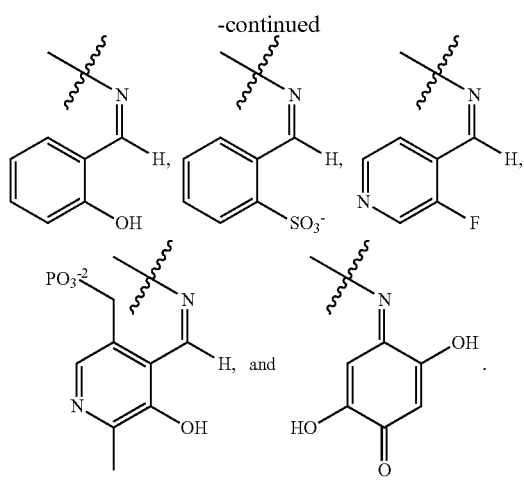

82. The method of any one of embodiments 70 to 81, wherein X at each occurrence is:
   unsubstituted $C_{1-10}$-alkyl-;
   $C_{1-10}$-alkyl- substituted with one or more groups independently selected from hydroxy, amino, oxo, nitrate, phosphate, and sulfate;
   unsubstituted $C_{2-10}$-alkenyl-;
   $C_{2-10}$-alkenyl- substituted with one or more groups independently selected from hydroxy, amino, oxo, nitrate, phosphate, and sulfate;
   unsubstituted $C_{2-10}$-alkynyl-;
   $C_{2-10}$-alkynyl- substituted with one or more groups independently selected from hydroxy, amino, oxo, nitrate, phosphate, and sulfate;
   unsubstituted $C_{6-12}$-aryl-;
   $C_{6-12}$-aryl- substituted with one or more groups independently selected from alkyl, halo, hydroxy, amino, oxo, nitrate, phosphate, and sulfate;
   unsubstituted $C_{4-12}$-heteroaryl- with 1 to 3 ring heteroatoms independently selected from the group consisting of nitrogen, oxygen and sulfur;
   $C_{4-12}$-heteroaryl- with 1 to 3 ring heteroatoms independently selected from the group consisting of nitrogen, oxygen and sulfur, wherein the heteroaryl is substituted with one or more groups independently selected from alkyl, halo, hydroxy, amino, oxo, nitrate, phosphate, and sulfate;
   unsubstituted $C_{3-12}$-cycloalkyl-;
   $C_{3-12}$-cycloalkyl- substituted with one or more groups selected from alkyl, halo, hydroxy, amino, oxo, nitrate, phosphate, and sulfate;
   unsubstituted $C_{3-12}$-heterocycloalkyl- with 1 to 3 ring heteroatoms independently selected from the group consisting of nitrogen, oxygen and sulfur;
   $C_{3-12}$-heterocycloalkyl- with 1 to 3 ring heteroatoms independently selected from the group consisting of nitrogen, oxygen and sulfur, wherein the heterocycloalkyl is substituted with one or more groups selected from alkyl, halo, hydroxy, amino, oxo, nitrate, phosphate, and sulfate;
   unsubstituted $C_{2-10}$-ether-;
   $C_{2-10}$-ether- substituted with one or more groups selected from alkyl, halo, hydroxy, amino, oxo, nitrate, phosphate, and sulfate; or
   —$(CH_2)_j$NHCO—, and j is an integer of at least 1.

83. The method of embodiment 82, wherein X at each occurrence is -ethylene glycol- or —$(CH_2)_j$NHCO—.

84. The method of embodiment 83, wherein X is —$(CH_2)_j$NHCO—, and j at each occurrence is between 1 and 10.

85. The method of any one of embodiments 1 to 84, wherein at least one of the polymers is thermally-responsive.

86. The method of embodiment 85, wherein at least one of the polymers has a LCST of at least 10° C.

87. The method of embodiment 85, the thermally-responsive polymer is at least partially insoluble in water at a temperature above about 15° C.

88. The method of embodiment 85, wherein the thermally-responsive polymer is at least partially insoluble in water at a temperature between about 20° C. and about 70° C.

89. The method of embodiment 87 or 88, wherein the thermally-responsive polymer is at least 1% insoluble.

90. The method of any one of embodiments 44 to 89, wherein at least one of the polymers has a molecular weight of between about 5,000 Da and about 1,000,000 Da.

91. The method of any one of embodiments 44 to 90, wherein at least one of the polymers has a polydispersity index (PDI) of between about 1.0 and about 2.0.

92. The method of any one of embodiments 44 to 91, wherein at least one of the polymers is nonionic, nonsurfactant, or a combination thereof.

93. The method of any one of embodiments 44 to 92, wherein the at least one enzyme is a cellulase, or a mixture of cellulases.

94. The method of embodiment 93, wherein the substrate is biomass, cellulose, disaccharides or other polysaccharides.

95. The method of embodiment 93, wherein the substrate Avicel or *Miscanthus*.

96. The method of any one of embodiments 44 to 86, wherein the at least one enzyme is a cellulase, a hemicellulase, or a lignase, or a mixture of two or more cellulases, hemicellulases, and lignases.

97. The method of any one of embodiments 44 to 86, the at least one enzyme is a lipase, or a mixture of lipases.

98. The method of any one of embodiments 44 to 86, wherein the at least one enzyme is an amylase, or a mixture of amylases.

99. The method of any one of embodiments 44 to 86, wherein the at least one enzyme is a phosphatase, or a mixture of phosphatases.

100. The method of any one of embodiments 44 to 86, wherein the at least one enzyme is a xylanase, or a mixture of xylanases.

101. A composition, comprising:
   at least one substrate;
   at least one enzyme; and
   at least one polymer comprising a plurality of monomer residues having the structure of formula (I):

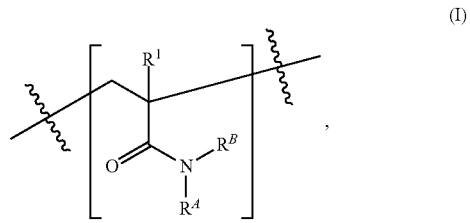

(I)

wherein:
R¹ at each occurrence is independently H or alkyl; and
R^A and R^B at each occurrence is independently H, unsubstituted or substituted aliphatic group, unsubstituted or substituted alicyclic group, unsubstituted or substituted aryl, unsubstituted or substituted heteroaryl, or unsubstituted or substituted heterocyclyl;
provided that at least one of R^A and R^B is other than H.

102. A composition, comprising:
at least one residual substrate;
at least one product;
at least one enzyme; and
at least one polymer comprising a plurality of monomer residues having the structure of formula (I):

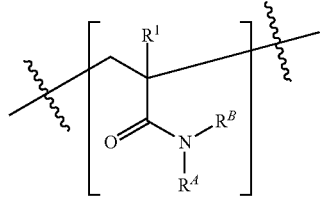
(I)

wherein:
R¹ at each occurrence is independently H or alkyl; and
R^A and R^B at each occurrence is independently H, unsubstituted or substituted aliphatic group, unsubstituted or substituted alicyclic group, unsubstituted or substituted aryl, unsubstituted or substituted heteroaryl, or unsubstituted or substituted heterocyclyl;
provided that at least one of R^A and R^B is other than H.

103. The composition of embodiment 101 or 102, wherein each R^A and R^B at each occurrence is independently:
H;
unsubstituted alkyl;
alkyl substituted with 1 to 5 groups selected from cycloalkyl, aryl, heterocycloalkyl, heteroaryl, amine, —C(O)NR'R", —C(O)R', —C(O)OR', —OR', a cationic moiety, or an anionic moiety;
unsubstituted cycloalkyl;
cycloalkyl substituted with 1 to 5 groups selected from alkyl, aryl, heterocycloalkyl, heteroaryl, amine, —C(O)NR'R", —C(O)R', —C(O)OR', —OR', a cationic moiety, or an anionic moiety;
unsubstituted aryl;
aryl substituted with 1 to 5 groups selected from alkyl, cycloalkyl, heterocycloalkyl, heteroaryl, amine, —C(O)NR'R", —C(O)R', —C(O)OR', —OR', a cationic moiety, or an anionic moiety;
unsubstituted heterocycloalkyl;
heterocycloalkyl substituted with 1 to 5 groups selected from alkyl, cycloalkyl, aryl, heteroaryl, amine, —C(O)NR'R", —C(O)R', —C(O)OR', —OR', a cationic moiety, or an anionic moiety;
unsubstituted heteroaryl; or
heteroaryl substituted with 1 to 5 groups selected from alkyl, cycloalkyl, aryl, heterocycloalkyl, amine, —C(O)NR'R", —C(O)R', —C(O)OR', —OR', a cationic moiety, or an anionic moiety;

wherein each R' and R" at each occurrence is independently H, alkyl, cycloalkyl, heterocycloalkyl, aryl, or heteroaryl.

104. The composition of embodiment 101 or 102, wherein R^A and R^B at each occurrence is independently H; unsubstituted alkyl; or alkyl substituted with 1 to 5 —OH groups.

105. The composition of any one of embodiments 101 to 104, wherein R^A at each occurrence is alkyl; and R^B is H.

106. The composition of any one of embodiments 101 to 105, wherein R¹ at each occurrence is H or alkyl.

107. The composition of embodiment 101 or 102, wherein the monomer residues having the structure of formula (I) are monomer residues of formula (I-A1):

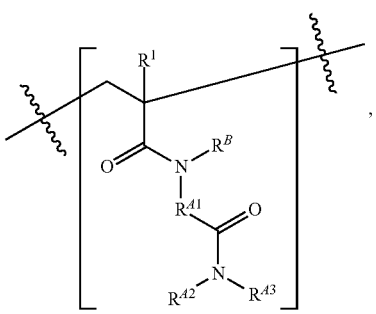
(I-A1)

wherein:
R^A1 at each occurrence is unsubstituted or substituted -aliphatic group-, unsubstituted or substituted -alicyclic group-, unsubstituted or substituted -aryl-, unsubstituted or substituted -heteroaryl-, or unsubstituted or substituted -heterocyclyl-; and
R^A2 and R^A3 at each occurrence is independently H, unsubstituted or substituted aliphatic group, unsubstituted or substituted alicyclic group, unsubstituted or substituted aryl, unsubstituted or substituted heteroaryl, or unsubstituted or substituted heterocyclyl.

108. The composition of embodiment 107, wherein:
R^A1 each occurrence is unsubstituted or substituted -alkyl-, unsubstituted or substituted -alkenyl-, unsubstituted or substituted -alkynyl-, unsubstituted or substituted -aryl-, unsubstituted or substituted -heteroaryl-, unsubstituted or substituted -cycloalkyl-, or unsubstituted or substituted -heterocycloalkyl-; and
R^A2 and R^A3 at each occurrence is independently H, unsubstituted or substituted alkyl, unsubstituted or substituted cycloalkyl, unsubstituted or substituted aryl, unsubstituted or substituted heterocycloalkyl, or unsubstituted or substituted heteroaryl.

109. The composition of embodiment 107, wherein R^A1 at each occurrence is unsubstituted or substituted -alkyl-.

110. The composition of embodiment 107 or 109, wherein R^A2 and R^A3 at each occurrence is independently H, or unsubstituted or substituted alkyl.

111. The composition of embodiment 101 or 102, wherein the monomer residues having the structure of formula (I) are monomer residues of formula (I-A2):

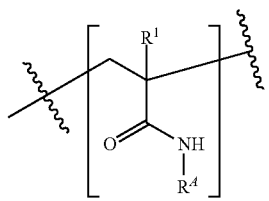
(I-A2)

112. The composition of embodiment 111, wherein the monomer residues of formula (I-A2) are monomer residues of formula (I-A2a):

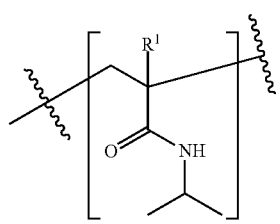
(I-A2a)

113. The composition of embodiment 111, wherein the monomer residues of formula (I-A2) are:

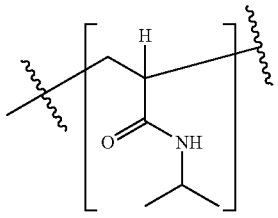

or

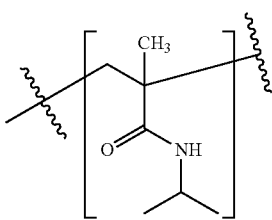

114. The composition of any one of embodiments 101 to 113, wherein at least one of the polymers is a homopolymer.
115. The composition of any one of embodiments 101 to 113, wherein at least one of the polymers is a copolymer.
116. The composition of embodiment 115, wherein the copolymer is a random copolymer.
117. The composition of embodiment 115 or 116, wherein the copolymer comprises:
a plurality of first monomer residues of formula (I-A2):

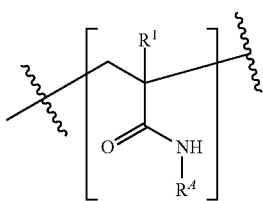
(I-A2)

wherein:
$R^1$ is H or alkyl;
$R^A$ is unsubstituted alkyl; and
$R^B$ is H; and
a plurality of second monomer residues of formula (I-A2), wherein:
$R^1$ is H or alkyl;
$R^A$ is unsubstituted alkyl, or alkyl substituted with 1 to 5 —OH groups;
$R^B$ is H,
provided that at least one of $R^1$, $R^A$ and $R^B$ of the first monomer residues is different from $R^1$, $R^A$ and $R^B$ of the second monomer residues.
118. The composition of embodiment 117, wherein:
the plurality of first monomer residues are

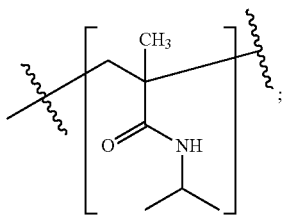

and
the plurality of second monomer residues are selected from the group consisting of

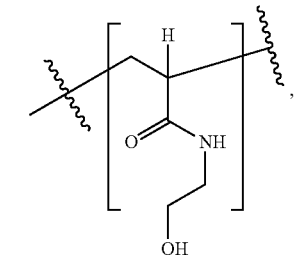

,

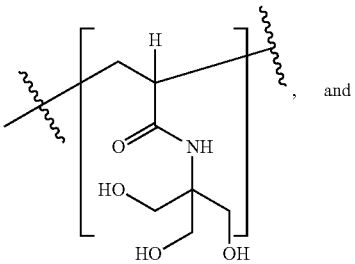

, and

-continued

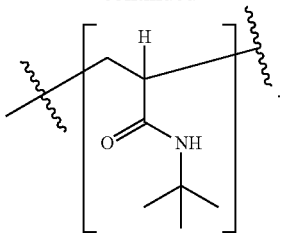

119. The composition of embodiment 115 or 116, wherein the copolymer further comprises a plurality of aminooxy-bearing methacrylamide monomer residues.

120. The composition of embodiment 119, wherein the aminooxy-bearing methacrylamide monomer residues have a structure of formula (II-B1) or (II-B2):

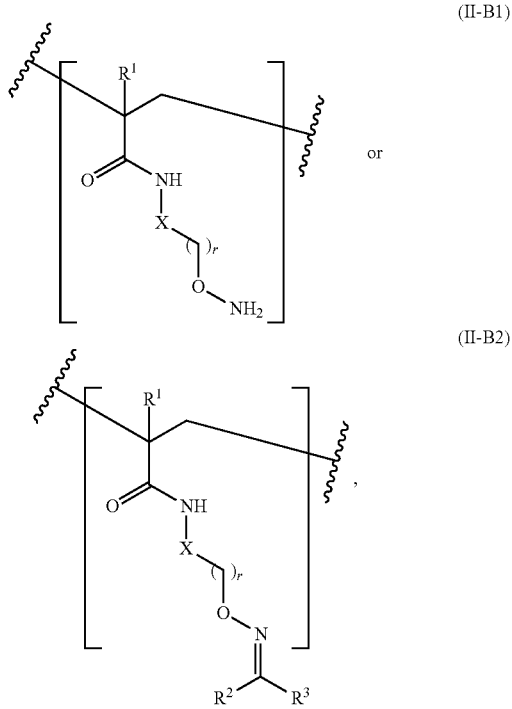

wherein:

$R^1$ at each occurrence is independently H or alkyl;

r at each occurrence is independently an integer greater than or equal to 1;

X at each occurrence is independently unsubstituted or substituted -aliphatic group-, unsubstituted or substituted -alicyclic group-, unsubstituted or substituted -aryl-, unsubstituted or substituted -heteroaryl-, unsubstituted or substituted -heterocyclyl-, unsubstituted or substituted -ether-, or —(CH$_2$)$_j$NHCO—, wherein j is an integer, and j at each occurrence is independently at least 1; and $R^2$ and $R^3$ at each occurrence are independently H, unsubstituted or substituted aliphatic group, unsubstituted or substituted alicyclic group, unsubstituted or substituted aryl, unsubstituted or substituted heteroaryl, unsubstituted or substituted heterocyclyl, or —C(O)R$^{a1}$, wherein R$^a$ is H, alkyl, or hydroxy; or $R^2$ and $R^3$ are taken together with the carbon to which they are attached to form a 5- or 6-membered unsubstituted or substituted heterocyclyl.

121. The composition of embodiment 120, wherein:

X at each occurrence is independently unsubstituted or substituted -alkyl-, unsubstituted or substituted -alkenyl-, unsubstituted or substituted -alkynyl-, unsubstituted or substituted -aryl-, unsubstituted or substituted -heteroaryl-, unsubstituted or substituted -cycloalkyl-, unsubstituted or substituted -heterocycloalkyl-, unsubstituted or substituted -ether-, or —(CH$_2$)$_j$NHCO—, wherein j is an integer, and j at each occurrence is independently at least 1; and $R^2$ and $R^3$ at each occurrence are independently H, unsubstituted or substituted alkyl, unsubstituted or substituted alkenyl, unsubstituted or substituted alkynyl, unsubstituted or substituted aryl, unsubstituted or substituted heteroaryl, unsubstituted or substituted cycloalkyl, unsubstituted or substituted heterocycloalkyl, or —C(O)R$^{a1}$, wherein R$^a$ is H, alkyl, or hydroxy; or $R^2$ and $R^3$ are taken together with the carbon to which they are attached to form a 5- or 6-membered unsubstituted or substituted heterocyclyl.

122. The composition of embodiment 120 or 121, wherein r is 1 to 10.

123. The composition of embodiment 122, wherein r is 1, 2, 3, 4, or 5.

124. The composition of embodiment 120, wherein the aminooxy-bearing methacrylamide monomer residues of formula (II-B1) has a structure of formula (II-B1a):

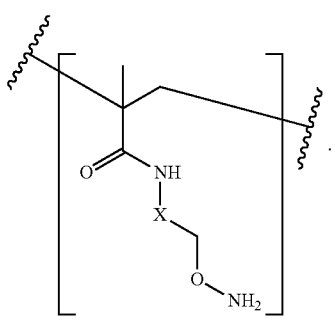

125. The composition of embodiment 120, wherein the aminooxy-bearing methacrylamide monomer residues of formula (II-B1) has a structure of formula (II-B2a):

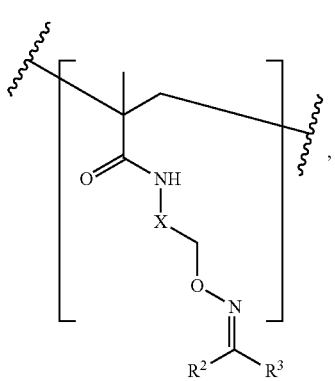

126. The composition of any one of embodiments 120 to 123 and 125, wherein $R^2$ and $R^3$ at each occurrence is independently:
H;
unsubstituted $C_{1-10}$ alkyl;
$C_{1-10}$ alkyl substituted with one or more groups independently selected from hydroxy, amino, oxo, nitrate, phosphate, and sulfate;
unsubstituted $C_{2-10}$ alkenyl;
$C_{2-10}$ alkenyl substituted with one or more groups independently selected from hydroxy, amino, oxo, nitrate, phosphate, and sulfate;
unsubstituted $C_{2-10}$ alkynyl;
$C_{2-10}$ alkynyl substituted with one or more groups independently selected from hydroxy, amino, oxo, nitrate, phosphate, and sulfate;
unsubstituted $C_{6-12}$ aryl;
$C_{6-12}$ aryl substituted with one or more groups independently selected from alkyl, halo, hydroxy, amino, oxo, nitrate, phosphate, and sulfate;
unsubstituted $C_{4-12}$ heteroaryl with 1 to 3 ring heteroatoms independently selected from the group consisting of nitrogen, oxygen and sulfur;
$C_{4-12}$ heteroaryl with 1 to 3 ring heteroatoms independently selected from the group consisting of nitrogen, oxygen and sulfur, wherein the heteroaryl is substituted with one or more groups independently selected from alkyl, halo, hydroxy, amino, oxo, nitrate, phosphate, and sulfate;
unsubstituted $C_{3-12}$ cycloalkyl;
$C_{3-12}$ cycloalkyl substituted with one or more groups selected from alkyl, halo, hydroxy, amino, oxo, nitrate, phosphate, and sulfate;
unsubstituted $C_{3-12}$ heterocycloalkyl with 1 to 3 ring heteroatoms independently selected from the group consisting of nitrogen, oxygen and sulfur;
$C_{3-12}$ heterocycloalkyl with 1 to 3 ring heteroatoms independently selected from the group consisting of nitrogen, oxygen and sulfur, wherein the heterocycloalkyl is substituted with one or more groups selected from alkyl, halo, hydroxy, amino, oxo, nitrate, phosphate, and sulfate;
$R^2$ and $R^3$ are taken together with the carbon to which they are attached to form a 5- or 6-membered unsubstituted $C_{4-12}$ heterocyclyl with 1 to 3 ring heteroatoms independently selected from the group consisting of nitrogen, oxygen and sulfur; or
$R^2$ and $R^3$ are taken together with the carbon to which they are attached to form a 5- or 6-membered $C_{4-12}$ heterocyclyl with 1 to 3 ring heteroatoms independently selected from the group consisting of nitrogen, oxygen and sulfur, wherein the heterocyclyl is substituted with one or more groups selected from alkyl, halo, hydroxy, amino, oxo, nitrate, phosphate, and sulfate.

127. The composition of any one of embodiments 120 to 123 and 125, wherein $R^2$ and $R^3$ at each occurrence is independently H, unsubstituted $C_{1-5}$ alkyl, or $C_{1-5}$ alkyl substituted with 1-5 hydroxyl groups.

128. The composition of any one of embodiments 120 or 125, wherein

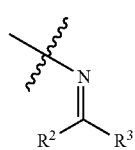

at each occurrence is independently selected from:

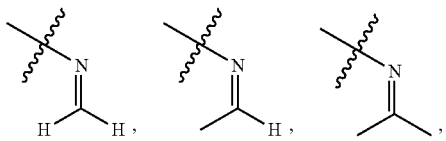

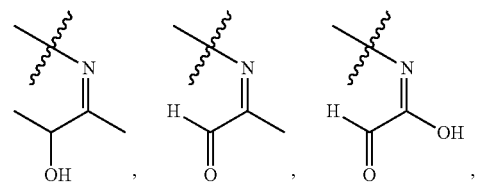

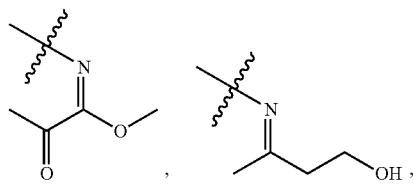

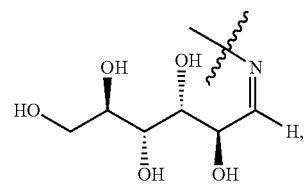

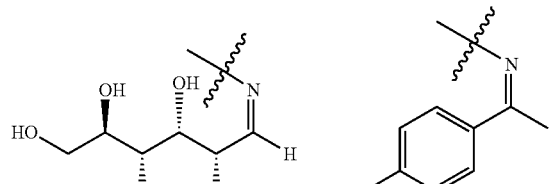

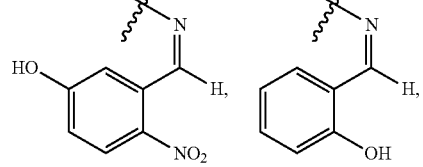

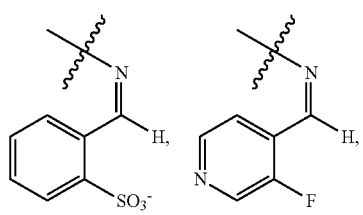

-continued

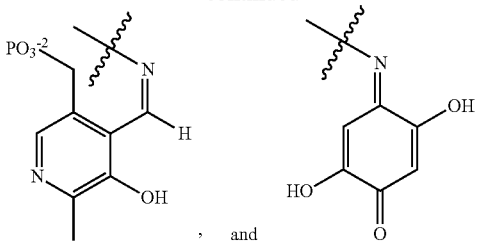
, and

129. The composition of any one of embodiments 120 to 128, wherein X at each occurrence is:
unsubstituted $C_{1-10}$-alkyl-;
$C_{1-10}$-alkyl- substituted with one or more groups independently selected from hydroxy, amino, oxo, nitrate, phosphate, and sulfate;
unsubstituted $C_{2-10}$-alkenyl-;
$C_{2-10}$-alkenyl- substituted with one or more groups independently selected from hydroxy, amino, oxo, nitrate, phosphate, and sulfate;
unsubstituted $C_{2-10}$-alkynyl-;
$C_{2-10}$-alkynyl- substituted with one or more groups independently selected from hydroxy, amino, oxo, nitrate, phosphate, and sulfate;
unsubstituted $C_{6-12}$-aryl-;
$C_{6-12}$-aryl- substituted with one or more groups independently selected from alkyl, halo, hydroxy, amino, oxo, nitrate, phosphate, and sulfate;
unsubstituted $C_{4-12}$-heteroaryl- with 1 to 3 ring heteroatoms independently selected from the group consisting of nitrogen, oxygen and sulfur;
$C_{4-12}$-heteroaryl- with 1 to 3 ring heteroatoms independently selected from the group consisting of nitrogen, oxygen and sulfur, wherein the heteroaryl is substituted with one or more groups independently selected from alkyl, halo, hydroxy, amino, oxo, nitrate, phosphate, and sulfate;
unsubstituted $C_{3-12}$-cycloalkyl-;
$C_{3-12}$-cycloalkyl- substituted with one or more groups selected from alkyl, halo, hydroxy, amino, oxo, nitrate, phosphate, and sulfate;
unsubstituted $C_{3-12}$-heterocycloalkyl- with 1 to 3 ring heteroatoms independently selected from the group consisting of nitrogen, oxygen and sulfur;
$C_{3-12}$-heterocycloalkyl- with 1 to 3 ring heteroatoms independently selected from the group consisting of nitrogen, oxygen and sulfur, wherein the heterocycloalkyl is substituted with one or more groups selected from alkyl, halo, hydroxy, amino, oxo, nitrate, phosphate, and sulfate;
unsubstituted $C_{2-10}$-ether-;
$C_{2-10}$-ether- substituted with one or more groups selected from alkyl, halo, hydroxy, amino, oxo, nitrate, phosphate, and sulfate; or
—$(CH_2)_j$NHCO—, and j is an integer of at least 1.
130. The composition of embodiment 129, wherein X at each occurrence is -ethylene glycol- or —$(CH_2)_j$NHCO—.
131. The composition of embodiment 130, wherein X is —$(CH_2)_j$NHCO—, and j at each occurrence is between 1 and 10.
132. The composition of any one of embodiments 101 to 131, wherein at least one of the polymers is thermally-responsive.
133. The composition of embodiment 132, wherein at least one of the polymers has a LCST of at least 10° C.
134. The composition of any one of embodiments 101 to 133, wherein the at least one enzyme is a cellulase, or a mixture of cellulases.
135. The composition of embodiment 134, wherein the substrate is biomass, cellulose, disaccharides or other polysaccharides.
136. The composition of embodiment 135, wherein the substrate Avicel or *Miscanthus*.
137. The composition of any one of embodiments 101 to 133, wherein the at least one enzyme is a cellulase, a hemicellulase, or a lignase, or a mixture of two or more cellulases, hemicellulases, and lignases.
138. The composition of any one of embodiments 101 to 133, wherein the at least one enzyme is a lipase, or a mixture of lipases.
139. The composition of any one of embodiments 101 to 133, wherein the at least one enzyme is an amylase, or a mixture of amylases.
140. The composition of any one of embodiments 101 to 133, wherein the at least one enzyme is a phosphatase, or a mixture of phosphatases.
141. The composition of any one of embodiments 101 to 133, wherein the at least one enzyme is a xylanase, or a mixture of xylanases.

EXAMPLES

The following Examples are merely illustrative and are not meant to limit any aspects of the present disclosure in any way.
General Procedures and Materials for Examples 1-11
Materials: Unless otherwise noted, all chemicals and solvents used in the Examples below were of analytical grade and were used as received from commercial sources. Analytical thin layer chromatography (TLC) was performed on EM Reagent. 0.25 mm silica gel 60-F254 plates with visualization by ultraviolet (UV) irradiation at 254 nm, ninhydrin, or potassium permanganate stain. Purifications by flash chromatography were performed using EM silica gel 60 (230-400 mesh). The eluting system for purification was determined by TLC. Room temperature and 4° C. centrifugations were conducted either with a Sorvall RC 5C (Sorvall, USA) Plus for samples greater than 50 mL, a Sorvall LEGEND Mach 1.6 R for samples between 1 and 50 mL, or an Eppendorf Mini Spin Plus for samples less than 1 mL (Eppendorf, USA). Centrifugations above room temperature were performed on a Hettich Rotofix 46 H (GMI, Ramsey, Minn.). Samples were lyophilized using a LAB CONCO Freezone 4.5 (Lab Conco, USA). UV-Vis spectroscopic measurements were conducted in a Varian Cary 50 spectrophotometer (Agilent, USA). Fluorescence measurements of samples in 96 well plates were obtained on a SpectraMax M2 (Molecular Devices, Sunnyvale, Calif.). Tryptophan fluorescence measurements were obtained using a 50 μL quartz cuvette on a Photon Technology International Quanta Master 4 L-format scanning spectrofluorometer (Lawrenceville, N.J.) equipped with an LPS-220B 75-W xenon lamp and power supply, A-101013 lamp housing with integrated igniter, switchable 814 photon-counting/analog photomultiplier detection unit and an MD5021 motor driver.
Gel Permeation Chromatography (GPC): GPC was performed on a Waters system, including a Waters 515 pump, Waters 717 autosampler, and Waters 2414 differential refractive index (RI) detector. SEC was performed at 1.0 mL/min in a PLgel Mixed B (10 μm) and a PLgel Mixed C (5 μm)

column (Polymer Laboratories, both 300×7.5 mm), in that order, using a mobile phase of DMF with 0.2% LiBr and linear PMMA (690-194,400 MW) as the calibration standards. The columns were kept at 70° C.

NMR: $^1$H and $^{13}$C spectra were measured with a Bruker AVB-400 (400 MHz) spectrometer. Chemical shifts are provided as δ in units of parts per million (ppm) relative to chloroform-d (δ 7.26, s) or methanol-d (δ3.31, p). Multiplicities are provided as follows: s (singlet), d (doublet), t (triplet), q (quartet), dd (doublet of doublets), p (pentet), m (multiplet), br (broadened), or app (apparent). Coupling constants are provided as a J value in Hertz (Hz). The number of protons (n) for a given resonance is indicated nH, and is based on spectral integration values.

SDS-PAGE Analysis: For protein analysis, sodium dodecyl sulfate-polyacrylamide gel electrophoresis (SDS-PAGE) was carried out on a Mini-Protean apparatus from Bio-Rad (Hercules, Calif.), following the general protocol of Laemmli. See Laemmii, Nature 1970, 227, 680. All protein electrophoresis samples were heated for at least 10 minutes at 100° C. in the presence of 1,4-dithiothreitol (DTT) to ensure reduction of any disulfide bonds. Gels were run for 70-90 min at 120 V to allow good separation of bands. Commercially available markers (Bio-Rad) were applied to at least one lane of each gel for assignment of apparent molecular masses. Gel imaging was performed on an EpiChem3 Darkroom system (UVP, USA). Protein conversion was estimated from standard optical density measurements of the observed gel bands with ImageJ software (NIH, rsb.info.nih.gov/ij/) after staining with Coomassie Brilliant Blue R-250 (Bio-Rad).

Example 1

Synthesis of LCST Copolymers (1a) and (1b)

Synthesis of N-Boc-O-(carboxymethyl)-hydroxylamine (S6)

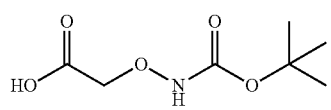

A 500 mL round-bottom flask was charged with a suspension of aminooxyacetic acid (4 g, 36.6 mmol) in CH$_2$Cl$_2$ (100 mL). The solution was cooled to 0° C. and triethylamine (16 mL, 114 mmol) was added dropwise while stirring to dissolve all solids. To this mixture was added a solution of di-tert-butyl dicarbonate (12 g, 55 mmol) in CH$_2$Cl$_2$ (20 mL). The reaction was stirred for 30 min at 0° C., then continued for 1 h at rt. The solution was washed with three 100 mL portions of water. The aqueous portion was combined and extracted with two 100 mL portions of EtOAc; this EtOAc was discarded. The pH of the aqueous portion was adjusted to 3.5 with 1 M HCl, then extracted with five 50 mL portions of EtOAc, adjusting to maintain pH 3.5 as needed. The combined EtOAc was dried over Na$_2$SO$_4$, filtered, and the solvent removed in vacuo to afford a white crystalline powder (5.8 g, 83%). TLC: (MeOH:CH$_2$Cl$_2$, 1:9) Rf=0.08. $^1$H NMR (400 MHz, CD$_3$OD): δ 1.48 (s, 9H), 4.47 (s, 2H), 7.94 (s, 1H). $^{13}$C NMR (100 MHz, CD OD): δ, 27.1, 47.0, 72.3, 81.4, 157.8, 171.3.

Synthesis of tert-butyl 2-(3-(2-methylprop-2-enamido)propylamino)-2-oxoethoxycarbamate (MEPO) (S7)

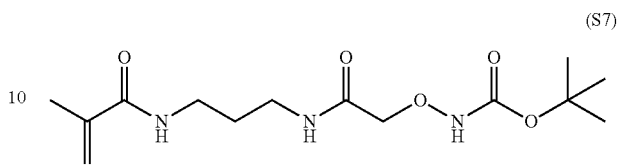

The synthesis of this monomer was adapted from a previously published procedure. See Esser-Kahn & Francis, Angew. Chem. Int. Ed. 2008, 47, 3751-3754. A 250 mL round-bottom flask was charged with a mixture of S6 (3.2 g, 16.68 mmol) and N-hydroxysuccinimide (2.3 g, 19.98 mmol) in CH$_2$Cl$_2$ (100 mL). The mixture was sonicated to dissolve the solids. To the solution was added N,N'-dicyclohexylcarbodiimide (4.15 g, 20.11 mmol) directly while stirring. The reaction mixture was stirred for 5 min at rt, then cooled to 0° C. for 10 min to precipitate the urea byproduct. The mixture was filtered through Celite, the precipitate washed with CH$_2$Cl$_2$ (50 mL), and the filtrate taken directly to the next step. A 500 mL round-bottom flask was charged with the filtrate and cooled to 0° C. Directly to this was added N-(3-aminopropyl)methacrylamide hydrochloride (1.5 g, 8.39 mmol) (Polysciences Inc.; Warrington, Pa., www.polysciences.com), followed by N,N-diisopropylethylamine (6.1 mL, 35 mmol) dropwise while stirring. The reaction mixture was allowed to come to room temperature over 1 h, then continued at rt for 3 h. The solution was diluted with 50 mL of CH$_2$Cl$_2$ and washed with three 150 mL portions of water followed by 100 mL of brine. The organic layer was dried over Na$_2$SO$_4$, filtered, and concentrated in vacuo. Purification by flash chromatography with EtOAc:MeOH, 19:1, afforded a clear, viscous oil (1.65 g, 62.4%). TLC: (EtOAc) Rf=0.2. $^1$H NMR (400 MHz, CD$_3$OD): δ, 1.48 (s, 9H), 1.76 (p, 2H, J=6.8), 1.95 (s, 3H), 3.31 (q, 4H, J=6.9), 4.27 (s, 2H), 5.38 (s, 1H), 5.73 (s, 1H). $^{13}$C NMR (100 MHz, CD$_3$OD): δ, 17.5, 27.2, 28.7, 36.0, 36.5, 75.0, 81.7, 119.2, 139.9, 158.3, 169.8, 170.2.

Synthesis of poly(MEPO-co-NIPAm) (1a)

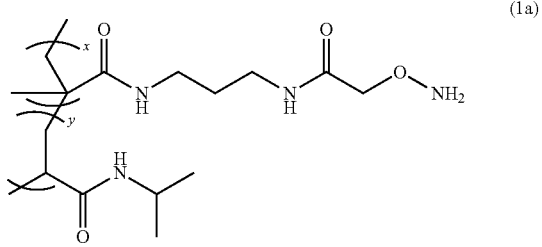

Figure 3A:
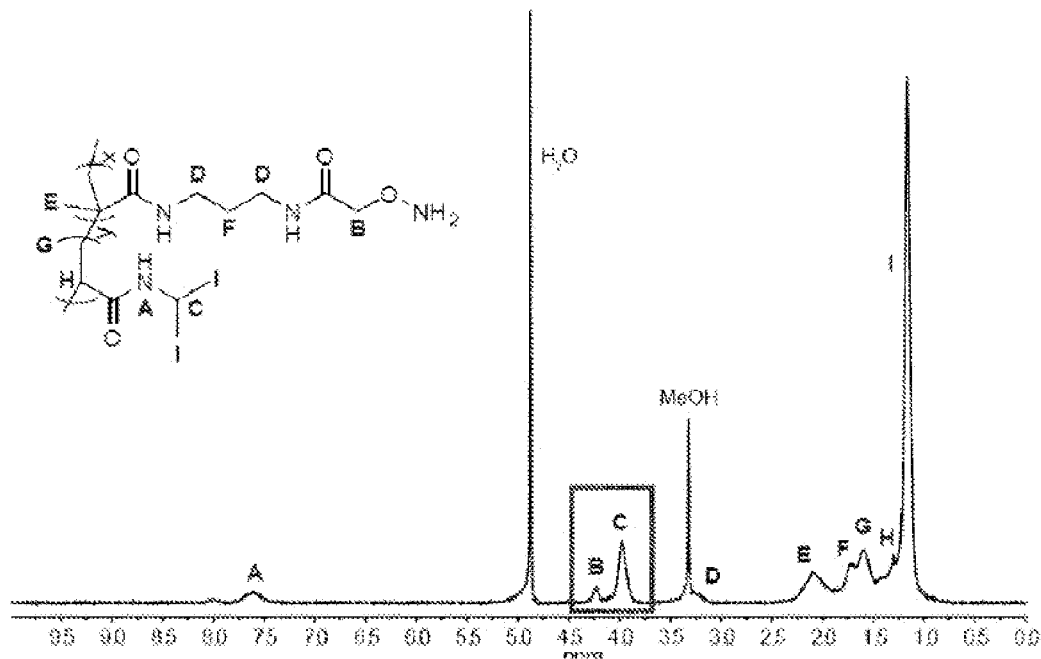
FIGS. 3A and 3B are $^1$H NMR spectra of Copolymers (1a) and (1b), respectively, described in Example 1 below, where comparison of integration values of peaks B and C provide an assessment of the co-monomer ratio.

Azobisisobutylonitrile (AIBN) was recrystallized from pure MeOH before use. N-isopropylacrylamide (NIPAm) was recrystallized from hexanes and toluene twice before use. Polymerization was conducted using a 1:9 molar ratio of S7:NIPAm and weight percent 11.1:0.6:88.3 for monomers:AIBN:CH$_3$OH. S7 (378.5 mg, 1.2 mmol), NIPAm (1.22 g, 10.78 mmol), and AIBN (80 mg, 0.49 mmol) were added to a clean scintillation vial. The vial was purged and refilled N$_2$. MeOH (12.67 g, 395.4 mmol) which had been previously sparged with N$_2$ for 1 h, was added and the components were dissolved under N$_2$. The mixture was divided into six clean scintillation vials, a stream of N$_2$ was bubbled through the solution in each vial for 10 min, and the vials were sealed under N$_2$ and placed in a 60° C. oil bath for 6 h. The polymer was recovered from the reaction mixture by one precipitation from MeOH into cold diethyl ether followed by centrifugation. Samples were dissolved in 1:1 CH$_2$Cl$_2$:trifluoroacetic acid for 1 h, concentrated in vacuo, then neutralized using 5 M NaOH. Samples were purified using Amicon Ultra 15 mL 10 kDa MWCO (Millipore) centrifugal ultrafiltration membranes and lyophilized to afford the final polymer. Analysis of the $^1$H-NMR spectrum showed the integration of peaks B:C to be 1.00:5.25 (FIG. 3A), from which the molar ratio of S7:NIPAm was calculated to be 1: 10.5, or 8.5% incorporation of S7. GPC analysis using PMMA standards indicated Mn=85,127, Mw=155,321, and PDI=1.82.

Synthesis of poly(MEPO-co-NIPMa) (1b)

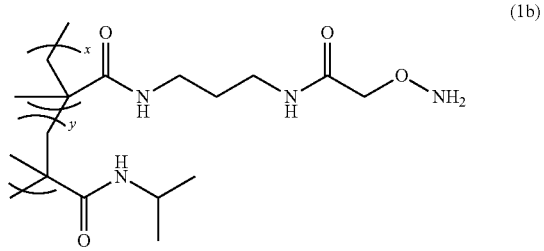

(1b)

Figure 3B:
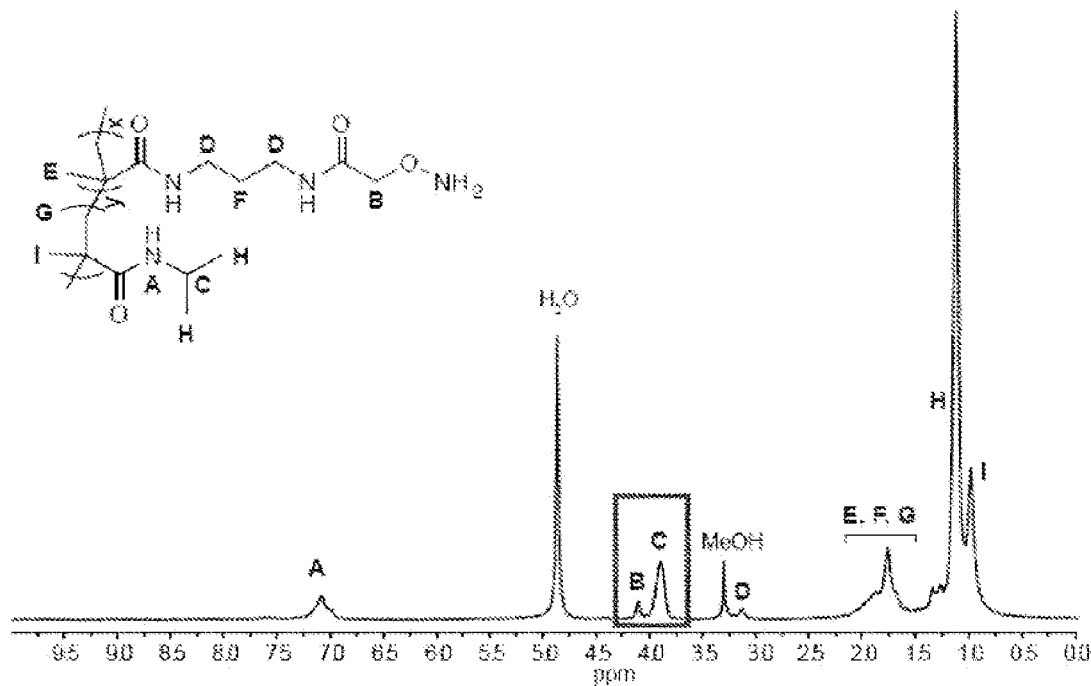

The same general procedure was followed as for Copolymer (1a). Analysis of the 1H-NMR spectrum showed the integration of peaks B:C to be 1.00:5.18 (FIG. 3B), from which the molar ratio of S7:NIPMa was calculated to be 1:10.36, or 8.8% incorporation of S7. GPC analysis using PMMA standards indicated Mn=11,144, Mw=14,037, and PDI=1.26.

Polymer size of Copolymers (1a) and (1b) were determined by size exclusion chromatography (SEC) using poly (methyl methacrylate) standards, with number-average molecular weights (M$_n$) of 85,127 and 11,144 Da and polydispersity indices (PDI) of 1.82 and 1.26 for Copolymers (1a) and (1b), respectively.

Example 2

Small Molecule Modification of Copolymers (1a) and (1b)

A 20 mg/mL stock solution of Copolymer (1a) was made in pH 4.5 buffer. A series of 1 mL, 120 mM stock solutions of formaldehyde, acetone, 3-fluoroisonicotinaldehyde (with 10% DMSO), and 4-hydroxy-2-butanone, and 1.2 M stock solutions of D-(+)-mannose and D-(+)-dextrose were made in pH 4.5 buffer. 750 µL of the polymer solution was mixed 1:1 with each of the small molecule solutions in 4 mL glass dram vials. The reactions were incubated at rt for 24 h, then excess small molecules were removed and the polymers buffer exchanged into pure water through 8 rounds of ultrafiltration (10 kDa MWCO) at 4° C. They were lyophilized, analyzed by NMR spectrometry to confirm modification, and the LCST was determined according to the procedure below. The same procedure was followed for small-molecule modification of Copolymer (1b).

Example 3

LCST Measurements

Polymer samples of modified Copolymers (1a) and (1b) prepared according to the procedure of Example 2 above were dissolved in pH 4.5 buffer at a concentration of 1 mg/mL and mixed for 30 min to ensure complete dissolution. They were transferred to a cuvette with a stir bar and warmed at a rate of 0.5° C./min while stirring in a Horiba Scientific F-3004 Peltier device (Kyoto, Japan) controlled by a LFI3751 5A digital temperature control instrument (Wavelength Electronics, Bozeman, Mont.). The cuvettes were quickly removed every 0.5° C. and the absorbance at 600 nm was measured, then the cuvette was returned to the Peltier device. The LCSTs in this Example are the temperature at 10% of the maximum absorbance for each sample.

As depicted in FIG. 2B, incorporation of the hydrophilic aminooxy-bearing monomer residues increased the LCST of the NIPAm copolymer to 42.5° C. from 32° C. for the homopolymer, and the LCST of the NIPMa copolymer increased to 58.1° C. from 43° C.

Figure 2C:
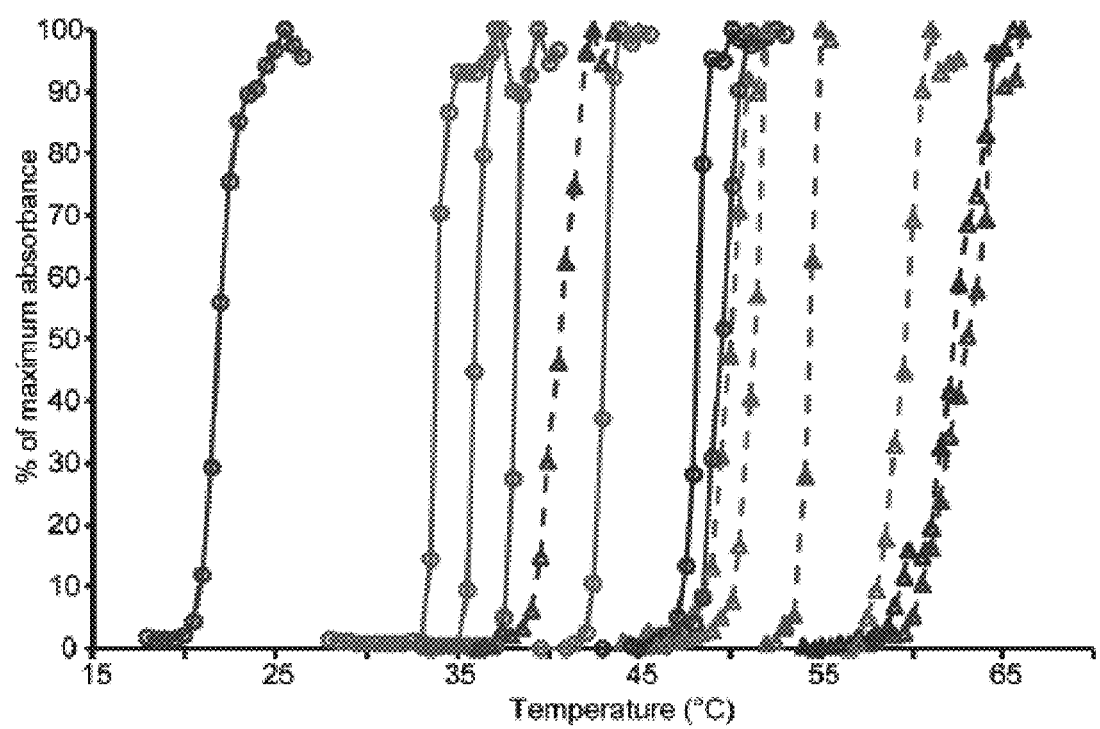
FIG. 2C is a graph of LCST measurements for NIPAm and NIPMa copolymers modified by small molecule quenchers A-F, normalized to the percentage of maximum absorbance.

Furthermore, the data from this Example demonstrates that the aminooxy group also provides a handle through which the LCST can be adjusted through small-molecule quenching. As seen in FIG. 2C, Copolymers (1a) and (1b) were modified to have LCSTs ranging from 20.9° C. to 60.5° C.

Example 4

Construction of EGPh Plasmids, Expression, and Purification

BL21starDE3 *E. coli* cells containing an EGPh-pet24b plasmid were obtained. The plasmid initially contained both N-terminal and C-terminal His6 tags, so site-directed mutagenesis and restriction digestion were used to remove the N-terminal His6 tag and to install an AKT sequence at the N-terminus to maximize transamination yield.

```
N-terminal sense primer:
5'GTGATGCCATATGGCTAAAACCCTGTTTGGTCAGGTCGTTCCGGTC

TACGC-3'

C-terminal antisense primer:
5'-GGTGGTGCTCGAGTTTCTTGGACGTATTGC-3'
```

The purified plasmid was doubly-digested with NdeI and XhoI restriction enzymes, then run on a 1% agarose gel to separate the linear plasmid from the original EGPh gene. The band corresponding to the desired vector was excised and purified using a QIAquick Gel Extraction Kit (Qiagen). The PCR product was also doubly-digested with NdeI and XhoI restriction enzymes. A plasmid ligation was then performed with a 1:3 molar ratio of PCR insert:vector, the product was transformed into XL1-blue competent *E. coli* cells (Invitrogen), and the cells were plated on LB agar plates containing kanamycin (50 µg/mL). Colonies were grown up in 4 mL overnight cultures, and the resulting plasmids were purified using a QIAprep Spin Miniprep Kit (Qiagen). The incorporation of the desired mutations were confirmed through sequencing (Sequetech, Mountain View, Calif.). AKT-EGPh plasmids were transformed into One Shot® BL21 (DE3) *E. coli* cells (Invitrogen) via heat shock and plated on Luria broth (LB) agar plates containing kanamycin (50 µg/mL). Cultures were grown in 1 L of LB containing kanamycin (50 µg/mL) at 37° C. until an optical density (OD) of 0.5 was observed at 600 nm. Expression of AKT-EGPh was induced by the addition of 0.1 mM isopropyl β-D-1-thiogalactopyranoside (IPTG). Cultures were grown for 12 h at 25° C., then spun down at 7,000 rcf, 4° C. for 40 min to pellet the cells. The cells were resuspended in 8 mL of lysis buffer (50 mM NaH2PO4, 300 mM NaCl, 10 mM imidazole, pH 8.0), lysed by sonication using a blunt tip for 20 min, and cell debris removed by centrifugation at 4,700 rpm at 4° C. for 40 min. The cleared cell lysate was washed over 2 mL of rinsed nickel-nitrilotriacetic acid resin (Ni-NTA) in a 15 mL cartridge for 1 h at 4° C. The resin-bound protein was washed with two 11 mL portions of wash buffer (50 mM $NaH_2PO_4$, 300 mM NaCl, 20 mM imidazole, pH 8.0), then eluted with four 1 mL portions of elution buffer (50 mM $NaH_2PO_4$, 300 mM NaCl, 250 mM imidazole, pH 8.0).

Example 5

Small-Molecule Modification of EGPh

Transamination of the EGPh N-terminus was performed following a previously reported method. See Witus, et al., *J. Am. Chem. Soc.* 2010, 132, 16812-16817. EGPh at a concentration of 50-60 µM in pH 4.5 buffer was mixed 1:1 with a pH 4.5 solution of 200 mM pyridoxal-5'-phosphate (PLP) (FIG. 4A). Samples were reacted for 1 h at 37° C., then excess PLP was removed by eight rounds of ultrafiltration (30 kDa MWCO) at 4° C. Controls were conducted following the same procedure but without PLP.

To modify the transaminated protein with benzylalkoxyamine ($BnONH_2$), 125 µL of a 250 mM solution of BnONH2 (pH adjusted to 5.5) was added to 625 µL of transaminated EGPh (30 µM) in pH 4.5 buffer and incubated at rt for 42 h. Excess $BnONH_2$ was removed through ultrafiltration (30 kDa MWCO). A control was conducted following the same procedure but with non-transaminated EGPh.

To modify transaminated protein with PEG, a stock solution of 1 mM 5 kDa alkoxyamine-poly(ethylene glycol) (PEG) in pH 4.5 buffer was mixed 1:1 with 50 µM transaminated EGPh and incubated at rt for 42 h. Excess PEG was removed through ultrafiltration (30 kDa MWCO). A control was conducted following the same procedure but with non-transaminated EGPh.

Figure 4B:
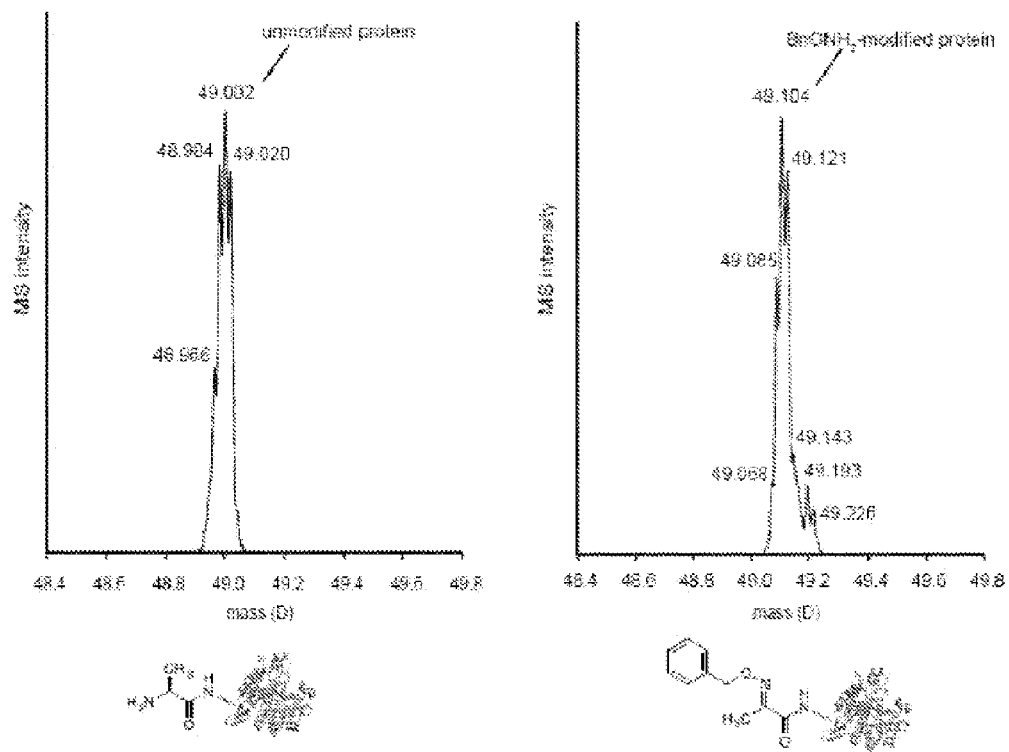
FIG. 4B provides two mass spectroscopy (MS) graphs of unmodified EGPh and EGPh after transamination by PLP and modification with benzylalkoxyamine, showing a +104 shift in mass, and where the low abundance, higher mass peaks are unassigned.
Figure 4C:
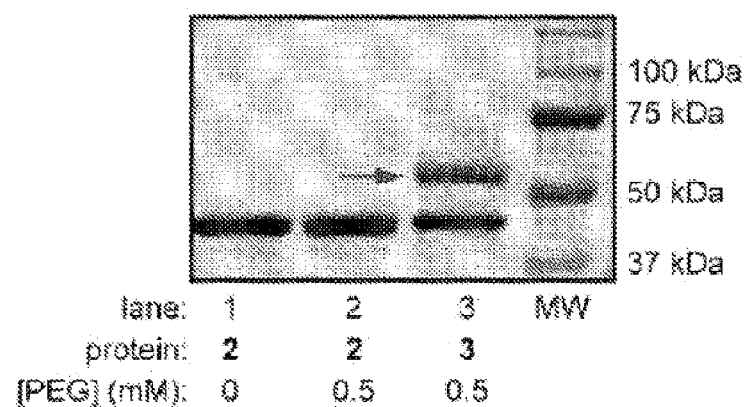
FIG. 4C is a SDS-PAGE analysis followed by Coomassie staining and densitometry, in which the arrow indicates a 5 kDa increase in mass corresponding to a single covalent modification with 5k-PEG-ONH$_2$.

To ascertain whether the enzyme modification site or the conditions used negatively affected its catalytic activity, both the benzylalkoxyamine and the 5 kDa-PEG-alkoxyaine modified EGPh were assayed, along with the two controls in which the protein was not transaminated. The controls showed no modification by LC-MS and SDS-PAGE (FIGS. 4B and 4C, respectively).

In addition, an unmodified, non-transaminated control was included, as well as a sample of EGPh that had been incubated with mannose (600 mM) for 24 h to ensure protein activity would not be affected by the quenching step used for the LCST polymers. Each protein reaction was assayed in a 40° C. water bath and 100 µL aliquots were removed at 2, 4, 6, 8, and 12 h. The supernatants were analyzed for the amount of soluble sugar released using the glucose oxidase-peroxidase assay with OxiRed as the fluorescent substrate.

The procedure for analyzing soluble reducing sugar was performed following a previously reported method, using the glucose oxidase-peroxidase assay with OxiRed as the substrate. See Kim, et al., *Biotechnol. Bioeng.* 2010, 107, 601-610. Analysis was performed in clear-bottom plastic 96 well plates, with each sample analyzed in triplicate. Internal standards of 300, 200, 100, 50, 25, and 0 µM glucose, and 150, 100, 50, 25, and 12.5 µM cellobiose in pH 4.5 buffer were included in each plate. Frozen aliquots from the activity assays were thawed on ice and then diluted 0- to 20-fold with cold buffer, then 8 µL of the solution was incubated with 8 µL of β-glucosidase (5 mg/mL in 10 mM NaOAc pH 4.6) for 60 min at 37° C. to convert all of the cellobiose to glucose. The amount of glucose present was then measured by adding 65 µL of glucose oxidase (1.25 U/mL), horseradish peroxidase (1.25 U/mL), and OxiRed (60 µM) in 125 mM phosphate buffer (pH 7.45) and incubating at rt for 10 min in the dark. The amount of Resorufin formed was measured on an optical plate reader with excitation at 535 nm and emission detection at 590 nm. The amount of Resorufin formed corresponded to the amount of glucose present. Linear standard curves were made from the internal standards in each plate (all $r^2 > 0.97$), which were then used to calculate the amount of glucose equivalents present in each activity assay sample. The triplicate measurements of each supernatant sample were averaged, and then the measurements of the triplicate activity assay samples were averaged to calculate each data point.

Figure 4D:
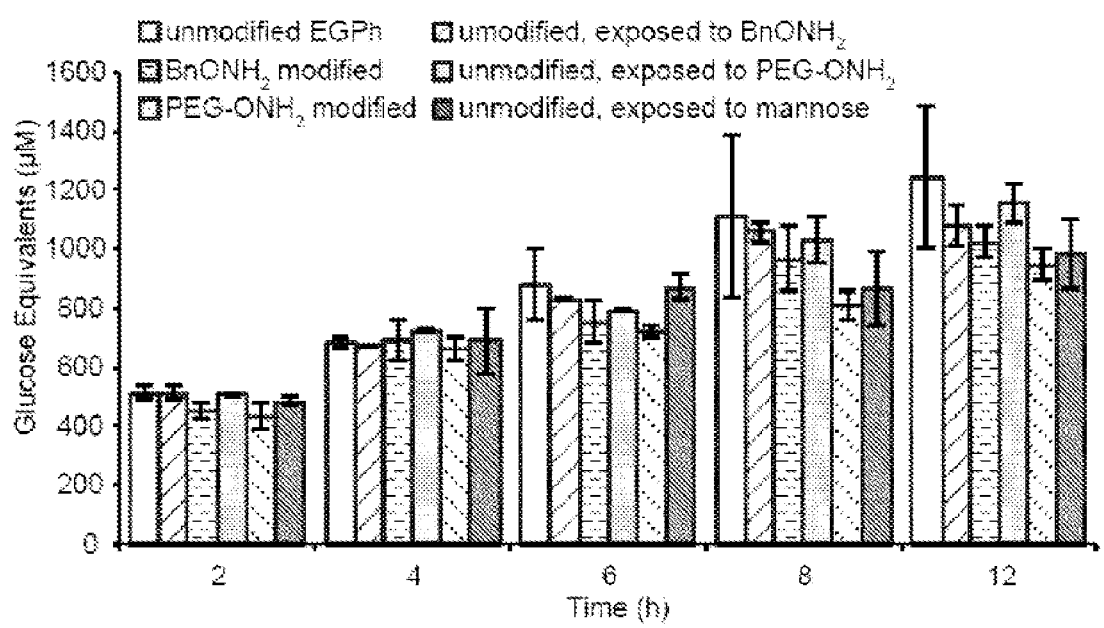
FIG. 4D is a graph illustrating the modified and unmodified protein samples assayed for hydrolytic activity, in which the error bars represent the standard deviation of three replicate experiments.

As shown in FIG. 4D, the activities of the two modified endoglucanases were slightly reduced relative to the unmodified control, but the differences were generally within the standard deviations of the assays. The activities of unmodified enzyme samples that had been exposed to benzylalkyoxy- amine, PEG-alkoxyamine, and mannose were also slightly lower, but within one standard deviation of the activity of the unmodified control at each time point. From this Example, neither the N-terminal modification itself nor the reaction conditions used were observed to have a significant effect on endocellulase activity.

Example 6

Construction of EGPh-Polymer Conjugates 1 mL of a 40 mg/mL stock solution of Copolymer (1a) in pH 4.5 buffer was combined with 1 mL of 50 µM transaminated EGPh in a 4 mL glass dram vial and pipetted vigorously to mix. The solution was incubated at rt for 24 h, then 2 mL of 1.2 M D-(+)- mannose in pH 4.5 buffer was added, mixed via pipet, and the new mixture was incubated an additional 24 h at rt. The solution was transferred to a 15 mL Falcon tube and heated for 10 min in a 55° C. water bath to precipitate the polymer, then centrifuged for 5 min at 55° C. and 2,000 rpm. The supernatant was removed and the pelleted polymer was resuspended in the same volume of rt buffer (pH 4.5). This procedure was repeated three more times for a total of 4 precipitation cycles, then any excess mannose was removed through three cycles of ultrafiltration at 4° C. (10 kDa MWCO). The concentrated polymer-EGPh conjugate was transferred to an Eppendorf tube and stored at 4° C. A small portion of the purified conjugate was buffer exchanged into pure water using ultrafiltration (30 kDa MWCO), lyophilized, and analyzed for protein concentration using tryptophan fluorescence. Attachment of Copolymer (1b) was performed using a similar procedure. A control with Copolymer (1a) was conducted following a similar procedure but with non-transaminated EGPh.

Protein Quantification: Unmodified, transaminated, PEGylated, and BnONH$_2$-modified EGPh concentrations were measured using a NanoDrop 1000 spectrophotometer (Thermo Scientific), with an extinction coefficient of 139,020 M$^{-1}$ cm$^{-1}$ and molecular weight of 49,023 Da. Protein concentration of the polymer conjugates was determined using tryptophan fluorescence. Buffered standards at pH 4.5 were prepared in triplicate containing 5 mg/mL of mannose-quenched copolymer and 7.06, 5.01, 3.0, 1.0, and 0 µM of EGPh. Triplicate 5 mg/mL samples of lyophilized polymer-EGPh conjugate were made in pH 4.5 buffer. The fluorescence spectrum of each of the standard and experimental samples was collected from 290 nm to 400 nm, with excitation at 280 nm. The maximum fluorescence intensity of each standard set was plotted versus the protein concentration and a linear fit was applied to the data points (all R$^2$>0.99). This linear fit was used to calculate the protein concentration in the lyophilized samples using their fluorescence maxima. Serial dilutions of the reserved, non-lyophilized protein-polymer conjugate were prepared and their fluorescence intensities were measured to determine the dilution level that matched that of the 5 mg/mL lyophilized samples. From these data, the protein and polymer concentrations of the reserved polymer-EGPh conjugates were determined. The protein concentrations in µM EGPh/mg material were 0.520 µM/mg for Copolymer (1a)-EGPh, 0.177 µM/mg for Copolymer (1b)-EGPh, and 0.066 µM/mg for a control of Copolymer (1a) combined with non-transaminated EGPh.

Example 7

Activity of Modified EGPh, Polymer-EGPh Conjugates, and Recycled Polymer-EGPh Conjugates Activity of Modified EGPh: To measure the enzymatic activity, each protein sample was assayed in triplicate. 1.3 mL portions of a 1% (w/v) suspension of Sigmacell cellulose powder (Sigma-Aldrich) in 50 mM NaOAc buffer (pH 4.5) was added to 1.5 mL Eppendorf tubes containing stir bars. Stock solutions of each protein sample were prepared ranging from 21.4 to 26.6 M, and 9.85 to 12.23 µL of these stocks were added to the appropriate Eppendorf tube to achieve a final protein concentration of 0.2 µM. A t=0 h sample was taken from each reaction tube, after which they were placed in a 40° C. water bath placed on a stir plate. Samples were taken after 2, 4, 6, 8, and 12 h for analysis. To measure the reactions, each tube was shaken vigorously to ensure even distribution of the substrate and protein, and a 100 µL aliquot was immediately removed and transferred to a clean, empty Eppendorf tube. This aliquot was centrifuged for 1 min at 13.3k rpm, and then the clarified supernatant was transferred to a 0.6 mL Eppendorf tube and immediately frozen in dry ice. The supernatant aliquots were stored at -20° C. until analysis for the amount of soluble reducing sugar.

Activity of Polymer-EGPh Conjugates: Both the NIPAm and NIPMa copolymer-protein conjugates and a free, unmodified EGPh control were assayed concurrently in triplicate. 900 µL of a 1.1% (w/v) suspension of Sigmacell cellulose powder (Sigma-Aldrich) in 50 mM NaOAc buffer (pH 4.5) was added to an Eppendorf tube containing a stir bar and 1.6 mg of mannose-quenched Copolymer (1a) or 1.1 mg of mannose-quenched Copolymer (1b) and a stir bar. The solution was mixed vigorously for 30 min at rt to ensure dissolution of the polymer. Polymer was not added to the control samples. 100 µL stock solutions of the two polymer-protein conjugates and the EGPh control were added to the appropriate Eppendorf tubes for a final protein concentration of 0.2 µM for all samples and 2 mg/mL polymer for both of the polymer-EGPh conjugate samples. A 100 µL aliquot was taken from each tube to measure the initial amount of reducing sugar, and then the tubes were placed in a 40° C. water bath on a stir plate. Subsequent aliquots were taken at 2, 4, 6, 8, and 12 h following the same procedure used in the activity assays of modified EGPh.

Figure 5A:
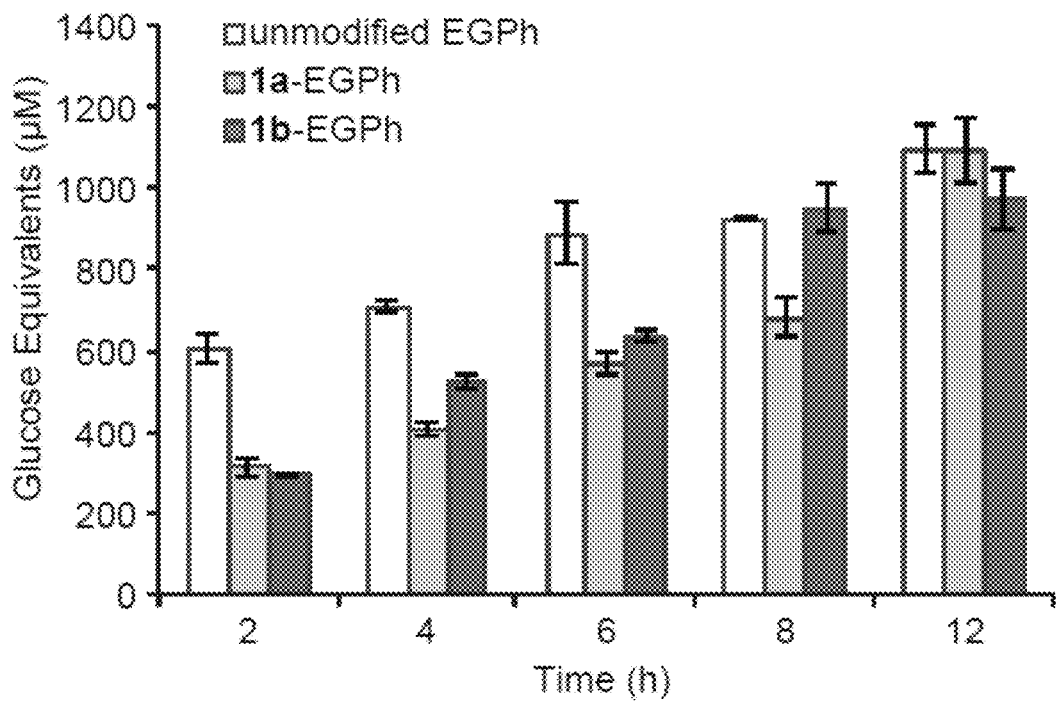
FIG. 5A is a graph showing the activity of conjugates Copolymer (1a)-EGPh, and Copolymer (1b)-EGPh.

With reference to FIG. 5A, both Copolymer (1a)-EGPh and Copolymer (1b)-EGPh were observed to display about half the endoglucanase activity of the free EGPh after 2 h, but at later time points the enzymatic activity in the samples were observed to converge. After 12 h, any initial differences in activity had subsided, and the differences in the total concentration of reducing sugars was statistically insignificant.

Activity of Unmodified EGPh in the Presence of β-Glucosidase: Unmodified EGPh with and without added β-glucosidase were assayed concurrently in triplicate, following a similar procedure for previous activity assays. The total volume of each reaction was 0.5 mL of a 1% (w/v) suspension of Sigmacell cellulose powder in 50 mM NaOAc buffer (pH 4.5) in Eppendorf tubes. EGPh concentration was 0.2 µM for all reactions, with β-glucosidase added to a concentration of 0.2 µM in 3 of the 6 reactions. They were placed in a 40° C. water bath on a stir plate and allowed to react for 12 h, at which point the levels of soluble reducing sugar were measured following the same procedure as for all other assays. Results show no increase in soluble reducing sugars.

Figure 5B:
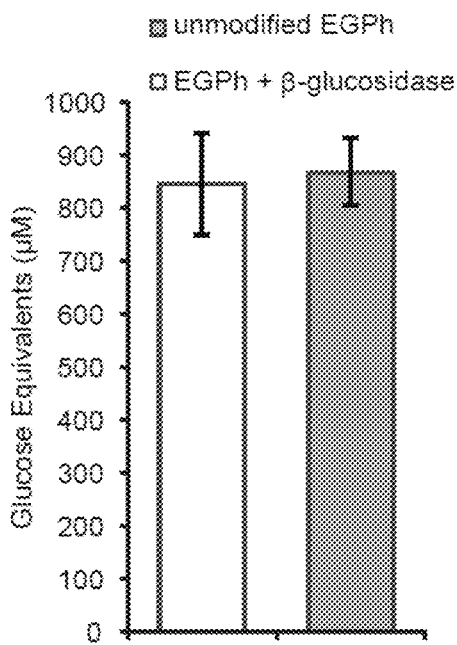
FIG. 5B is a graph comparing the activity of unmodified EGPh with and without added β-glucosidase, in which the error bars represent the standard deviation of three replicate experiments.

With reference to FIG. 5B, added β-glucosidase was not observed to increase the overall activity of the unmodified enzyme. This indicates that product inhibition by cellobiose is unlikely to be the cause of activity loss.

Activity of Recycled Polymer-EGPh Conjugates: The polymer-protein conjugate and a free, unmodified EGPh control were assayed concurrently in triplicate. 1.0 mL of a 1% (w/v) suspension of Sigmacell cellulose powder (Sigma-Aldrich) in 50 mM NaOAc buffer (pH 4.5) was added to an Eppendorf tube containing 1.6 mg of mannose-quenched Copolymer (1a) and a stir bar. The solution was mixed vigorously for 30 min at rt to ensure dissolution of the polymer. Polymer was not added to the control samples. Stock solutions of the two protein samples were added to the appropriate Eppendorf tube for a final protein concentration of 0.2 µM for all samples and 2 mg/mL polymer for the polymer-EGPh conjugate samples. A 100 µL aliquot was taken from each tube to measure the initial amount of reducing sugar, and then the tubes were placed in a 40° C. water bath on a stir plate and allowed to react for 12 h. A 50 µL aliquot was removed at the end of 12 h to measure the amount of reducing sugar. The stir bars were removed and the polymer-containing tubes were heated at 55° C. for 5 min to precipitate the polymer, then centrifuged at 2k rpm for 10 min at 55° C. to pellet the polymer. All tubes were then centrifuged at 13.2k rpm for 1 min at rt to pellet the substrate. The cleared supernatant was removed and replaced with ice cold 50 mM NaOAc buffer (pH 4.5), clean stir bars were added, and the tubes shaken vigorously for 3 minutes to ensure an even suspension of substrate and polymer. The assay procedure was then repeated twice more, beginning with removing a 100 µL aliquot to measure initial reducing sugar, for a total of two precipitation events and three 12 h assay periods. To aliquot the reactions, each tube was shaken vigorously to ensure even distribution of substrate and protein, and an aliquot was immediately removed and transferred to a clean, empty Eppendorf tube. This aliquot was centrifuged for 1 min at 13.3k rpm, and then the clear supernatant was transferred to a 0.6 mL Eppendorf tube and immediately frozen in dry ice. The samples were stored at −20° C. until analysis for the amount of soluble reducing sugar was performed.

Figure 5C:
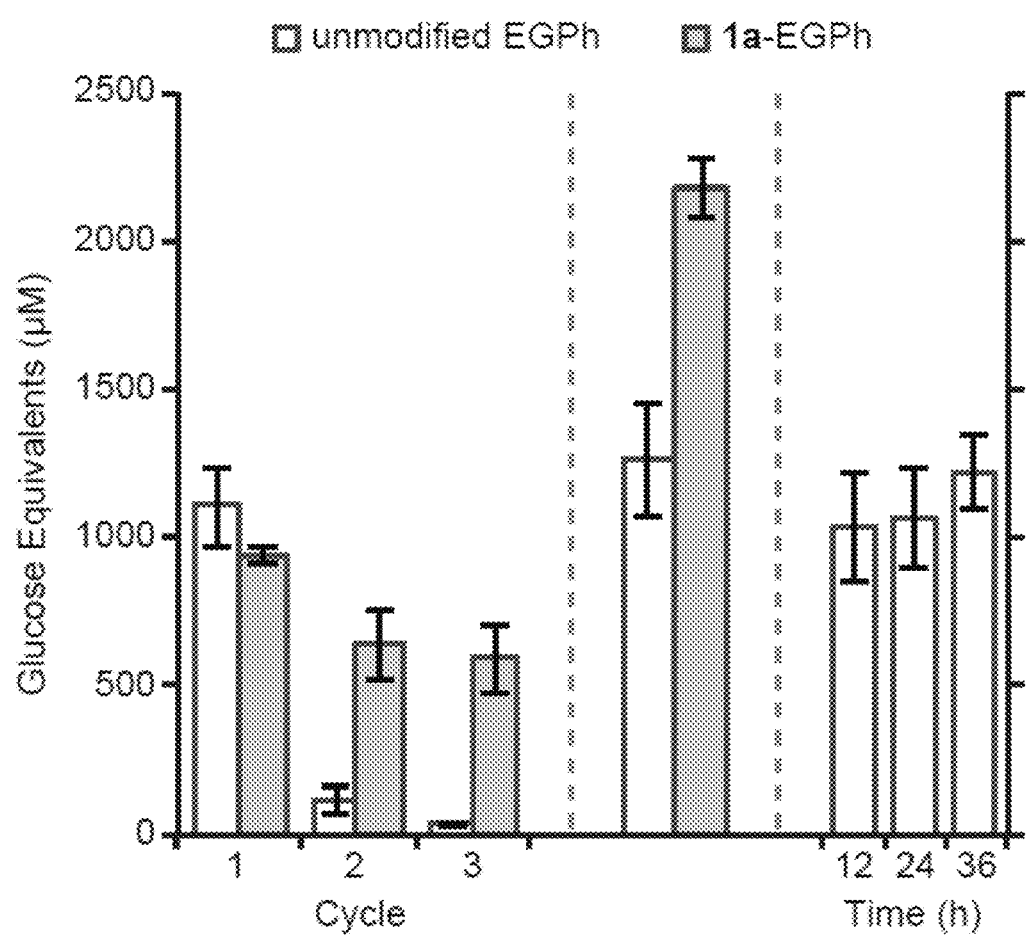
FIG. 5C is a graph from the recycling assay for Copolymer (1a)-EGPh using microcrystalline Sigmacell as a substrate, in which soluble reducing sugar was measured at 0 h and 12 h of each cycle (left of dotted lines); showing the total additional glucose equivalents produced over three cycles (between dotted lines), based on the sum of values from the recycling assay with Sigmacell; and showing the hydrolytic activity of unmodified EGPh over 36 h based on the difference in soluble reducing sugar between 0 h and 12, 24, and 36 h (right of dotted lines)

With reference to FIG. 5C, after the initial 12 h of reaction, Copolymer (1a)-EGPh conjugate produced reducing sugars at 86% of the level of the control (see graph left of the dotted lines). However, it retained 68% and 63% of its initial activity over two cycles of precipitation and recovery of the material. The free enzyme, in contrast, retained only 11% and 4% of its initial activity. While the supernatant was removed from all samples, only the polymer conjugate sample had the majority of the protein precipitated in the substrate pellet. Any subsequent activity for the free control was due to enzyme carryover contained in the pelleted insoluble cellulose. Over three cycles, the polymer-enzyme conjugate was able to produce a 1.7-fold increase in the amount of free reducing sugar over that produced by the control (see graph between dotted lines).

While the results of this Example indicate that the polymer-enzyme conjugate can be recycled, the activity of the conjugate over three 12 h reaction cycles was compared to the activity of free protein over one 36 h reaction to determine if recycling the enzyme actually provided any benefit over simply letting free enzyme react for an extended period of time. Free, unmodified EGPh was allowed to react with Sigmacell for 36 h at 40° C., with free reducing sugar measured at 0 h, 12 h, 24 h, and 36 h. Consistent with the results above, the free enzyme reached an upper activity limit by 12 h, with only modest increases in reducing sugar achieved in the next 24 h (see FIG. 5C to the right of the dotted lines). At 12 h, the polymer-enzyme conjugate was 91% as active as the free control; by recycling the enzyme, however, 78% more reducing sugars were produced over 36 h than if the free enzyme was allowed to react.

Example 8

Hydrolytic Activity of Copolymer (1a)-EGPh Conjugate on *Miscanthus*

Acid-pretreated *Miscanthus* (*Miscanthus giganteus*) was obtained. The substrate was cut into approximately 1-inch pieces and then subjected to 1.5% (w/w) sulfuric acid, 25% biomass loading (w/w), at 190° C. for approximately 1 min. After treatment, the biomass was ground into smaller pieces. It was then washed extensively with deionized water until the filtrate had a neutral pH and no detectable glucose. The material was dried for 24 h at 104° C., then ground into a fine powder with a mortar and pestle. The activity and recycling ability of the Copolymer (1a)-EGPh conjugate was then assessed according to the procedure in Example 7 above.

Figure 6:
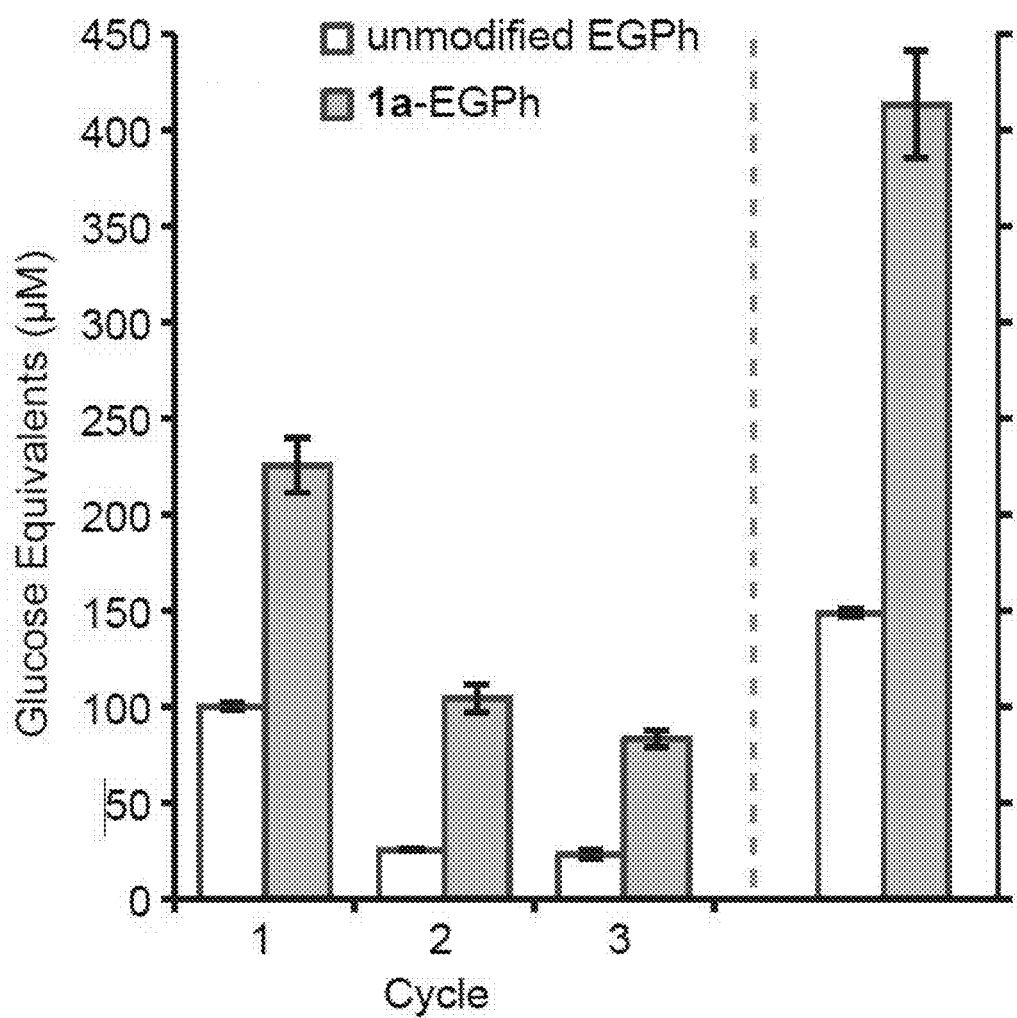
FIG. 6 is a graph from the recycling assay for Copolymer (1a)-EGPh using *Miscanthus* as a substrate, in which soluble reducing sugar was measured at 0 h and 12 h of each cycle (left of dotted line); and showing the total additional glucose equivalents produced over three cycles, based on the sum of the values from the recycling assay with *Miscanthus* (right of dotted line)

As seen in FIG. 6, the activity of the unmodified enzyme control was significantly lower for *Miscanthus* that it was for Sigmacell in Example 7 above. The activity of the conjugate also decreased for this substrate, but to a lower extent than the control. At the same enzyme loading, the conjugate produced substantially more reducing sugars after the first cycle.

In subsequent cycles of reuse, a drop in activity of the conjugate was observed, possibly because some protein may have still been adsorbed onto the biomass and ultimately deactivated. However, the conjugate remained 104% and 83% as active as the initial control in cycles 2 and 3. The ability to recover the conjugate, combined with the added activity due to the surfactant effect, increased the amount of reducing sugars by 2.8-fold over three rounds.

Example 9

Catalytic Activity of Modified and Unmodified EGPh

Figure 7A:
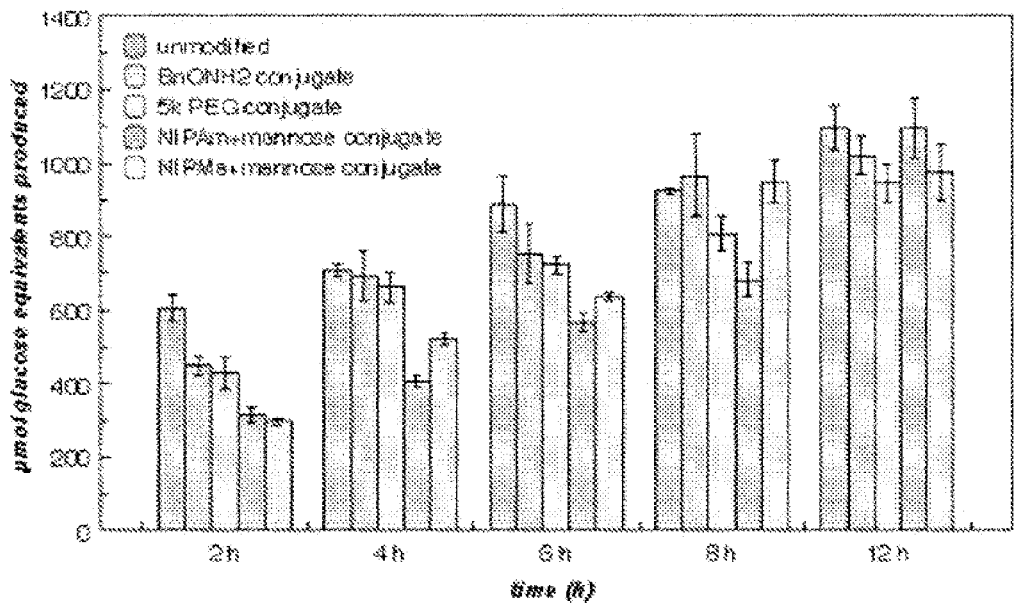
FIG. 7A is a graph depicting the hydrolytic activity of various modified and unmodified EGPh when added to microcrystalline Sigmacell.

Unmodified EGPh, as well as BnONH$_2$ conjugate, 5k PEG conjugate, NIPAM+mannose conjugate, and NIPMA+ mannose conjugate were provided. For each sample, a 1% w/v suspension of Sigmacell was exposed to 0.2 μM protein in a 50 mM sodium acetate buffer, pH 4.5, at 40° C. At each time point, the supernatant was collected and exposed to a calorimetric assay for the determination of free glucose and cellobiose. See FIG. 7A.

Figure 7B:
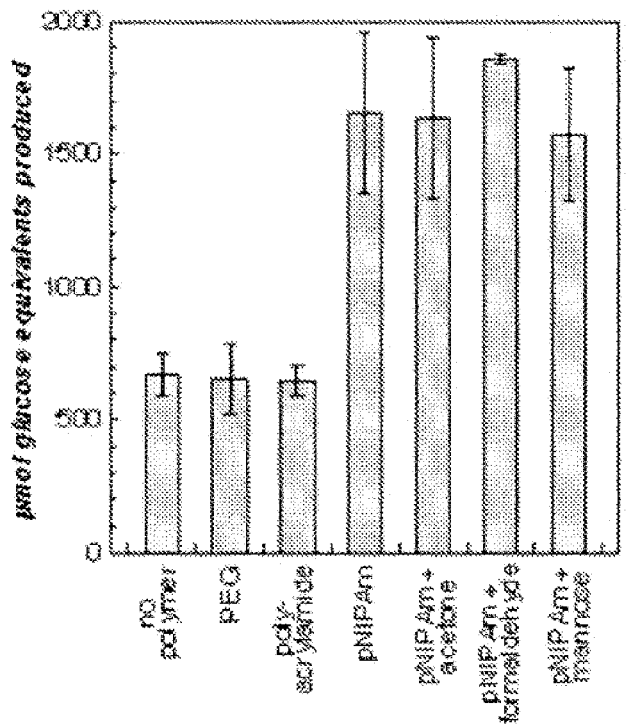
FIG. 7B is a graph depicting the hydrolytic activity of unmodified EGPh in the presence of several different polymer additives at 0.2%, at the 12 h time point.

With reference to FIG. 7B, the activity of unmodified EGPh was evaluated in the presence of several different polymer additives at 0.1%. When unmodified EGPh was added to microcrystalline Sigmacell in the presence of unattached pNIPAm, the enzymatic activity was unexpectedly observed to increase. The unattached pNIPAm was observed to increase enzymatic activity by two- to three-fold, affording up to triple the amount of usable cellobiose/ glucose in a 12 h period. This effect was more pronouncedly observed for pNIPAm, but was also observed for pNIPMa.

Example 10

Polymer Enhancement of Cellulase Activity

For all activity assays in this Example, each sample was evaluated in triplicate in 50 mM sodium acetate buffer (pH 4.5) using 0.2 μM EGPh and the insoluble cellulose substrate Sigmacell at 1% w/v loading. Additives were included at 2 mg/mL (0.2% w/v). Volumes ranged from 0.5 to 1.3 mL. The assays were run at either 28° C., 30° C., or 40° C. depending on the polymer, and for 12 h except where indicated. Specifically, the temperature used for poly(acrylamide), poly(NIPAm) (homopolymer) was 28° C. The temperature for all the quenched NIPAm copolymers, including mannose, PEG, poly(acrylamide-co-acrylic acid), poly(acrylic acid-co-maleic acid) was 30° C. The temperature for the mannose-quenched NIPMa was 40° C. A control using the same conditions but with no additive was included in each assay.

Additionally, the polymers used in this Example had the following sizes:
PEG: Mw 20 k
poly(acrylamide-co-acrylic acid): Mw/Mn 520/150 k, 80 wt % acrylamide
poly(acrylic acid-co-maleic acid): Mw 70k, 2.2:1 acrylic: maleic acid
poly(NIPAm): Mw 155 k
poly(acrylamide): Mw 1,000 k
NIPAm copolymers: generally Mw 130-160 k*
NIPMa copolymer: Mw 14 k
* measured based on gel permeation chromatography (GPC) using DMF as a solvent and PMMA standards To measure activity, an aliquot was removed from each reaction, centrifuged to pellet the substrate, and the amount of soluble reducing sugar in the supernatant was measured using the glucose oxidase-peroxidase assay with OxiRed as the fluorescent substrate. To compare the data, the concentration of glucose equivalents was normalized against the control of each set. For the time course assay, aliquots were removed at each indicated time point, then the reaction was returned to the water bath. The data was normalized against the activity of the control at each time point.

Figure 8A:
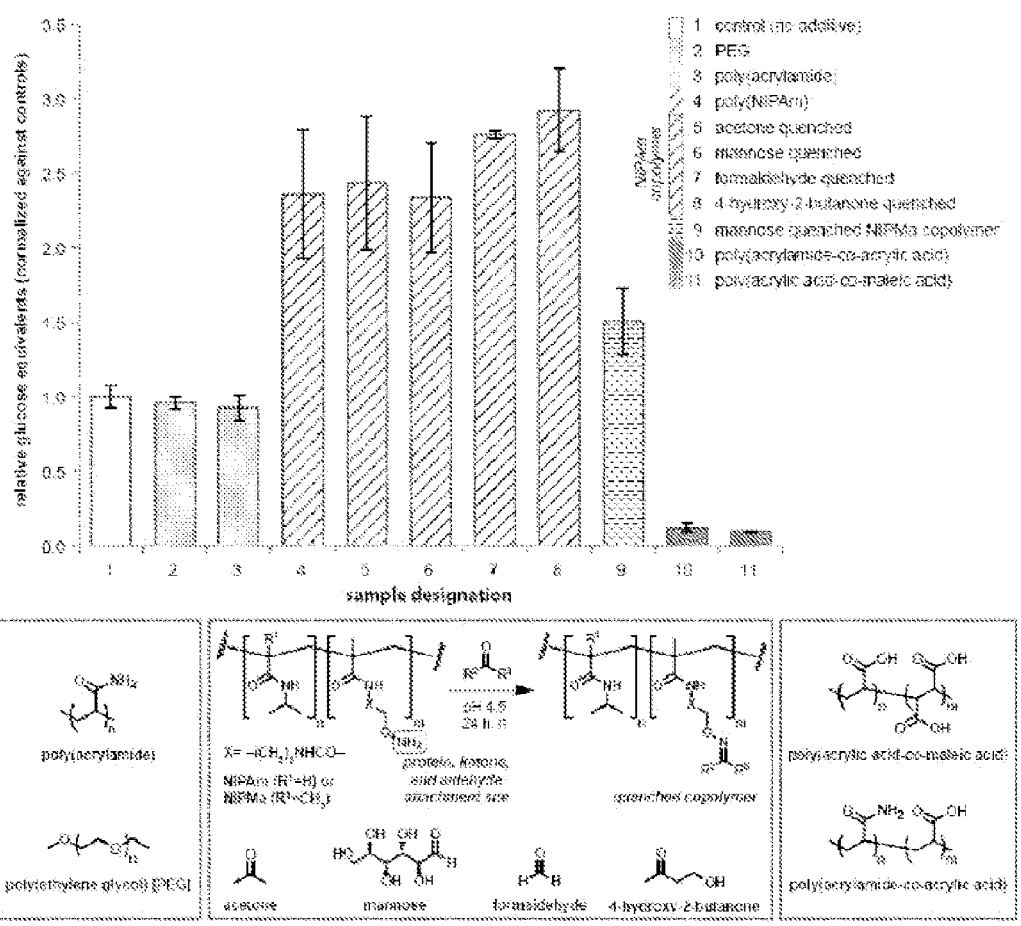
FIG. 8A is a graph showing the hydrolytic activity of EGPh in the presence of no added polymer (sample 1) and several different polymers (samples 2-11)

To investigate the role of certain small molecule quenchers, NIPAm copolymer samples were quenched with three small molecules that had different functional groups: acetone, formaldehyde, and 4-hydroxy-2-butanone (samples 6, 7, and 8, respectively). With reference to FIG. 8A, the different small-molecule quenchers were not observed to change the polymer effect observed with the mannose-quenched polymer.

Other polymers were also tested to determine if the activity increase was due to soluble polymers in general. With reference again to FIG. 8A, no polymer effect was observed in the presence of poly(ethylene glycol) (sample 2), and a drop in activity was observed with the addition of poly(acrylamide-co-acrylic acid) and poly(acrylic acid-co-maleic acid) (samples 10 and 11, respectively). Most significantly, there was no polymer effect with the addition of poly(acrylamide) (sample 3) but there was an activity increase in the presence of poly(NIPAm), a polymer composed only of NIPAm without any aminooxy-bearing monomer residues (sample 4). Structurally, poly(acrylamide) differs from poly(NIPAm) only by the presence of an isopropyl group on the nitrogen of NIPAm.

Time Courses

Figure 8B:
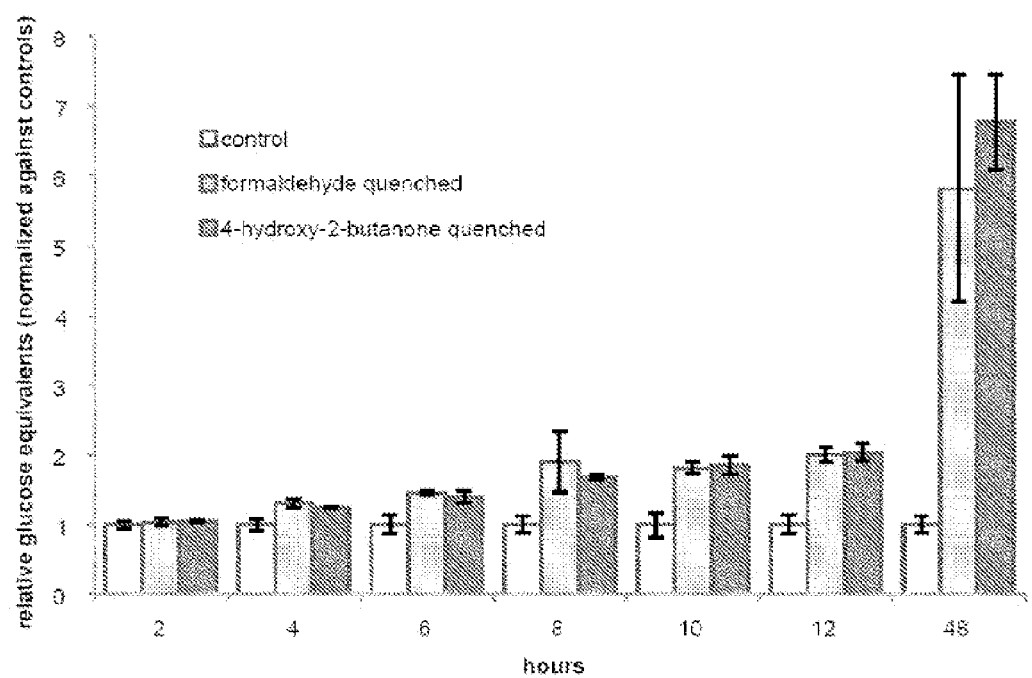
FIG. 8B is a graph showing the hydrolytic activity of EGPh over 48 hours in the presence of a formaldehyde-quenched NIPAm copolymer and a 4-hydroxy-2-butanone quenched NIPAm.

A time course was conducted with either formaldehyde or 4-hydroxy-2-butanone quenched NIPAm copolymer. With reference to FIG. 8B, this time-course study showed a gradual increase of soluble reducing sugars in the supernatant over time.

Figure 8C:
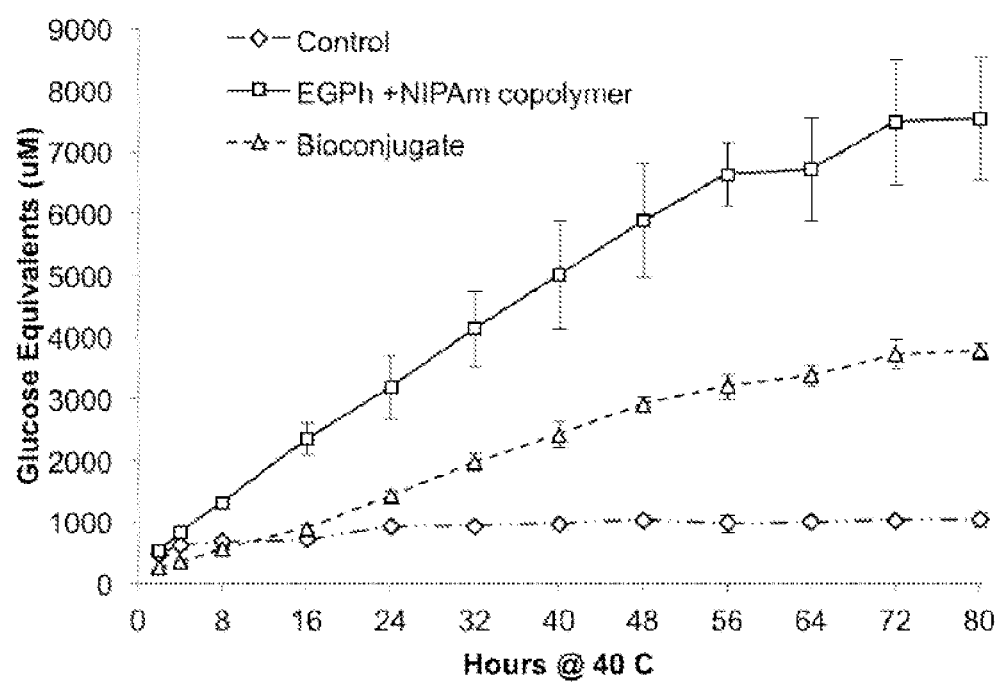
FIG. 8C is a graph showing a time-course experiment to compare the activity of free EGPh in the presence of mannose quenched poly(aminooxy methacrylamide-co-NIPAm) with the activity of EGPh-copolymer bioconjugate (in the presence of added free copolymer for a total of 2 mg/ml polymer) on Avicel substrate.
Figure 8D:
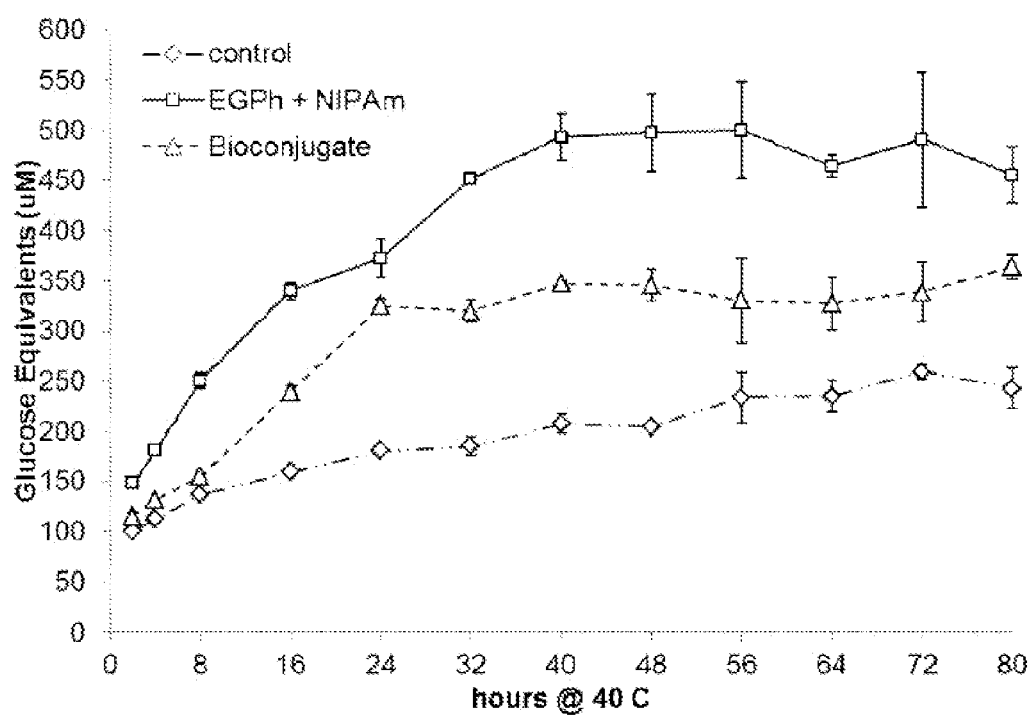
FIG. 8D is a graph showing a time-course experiment to compare the activity of free EGPh in the presence of mannose quenched poly(aminooxy methacrylamide-co-NIPAm) with the activity of EGPh-copolymer bioconjugate (in the presence of added free copolymer for a total of 2 mg/ml polymer) on steam pre-treated *Miscanthus giganteus* substrate.

Additional time courses were conducted to compare the activity of unmodified *Pyrococcus horikoshii* endoglucanase (EGHPh) in the presence of free NIPAm copolymer (12% mannose-quenched aminooxy comonomer) with the activity of the EGPh-copolymer bioconjugate (in the presence of added free copolymer for a total of 2 mg/ml polymer) using either Avicel (FIG. 8C) or acid and steam pretreated *Miscanthus giganteus* (FIG. 8D) substrates. With reference to both FIGS. 8C and 8D, the time-course study showed more rapid production and higher plateau levels of reducing sugars by the combination of free enzyme and copolymer relative to the bioconjugate when using either Avicel (FIG. 8C) or *Miscanthus* substrates (FIG. 8D).

Figure 8E:
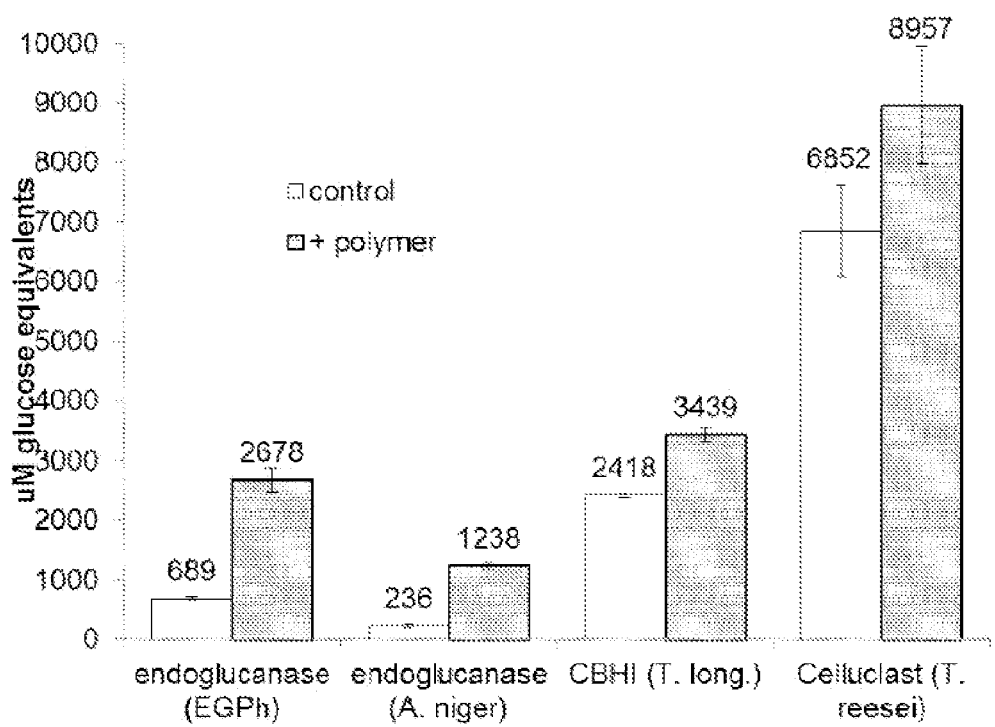
FIG. 8E is a graph showing the effect of NIPAm copolymer on cellulases derived from different organisms, including endoglucanase EGPh from *Pyrococcus horikoshii*, endoglucanase from *Aspergillus niger*, CBHI from *Trichoderma longibrachiatum*, and Celluclast from *Trichoderma reesei*, to hydrolyze Avicel, a cellulosic substrate.
Figure 8F:
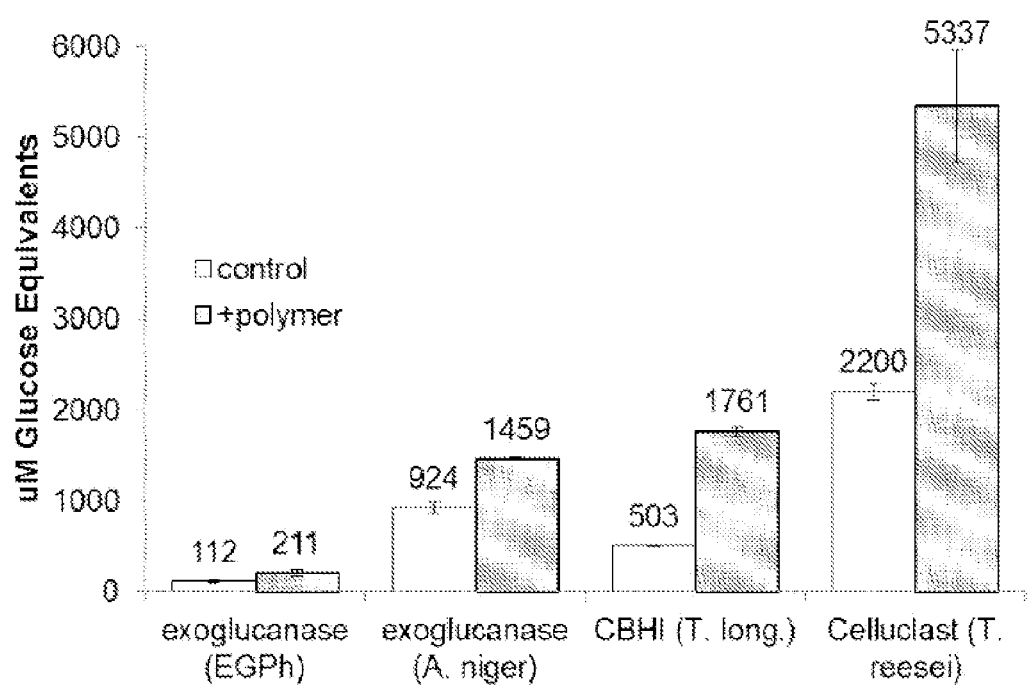
FIG. 8F is a graph showing the effect of NIPAm copolymer on the ability of the cellulases described in FIG. 8E above to hydrolyze acid and steam pre-treated *Miscanthus giganteus*, a lignocellulosic substrate.

Breadth of Copolymer Effect on Cellulases of Various Origins and with Different Activities The effect of NIPAm copolymer was tested on cellulases derived from a range of different organisms and on enzymes producing cellulose through different actions, including endoglucanase EGPh from *Pyrococcus horikoshii*, endoglucanase from *Aspergillus niger*, CBHI from *Trichoderma longibrachiatum*, and celluclast from *Trichoderma reesei*. With reference to FIGS. 8E and 8F, this test showed that NIPAm copolymers consistently improve the yield of reducing sugars from these cellulases with respect to both cellulosic substrates (FIG. 8E) and lignocellulosic substrates (FIG. 8F). In these tests, copolymers were composed of 8% aminooxy comonomer and quenched with mannose. Endoglucanase from *Pyrococcus horikoshii* (EGPh), purified endoglucanase from *Aspergillus niger*, or purified CBHI from *Trichoderma longibrachiatum* were included at 0.2 μM; Celluclast 1.5 L, the commercial cellulase mixture from *Trichoderma reesei* was included at 0.02 mg/mL.

Rescue Assay

A series of rescue assays were performed to determine whether the activity enhancements observed for enzyme-copolymer combinations were mediated by enzyme-copolymer interactions or substrate-copolymer interactions.

In these rescue assays, each set of samples (600 μL) was incubated for 12 h at 40° C., at which time an aliquot (100 mL) was removed to measure reducing sugars. Next, enzyme or copolymer was added to some reactions and all were allowed to incubate for another 12 h. The experimental conditions for the respective samples were: 1) protein control, only 0.2 μM EGPh over the entire 24 h incubation period; 2) copolymer effect control, 0.2 μM EGPh and 0.2% copolymer over the entire 24 h incubation period; 3) 0.2 μM EGPh over the entire 24 h incubation period, 0.2% copolymer was added at t=12 h to determine if the enzyme activity could be "rescued"; and 4) 0.2% copolymer over the entire 24 h incubation period, 0.2 μM EGPh was added at t=12 h to determining if just the interaction of the copolymer and substrate was increasing effective protein activity.

Figure 10A:
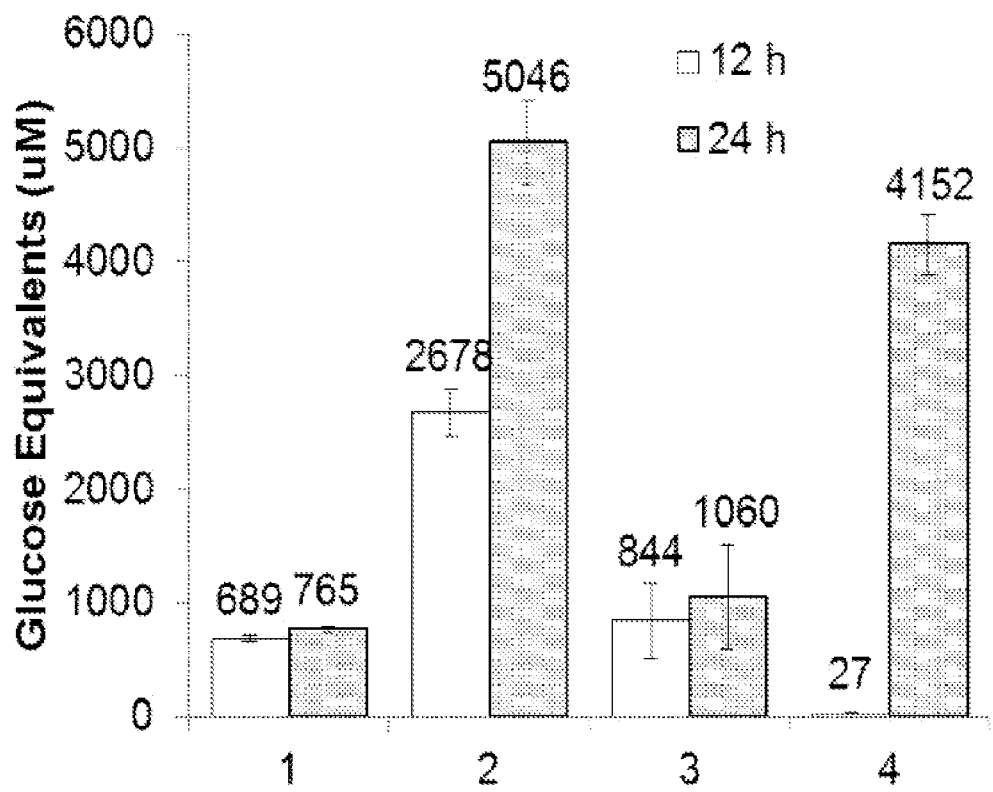
FIG. 10A is a graph showing a rescue experiment comparing EGPh enzyme activities under conditions where the enzyme was either incubated in the absence of copolymer and substrate for 24 h (sample 1), where the enzyme was incubated with substrate and copolymer throughout the entire 24 h reaction time (sample 2), where the enzyme was first incubated for 12 h in the absence of copolymer and then incubated in the presence of copolymer for another 12 h (sample 3), and where the copolymer was first incubated in the absence of enzyme for 12 h and then coincubated with enzyme for another 12 h (sample 4). In samples 1-4 substrate was provided throughout the entire 24 h reaction period.

With reference to FIG. 10A the rescue assays reproduced the enzyme activity enhancing effect of free copolymer under conditions where the copolymer was present throughout the entire incubation time (compare sample 2 to sample 1). Adding the copolymer only at the 12 h timepoint did not rescue the enzyme activity (see sample 3). Adding enzyme after the copolymer was preincubated for a 12 h period resulted in substantial production of reducing sugars after another 12 h incubation period.

Polymer Effect on Higher EGPh Loadings

To determine if the enzyme activity enhancing effect of the copolymer is protein-concentration dependent, enzyme activation was tested at different protein concentrations.

Figure 10B:
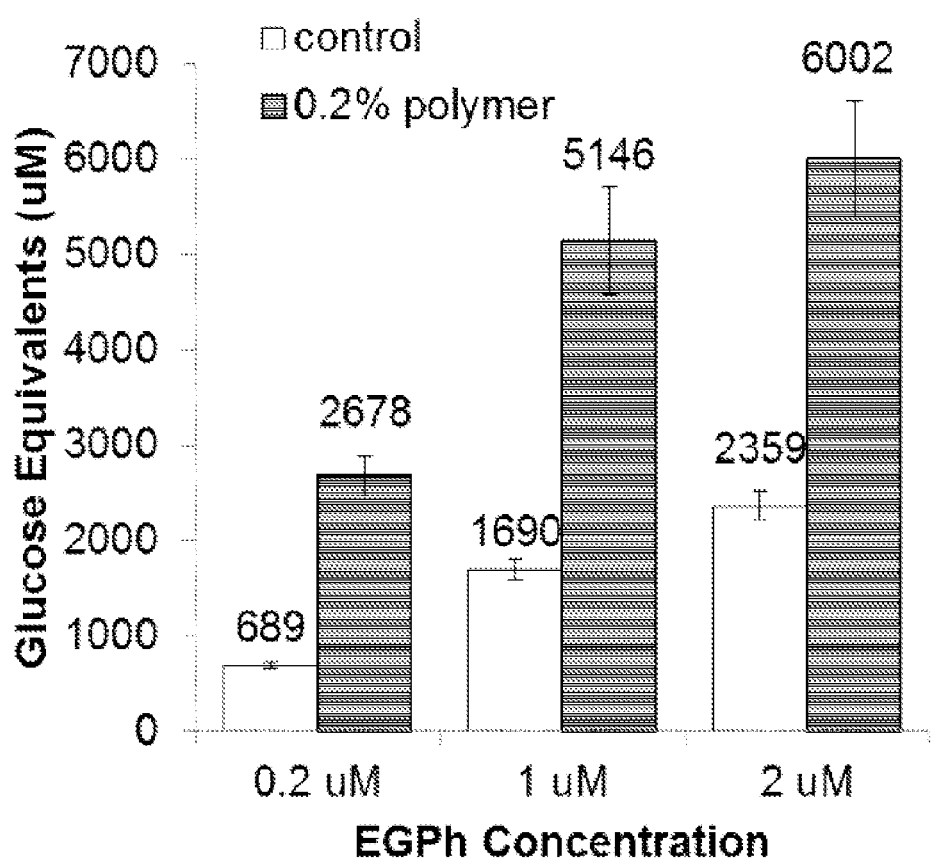
FIG. 10B is a graph showing the effect of NIPAm mediated EGPh activation at different enzyme concentrations.

With reference to FIG. 10B, this study showed that the copolymer mediated enzyme activity enhancement was 3.9 fold at an enzyme concentration of 0.2 μM, 3.0-fold at 1 μM enzyme, and 2.5-fold at 2 μM enzyme.

Polymer Effect on Celluclast Over Time

To determine if a time-dependent polymer effect can be observed with commercial cellulase mixtures a time course study was conducted using Celluclast on an Avicel substrate.

Figure 10C:
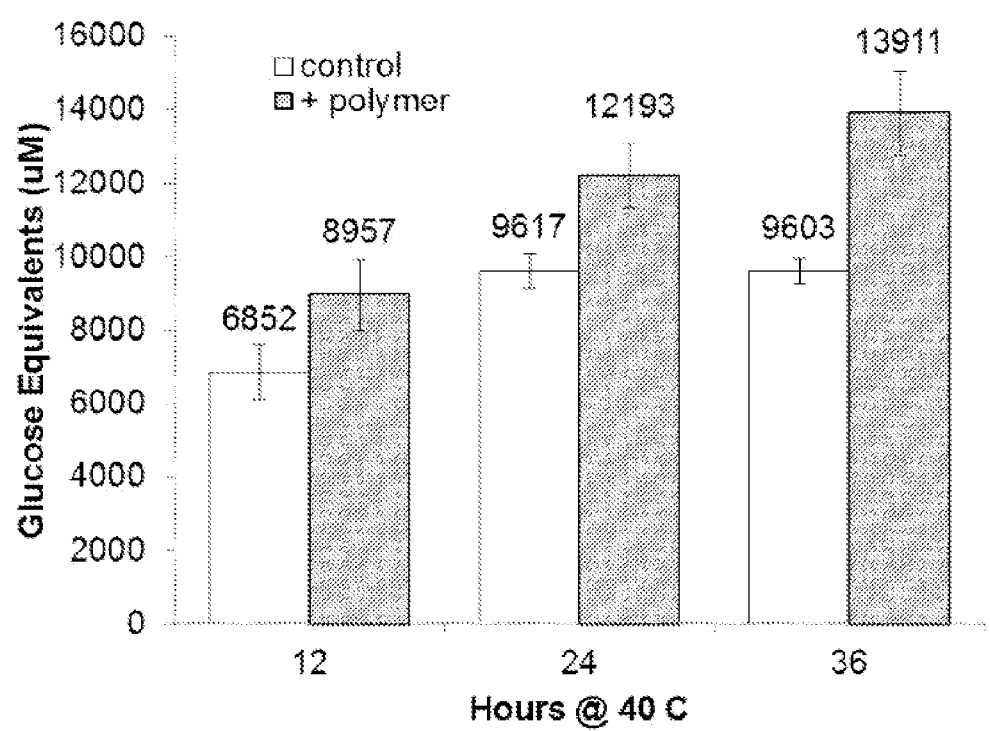
FIG. 10C is a graph showing the effect of NIPAm on Celluclast activity over time.

With reference to FIG. 10C, 1.3-fold copolymer activation of Celluclast was found after 12 h and 24 h incubation periods, whereas 1.4-fold copolymer activation was found after a 36 hour incubation period.

Pretreating Avicel with Copolymer

To determine if increasing the duration of "pretreatment" of Avicel with copolymer produces time-dependent increases in apparent enzyme activity an additional time-course study was performed.

In this study, Avicel was incubated with copolymer for 0, 12, 24, or 36 hours at 40° C. and kept stirring; then EGPh was added to 0.2 μM and free reducing sugars were measured 12 hours later. As a control, Avicel was incubated for 36 hours at 40° C. in the absence of polymer prior to EGPh addition.

Figure 10D:
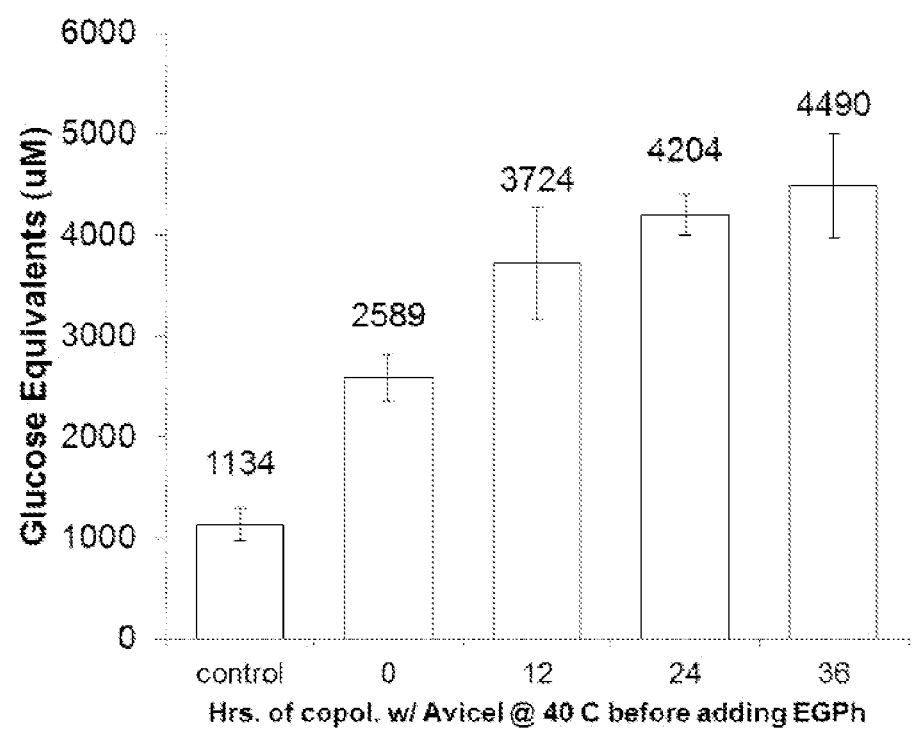
FIG. 10D is a graph showing the time-dependent effect of Avicel pretreatment with NIPAm on EGPh enzyme activities.

With reference to FIG. 10D, the graph shows gradually increasing enzyme activity as the preincubation period is increased from 0 h to 12 h, 24 h, and 36 h.

Effect of Polymer Charge on EGPh Activity

To determine how polymer charges affect enzyme activation, the effects of negatively charged polymers, positively charged polymers, and neutral polymers were compared.

To this end, charged polymers were made from the same copolymer base as for the mannose-quenched polymer used in the other assays, but the copolymer base was quenched with 2-formyl benzene sulfonic acid (CAS 1008-72-6) or Rappoport's salt (4-formyl-1-methylpyridinium benzenesulfonate, CAS 82228-89-5) to make negatively and positively charged copolymers, respectively. The assay was repeated to confirm results. The repeat assay included a neutral copolymer control (mannose-quenched copolymer). The pI of EGPh is estimated to be about 5.85; at pH 4.5 it is positively charged.

Figure 10E:
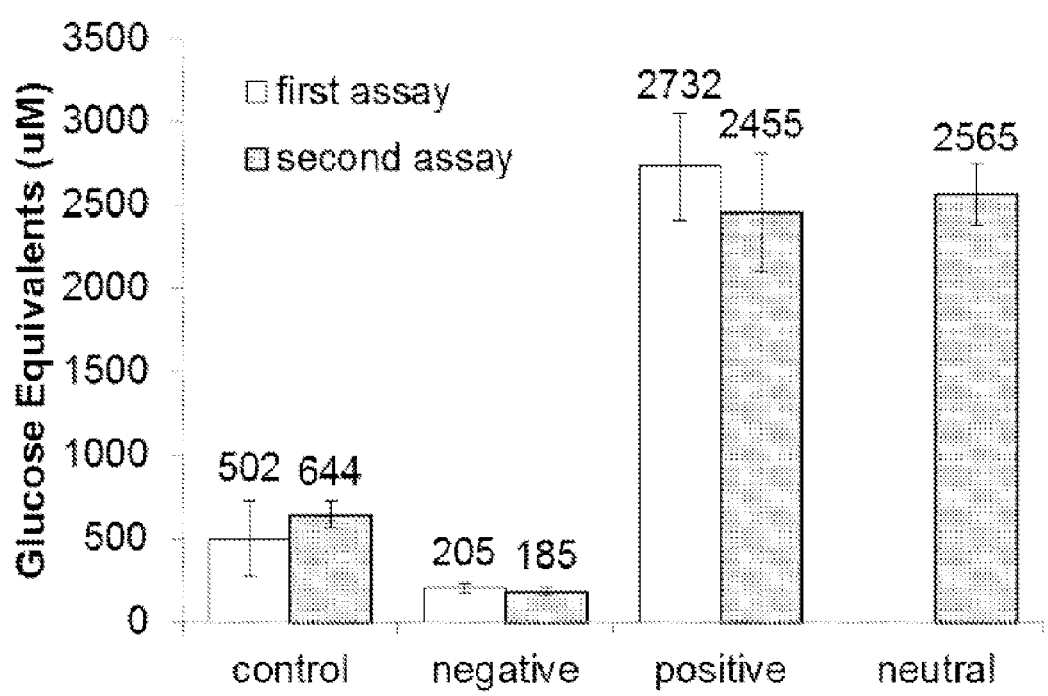
FIG. 10E is a graph showing the effect of polymer charges on EGPh activity against Avicel as a substrate.

With reference to FIG. 10E, the graph shows that the addition of negatively charged copolymer resulted in lower enzyme activity than the control, whereas addition of positively charged or neutral copolymers resulted in higher enzyme activities compared to the control reaction.

Effect of Copolymer in the Presence of Other Additives

To determine if the activity enhancement from the copolymer is occurring through the same mechanism as that observed for other additives or through a different mechanism, enzyme activities were compared in the presence of either copolymer, other additives, including BSA and Tween, or in the presence of combinations of copolymers and other additives.

Assays were carried out under standard conditions, but instead of adding polymer, bovine serum albumin (BSA, desalted before use) and the surfactant Tween 20 were added at a final concentration of 2 mg/mL. To determine if the copolymer acted through a different mechanism, samples were also prepared with either 1 mg/mL BSA or Tween 20 and 1 mg/mL of the copolymer, for a total additive loading of 2 mg/mL. The total loading was kept at 2 mg/mL for all samples to be sure that any increase in activity was not due to an increase in total additive. The experimental series was conducted using either Avicel or *Miscanthus* as a substrate.

Figure 10F:
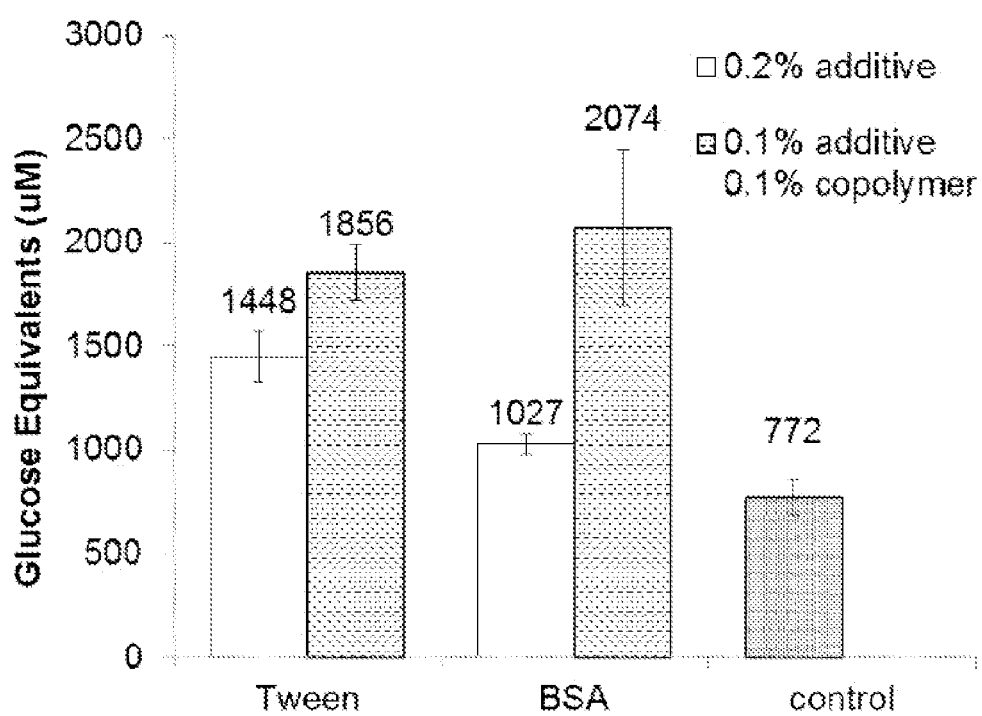
FIG. 10F is a graph showing the effect of NIPAm on EGPh activity in the presence of other additives using Avicel as a substrate.

With reference to FIG. 10F, the graph shows that when using Avicel as a substrate, the addition of Tween and BSA alone increased the enzyme activities relative to the control reaction. Combining additives with the copolymer increased the enzyme activity even further than adding additives alone.

Figure 10G:
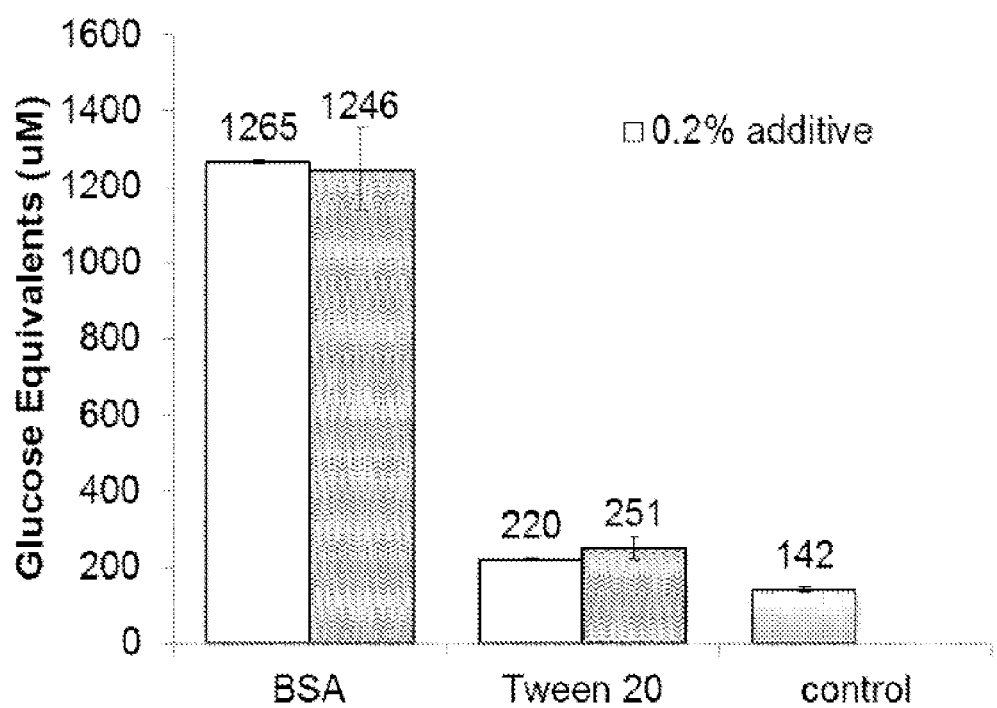
FIG. 10G is a graph showing the effect of NIPAm on EGPh activity in the presence of other additives using acid and steam pre-treated *Miscanthus giganteus* as a substrate.

With reference to FIG. 10G, the graph shows that when using *Miscanthus* as a substrate, the addition of BSA and Tween 20 to the enzyme reaction increases the enzyme activity. Combining additives with copolymer does not result in further increases of enzyme activities over additives alone.

Effect of Similar Polymers

To determine if polymers with a similar structure to the NIPAm copolymer mediate similar enhancement effect on a lignocellulosic substrate and to help determine what functional groups of the NIPAM copolymer are necessary for enhanced activity a study was conducted using a range of different polymers.

In this study, two polymers were included with very similar structures to the standard NIPAm copolymer. Poly (NIPAm), was included, which did not contain any aminooxy comonomer. Poly(acrylamide) was included, which is identical to NIPAm but does not contain the N-isopropyl group. The p(NIPAm) was synthesized under the same conditions used to make the NIPAm copolymer; Mn 49,575 Da; Mw 155,535; PDI 3.14. The p(acrylamide) was from Polysciences, Inc., ~Mw 1,000,000 Da; PDI ~2.5; it was washed with water before use. The substrate was acid and steam pretreated *Miscanthus*; the assay temperature was lowered to 28 C to keep all additives soluble (the LCST of pNIPAm is 32° C.). The experiment was repeated using Avicel as a substrate; in this experiment the assay temperature was lowered to 28 C.

Figure 10H:
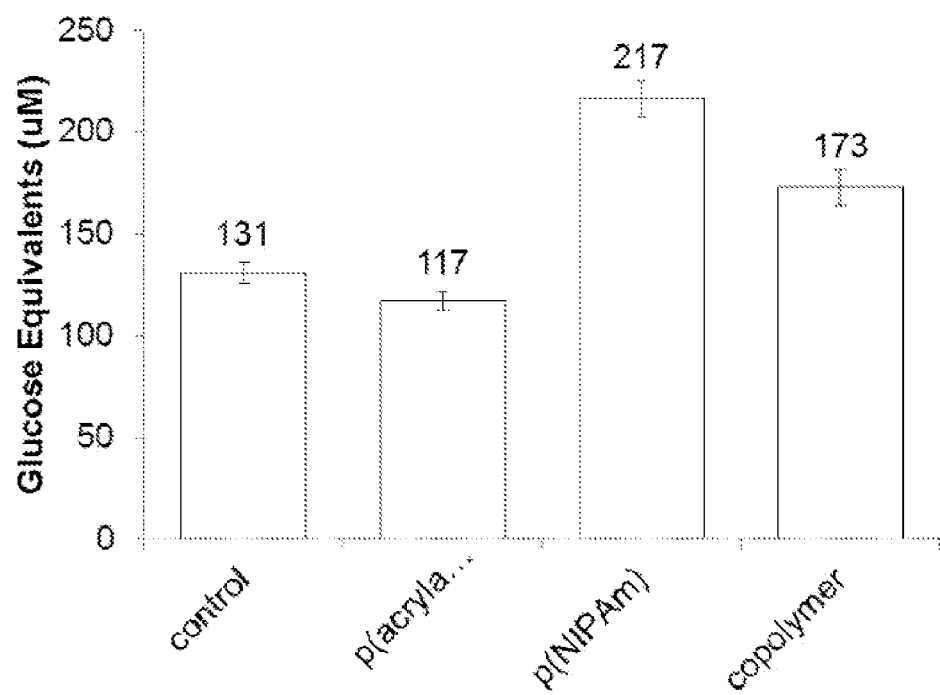
FIG. 10H is a graph comparing the effect of different polymers, including poly(acrylamide), NIPAm, and NIPAm lacking aminooxy comonomers, on EGPh activity using acid and steam pre-treated *Miscanthus giganteus* as a substrate.

With reference to FIG. 10H, the graph shows that when using *Miscanthus* as a substrate, poly(acrylamide) did not mediate increased enzyme activities compared to the control reaction, whereas the addition of either the standard NIPAm copolymer or the NIPAm polymer lacking the aminooxy comonomers resulted in increased levels of enzyme activation.

Figure 10I:
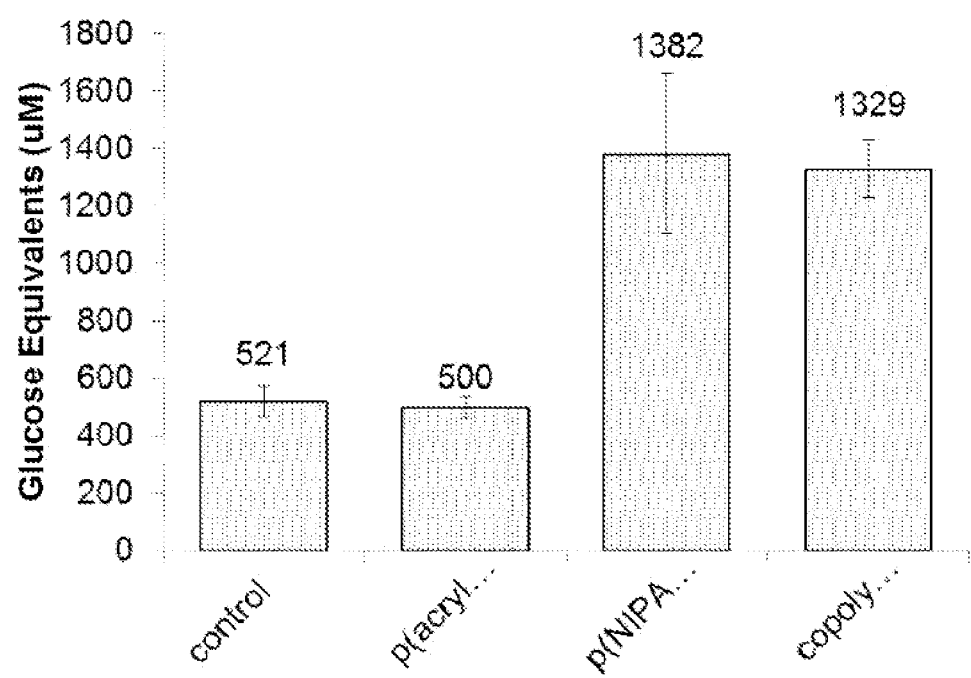
FIG. 10I is a graph comparing the effects of different polymers, including poly(acrylamide), NIPAm, and NIPAm lacking aminooxy comonomers, on EGPh activity using Avicel as a substrate.

With reference to FIG. 10I, the graph shows that when using Avicel as a substrate, poly(acrylamide) did not mediate increased enzyme activities compared to the control reaction, whereas the addition of either the standard NIPAm copolymer or the NIPAm polymer lacking the aminooxy comonomers resulted in comparable increases in enzyme activities.

Effect of Additives on EGPh Endoglucanase Activity

To determine whether additives such as BSA, PEG, Tween 20, or the NIPAm copolymer have a direct effect on the endoglucanase activity of EGPh (e.g., by changing the substrate turnover rate of the enzyme) or whether the copolymer is increasing activity through a different mechanism (e.g., decreasing nonspecific binding, increasing access to amorphous regions, etc.) a series of azo-CMC experiments were conducted.

Azo-CMC assays involve the use of dye-impregnated carboxymethyl cellulose (CMC) as the substrate. CMC is a specific soluble substrate of endoglucanases. When incubated with an endoglucanase, low molecular weight dyed fragments are released. A precipitant solution is added, all the high MW fragments are cleared from the solution by centrifugation, the color of the supernatant is measured using a UV-Vis spectrophotometer, and enzyme activity is determined by comparison with a standard curve. For the following sets of data a standard curve was prepared in triplicate using known quantities of EGPh. From this standard curve, the EGPh activity of each experimental sample was calculated in uM.

CMC assays were conducted according to manufacturer's instructions (Megazyme, Inc.), but decreasing the assay volume to 100 uL. 1 mg/mL azo-CMC, 75 mM sodium acetate pH 4.5, standard curve consisted of 4 concentrations of EGPh and a 0 µM value. In general, 50 µL of a 2× azo-CMC solution was added to 50 µL of each experimental sample and allowed to react at 40 C for 60-90 minutes (all samples/stds from the same data set reacted for the same amount of time). After addition of 250 µL of the precipitant solution (80% ethanol, some zinc, sodium acetate, pH 5) and centrifugation, 200 uL of the supernatant was transferred to a 96-well plate and absorbance of all samples at 590 nm was measured using a plate reader.

Additives were included in the 100 uL azo-CMC incubation along with 0.2 µM EGPh. BSA was desalted at 4.7 mg/mL and only two replicates are shown; PEG 20K, Tween 20, and mannose-quenched NIPAm copolymer at 2 mg/mL with three replicates. The control referenced in the data corresponds to the 0.2 µM replicates from the standard curve.

Figure 10J:
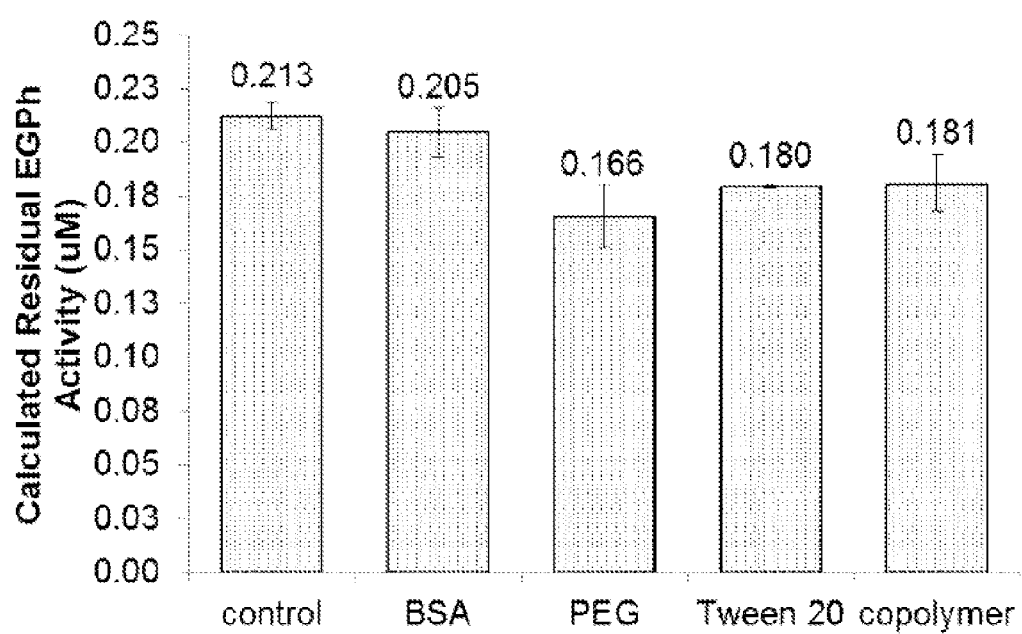
FIG. 10J is a graph showing the effect of additives on EGPh endoglucanase activity as measured in an azo-CMC assay.

With reference to FIG. 10J, the graph shows that BSA does not significantly affect the enzyme activity, whereas the addition of PEG lowers the enzyme activity by >20%, whereas Tween 20 and the NIPAm copolymer lower the enzyme activity by about 15%.

Residual Activity of EGPh in Supernatant after 12 h w/ Avicel and Additives

A study was conducted to determine the residual activity of EGPh in cleared supernatants of Avicel assays, in the presence or absence of additives. This study was further conducted to determine how much EGPh is nonspecifically bound to the Avicel substrate or otherwise inactivated under standard assay conditions.

The standard Avicel conditions were followed as outlined previously, using 0.8 µM EGPh (instead of 0.2 µM). Additives were included in those assays at a concentration of 2 mg/mL; PEG 20k, Tween 20, desalted BSA, and mannose-quenched NIPAm copolymer were used. After a 12 h incubation at 40° C., 50 µL of the cleared supernatant from each experimental replicate was added to 50 µL 2× azo-CMC and the azo-CMC procedure followed to measure residual activity. The control referenced in the data is a 0.8 µM EGPh-only control from the Avicel assay. Each Avicel experimental replicate was measured with one azo-CMC reading.

Figure 10K:
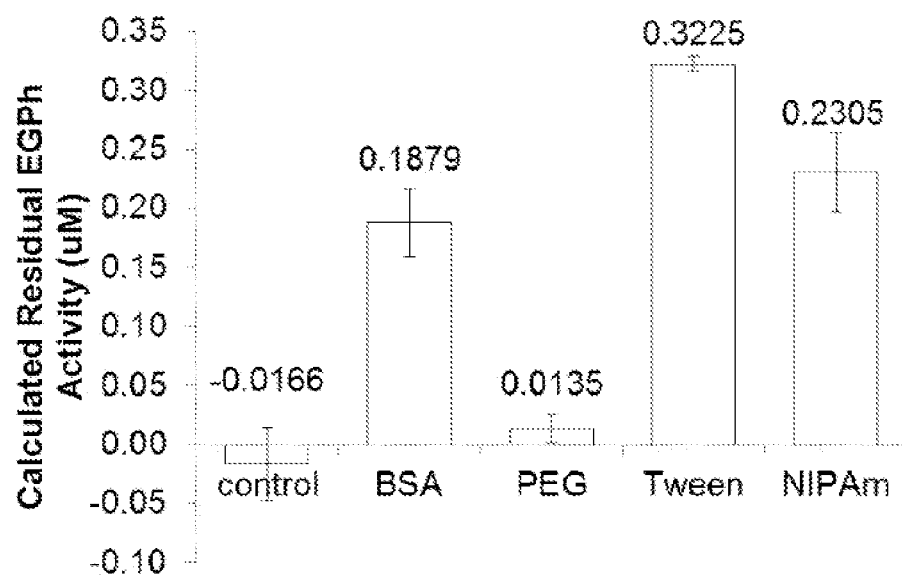
FIG. 10K is a graph showing the residual activity of EGPh in supernatants following a 12*h* incubation w/ Avicel and additives as measured in azo-CMC assays.

With reference to FIG. 10K, the graph shows that no residual enzyme activity remains in assays conducted in the presence of PEG, whereas substantial enzyme activity remains if assays are conducted in the presence of BSA, Tween 20, or the NIPAm copolymer.

Example 11

LCST Tuning of NIPAm or NIPMa Copolymers

The copolymers used in this Example were made up of 8-9% aminooxy-bearing monomer residues and the remainder N-isopropylacrylamide (NIPAm) or N-isopropylmethacrylamide (NIPMa). These copolymers were synthesized according to the procedure set forth in Example 1 above. Using these two copolymers and six different small molecules (acetone, formaldehyde, mannose, dextrose, 4-hydroxy-2-butanone, 3-fluoroisonicotinaldehyde), the polymers were modified according to the procedure of Example 2 above to achieve materials with LCSTs ranging from 20° C. to 60° C.

Figure 9A:
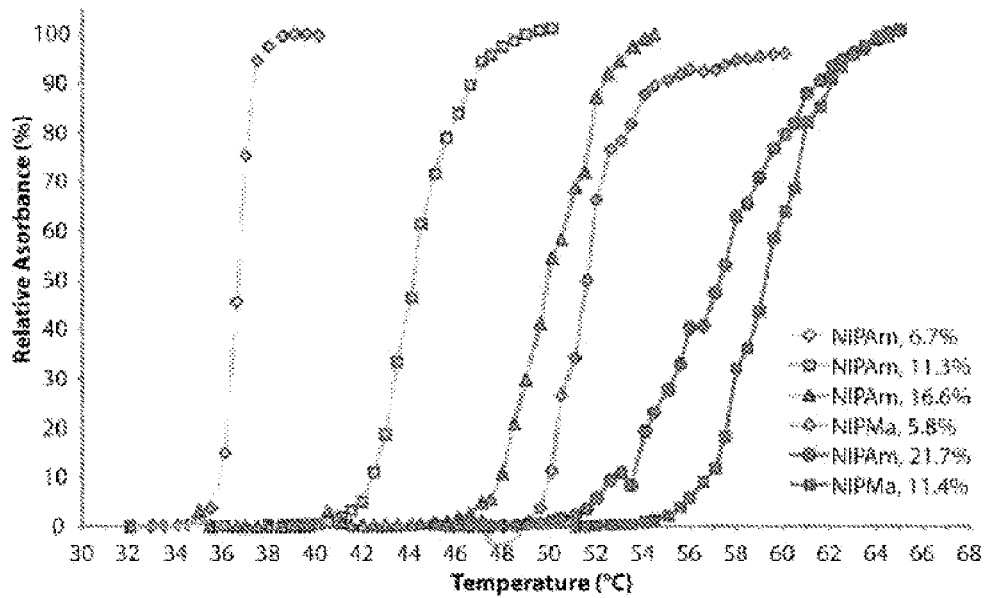
FIG. 9A is a graph of LCST measurements for NIPAm and NIPMa copolymers with varying amounts of aminooxy-bearing monomer residues.
Figure 9B:
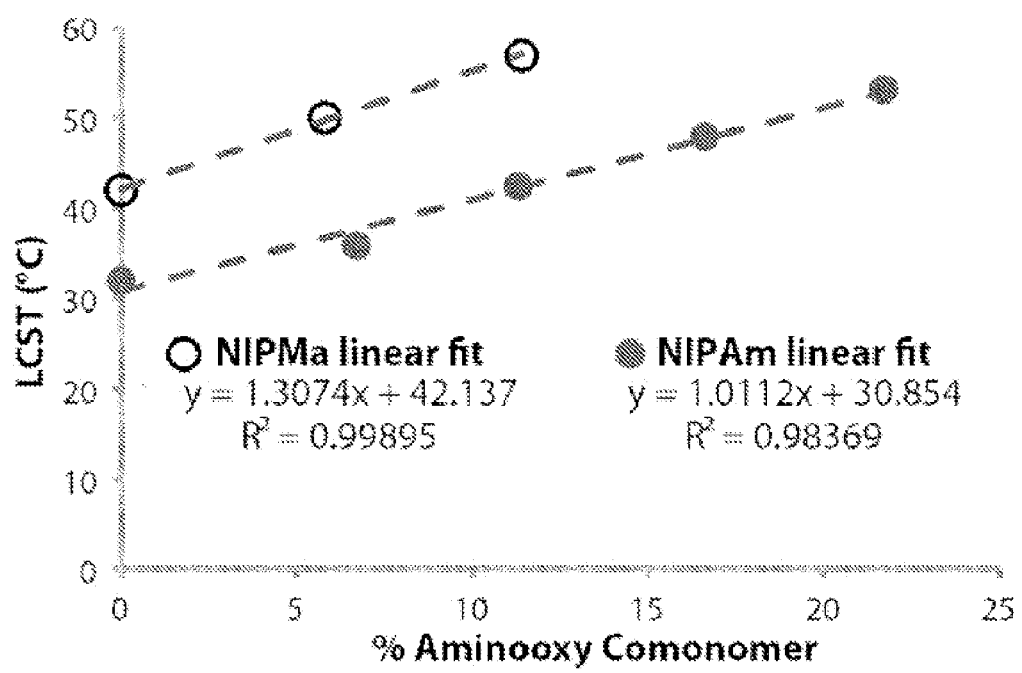
FIG. 9B is a plot of the NIPAm and NIPMa copolymer LCSTs against the mole percent of aminooxy-bearing monomer residues.

Copolymers were made with NIPAm and 6.7, 11.3, 16.6, and 21.7% aminooxy methacrylamide, and with NIPMa and 5.8 and 11.4% aminooxy methacrylamide. The LCSTs of these copolymers were measured as described in Example 3 above. By incorporating increasing amounts of aminooxy-bearing monomer residues, NIPAm copolymers were obtained with LCSTs as high as 53.1° C. For NIPMa copolymers, LCSTs of up to 56.9° C. were obtained (FIG. 9A). When the LCST of these copolymers was plotted against the mole percent of aminooxy-bearing monomer residue included, the data followed a linear fit closely (FIG. 9B).

General Procedures and Materials for Examples 12-18

Materials: Unless otherwise noted, all chemicals and solvents used were of analytical grade and were used as received from commercial sources. Analytical thin layer chromatography (TLC) was performed on EM Reagent 0.25 mm silica gel 60-$F_{254}$ plates with visualization by ultraviolet (UV) irradiation at 254 nm, ninhydrin, or potassium permanganate stain. Purifications by flash chromatography were performed using EM silica gel 60 (230-400 mesh). The eluting system for purification was determined by TLC. Room temperature and 4° C. centrifugations were conducted either with a Sorvall RC 5C (Sorvall, USA) Plus for samples greater than 50 mL, a Sorvall LEGEND Mach 1.6R for samples between 1 and 50 mL, or an Eppendorf Mini Spin Plus for samples less than 1 mL (Eppendorf, USA). Centrifugations above room temperature were performed on a Hettich Rotofix 46 H (GMI, Ramsey, Minn.). Samples were lyophilized using a LAB CONCO FreeZone 1 L (Lab Conco, USA). Regular scale UV-Vis spectroscopic measurements were conducted in a Varian Cary 50 spectrophotometer (Agilent, USA). Absorbance and fluorescence measurements of samples in 96 well plates were obtained on a SpectraMax M2 (Molecular Devices, Sunnyvale, Calif.).

Gel Permeation Chromatography (GPC): GPC was performed on a Waters system, including a Waters 515 pump, Waters 717 autosampler, and Waters 2414 differential refractive index (RI) detector. SEC was performed at 1.0 mL/min in a PLgel Mixed B (10 µm) and a PLgel Mixed C (5 µm) column (Polymer Laboratories, both 300×7.5 mm), in that order, using a mobile phase of DMF with 0.2% LiBr and linear PMMA (690-194,400 MW) as the calibration standards. The columns were kept at 70° C.

Synthesis of Poly(NIPAm-Co-MEPO) (S1): This was synthesized multiple times following a previously reported procedure on a 2 g scale. Analysis of the $^1$H-NMR spectrum showed the molar ratio of MEPO:NIPAm to be from 1:10.2 to 1:11.3 depending on the batch, or 8.1-8.9% incorporation of MEPO. GPC analysis using PMMA standards indicated the batches were of similar mass distribution, approximately $M_n$=68,300, $M_w$=163,000, and PDI=2.4.

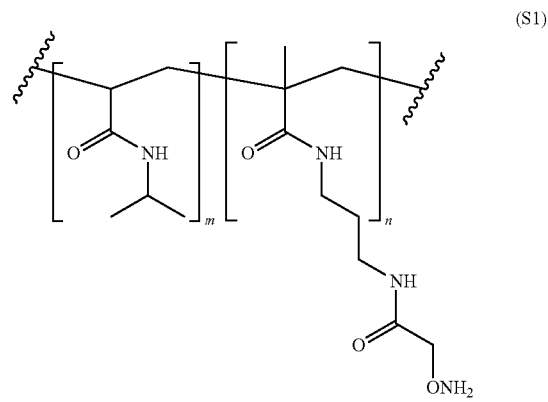

(S1)

Small-Molecule Modification of (S1): Solutions of 10 mg/mL of (S1) and 60 mM of acetone, formaldehyde, or 4-hydroxy butanone, or 600 mM mannose in 50 mM NaOAc (pH 4.5) were reacted for 24 h at room temperature. Unreacted small molecules were removed and the modified polymer buffer exchanged into pure water through 8 rounds of ultrafiltration (10 kDa MWCO). The polymers were lyophilized and analyzed by NMR spectrometry to confirm modification of all aminooxy groups.

Expression and Purification of EGPh: The endoglucanase from *Pyrococcus horikoshii* (EGPh) was expressed and purified according to the procedure set forth in Example 4 above.

Preparation of *Miscanthus*: *Miscanthus giganteus* was cut into approximately 1-inch pieces, then subjected to acid pretreatment at 25% biomass loading with 1.5% (w/w) sulfuric acid at 190° C. for approximately 1 min. After a subsequent steam explosion step the solids were pressed to remove liquids, then washed extensively with deionized water until the filtrate had no detectable glucose and neutral pH. The solids were dried for 24 h at 104° C., ground into a fine powder with a mortar and pestle, then stored at room temperature until use.

Other Additives: The homopolymer of NIPAm was prepared following the procedure set forth above, at ⅕ the scale and without MEPO. GPC analysis using PMMA standards indicated $M_n$=49,575, $M_w$=155,535, PDI=3.1. Bovine Serum Albumin (BSA) was desalted before use. Poly(ethylene glycol) (PEG) ($M_n$=20k; Sigma-Aldrich) and poly (acrylamide) ($M_w$=1,000 k; Polysciences, Inc.) were washed extensively with deionized water before use. Tween 20 was used as received.

Other Enzymes: Celluclast was obtained from Sigma-Aldrich and desalted before use. An endoglucanase from *Aspergillus niger* and cellobiohydrolase I (CBHI) from *Trichoderma longibrachiatum* were obtained from Megazyme International (Bray, Ireland) and used as received.

EGPh Activity Assays: All assays were performed in triplicate. Unless otherwise indicated, assays were performed in 1.3 mL Eppendorf tubes on a 0.5 mL scale, in 50 mM NaOAc (pH 4.5), with 1% (w/v) Avicel pH 101 microcrystalline cellulose (Sigma-Aldrich) or acid-pretreated and steam-exploded *Miscanthus*, 0.2 µM EGPh, for 12 h in a 40° C. water bath. Mannose-modified (S1) was included at 2 mg/mL unless otherwise stated, and was allowed to mix thoroughly with the substrate before addition of enzyme. Controls contained no additive. After 12 h, the tubes were centrifuged at 13.2k rpm for two 5 min intervals, with a 180° rotation in between. An aliquot of the clarified supernatant was transferred to a 0.6 mL Eppendorf tube and frozen on dry ice, then stored at −20° C. until soluble reducing sugar was quantified. For time-point experiments, the total volume of each sample was 1.3 mL, with identical concentrations as indicated above. At each indicated time point, the reaction tubes were removed from the water bath, shaken to ensure even distribution of the contents, a 100 µL aliquot was transferred to a clean, empty Eppendorf tube, and the reaction tube returned to the water bath. The removed aliquot was centrifuged for 10 min at 13.3k rpm and the clarified supernatant was transferred to a new tube and frozen until later analysis.

Soluble Reducing Sugar Analysis: Substrate hydrolysis was determined by measuring soluble reducing sugar following a previously reported method, using the paired glucose oxidase-horseradish peroxidase assay with OxiRed as the fluoregenic substrate.1 All samples were measured in triplicate using clear-bottom plastic 96-well plates, with an internal standard curve of 250, 200, 150, 100, 50, and 0 µM glucose. Samples of 100 and 50 µM cellobiose were also included to confirm full hydrolysis to glucose. Frozen aliquots from activity assays were thawed on ice and diluted with pH 4.5 buffer, then 8 uL aliquots were mixed with 8 uL of β-glucosidase (5 mg/mL in 10 mM NaOAc pH 4.6) in a 96-well plate and incubated at 37° C. for 60 minutes to fully hydrolyze any soluble oligosaccharides. Glucose was then quantified by adding 65 µL of glucose oxidase (1.25 U/mL), horseradish peroxidase (1.25 U/mL), and OxiRed (60 µM) in 125 mM phosphate buffer (pH 7.45) and incubating at rt for 15 min in the dark. The amount of Resorufin formed was measured on an optical plate reader with excitation at 535 nm and emission detection at 590 nm, and the value corresponded to the quantity of glucose present. The internal standards were used to make linear standard curves for each plate (r2>0.98) which were used to calculate the glucose equivalents present in each well. The triplicate measurements of each supernatant sample were averaged, then the values of the triplicate assay samples were averaged to calculate each data point.

HPLC: Analysis of glucose, cellobiose, and cellotriose was performed for a range of enzymes assayed on Avicel. Samples of cleared supernatant were filtered through 0.45 µM PTFE filters, then injected onto a 3×250 mm PA200 column (Dionex, now Thermo Fisher Scientific) with a guard column (3×50 mm) of the same material and analyzed using a ICS-3000 chromatography system (Dionex). Compounds were eluted at 30° C. with a flow rate of 0.4 mL/min and mobile phase buffer A (0.1 M NaOH) and buffer B (0.1 M NaOH, 1 M NaOAc) with the following gradient: in 25 min from 0% B to 13.4% B, then in 0.1 min to 30% B, 2.9 min isocratic, then 0% B for 7 min. Compounds were detected using pulsedamperometric detection with the carbohydrate standard 4-potential waveform. Glucose, cellobiose (Sigma), and cellotriose (Seikagaku Biobusiness, Tokyo, Japan) standards were used for calibration. The results of this analysis are shown in Table 1 below.

TABLE 1

HPLC analysis of enzymes assayed on Avicel

| | | glucose | | cellobiose | | cellotriose | | | as a % of total glucose equivalents | | | glucose equivalents |
|---|---|---|---|---|---|---|---|---|---|---|---|---|
| copol. | | avg. | std. dev. | avg. | std. dev. | avg. | std. dev. | total | glucose | cellobiose | cellotriose | from OxiRed |
| EGPh | − | 49.9 | 1.2 | 562.2 | 42.0 | 104.7 | 7.7 | 717 | 7.0% | 78.4% | 14.6% | 689 |
|  | + | 356.9 | 5.5 | 2716.3 | 47.4 | 134.5 | 21.2 | 3208 | 11.1% | 84.7% | 4.2% | 2678 |
| A. niger | − | 16.6 | 3.8 | 114.1 | 8.8 | 135.7 | 25.4 | 266 | 6.2% | 42.8% | 50.9% | 236 |
|  | + | 211.0 | 1.9 | 626.8 | 48.3 | 820.9 | 31.8 | 1659 | 12.7% | 37.8% | 49.5% | 1238 |
| T. long. | − | 108.7 | 5.8 | 2493.5 | 69.6 | 142.5 | 6.9 | 2745 | 4.0% | 90.8% | 5.2% | 2418 |
|  | + | 296.4 | 9.5 | 3450.1 | 136.9 | 181.1 | 13.9 | 3928 | 7.5% | 87.8% | 4.6% | 3439 |
| Celluclast | − | 823.6 | 11.8 | 6718.4 | 90.5 | 75.3 | 14.8 | 7617 | 10.8% | 88.2% | 1.0% | 6852 |
|  | + | 1606.3 | 111.6 | 7801.5 | 746.8 | 120.4 | 9.6 | 9528 | 16.9% | 81.9% | 1.3% | 8957 |

Residual EGPh Activity Measurements: Residual endoglucanase activity of EGPh in cleared supernatant was measured using azo-carboxymethyl cellulose (azo-CMC) (Megazyme International, Ireland), generally following the supplier's instructions. To measure residual activity after incubation in contact with air, hydrolysis reactions were prepared in triplicate following the general procedure for EGPh assays as indicated above, using 0.8 µM EGPh and Avicel, *Miscanthus*, or no substrate. To measure residual activity after incubation excluding air, reactions were set up in plastic 1 mL HPLC vials containing stir bars, using a total volume of 950 uL using the same concentrations as the air-contact reactions, which just overfilled the vials. Plastic HPLC caps were used to seal each reaction. The caps were in direct contact with the solution surface and were translucent enough to visually confirm exclusion of almost all air in each sample. Both sets of samples were stirred for 12 h at 40° C., then the reactions were centrifuged for 10 min at 13.2k rpm to pellet the substrate. To measure residual activity, 60 µL of the cleared supernatant was mixed with 60 µL of azo-CMC suspension (prepared according to supplier's instructions) in a 0.6 mL Eppendorf tube and incubated for 75 min at 40° C. 300 µL of the stop solution was added, the contents mixed, the reaction allowed to rest for 10 min at rt, then the tubes centrifuged at 13.2k rpm for 10 min to pellet unreacted substrate. 300 µL of the supernatant was transferred to clear-bottom 96 well plate and the absorbance measured at 590 nm using an optical plate reader. Controls were included containing 0.8 µM enzyme but without any substrate or prior incubation. Enzyme activity was measured in comparison to a standard curve of 1.2, 0.8, 0.4, 0.2, and 0 µM EGPh; polymer-containing samples were compared to a standard curve including 2 mg/mL of mannose-modified (S1).

Residual EGPh Concentration Measurements: The concentration of residual EGPh after hydrolysis was measured using a modified Bradford assay (Bio-Rad). Following the 12 h incubation of EGPh with various substrates used to measure residual activity outlined above, 20 µL aliquots of cleared supernatant were mixed with 200 µL of the diluted reagent in clear-bottom 96 well plates and allowed to site at rt for 40 min. Absorbance of the solution at 595 nm was measured using an optical plate reader. Enzyme content was compared to a standard curve of 1.2, 0.8, 0.4, 0.2, and 0 µM EGPh; polymer-containing samples were compared to a standard curve including 2 mg/mL of mannose-modified (S1).

Substrate Volume Measurements: For Avicel measurements, between 4.970 and 5.007 mg of substrate was added to each of six 2 mL glass vials along with a stir bar. 490 µL of buffer was added to three vials as controls. To the other three, 480 µL of buffer and 10 µL of 100 mg/mL mannose-modified (S1) was added for a total concentration of 2 mg/mL polymer. The vials were capped and allowed to stir for 12 h in a 40° C. water bath. Then the stir bars were removed and the vials were allowed to rest for 30 min at rt to allow the substrate to settle, then a picture was taken of all six vials. The picture was adjusted for contrast and brightness in Adobe Photoshop to sharpen the image. To measure substrate volume, Adobe Illustrator was used to outline the edges of the substrate and the total reaction volume using a closed path, then the area of each shape was calculated by the software. The analysis was performed on one picture of all six vials to ensure the same angle of observation was used for all samples. The procedure was repeated to measure *Miscanthus* volume.

Example 12

Effect of NIPAm Copolymer on Endoglucanase Activity

This Example demonstrates the effect of the NIPAm copolymer on endoglucanase activity. To determine the full extent of polymer enhancement for EGPh over time, hydrolysis was performed on a 1.3 mL scale and aliquots removed at the indicated time points to measure reducing sugars.

Figure 11A:
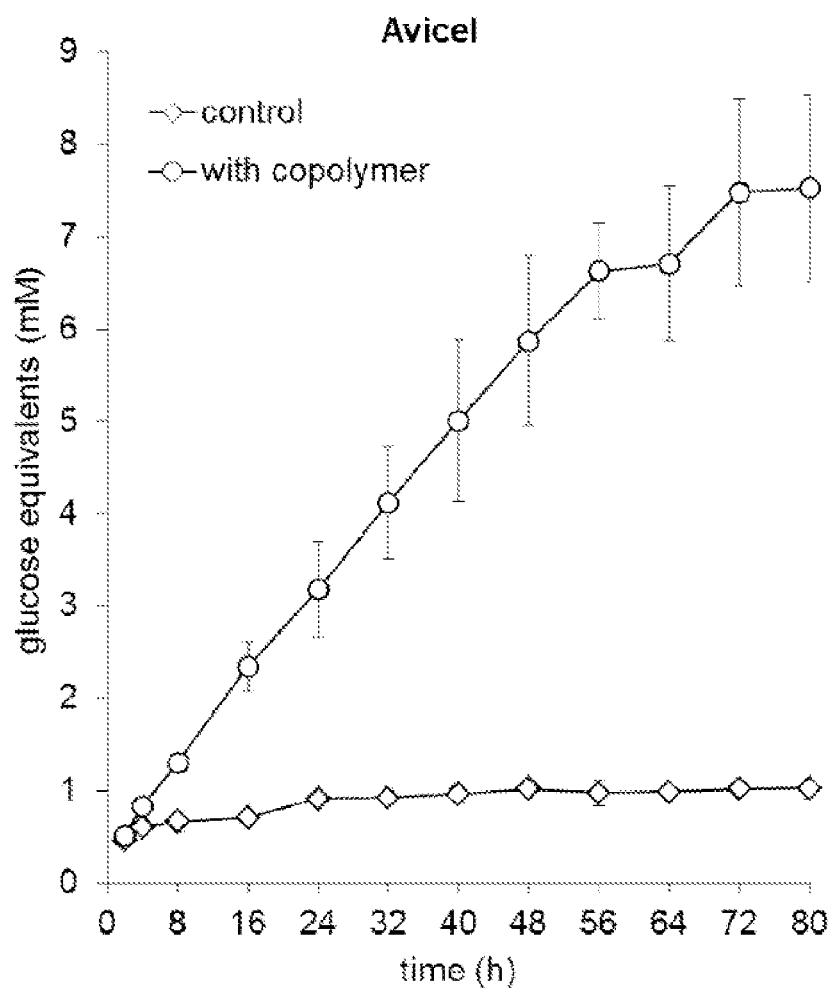
FIGS. 11A and 11B are graphs depicting the effect of NIPAm-containing polymers on EGPh hydrolysis on Avicel and *Miscanthus*, respectively.

Without copolymer addition, the hydrolysis of Avicel was found to stabilize after 12 h with a maximum yield of 1.03 mM glucose equivalents achieved at 80 h. In the presence of copolymer, a distinct linear increase in product concentration was observed until 56 h, with a maximum of 7.5 mM glucose equivalents reached at 80 h. This corresponded to 7.3 times the activity of the control (FIG. 11A). The positive slope of the curve indicated that there was still active enzyme in the samples including copolymer, but in samples without copolymer the EGPh was almost fully deactivated after only 24 h.

Figure 11B:
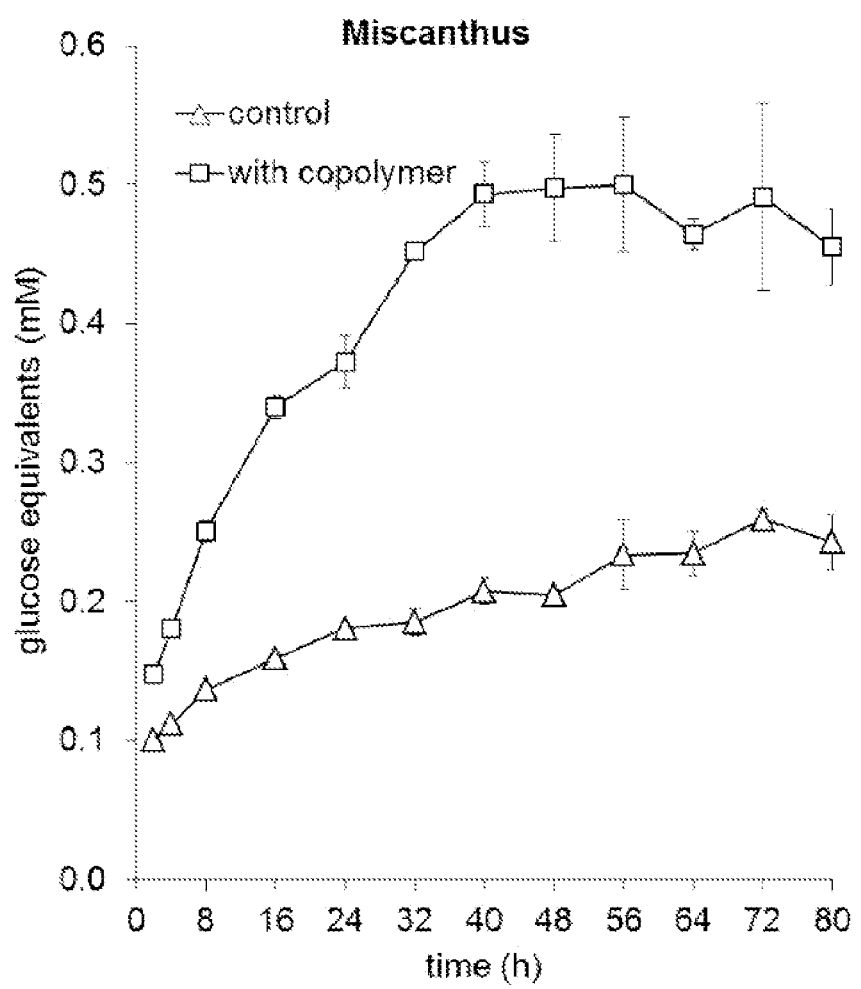

On *Miscanthus* in the absence of copolymer, EGPh activity slowed at 56 h with a maximum of 0.26 mM glucose equivalents reached at 72 h. The addition of copolymer resulted in maximum hydrolysis being reached after 40 h, with a 2.4-fold increase in yield being observed at this time point (FIG. 11B).

Thus, this Example demonstrates the ability of the copolymer to increase hydrolysis yields on both Avicel and *Miscanthus*.

Example 13

Effect of NIPAm Copolymer Across Different Enzyme Types

This Examples demonstrates the effect of the NIPAm copolymer on various types of cellulases.

Figure 12A:
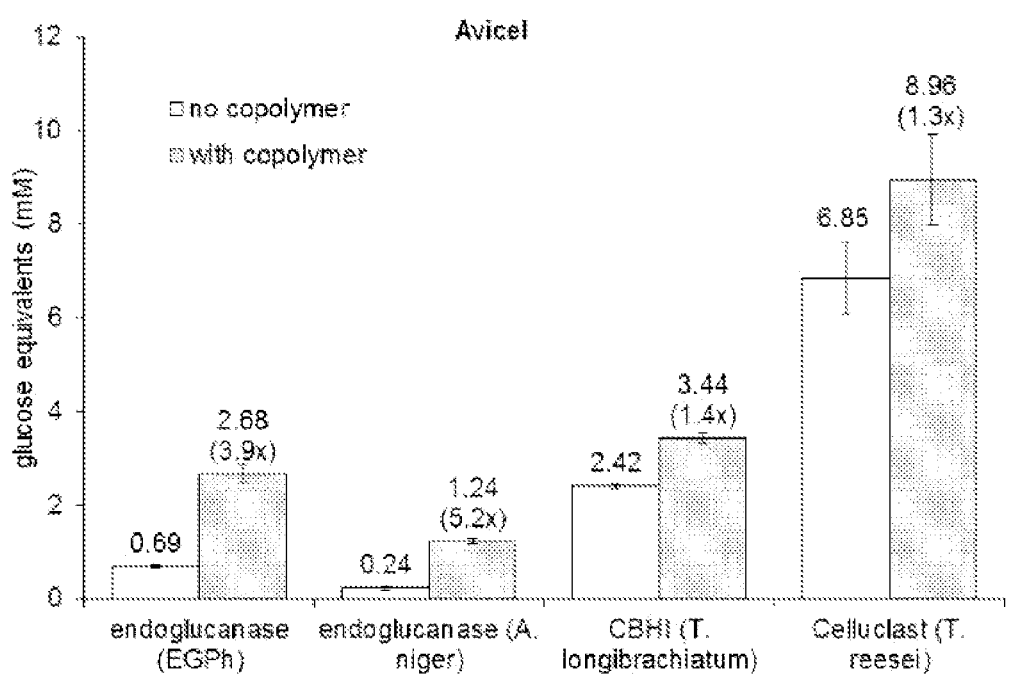
FIGS. 12A and 12B are graphs depicting the effect of NIPAm-containing polymers on endoglucanases, cellobiohydrolases, and mixtures thereof, on microcrystalline cellulose and lignocellulose, respectively. For each sample, the degree of increase over the control is indicated in the parentheses. Error bars indicate the standard deviations.
Figure 12B:
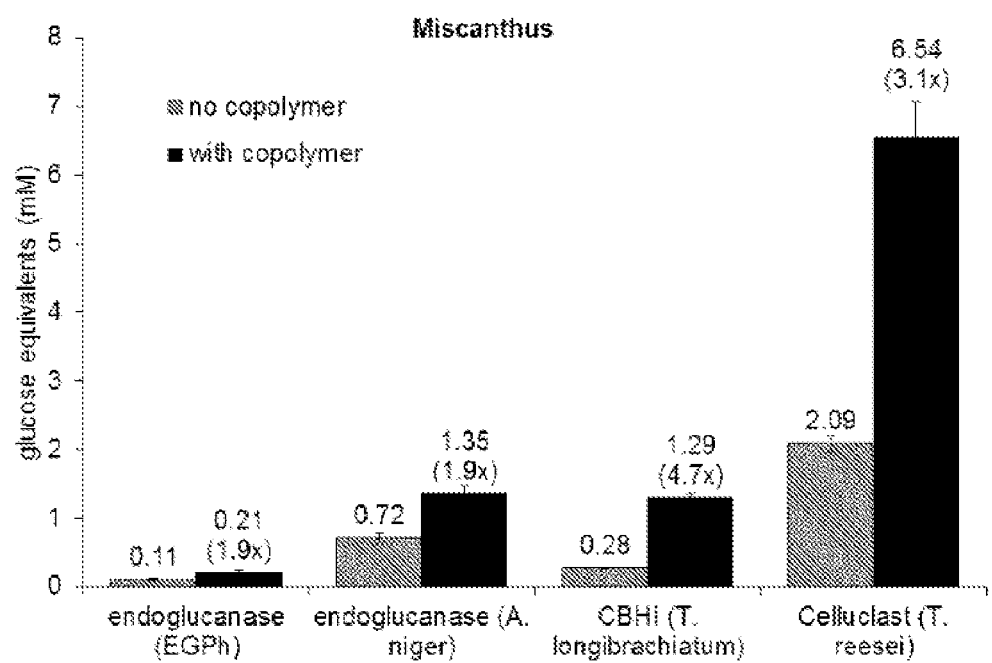

Electrophoretically homogeneous endoglucanase from *A. niger* and CBHI from *T. longibrachiatum* were assayed in addition to Celluclast on both Avicel and *Miscanthus* substrates in the presence of copolymer for 12 h. Analogous protein concentrations were used to allow comparison to EGPh. As seen in FIGS. 12A and 12B, increased hydrolysis yields were observed for all cellulases on both substrates assayed. Most significantly, the copolymer effect on Celluclast activity was greater on *Miscanthus* than on Avicel, enabling lignocellulosic hydrolysis to reach a level similar to that observed on purified cellulose alone.

The samples assayed on Avicel were also analyzed by HPLC to quantify glucose, cellobiose, and cellotriose concentrations. The calculated glucose equivalents from HPLC analysis confirmed the accuracy of the OxiRed assay, and showed that the ratios of the three hydrolysis products did not change considerably between samples with and without copolymer for any of the enzymes assayed.

Example 14

The Role of Polymer Structure and Effect of Polymer Loading

This Example explores the role of the NIPAm copolymer and the effect of polymer loading. Hydrolysis of both substrates by EGPh was tested in the presence of poly (NIPAm) and also poly(acrylamide), which has the same backbone structure as p(NIPAm) but lacks the N-isopropyl groups.

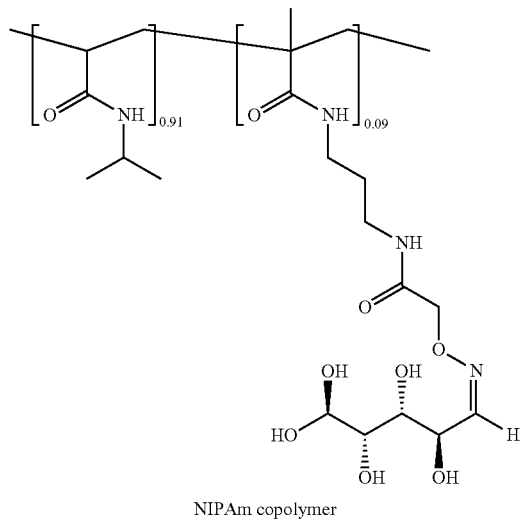

NIPAm copolymer

-continued

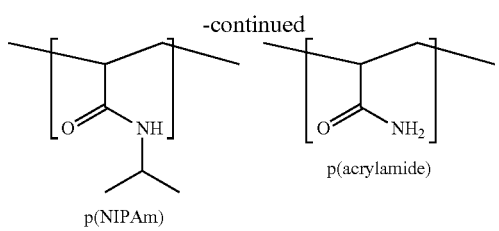

p(NIPAm)  p(acrylamide)

Figure 13A:
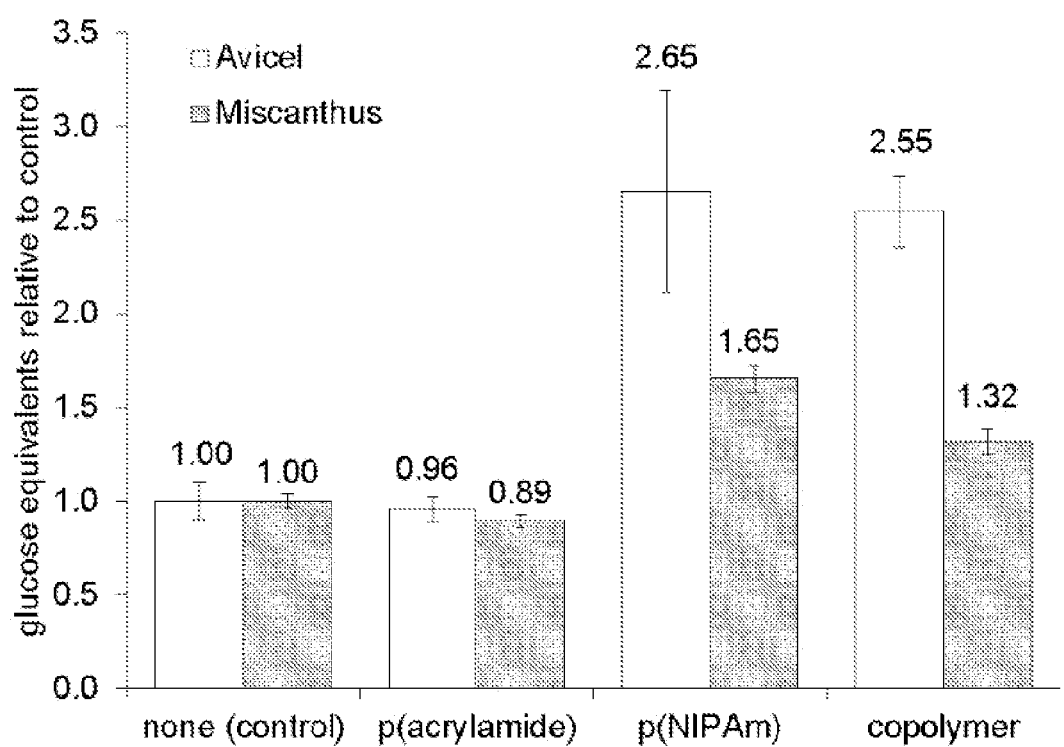
FIG. 13A is a bar graph comparing the effect of poly (acrylamide), poly(NIPAm), and the NIPAm copolymer on Avicel and *Miscanthus*.

As shown in FIG. 13A, p(acrylamide) did not have an effect on hydrolysis. In contrast, p(NIPAm) increased the saccharification yield on both Avicel and *Miscanthus* to a level slightly higher than that observed in the presence of the copolymer. This indicated that the NIPAm monomer itself is the basis for increased substrate hydrolysis, and that the N-isopropyl groups are specifically required structural elements. However, the aminooxy monomers provide necessary handles with which to adapt the LCST of the material to a useful range, making any corresponding drop in enhancement a tolerable if not ideal tradeoff. Copolymers capped with small molecules other than mannose were also tested, revealing that the structure of the small molecule had little-to-no effect on the overall enhancement observed (FIG. 13C).

Figure 13B:
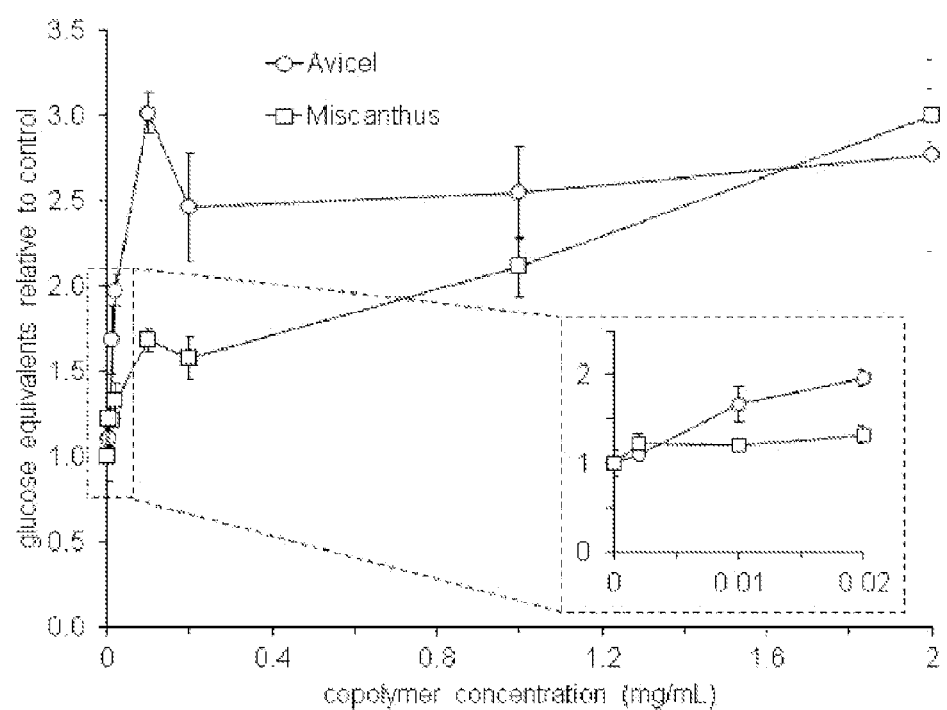
FIG. 13B is a graph depicting hydrolysis yields on Avicel and *Miscanthus* at various polymer loadings. Error bars indicate the standard deviations.
Figure 13C:
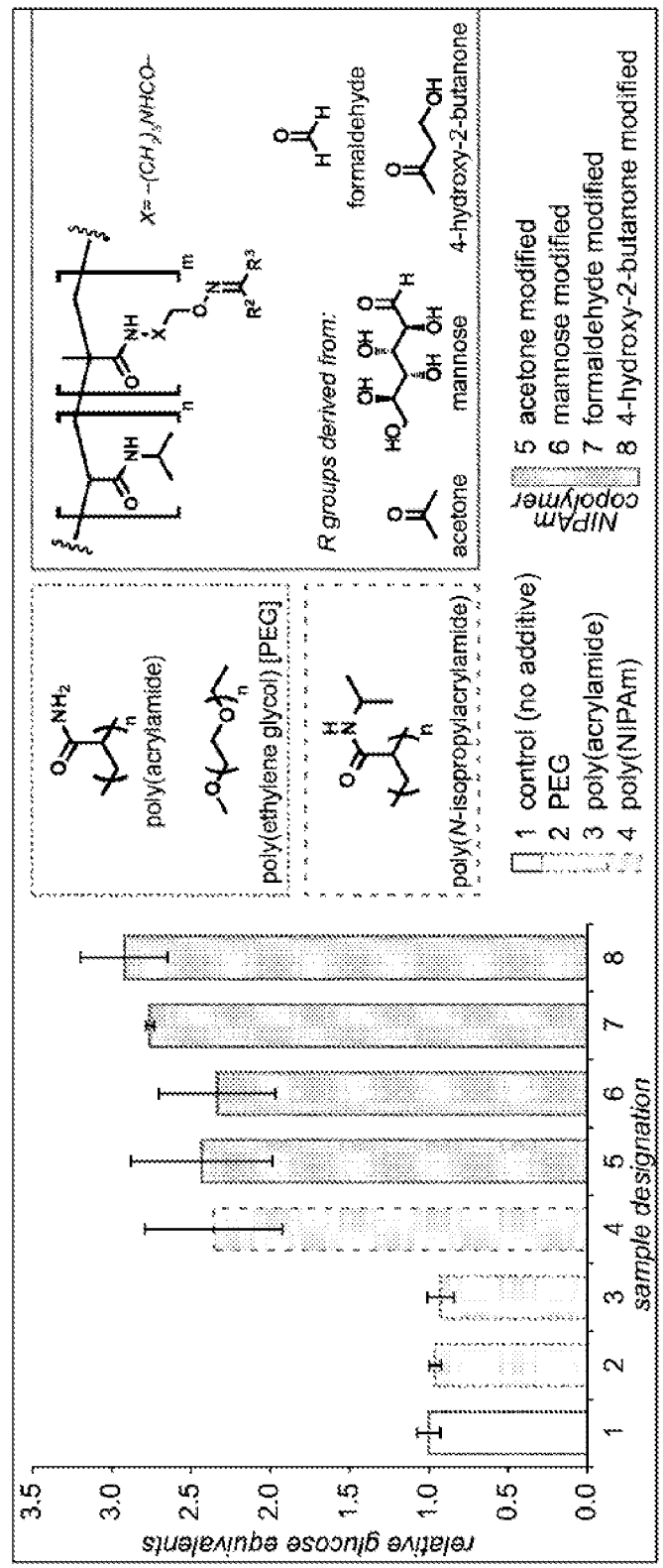
FIG. 13C is a graph depicting the effect of adding NIPAm copolymer to the hydrolysis of *Miscanthus* with Celluclast. Error bars indicate the standard deviations.

The correlation between copolymer concentration and hydrolysis yield after 12 h was also explored (FIG. 13B). A 68% increase in Avicel hydrolysis was apparent at copolymer loadings as low as 0.001 g/g DM, with additional yield gains being negligible above 0.02 g/g DM. Greater copolymer loading was required with *Miscanthus*, with 0.001 g/g DM loading producing only a 21% increase in hydrolysis. From that point, yield increases continued to correlate positively with copolymer loading. Interestingly, the hydrolysis yields exhibited a local maximum at 0.01 g/g DM loading then decreased at 0.02 g/g DM. This result was observed in numerous trials and was independent of substrate type. It is suggestive of the copolymers displaying concentration-dependent aggregation behavior, or having multiple modes of action that switch in that concentration range. We are currently evaluating these possibilities in ongoing experiments.

Example 15

Effects of NIPAm Copolymer on EGPh Adsorption and Stability

This Example investigates the effects of the NIPAm copolymer on EGPh adsorption and stability. To measure the effect of the copolymer on protein stability at interfaces in the absence of substrate (*Miscanthus* or Avicel), solutions of 0.8 µM EGPh were stirred for 12 h with or without 2 g/L copolymer. As a second variable, air was either included or excluded from these reactions.

Figure 14A:
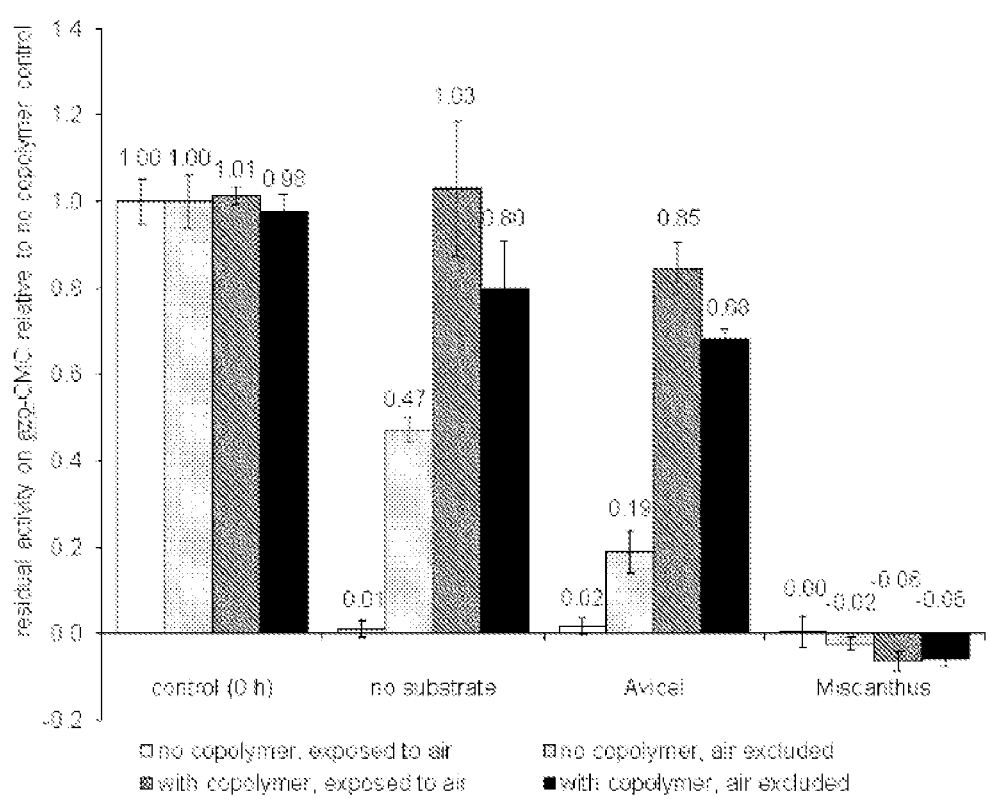
FIGS. 14A and 14B are graphs depicting residual EPGh activity on a soluble azo-CMC substrate and residual soluble protein, respectively, following incubation with Avicel, *Miscanthus* or no substrate.
Figure 14B:
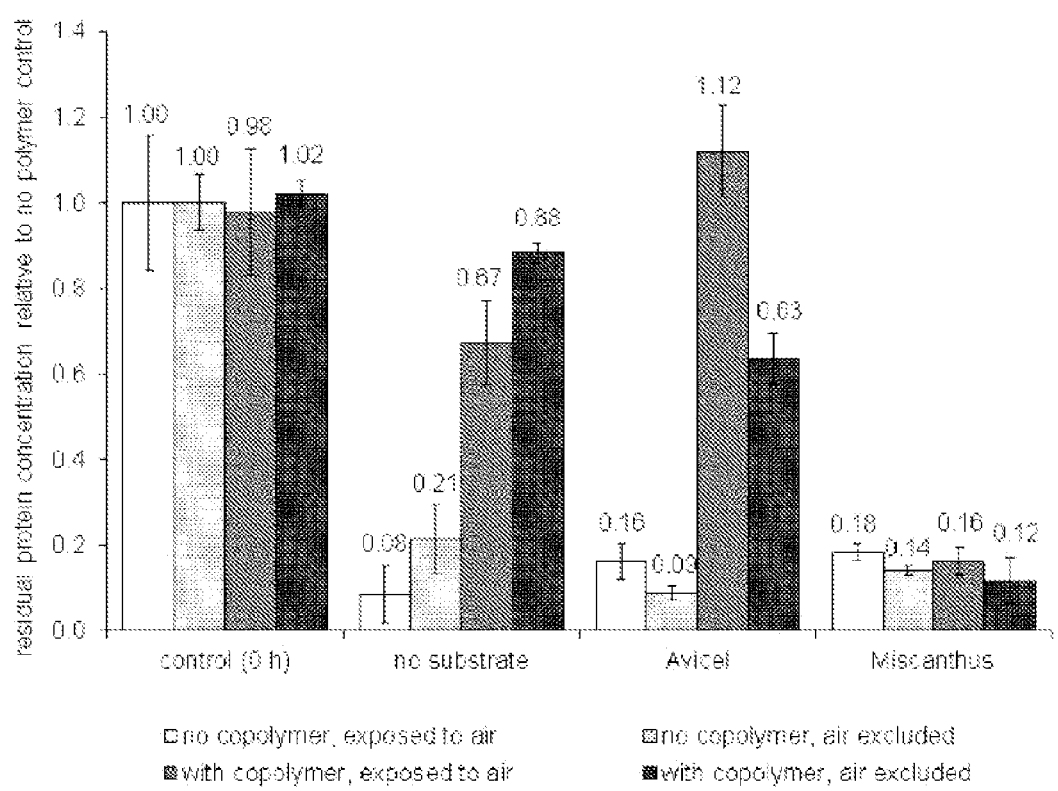

After centrifugation to remove denatured protein, the amount of active endoglucanase in the cleared supernatant was quantified using azo-carboxymethyl cellulose (azo-CMC), a soluble endoglucanase substrate that releases a dye upon degradation. As shown in FIG. 14A, the presence of copolymer enabled activity retention in excess of 80% whether or not air was excluded. However, in the absence of copolymer, enzyme activity was observed to be negligible if stirred in contact with air and less than 50% retained if air was excluded. Both shear stress from stirring and contact with the hydrophobic-hydrophilic interface at the solution surface were observed to be significant factors in cellulase inactivation. Both of these factors were ameliorated by the addition of NIPAm copolymers. Soluble protein concentration evaluated using a Bradford assay correlated with the activity findings (FIG. 14B).

To measure how NIPAm copolymers may affect protein adsorption, residual endoglucanase activity was measured after stifling 1% suspensions of Avicel or *Miscanthus* with 4 mg/g DM EGPh and 0.2 g/g DM copolymer for 12 h. This experiment was also performed in the presence and absence of air to separate the effects of non-productive substrate binding from those of the air-water interface. As shown in FIG. 14A, the results with Avicel were very similar if slightly lower than those without any substrate. The results with *Miscanthus* showed negligible enzyme activity in the supernatant in any of the tested scenarios, whether or not air or copolymer was included. Residual protein concentration quantified with a Bradford assay was also very low across all *Miscanthus* cases.

Example 16

Interaction of NIPAm Copolymer with Cellulose Substrates

Figure 15:
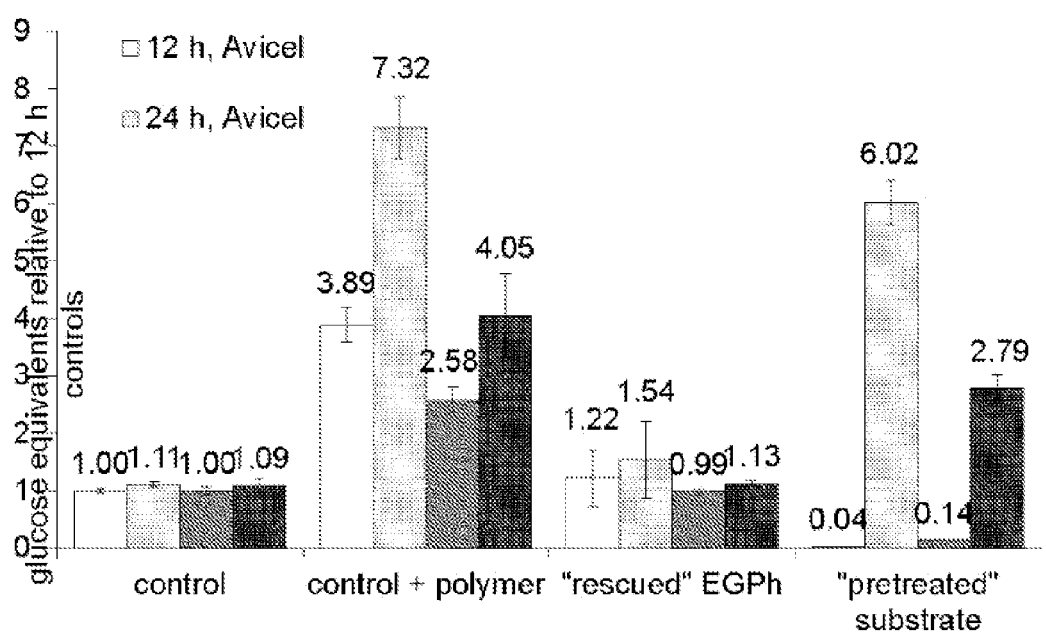
FIG. 15 is a graph comparing the effect of adding the NIPAm copolymer to hydrolysis reactions involving "rescued" EPGh and "pretreated" substrate.

This Example explores the interaction of the NIPAm copolymer with Avicel and *Miscanthus* substrates. To determine if NIPAm copolymers could "rescue" enzymes non-productively adsorbed on the substrate surface, EGPh was first incubated with Avicel or *Miscanthus* for 12 h in the absence of polymer. After this, the copolymer was added and the hydrolysis reaction was continued for another 12 h. On both substrates, the addition of NIPAm copolymers halfway through a 24 h hydrolysis period had no positive effect on yield, indicating that either the copolymer had no influence on enzyme desorption or that the enzymes had already been denatured (FIG. 15).

To ascertain if NIPAm copolymers were altering the structure of the substrate independent of enzymes, NIPAm copolymer was incubated with Avicel or *Miscanthus* for 12 h to pretreat the cellulose. EGPh was then added, and the hydrolysis activity was measured after 12 additional hours. The yield at this point clearly showed that pretreating Avicel with the copolymer resulted in significantly higher saccharification than if enzyme and polymer had been added simultaneously. Hydrolysis of pretreated Avicel achieved a 6.0-fold greater yield after 12 h than a control containing only cellulase and substrate. The reaction containing copolymer, cellulase, and Avicel combined at the same time attained 3.9- and 7.3-fold greater yields at 12 and 24 h, respectively. The copolymer itself was not observed to catalyze substrate hydrolysis, as indicated by the negligible level of reducing sugars after 12 h without enzyme. This pretreatment effect was observed to be more subtle with *Miscanthus*. Pretreating *Miscanthus* with copolymer for 12 h before the addition of EGPh resulted in only slightly increased 12 h hydrolysis yields compared to the control in which all elements were combined at the same time.

These findings strongly support a cellulose-copolymer interaction that is independent of enzyme, in which the NIPAm copolymers are altering cellulose in a manner that is beneficial to hydrolysis activity. The presence of lignin in *Miscanthus* either prevents this interaction, perhaps by blocking most of the surface of the cellulose and preventing access by the copolymer, or the copolymer is preferentially interacting with hydrophobic lignin and is therefore not as available to interact with cellulose itself.

To probe this cellulose-copolymer association further, a 1% DM suspension of Avicel was incubated with 0.2 g/g DM NIPAm copolymer for 0, 12, 24, or 36 h. EGPh was then added and hydrolysis yields were measured at the end of an additional 12 h period. As shown in Table 2 below, longer Avicel pretreatment with copolymer correlated to higher levels of saccharification. Incubating Avicel in buffer for 36 h without copolymer also improved the yield slightly, most likely do to the swelling of the substrate, but that increase could not account for the enhancement seen with extended copolymer pretreatment.

TABLE 2

Summary of data from pretreating Avicel with NIPAm copolymer

| length of Avicel pretreatment (h) | μM glucose equiv. | | relative to 0 h control | |
|---|---|---|---|---|
| | avg. | std. dev. | avg. | std. dev |
| control 0 h (no copol.) | 689 | 29 | 1.00 | 0.04 |
| 0 | 2589 | 232 | 3.76 | 0.34 |
| 12 | 3724 | 560 | 5.40 | 0.81 |
| 24 | 4204 | 205 | 6.10 | 0.30 |
| 36 | 4490 | 513 | 6.51 | 0.74 |
| control 36 h (no copol.) | 1134 | 161 | 1.65 | 0.23 |

During the execution of hydrolysis experiments, it was qualitatively observed that NIPAm copolymers had a substantial effect on the volume of the substrates after incubation, even without added enzyme. This effect was quantified by stiffing Avicel or *Miscanthus* with copolymer for 12 h at 40° C., and then letting the substrates settle for 30 min at room temperature. Increases in volume of about 40% for both substrates, as shown by the data in Table 3 below.

TABLE 3

Effect of NIPAm copolymer on swelling of substrates

| | | Avicel | | Miscanthus | |
|---|---|---|---|---|---|
| copolymer | | − | + | − | + |
| substrate volume (% of total) | avg. | 47.9 | 69.4 | 23 | 32.3 |
| | std. dev. | 9.0 | 5.1 | 3.9 | 2.8 |
| increase over control | | — | 44.9% | — | 40.4% |

Example 17

Figure 16:
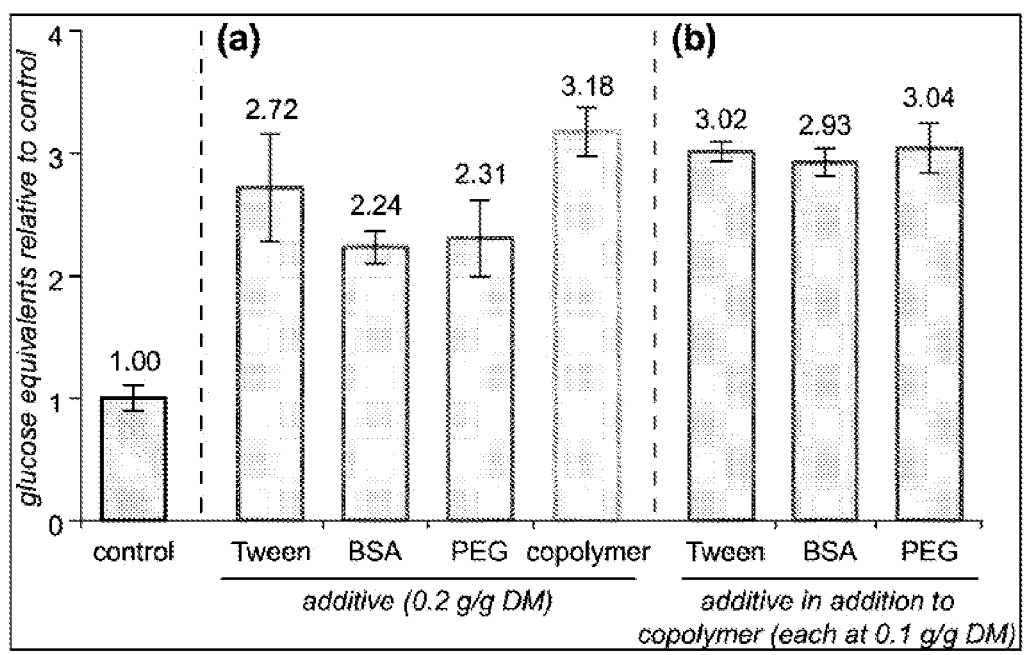
FIG. 16 is a graph comparing the effects the NIPAm polymer with other additives such as Tween, BSA and PEG.

Comparing the Effect of the NIPAm Copolymer with Other Additives on Celluclast Activity This Example compares the effects of the NIPAm copolymer with other additives, such as poly(ethylene glycol) (PEG), Tween, and bovine serum albumin (BSA). The effect of the four additives was compared by hydrolyzing a 1% DM suspension of *Miscanthus* for 12 h, using 0.2 g/g DM additive loading in the presence of 2 mg/g DM Celluclast supplemented with 0.4 mg/g DM β-glucosidase. All four additives resulted in enhancement of hydrolysis, but the NIPAm copolymer elicited the highest yield increase, ranging from 14 to 30% greater yield of hydrolysis products than the other additives (FIG. 16).

Moreover, to investigate the potential cooperative effect between NIPAm and another additive, *Miscanthus* was hydrolyzed by Celluclast in the presence of 0.1 g/g DM BSA, Tween, or PEG, in addition to 0.1 g/g DM NIPAm copolymer (for a total additive loading of 0.2 g/g DM). Comparing these hydrolysis yields to those obtained in the presence of each additive alone, the addition of NIPAm copolymer to the other additives increased cellulose conversion to the level measured in the presence of only copolymer, but was not observed to increase yields further (FIG. 16).

Example 18

Effect of NIPAm Copolymers on Enzyme Loading

Figure 17:
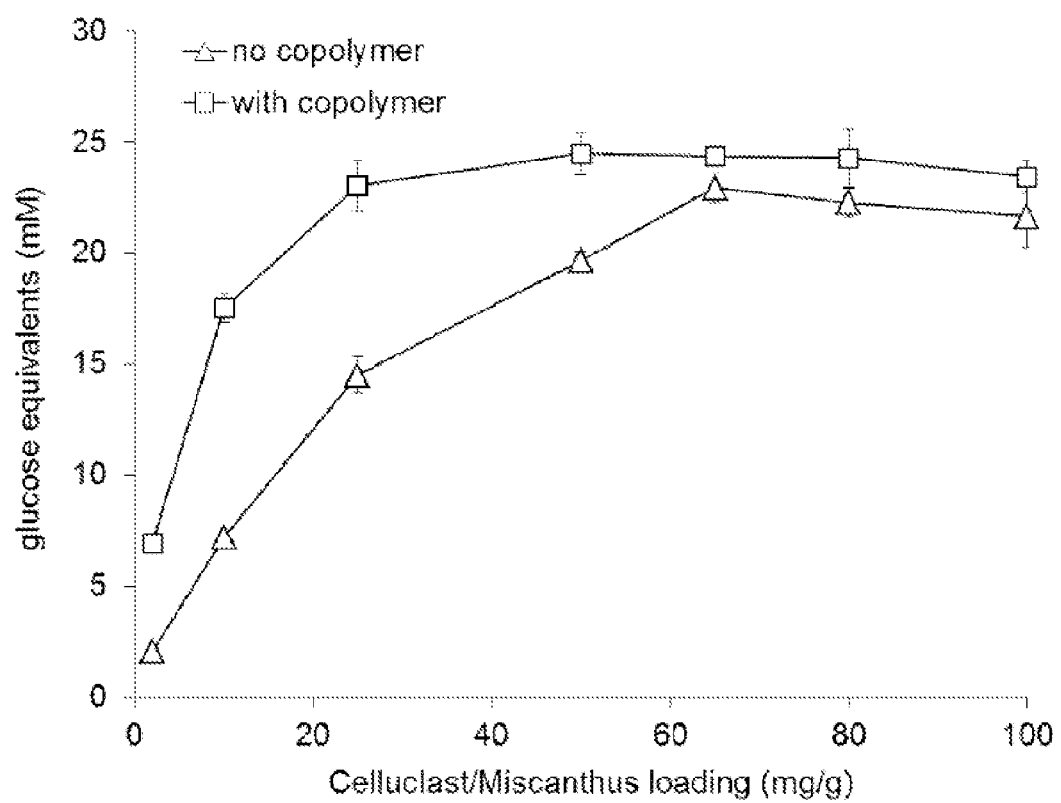
FIG. 17 is a graph depicting the effect of 0.2% NIPAm copolymer on the hydrolysis of *Miscanthus* by Celluclast at varying levels of Celluclast concentration.

This Example demonstrates the effect of various enzyme loadings of the NIPAm copolymers. To investigate the copolymer enhancement using more typical enzyme concentrations, the effect of NIPAm copolymers on 12 h hydrolysis yield for *Miscanthus* was studied across Celluclast loadings ranging from 2 to 100 mg/g DM. These reactions were also supplemented with β-glucosidase at 20% of the Celluclast level. As shown in FIG. 17, by adding NIPAm copolymers the maximum substrate hydrolysis was reached with an enzyme loading of only 25 mg/g DM, a 62.5% reduction compared to the 65 mg/g DM required without additive. Even at the highest enzyme loading, including the NIPAm copolymers led to a 6-9% yield increase, further suggesting the copolymers have a greater effect than just preventing protein adsorption.

Example 19

Effect of NIPAm Copolymer on Lipase with Olive Oil as Substrate

This Example demonstrates the effect of the NIPAm copolymer on lipase using olive oil as a substrate. To twelve 1.5 mL Eppendorf tubes was added 0.5 mL 1 mg/mL lipase from *Candida rugosa* in 100 mM Tris buffer, pH 7.7. To six of these tubes was added the NIPAm copolymer at a total concentration of 2 mg/mL. Three tubes without copolymer (control) and three tubes with copolymer (control+copolymer) were kept at 4° C. without stiffing. Stir bars were added to the other three tubes without copolymer (−polymer) and the other three tubes with copolymer (+polymer), and they were stirred at 30° C. At the indicated time points, all 12 protein samples were assayed for lipase activity using olive oil as a substrate.

To assay activity, 350 μL 100 mM Tris buffer pH 7.7, 25 μL of protein sample, and 75 μL olive oil were added to a 2 mL Eppendorf tube with a stir. The mixtures were allowed to stir for 30 min at 37° C. To stop the reaction, 300 μL of 100% ethanol with 0.5% w/v thymolphthalein pH indicator was added and the tubes inverted to mix. Each mixture was then titrated with 50 mM sodium hydroxide until the same light blue color was achieved. Blanks were also prepared for each protein sample by combining 350 µL buffer and 25 µL of the protein sample. This solution was allowed to sit at room temperature until the active samples were stopped, at which point 300 µL of the ethanol with indicator and 75 µL were added together to prevent any substrate hydrolysis. These blanks were also titrated, and the blank values subtracted from the active protein values to arrive at the volume of sodium hydroxide needed to neutralize any new acid produced.

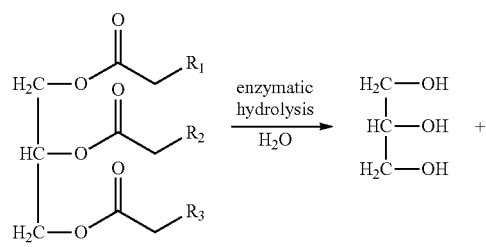

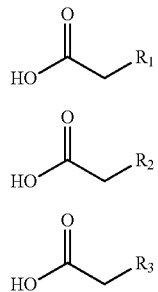

concentration measured by titration with NaOH and a pH indicator

Figure 18:
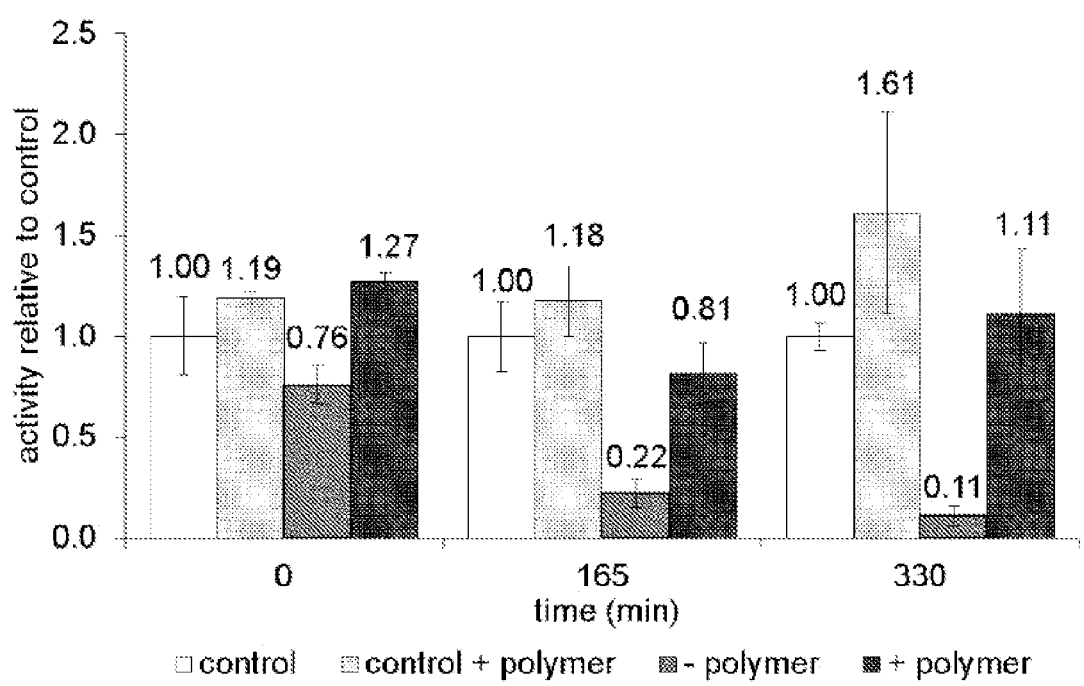
FIG. 18 is a bar graph depicting the ability of lipase from *Candida rugosa* to hydrolyze olive oil following time stirred at 30° C. with or without NIPAm copolymer.

The enzymatic activity measured relative to the control is summarized in FIG. 18 and Table 4 below. Inclusion of NIPAm copolymer during hydrolysis of olive oil by lipase was generally observed to increase hydrolysis yield, as indicated by the higher activity of the "control+polymer" samples. Lipase enzyme was observed to gradually becomes less active over time when stirred at 30° C., as shown by the decrease in activity of the "-polymer" samples at the time points indicated. By including NIPAm copolymer in samples that were stirred at 30° C., this activity loss over time is prevented ("+polymer" sample). As such, the copolymer was observed to have a protective effect against the protein deactivation otherwise observed.

TABLE 4

| | activity relative to control | | | | | | | |
|---|---|---|---|---|---|---|---|---|
| | stored at 4° C. without stirring | | | | stirred at 30° C. | | | |
| | control | | control + polymer | | −polymer | | +polymer | |
| min. | avg. | std. dev. | avg. | std. dev. | avg. | std. dev. | avg. | std. dev. |
| 0 | 1.00 | 0.19 | 1.19 | 0.03 | 0.76 | 0.10 | 1.27 | 0.04 |
| 165 | 1.00 | 0.17 | 1.18 | 0.17 | 0.22 | 0.07 | 0.81 | 0.16 |
| 330 | 1.00 | 0.07 | 1.61 | 0.50 | 0.11 | 0.05 | 1.11 | 0.32 |

Example 20

Effect of NIPAm Copolymer on Lipase with p-NPD as Substrate

The effect of NIPAm copolymer on the rate of lipase hydrolysis of the chromogenic substrate paranitrophenyl dodecanoate (p-NPD) was measured in triplicate for each polymer concentration in a clear-bottomed, 96-well plate. To each well, 10 µL of 0.2 mg/mL lipase from *Candida rugosa* was added. Then, 10 µL of 0, 0.1, 0.5, 1, 2, 4, 6, or 10 mg/mL of the standard NIPAm copolymer was added and mixed via pipette. Using a multichannel pipette, 80 µL of 500 µM p-NPD in 100 mM Tris pH 7.7 was then added to each well and absorbance at 405 nm monitored every 30 seconds for 42 minutes using a plate reader. The final concentration in each well during the assay was 0.02 mg/mL lipase from *Candida rugosa*; 400 µM p-NPD; either 0, 0.01, 0.05, 0.1, 0.2, 0.4, 0.6, or 1 mg/mL NIPAm copolymer; 100 mM Tris HCl buffer, pH 7.7.

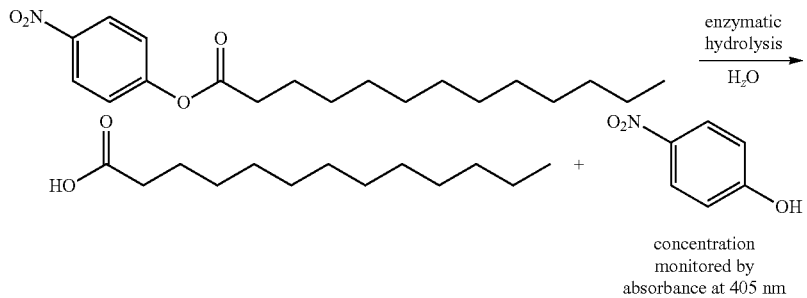

concentration monitored by absorbance at 405 nm

Figure 19A:
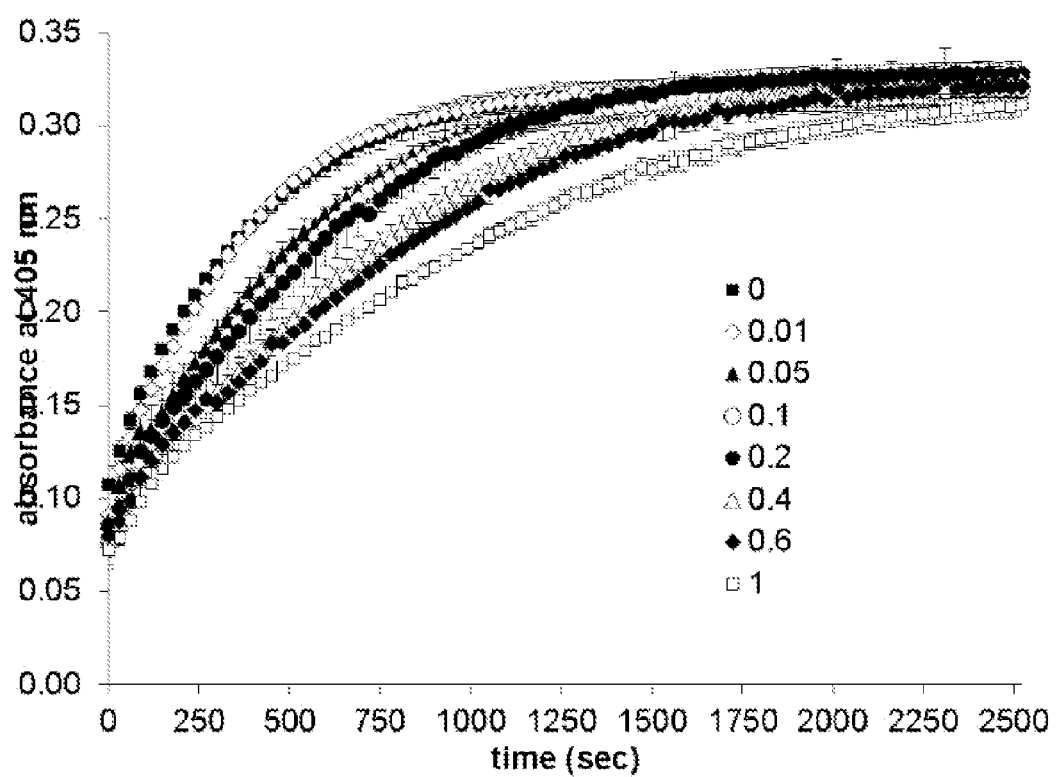
FIG. 19A is a graph depicting the effect varying concentrations of NIPAm copolymer have on hydrolysis of the fluorogenic substrate p-nitrophenyl dodecanoate by the lipase from *Candida rugosa*.

The kinetics of the lipase is summarized in FIG. 19A. When assayed with the chromogenic substrate p-nitro dodecanoate, the rate of lipase activity was observed to decrease with increasing concentrations of NIPAm copolymer. The same total level of substrate hydrolysis was reached regardless of copolymer concentration, but a greater concentration of copolymer was observed to require a longer reaction time for the lipase to fully hydrolyze the substrate present. This negative impact on activity, however, was not observed when the lipase was assayed with olive oil as a substrate (see FIG. 18). Without wishing to be bound by any theory, it is believed that the polymer was not acting directly on the lipase enzyme itself but rather the polymer was either interacting with the substrate alone or mediating a lipase-substrate interaction.

To twelve 1.5 mL Eppendorf tubes was added 0.3 mL 0.2 mg/mL lipase from *Candida rugosa* in 100 mM Tris buffer, pH 7.7. To six of these tubes was added the NIPAm copolymer to a total concentration of 2 mg/mL. Three tubes without copolymer (control) and three tubes with copolymer (control+copolymer) were kept at 4° C. without stirring. Stir bars were added to the other three tubes without copolymer (−polymer) and the other three tubes with copolymer (+polymer), and they were stirred at room temperature. At the indicated time points, all 12 protein samples were assayed for lipase activity using p-NPD as a substrate.

Lipase activity was assayed in a clear-bottomed, 96-well plate. To each well, 10 μL of a protein sample was added. Using a multichannel pipette, 90 μL of 500 μM p-NPD in 100 mM Tris pH 7.7 with 5% v/v ethanol was then added to each well. The plate was allowed to sit at room temperature for 12.5 minutes, then the absorbance of each well at 405 nm was measured using a plate reader. The final concentration in each well during the assay was 0.02 mg/mL lipase from *Candida rugosa*; 450 μM p-NPD; either 0 or 0.2 mg/mL NIPAm copolymer; 100 mM Tris HCl buffer, pH 7.7; and 5% v/v ethanol.

Figure 19B:
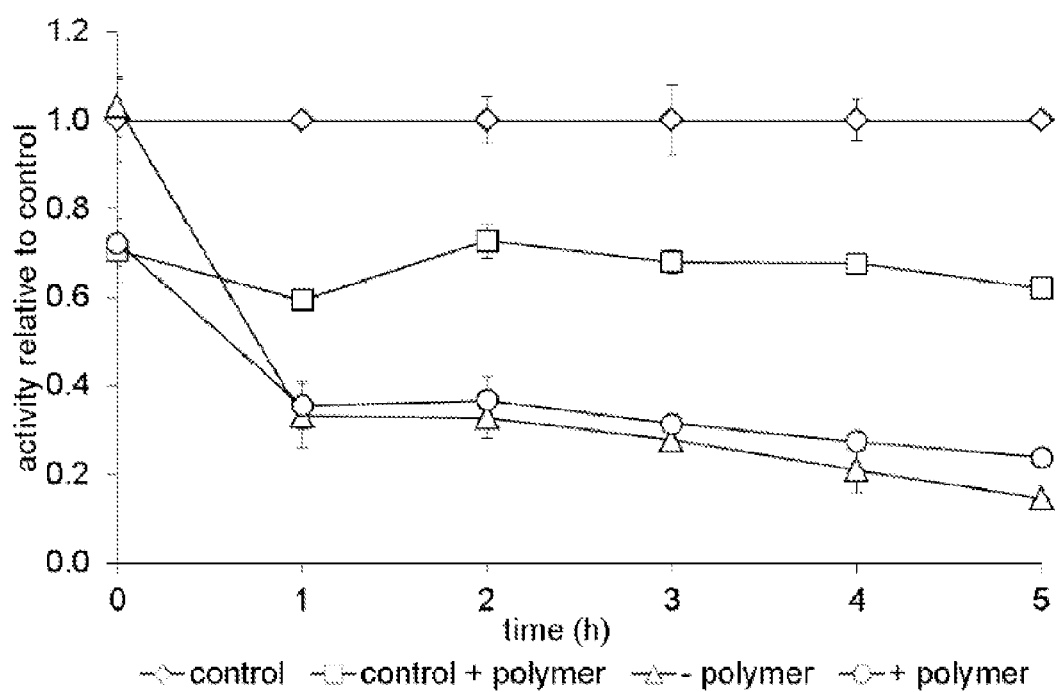
FIG. 19B is a graph depicting the ability of lipase from *Candida rugosa* to hydrolyze p-nitrophenyl dodecanoate following time stirred at room temperature with or without NIPAm copolymer

The enzymatic activity measured relative to the control is summarized in FIG. 19B and Table 5 below. Inclusion of NIPAm copolymer during hydrolysis of p-nitro dodecanoate by lipase was observed to slightly decrease hydrolysis yield, as indicated by the lower activity of the "control+polymer" sample compared to the "control". Lipase stirred at room temperature was observed to rapidly lose activity over time, as shown by the "-polymer" sample. Including NIPAm copolymer during this extended stirring helps prevent some of the activity loss, as shown by the "+polymer" sample. When this data is combined with the data shown in FIGS. 18 and 19A, without wishing to be bound by any theory, it is believed that NIPAm copolymer may help prevent lipase enzyme deactivation due to agitation over time.

TABLE 5 activity relative to control

| | kept at 4° C. without stirring | | | | stirred at room temperature | | | |
| | control | | control + polymer | | −polymer | | +polymer | |
| hours | avg. | std. dev. | avg. | std. dev. | avg. | std. dev. | avg. | std. dev. |
|---|---|---|---|---|---|---|---|---|
| 0 | 1.00 | 0.09 | 0.71 | 0.07 | 1.03 | 0.07 | 0.72 | 0.05 |
| 1 | 1.00 | 0.01 | 0.59 | 0.01 | 0.33 | 0.07 | 0.36 | 0.05 |
| 2 | 1.00 | 0.05 | 0.73 | 0.04 | 0.33 | 0.05 | 0.37 | 0.05 |
| 3 | 1.00 | 0.08 | 0.68 | 0.03 | 0.28 | 0.03 | 0.31 | 0.02 |
| 4 | 1.00 | 0.05 | 0.68 | 0.02 | 0.21 | 0.05 | 0.27 | 0.02 |
| 5 | 1.00 | 0.01 | 0.62 | 0.01 | 0.15 | 0.03 | 0.24 | 0.01 |

Example 21

Effect of NIPAm Copolymer on Alkaline Phosphatase with 4-MUP as Substrate

To twelve 1.5 mL Eppendorf tubes was added 0.5 mL 0.001 mg/mL alkaline phosphatase (AP) in 100 mM MOPS buffer, pH 8. To six of these tubes was added the NIPAm copolymer to a total concentration of 2 mg/mL. Three tubes without copolymer (control) and three tubes with copolymer (control+copolymer) were kept at 4° C. without stirring. Stir bars were added to the other three tubes without copolymer (−polymer) and the other three tubes with copolymer (+polymer), and they were stirred at 30° C. At the indicated time points, all 12 protein samples were assayed for alkaline phosphatase activity using the fluorogenic substrate 4-methylumbelliferyl phosphatase (4-MUP).

Alkaline phosphatase activity was assayed in a clear-bottomed, 96-well plate. To each well, 10 μL of a protein sample was added. Using a multichannel pipette, 190 μL of 100 μM 4-MUP in 100 mM MOPS pH 8 was then added to each well. Fluorescence was monitored by a plate reader with excitation at 360 nm and emission at 449 nm every 20 seconds for 10 minutes. The final concentration in each well during the assay was 0.0001 mg/mL AP, 90 μM 4-MUP, either 0 or 0.2 mg/mL NIPAm copolymer, and 100 mM MOPS buffer pH 8.

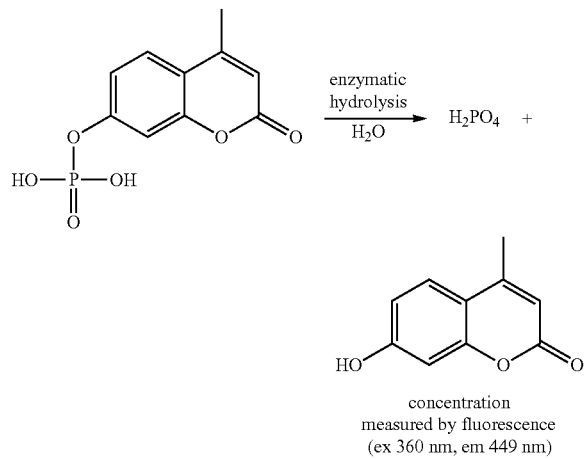

Figure 20A:
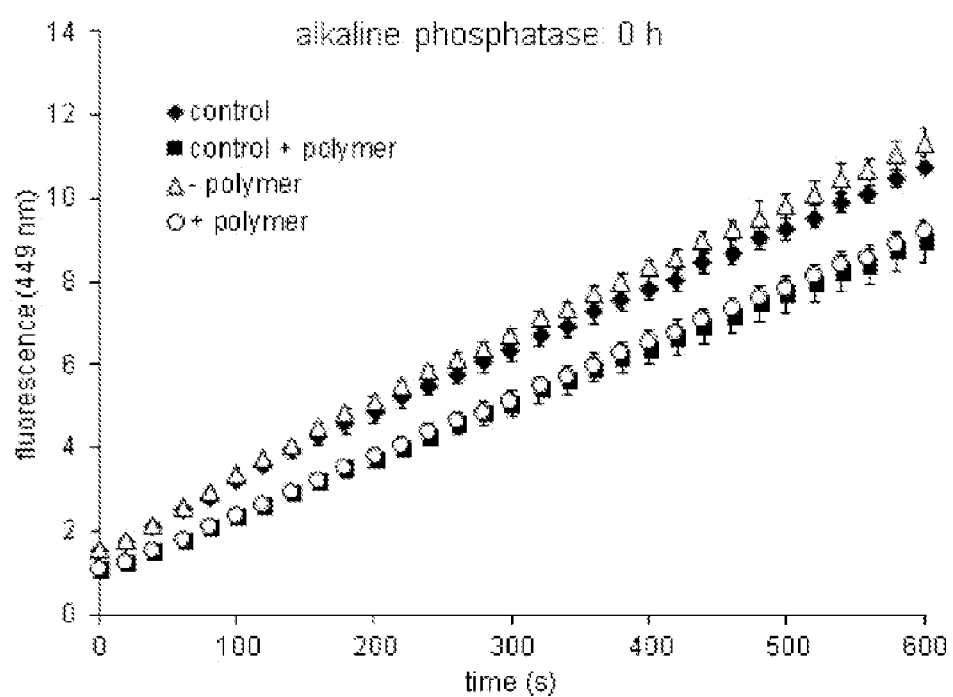
FIGS. 20A-C depict the ability of alkaline phosphatase to hydrolyze a fluorogenic substrate over time, stirred at 30° C., with or without NIPAm copolymer.
Figure 20B:
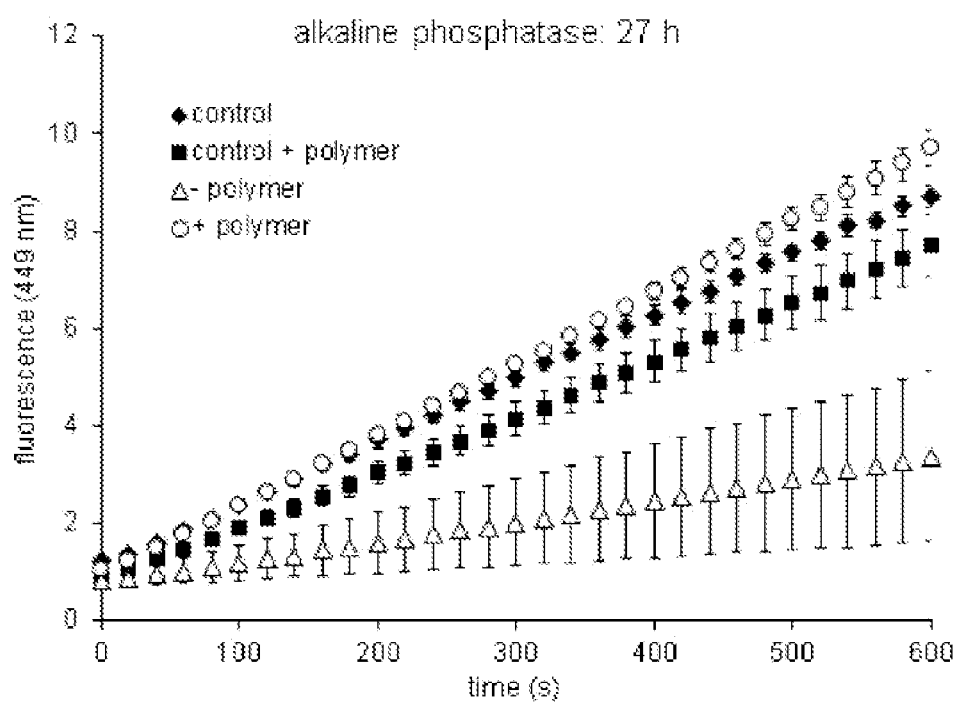
Figure 20C:
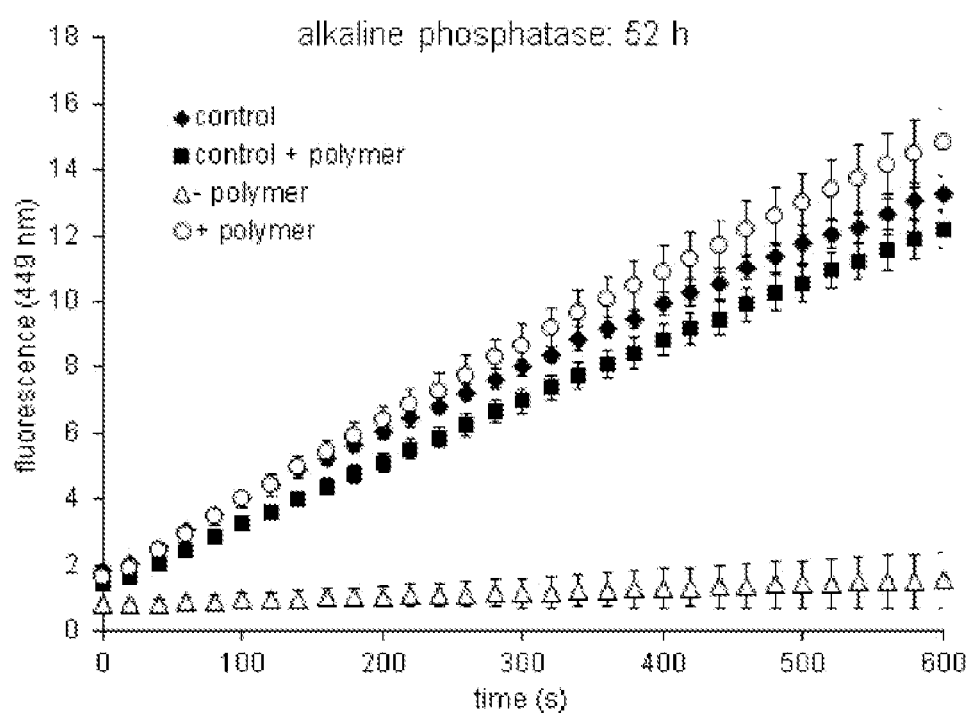

As seen in FIGS. 20A-C, inclusion of NIPAm copolymer was not observed to have a significant impact on the ability of alkaline phosphatase to dephosphorylate the substrate 4-MUP. When stirred at 30° C. for an extended period of time, alkaline phosphatase gradually loses activity as illustrated by the the "-polymer" sample in FIGS. 20B and 20C. After 27 h, stirred enzyme was observed to have about half the activity as the control that was kept unstirred at 4° C.; at 52 h of stirring, negligible activity was detected detected. By including NIPAm copolymer, the enzyme was observed to retain full activity over time when stirred at 30° C., as shown by the sample "+polymer".

Example 22

Synthesis of Additional Copolymers

This Example describes the synthesis of several additional copolymers.

General Polymerization Procedure: Azobisisobutylonitrile (AIBN) was recrystallized from pure methanol before use. N-isopropylacrylamide (NIPAm) and N-isopropylmethacrylamide (NIPMa) were recrystallized from hexanes and toluene twice before use. The tert-butyl 2-(3-(2-methylprop-2-enamido)propylamino)-2-oxoethoxycarbamate (MEPO) was synthesized according to the procedure set forth in Example 1 above. Other monomers were used as obtained. In general, polymerizations were carried out on a 1.2 g total monomer weight scale. Monomers and AIBN were added to a clean scintillation vial. The vial was purged and refilled $N_2$. Methanol which had been previously sparged with $N_2$ for 1 h was added and the components were dissolved under $N_2$. A stream of $N_2$ was bubbled through the solution in the vial for 10 min, and the vial was sealed under $N_2$ and placed in a 60° C. oil bath for 5-6 h. The polymer was recovered from the reaction mixture by one precipitation from methanol into cold diethyl ether followed by centrifugation. The ratio of comonomers was determined by $^1$H-NMR.

LCST Measurements: For Polymers 1-10 described below, LCST was measured by heating 1 mL solutions of 1 mg/mL of each polymer in 50 mM sodium acetate buffer, pH 4.5, at a rate of 2° C./min in a water bath. The LCST value given is the temperature at which the transition from clear, colorless solution to slightly opaque began, as determined visually.

Figure 21:
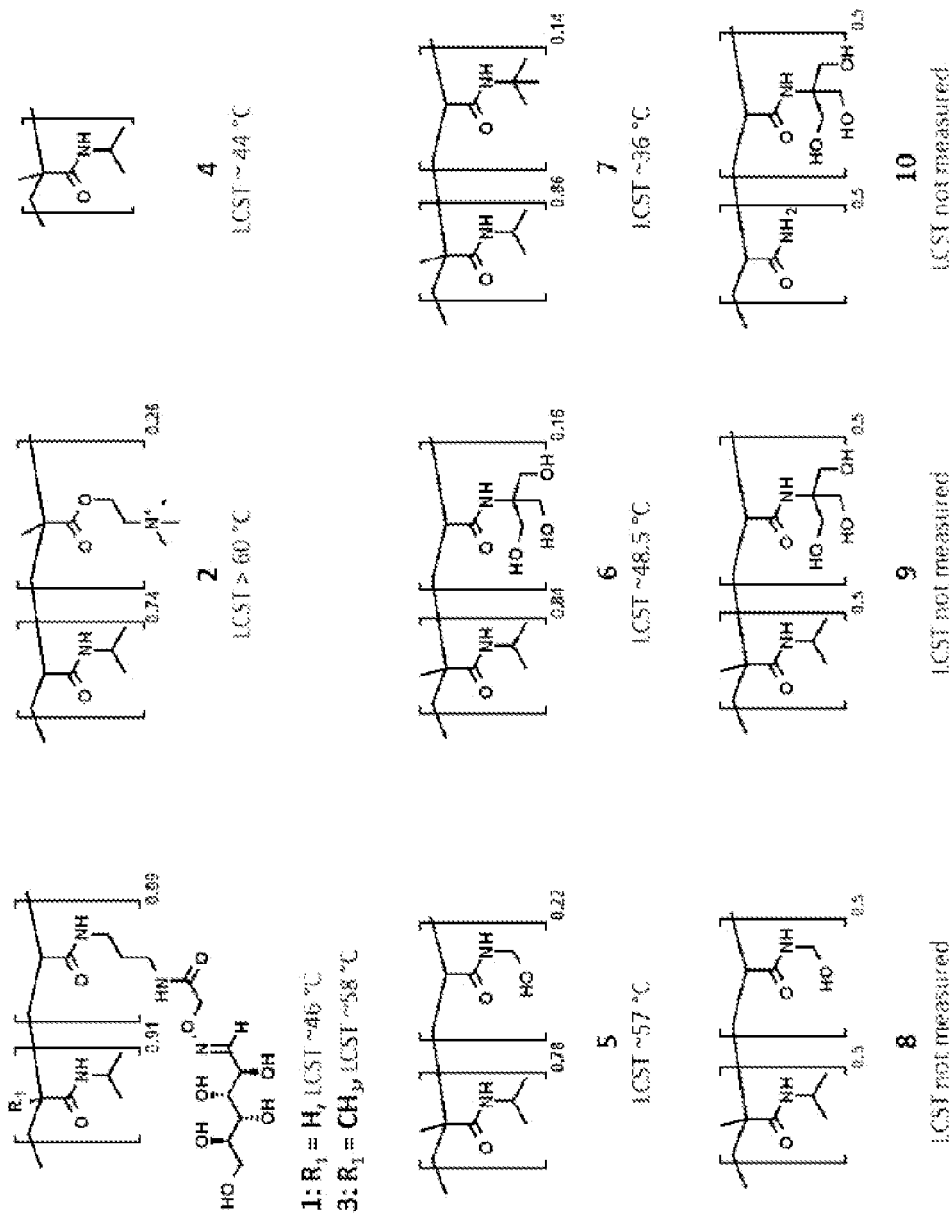
FIG. 21 provides the structures of Polymers 1-10 synthesized in Example 22 below.

The synthesis for each of the polymers are described in further detail below. The structures and corresponding LCSTs (if measured) are summarized in FIG. 21.

Polymer 1: Polymerization was conducted using a 1:9 molar ratio of MEPO:NIPAm and weight percent 11.1:0.6:88.3 for monomers:AIBN:$CH_3OH$. Polymerization was carried out on a 1.2 g scale, and the reaction mixture was divided between six vials following dissolution of all components. Nitrogen was bubbled through the contents and the vials were sealed as described above. Following polymer precipitation in diethyl ether, the dried samples were dissolved in 1:1 $CH_2Cl_2$:trifluoroacetic acid for 1 h to cleave the protecting group, concentrated in vacuo, then neutralized using 5 M NaOH. Samples were purified using Amicon Ultra 15 mL 10 kDa MWCO (Millipore) centrifugal ultrafiltration membranes and lyophilized to afford the dried polymer. The pendant aminooxy groups were then modified with mannose by incubating a solution of 10 mg/mL deprotected polymer with 600 mM mannose in 50 mM sodium acetate buffer, pH 4.5, for 24 h at room temperature. Unreacted small molecule was removed by exchanging the modified polymer into pure water through 8 rounds of ultrafiltration (10 kDa MWCO). The polymer was lyophilized and analyzed by NMR spectroscopy to confirm modification of all aminooxy groups.

Polymer 2: The general polymerization procedure was followed, using 1.2 mmol NIPAm, 0.3 mmol 2-(methacryloyloxy)ethyltrimethylammonium benzyl sulfate, 10 mg AIBN, and 2 mL of methanol. The polymer was isolated by precipitation into cold diethyl ether.

Polymer 3: The same procedure as for Polymer 1 was followed, using 4.93 mmol NIPMa, 0.55 mmol MEPO, 40 mg AIBN, and 8.2 mL methanol, and dividing the reaction into four vials. The polymer was recovered, deprotected, and modified with mannose following the procedure for Polymer 1.

Polymer 4: The general polymerization procedure was followed, using 1.53 mmol NIPMa, 10 mg AIBN, and 2 mL of methanol. The polymer was isolated by precipitation into cold diethyl ether.

Polymer 5: The general polymerization procedure was followed, using 1.26 mmol NIPMa, 0.2 mmol N-hydroxymethyl acrylamide, 10 mg AIBN, and 2 mL of methanol. The polymer was isolated by precipitation into cold diethyl ether.

Polymer 6: The general polymerization procedure was followed, using 1.27 mmol NIPMa, 0.22 mmol N-tris[hydroxymethyl]methyl acrylamide, 10 mg AIBN, and 2 mL of methanol. The polymer was isolated by precipitation into cold diethyl ether.

Polymer 7: The general polymerization procedure was followed, using 1.26 mmol NIPMa, 0.25 mmol N-tertbutyl acrylamide, 10 mg AIBN, and 2 mL of methanol. The polymer was isolated by precipitation into cold diethyl ether.

Polymer 8: The general polymerization procedure was followed, using 0.75 mmol NIPMa, 0.74 mmol N-hydroxymethyl acrylamide, 10 mg AIBN, and 2 mL of methanol. The polymer was isolated by precipitation into cold diethyl ether.

Polymer 9: The general polymerization procedure was followed, using 0.74 mmol NIPMa, 0.74 mmol N-tris[hydroxymethyl]methyl acrylamide, 10 mg AIBN, and 2 mL of methanol. The polymer was isolated by precipitation into cold diethyl ether.

Polymer 10: The general polymerization procedure was followed, using 1.00 mmol acrylamide, 0.51 mmol N-tris[hydroxymethyl]methyl acrylamide, 10 mg AIBN, and 2 mL of methanol. The polymer was isolated by precipitation into cold diethyl ether.

Example 23

Comparison of the Effect of Copolymers from Example 22

This Example compares the effect of the thermally-response copolymers synthesized in Example 22 above on hydrolysis of Avicel and *Miscanthus*.

Assays were performed in triplicate in 1.5 mL Eppendorf tubes on a 0.5 mL scale, in 50 mM NaOAc (pH 4.5), with 1% (w/v) Avicel pH 101 microcrystalline cellulose (Sigma-Aldrich) or acid-pretreated and steam-exploded *Miscanthus*, 0.2 µM EGPh (0.01 mg/g Dry Matter substrate), in a 30° C. water bath for the length of time indicated. Polymers were included at 2 mg/mL (0.2 g/g DM) unless otherwise stated, and were allowed to mix thoroughly with the substrate before addition of enzyme. Controls contained no additive. Samples were stirred by a magnetic stir plate at a rate sufficient to fully suspend the substrate but not so vigorously as to cause a vortex. After 12 h, the tubes were centrifuged at 13.2k rpm for two 5 min intervals, with a 180° rotation in between. An aliquot of the clarified supernatant was transferred to a 0.6 mL Eppendorf tube and frozen on dry ice, then stored at −20° C. until soluble reducing sugar was quantified.

Figure 22:
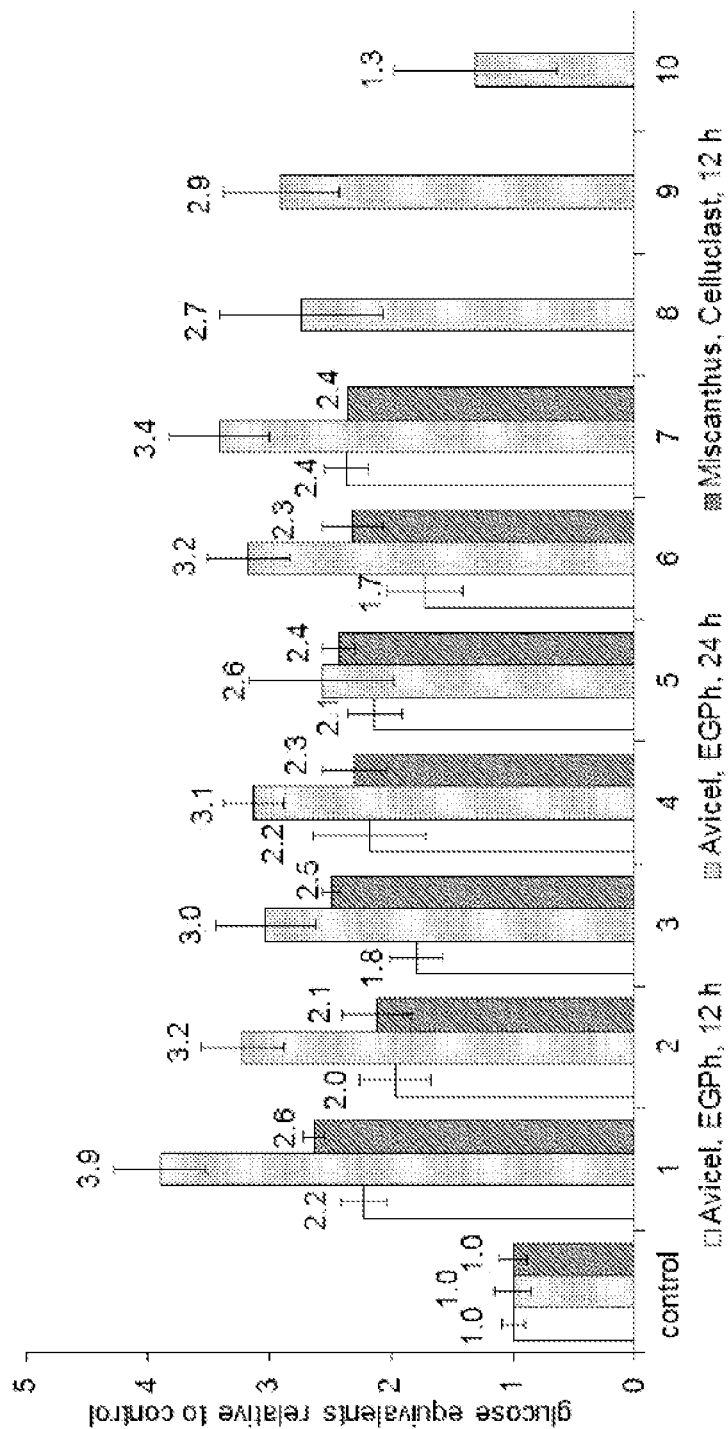
FIG. 22 is a graph comparing the effect of adding Polymers 1-10 on the hydrolysis of Avicel and *Miscanthus*.

As seen in FIG. 22, the addition of Polymers 1-10 increased enzymatic activity compared to the control. Of all the polymers tested, the copolymer made up of NIPAm and mannose-capped aminooxy methacrylamide was observed to have the greatest increase in enzymatic activity in all except for one case. Polymer 7, a copolymer of NIPAm and N-(tert-butyl)acrylamide, was observed to enhance EGPh hydrolysis of Avicel at 12 h to a level slightly greater than Polymer 1, but such difference was not statistically significant. Copolymers containing NIPAm were observed to be more effective than those containing NIPMa (Polymer 1 vs. Polymer 3). Comparing the non-thermoresponsive monomers included in the copolymers, it was observed that the more structurally similar the monomer is to NIPAm (Polymer 7), the more similar the activity enhancement level is to the standard copolymer. This comparison of activity enhancement by a series of structurally similar copolymers illustrates that the NIPAm copolymer is the most effective of the polymers tested in this Example at increasing enzymatic hydrolysis of cellulosic and lignocellulosic substrates.

What is claimed is:

1. A method, comprising contacting a biomass substrate with a hydrolysis enzyme and a thermally-responsive polymer under conditions wherein the enzyme hydrolyzes at least portion of the substrate to produce a product, wherein the polymer is:
    poly N-isopropylacrylamide,
    poly N-isopropylmethacrylamide, or
    a copolymer comprising a plurality of first monomer residues and a plurality of second monomer residues, wherein each of the first monomer residues is independently selected from the group consisting of N-isopropylacrylamide, N-isopropylmethacrylamide, and any combinations thereof, and each of the second monomer residues is an aminooxy-bearing methacrylamide monomer residue.

2. The method of claim 1, wherein the thermally-responsive polymer is a copolymer comprising a plurality of first monomer residues and a plurality of second monomer residues, wherein each of the first monomer residues is independently selected from the group consisting of N-isopropylacrylamide, N-isopropylmethacrylamide, and any combinations thereof, and wherein each of the second monomer residues is an aminooxy-bearing methacrylamide monomer residue.

3. The method of claim 2, wherein each of the second monomer residues of the copolymer independently has the structure of formula (B1) or (B2):

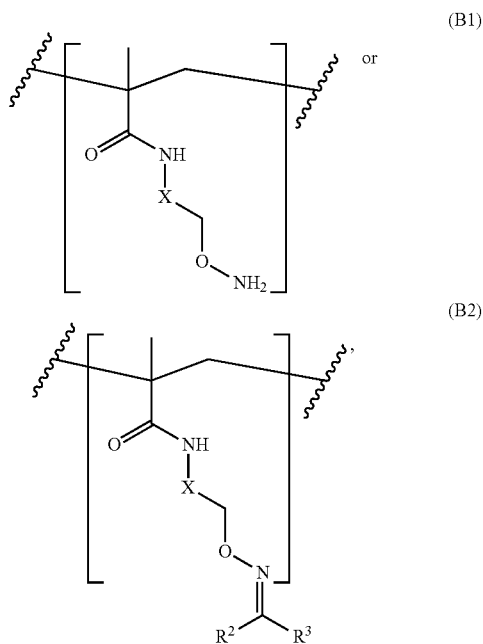

wherein X at each occurrence is:
    unsubstituted $C_{1-10}$-alkyl-;
    $C_{1-10}$-alkyl- substituted with one or more groups independently selected from hydroxy, amino, oxo, nitrate, phosphate, and sulfate;
    unsubstituted $C_{2-10}$-alkenyl-;
    $C_{2-10}$-alkenyl- substituted with one or more groups independently selected from hydroxy, amino, oxo, nitrate, phosphate, and sulfate;
    unsubstituted $C_{2-10}$-alkynyl-;
    $C_{2-10}$-alkynyl- substituted with one or more groups independently selected from hydroxy, amino, oxo, nitrate, phosphate, and sulfate;
    unsubstituted $C_{6-12}$-aryl-;
    $C_{6-12}$-aryl- substituted with one or more groups independently selected from alkyl, halo, hydroxy, amino, oxo, nitrate, phosphate, and sulfate;
    unsubstituted $C_{4-12}$-heteroaryl- with 1 to 3 ring heteroatoms independently selected from the group consisting of nitrogen, oxygen and sulfur;
    $C_{4-12}$-heteroaryl- with 1 to 3 ring heteroatoms independently selected from the group consisting of nitrogen, oxygen and sulfur, wherein the heteroaryl is substituted with one or more groups independently selected from alkyl, halo, hydroxy, amino, oxo, nitrate, phosphate, and sulfate;

unsubstituted $C_{3-12}$ -cycloalkyl-;

$C_{3-12}$ -cycloalkyl- substituted with one or more groups selected from alkyl, halo, hydroxy, amino, oxo, nitrate, phosphate, and sulfate;

unsubstituted $C_{3-12}$ -heterocycloalkyl- with 1 to 3 ring heteroatoms independently selected from the group consisting of nitrogen, oxygen and sulfur;

$C_{3-12}$ -heterocycloalkyl- with 1 to 3 ring heteroatoms independently selected from the group consisting of nitrogen, oxygen and sulfur, wherein the heterocycloalkyl is substituted with one or more groups selected from alkyl, halo, hydroxy, amino, oxo, nitrate, phosphate, and sulfate;

unsubstituted $C_{2-10}$ -ether-;

$C_{2-10}$ -ether- substituted with one or more groups selected from alkyl, halo, hydroxy, amino, oxo, nitrate, phosphate, and sulfate; or —$(CH_2)_j$NHCO—; and $R^2$ and $R^3$ at each occurrence are independently:

H;

unsubstituted $C_{1-10}$ alkyl;

$C_{1-10}$ alkyl substituted with one or more groups independently selected from hydroxy, amino, oxo, nitrate, phosphate, and sulfate;

unsubstituted $C_{2-10}$ alkenyl;

$C_{2-10}$ alkenyl substituted with one or more groups independently selected from hydroxy, amino, oxo, nitrate, phosphate, and sulfate;

unsubstituted $C_{2-10}$ alkynyl;

$C_{2-10}$ alkynyl substituted with one or more groups independently selected from hydroxy, amino, oxo, nitrate, phosphate, and sulfate;

unsubstituted $C_{6-12}$ aryl;

$C_{6-12}$ aryl substituted with one or more groups independently selected from alkyl, halo, hydroxy, amino, oxo, nitrate, phosphate, and sulfate;

unsubstituted $C_{4-12}$ heteroaryl with 1 to 3 ring heteroatoms independently selected from the group consisting of nitrogen, oxygen and sulfur;

$C_{4-12}$ heteroaryl with 1 to 3 ring heteroatoms independently selected from the group consisting of nitrogen, oxygen and sulfur, wherein the heteroaryl is substituted with one or more groups independently selected from alkyl, halo, hydroxy, amino, oxo, nitrate, phosphate, and sulfate;

unsubstituted $_{C3-12}$ cycloalkyl;

$C_{3-12}$ cycloalkyl substituted with one or more groups selected from alkyl, halo, hydroxy, amino, oxo, nitrate, phosphate, and sulfate;

unsubstituted $C_{3-12}$ heterocycloalkyl with 1 to 3 ring heteroatoms independently selected from the group consisting of nitrogen, oxygen and sulfur;

$C_{3-12}$ heterocycloalkyl with 1 to 3 ring heteroatoms independently selected from the group consisting of nitrogen, oxygen and sulfur, wherein the heterocycloalkyl is substituted with one or more groups selected from alkyl, halo, hydroxy, amino, oxo, nitrate, phosphate, and sulfate;

$R^2$ and $R^3$ are taken together with the carbon to which they are attached to form a 5- or 6-membered unsubstituted $C_{4-12}$ heterocyclyl with 1 to 3 ring heteroatoms independently selected from the group consisting of nitrogen, oxygen and sulfur; or $R^2$ and $R^3$ are taken together with the carbon to which they are attached to form a 5- or 6-membered $C_{4-12}$ heterocyclyl with 1 to 3 ring heteroatoms independently selected from the group consisting of nitrogen, oxygen and sulfur, wherein the heterocyclyl is substituted with one or more groups selected from alkyl, halo, hydroxy, amino, oxo, nitrate, phosphate, and sulfate.

4. The method of claim 3, wherein X at each occurrence is —$(CH_2)_3$NHCO—.

5. The method of claim 3, wherein $R^2$ and $R^3$ at each occurrence are independently H, unsubstituted $C_{1-5}$ alkyl, or $C_{1-5}$ alkyl substituted with 1-5 hydroxyl groups.

6. The method of claim 3, wherein

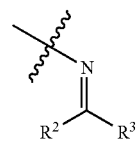

at each occurrence is independently selected from the group consisting of:

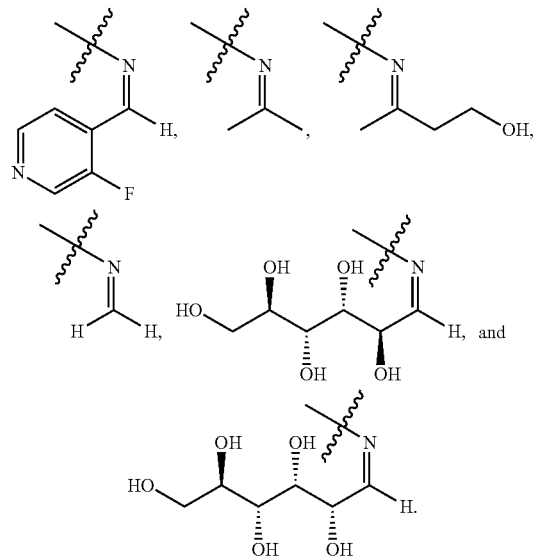

7. The method of claim 2, wherein the plurality of the first monomer residues and the plurality of the second monomer residues are present in a molar ratio of between 50:50 and 99:1.

8. The method of claim 1, wherein the thermally-responsive polymer is at least partially insoluble in water at a temperature above 15° C.

9. The method of claim 1, wherein the thermally-responsive polymer is at least partially insoluble in water at a temperature between 20° C. and 70° C.

10. The method of claim 1, wherein the thermally-responsive polymer has a molecular weight of between about 5,000 Da and about 1,000,000 Da.

11. The method of claim 1, wherein the thermally-responsive polymer has a polydispersity index (PDI) of between about 1.0 and about 2.0.

12. The method of claim 1, wherein the enzyme is an endoglucanase, an exoglucanase, a β-glucosidase, or a polysaccharide monooxygenase.

13. The method of claim 1, further comprising recovering the thermally-responsive polymer after hydrolysis.

14. The method of claim 13 further comprising:
   i) providing second biomass substrate, a second hydrolysis enzyme, and the recovered thermally-responsive polymer;
   ii) contacting the second substrate with the second hydrolysis enzyme in the presence of the recovered the thermally-responsive polymer; and
   iii) hydrolyzing at least a portion of the second substrate to produce second products.

* * * * *